US008324199B2

(12) United States Patent
Corte et al.

(10) Patent No.: US 8,324,199 B2
(45) Date of Patent: Dec. 4, 2012

(54) PYRIDAZINE DERIVATIVES AS FACTOR XIA INHIBITORS

(75) Inventors: James R. Corte, Lawrenceville, NJ (US); Zilun Hu, Jamison, PA (US); Mimi L. Quan, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 128 days.

(21) Appl. No.: 12/921,177

(22) PCT Filed: Mar. 12, 2009

(86) PCT No.: PCT/US2009/036934
§ 371 (c)(1),
(2), (4) Date: Sep. 7, 2010

(87) PCT Pub. No.: WO2009/114677
PCT Pub. Date: Sep. 17, 2009

(65) Prior Publication Data
US 2011/0021492 A1 Jan. 27, 2011

Related U.S. Application Data

(60) Provisional application No. 61/036,127, filed on Mar. 13, 2008, provisional application No. 61/145,203, filed on Jan. 16, 2009.

(51) Int. Cl.
*A61K 31/00* (2006.01)
*C07D 401/00* (2006.01)
(52) U.S. Cl. .............. 514/210.18; 544/238; 544/224
(58) Field of Classification Search .......... 544/238, 544/224; 514/210.18
See application file for complete search history.

(56) References Cited

U.S. PATENT DOCUMENTS

| | | | |
|---|---|---|---|
| 7,429,604 B2 | 9/2008 | Corte et al. | |
| 7,453,002 B2 | 11/2008 | Hangeland et al. | |
| 7,459,564 B2 | 12/2008 | Corte et al. | |
| 7,626,039 B2 | 12/2009 | Pinto et al. | |
| 2004/0180855 A1 | 9/2004 | Schumacher et al. | |
| 2009/0181938 A1 | 7/2009 | Binch et al. | |
| 2009/0181983 A1* | 7/2009 | Corte | 514/256 |
| 2009/0253766 A1 | 10/2009 | Han | |
| 2010/0016316 A1 | 1/2010 | Pinto | |
| 2010/0173899 A1 | 7/2010 | Pinto et al. | |

FOREIGN PATENT DOCUMENTS

| | | |
|---|---|---|
| EP | 1 810 965 A1 | 7/2007 |
| WO | WO2007/070818 A1 | 6/2007 |
| WO | WO2007/070826 A1 | 6/2007 |

OTHER PUBLICATIONS

Chan, J. et al., "The Characterization of Mice with a Targeted Combined Deficiency of Protein C and Factor XI", American J. of Pathology, vol. 158(2), pp. 469-477 (2001).
Gailani, D. et al., "A murine model of factor XI deficiency", Blood Coagulation and Fibrinolysis, vol. 8, pp. 134-144 (1997).
Gailani, D., "Gene Targeting in Hemostasis. Factor XI", Frontiers in Bioscience, vol. 6, pp. 201-207 (2001).
Gruber, A. et al., "Factor XI-dependence of surface-and tissue factor-initiated thrombus propagation in primates", Blood, vol. 102(3), pp. 953-955 (2003).
Hoffman, M., "A cell-based model of coagulation and the role of factor VIIa", Blood Reviews, vol. 17, pp. S1-S5 (2003).
Meijers, J. et al., "High Levels of Coagulation Factor XI as a Risk Factor for Venous Thrombosis", The New England J. of Medicine, vol. 342, pp. 696-701 (2000).
Minnema, M. et al., "Activation of Clotting Factors XI and IX in Patients with Acute Myocardial infarction", vol. 20, pp. 2489-2493 (2000).
Murakami, T. et al., "Evaluation of Factor XIa-$\alpha_1$-Antitrypsin in Plasma, a Contact Phase-Activated Coagulation Factor-Inhibitor Complex, in Patients with Coronary Artery Disease", Arterioscler, Thromb, Vasc, Biology, vol. 15, pp. 1107-1113 (1995).
Rosen, E. et al., "FXI is Essential for Thrombus Formation Following $FeCl_3$—Induced Injury of the Carotid Artery in the Mouse", Thromb Haemost., vol. 87, pp. 774-776 (2002).
Walsh, P., "Platelets and Factor XI Bypass the Contact System of Blood Coagulation", Thrombosis and Haemostasis, vol. 82(2), pp. 234-242 (1999).
Wang, X. et al., "Effects of factor IX or factor XI deficiency on ferric chloride-induced carotid artery occlusion in mice", J. of Thrombosis and Haemostasis, vol. 3, pp. 695-702 (2004).

* cited by examiner

*Primary Examiner* — Rei-tsang Shiao
(74) *Attorney, Agent, or Firm* — Hong Liu

(57) ABSTRACT

The present invention provides compounds of Formula (I):

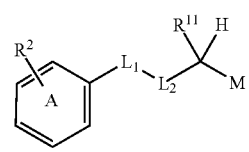

or stereoisomers, tautomers, or pharmaceutically acceptable salts thereof, wherein the variables A, $L_1$, $L_2$, $R^2$, $R^{11}$, and M are as defined herein. These compounds are selective factor XIa inhibitors or dual inhibitors of fXIa and plasma kallikrein. This invention also relates to pharmaceutical compositions comprising these compounds and methods of treating thromboembolic and/or inflammatory disorders using the same.

9 Claims, No Drawings

PYRIDAZINE DERIVATIVES AS FACTOR XIA INHIBITORS

CROSS-REFERENCE TO RELATED APPLICATIONS

The present application is a 371 application of PCT/US2009/036934 filed Mar. 12, 2009, which claims the priority benefit of U.S. Provisional Application No. 61/036,127, filed Mar. 13, 2008 and the priority benefit of U.S. Provisional Application No. 61/145,203, filed Jan. 16, 2009, all of which are expressly incorporated fully herein by reference.

FIELD OF THE INVENTION

The present invention relates generally to novel pyridazine derivatives and analogues thereof, which inhibit factor XIa and/or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N., *Thromb. Haemostasis* 1999, 82:234-242.) The resulting burst of thrombin converts fibrinogen to fibrin that polymerizes to form the structural framework of a blood clot, and activates platelets, which are a key cellular component of coagulation (Hoffman, M., *Blood Reviews* 2003, 17:S1-S5). Therefore, factor XIa plays a key role in propagating this amplification loop and is thus an attractive target for anti-thrombotic therapy.

SUMMARY OF THE INVENTION

The present invention provides novel pyridazine derivatives and analogues thereof, which are useful as selective inhibitors of serine protease enzymes, especially factor XIa and/or plasma kallikrein, or stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

These and other features of the invention will be set forth in expanded form as the disclosure continues.

DETAILED DESCRIPTION OF THE INVENTION

I. Compounds Of The Invention

In a first aspect, the present invention provides, inter alia, a compound of Formula (I):

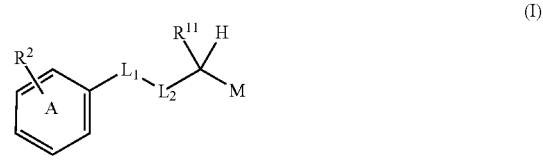

or a stereoisomer, a tautomer, a pharmaceutically acceptable salt, a solvate, or a prodrug thereof, wherein:

A is phenyl further substituted with 0-3 $R^1$, or pyridyl further substituted with 0-3 $R^1$;

$L_1$ is —CH($R^5$)CH$_2$—, —CH(NR$^7$R$^8$)CH$_2$—, —C($R^5$)=CH—, —C≡C—, —OCH$_2$—, —CR$^5$R$^6$NH—, —CH$_2$O—, —SCH$_2$—, —S(O)CH$_2$—, —SO$_2$CH$_2$—, —CH$_2$NR$^{10}$—, or —NHNH—;

$L_2$ is —CONH— or —NHCO—;

provided that when $L_1$ is —NHNH—, —OCH$_2$—, or —SCH$_2$—, then $L_2$ is —CONH—;

M is selected from the group consisting of:

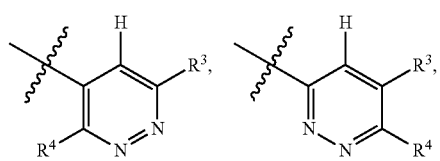

-continued

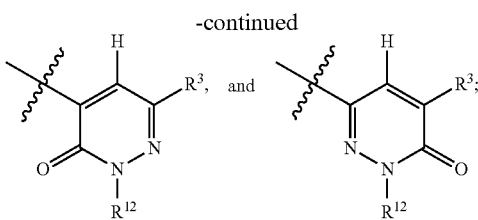

R¹ is, independently at each occurrence, F, Cl, Br, I, OCF₃, CHF₂, CF₃, —(CH₂)ᵣORᵃ, —(CH₂)ᵣSRᵃ, CN, NO₂, —(CH₂)ᵣNR⁷R⁸, —(CH₂)ᵣC(O)ORᵃ, —(CH₂)ᵣOC(O)Rᵃ, —C(=NR⁸)NR⁸R⁹, —(CH₂)ᵣC(O)NR⁸R⁹, —(CH₂)ᵣNR⁸C(O)Rᶜ, —(CH₂)ᵣNR⁸C(O)ORᶜ, —NR⁸C(O)NR⁸Rᶜ, —S(O)ₚNR⁸R⁹, —S(O)Rᶜ, —S(O)₂Rᶜ, or C₁₋₆ alkyl substituted with 0-1 R¹³;

R² is H, —(CH₂)ᵣC(O)Rᵃ, —(CH₂)ᵣORᵃ, —(CH₂)ᵣNR⁷R⁸, C₁₋₆ alkyl substituted with 0-1 R²ᵃ, —(CH₂)ᵣ-3- to 7-membered carbocycle substituted with 0-2 R²ᵇ, or —(CH₂)ᵣ-5- to 7-membered heterocycle comprising carbon atoms and 1-4 heteroatoms selected from N, O, and S(O)ₚ, wherein said heterocycle is substituted with 0-2 R²ᵇ;

R²ᵃ is F, OCF₃, CF₃, ORE, SRᵃ, CN, —NR⁷R⁸, —C(O)NR⁸R⁹, —NR⁸C(O)Rᶜ, —NR⁸C(O)ORᶜ, —NR⁸C(O)NR⁸Rᶜ, —S(O)ₚNR⁸R⁹, —NR⁸SO₂Rᶜ, or —(CF₂)ᵣCF₃;

R²ᵇ is, independently at each occurrence, =O, F, Br, Cl, OCF₃, CF₃, —(CH₂)ᵣORᵃ, —(CH₂)ᵣSRᵃ, —(CH₂)ᵣCN, —(CH₂)ᵣNR⁷R⁸, —(CH₂)ᵣC(O)ORᵃ, —(CH₂)ᵣOC(O)Rᵃ, —(CH₂)ᵣC(O)NR⁸R⁹, —(CH₂)ᵣNR⁸C(O)Rᶜ, —(CH₂)ᵣNR⁸C(O)ORᶜ, —(CH₂)ᵣS(O)ₚNR⁸R⁹, —(CH₂)ᵣNR⁸SO₂Rᶜ, C₁₋₄ alkyl or —(CF₂)ᵣCF₃;

R³ is, independently at each occurrence, —(CH₂)ᵣ—C₃₋₁₀ carbocycle substituted with 0-3 R³ᵃ and 0-1 R³ᵈ, or —(CH₂)ᵣ-5- to 12-membered heterocycle comprising: carbon atoms and 1-4 heteroatoms selected from N, O, and S(O)ₚ, wherein said heterocycle is substituted with 0-3 R¹ᵃ and 0-1 R³ᵈ;

R³ᵃ is, independently at each occurrence, F, Cl, Br, I, OCF₃, CF₃, —(CH₂)ᵣCN, NO₂, —(CH₂)ᵣORᵃ, —(CH₂)ᵣSRᵃ, —(CH₂)ᵣNR⁷R⁸, —NHC(O)NR⁸R⁹, —(CH₂)ᵣC(O)ORᵃ, —C(O)C₁₋₄ alkyl, —(CH₂)ᵣNR⁸C(O)Rᵃ, —(CH₂)ᵣNR⁸CO₂Rᶜ, —(CH₂)ᵣS(O)ₚNR⁸R⁹, —(CH₂)ᵣNR⁸S(O)ₚRᶜ, —NHSO₂CF₃, —S(O)Rᶜ, —S(O)₂Rᶜ, —(CH₂)ᵣOC(O)Rᶜ, —(CH₂)ᵣC(O)NR⁸R⁹, —(CH₂)ᵣOC(O)NR⁸R⁹, C₁₋₄ haloalkyl, C₁₋₄ haloalkyloxy-, C₁₋₆ alkyl, C₃₋₆ cycloalkyl substituted by 0-1 R³ᵈ, —(CH₂)ᵣ—C₆₋₁₀ carbocycle substituted by 0-3 R³ᵈ or —(CH₂)ᵣ-5- to 10-membered heterocycle comprising: carbon atoms and 1-4 heteroatoms selected from N, O, and S(O)ₚ, wherein said heterocycle is substituted with 0-3 R³ᵈ;

R³ᵈ is, independently at each occurrence, H, =O, F, Cl, Br, CN, NO₂, —(CH₂)ᵣNR⁷R⁸, —(CH₂)ᵣORᵃ, —C(O)Rᵃ, —C(O)ORᵃ, —OC(O)Rᵃ, —NR⁸C(O)Rᶜ, —C(O)NR⁸R⁹, —S(O)₂NR⁸R⁹, —NR⁷R⁸, —NR⁸S(O)₂NR⁸R⁹, —NR⁸S(O)₂Rᶜ, —S(O)ₚRᶜ, —(CF₂)ᵣCF₃, C₁₋₆ alkyl substituted with 0-2 Rᵉ, C₂₋₆ alkenyl substituted with 0-2 Rᵉ, C₂₋₆ alkynyl substituted with 0-2 Rᵉ, —(CH₂)ᵣ—C₃₋₁₀ carbocycle substituted with 0-3 Rᵈ, or —(CH₂)ᵣ-5- to 10-membered heterocycle comprising: carbon atoms and 1-4 heteroatoms selected from N, O, and S(O)ₚ, wherein said heterocycle is substituted with 0-3 Rᵈ;

R⁴ is, independently at each occurrence, H, F, Cl, Br, I, OCF₃, CF₃, CN, NO₂, —(CH₂)ᵣORᵃ, —(CH₂)ᵣSRᵃ, —(CH₂)ᵣC(O)Rᵃ, —(CH₂)ᵣC(O)ORᵃ, —OC(O)Rᵃ, —(CH₂)ᵣNR⁷R⁸, —NR⁸(CH₂)ᵣC(O)ORᵃ, —(CH₂)ᵣC(O)NR⁸R⁹, —(CH₂)ᵣNR⁸C(O)Rᶜ, —(CH₂)ᵣNR⁸C(O)₂Rᵇ, —(CH₂)ᵣNR⁸C(O)NR⁸R⁹, —S(O)ₚNR⁸R⁹, —NR⁸S(O)ₚRᶜ, —(CH₂)ᵣS(O)₂Rᶜ, —(CH₂)ᵣOP(O)(ORᵃ)₂, C₁₋₄ alkyl substituted with 0-2 R⁴ᵃ, or C₂₋₄ alkenyl substituted with 0-2 R⁴ᵃ;

R⁴ᵃ is, independently at each occurrence, H, F, =O, C₁₋₆ alkyl, ORᵃ, SRᵃ, CF₃, CN, NO₂, —C(O)Rᵃ, —C(O)ORᵃ, —NR⁷R⁸, —C(O)NR⁸R⁹, —NR⁸C(O)Rᶜ, —S(O)ₚNR⁸R⁹, —NR⁸S(O)ₚRᶜ, —S(O)Rᶜ, or —S(O)₂Rᶜ;

R⁵ is, independently at each occurrence, H, F, CF₃, —(CH₂)ᵣORᵃ, =O, —(CH₂)ᵣNR⁷R⁸, —S(O)ₚNR⁸R⁹, —(CH₂)ᵣCO₂Rᵃ, —(CH₂)ᵣCONR⁸R⁹, or C₁₋₄ alkyl;

R⁶ is, independently at each occurrence, H, F, or C₁₋₄ alkyl;

R⁷ is, independently at each occurrence, H, C₁₋₆ alkyl, —(CH₂)ₙ—C₃₋₁₀ carbocycle, —(CH₂)ₙ-(5- to 10-membered heteroaryl), —C(O)Rᶜ, —CHO, —C(O)₂Rᶜ, —S(O)₂Rᶜ, —CONR⁸Rᶜ, —OCONHRᶜ, —C(O)O—(C₁₋₄alkyl)OC(O)—(C₁₋₄ alkyl), or —C(O)O—(C₁₋₄ alkyl)OC(O)—(C₆₋₁₀ aryl); wherein said alkyl, carbocycle, heteroaryl, and aryl are substituted with 0-2 Rᶠ; wherein said heteroaryl comprises: carbon atoms and 1-4 heteroatoms selected from N, O, and S(O)ₚ;

R⁸ is, independently at each occurrence, H, C₁₋₆ alkyl, —(CH₂)ₙ-phenyl, or —(CH₂)ₙ-5- to 10-membered heterocycle comprising: carbon atoms and 1-4 heteroatoms selected from N, O, and S(O)ₚ; wherein said alkyl, phenyl and heterocycle are optionally substituted with 0-2 Rᶠ;

alternatively, R⁷ and R⁸, when attached to the same nitrogen, combine to form a 5- to 10-membered heterocycle comprising: carbon atoms and 0-3 additional heteroatoms selected from N, O, and S(O)ₚ, wherein said heterocycle is substituted with 0-2 Rᶠ;

R⁹ is, independently at each occurrence, H, C₁₋₆ alkyl, or —(CH₂)ₙ-phenyl; wherein said alkyl and phenyl are optionally substituted with 0-2 Rᶠ;

alternatively, R⁸ and R⁹, when attached to the same nitrogen, combine to form a 5- to 12-membered heterocycle comprising: carbon atoms and 0-2 additional heteroatoms selected from N, O, and S(O)ₚ, wherein said heterocycle is substituted with 0-2 Rᵈ;

R¹⁰ is, independently at each occurrence, H or C₁₋₆ alkyl substituted with 0-3 R¹⁰ᵃ;

R¹⁰ᵃ is, independently at each occurrence, H, =O, C₁₋₄ alkyl, ORᵃ, SRᵃ, F, CF₃, CN, NO₂, —C(O)Rᵃ, —C(O)ORᵃ, —C(O)NR⁸R⁹, —NR⁸C(O)Rᶜ, —S(O)ₚNR⁸R⁹, —NR⁸S(O)ₚRᶜ, or —S(O)ₚRᶜ;

R¹¹ is C₁₋₄ haloalkyl, C₁₋₆ alkyl substituted with 0-3 R¹¹ᵃ, C₂₋₆ alkenyl substituted with 0-3 R¹¹ᵃ, C₂₋₆ alkynyl substituted with 0-3 R¹¹ᵃ, —(CH₂)ₛ—C₃₋₁₀ carbocycle substituted with 0-3 Rub or —(CH₂)ₛ-4- to 10-membered heterocycle comprising: carbon atoms and 1-4 heteroatoms selected from N, O, and S(O)ₚ, wherein said heterocycle is substituted with 0-3 R¹¹ᵇ;

R¹¹ᵃ is independently at each occurrence H, =O, ORᵃ, SRᵃ, F, CF₃, CN, NO₂, —C(O)Rᵃ, —C(O)ORᵃ, —NR⁷R⁸, —C(O)NR⁸R⁹, —NR⁸C(O)Rᶜ, —NR⁸C(O)ORᶜ, —NR⁸CHO, —S(O)ₚNR⁸R⁹, —NR⁸S(O)ₚRᶜ, —S(O)ₚRᶜ, C₁₋₄ alkyl, C₃₋₆ cycloalkyl, C₁₋₄ haloalkyl, C₁₋₄ haloalkyloxy-, —(CH₂)ᵣ—C₃₋₁₀ carbocycle substituted with 0-3 Rᵈ, or —(CH₂)ᵣ-5- to 10-membered heterocycle comprising carbon atoms and 1-4 heteroatoms selected from N, O, and S(O)ₚ, and substituted with 0-3 Rᵈ;

R¹¹ᵇ is, independently at each occurrence, H, =O, =NR⁸, ORᵃ, —CH₂ORᵃ, F, Cl, Br, CN, NO₂, CF₃, OCF₃, OCHF₂, —C(CH₃)₂ORᵃ, —C(O)Rᵃ, —C(O)ORᵃ, —NR⁷R⁸, —C(O)NR⁸R⁹, —NR⁷C(O)Rᵇ, —NR⁸C(O)₂Rᶜ, —NR⁸C(O)NR⁸R⁹, —S(O)ₚNR⁸R⁹, —NR⁸S(O)ₚRᶜ, —S(O)ₚRᶜ, C₁₋₆ alkyl, C₂₋₆ alkenyl, C₂₋₆ alkynyl, C₃₋₆ cycloalkyl, C₁₋₄ haloalkyl, C₁₋₄ haloalkyloxy-, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

R$^{12}$ is independently at each occurrence, H, C$_{1-6}$ alkyl substituted with 0-2 R$^f$, or —(CH$_2$)$_n$-phenyl;

R$^{13}$ is F, OCF$_3$, CF$_3$, OR$^e$, SR$^a$, CN, —NR$^7$R$^8$, —C(O)NR$^8$R$^9$, —NR$^8$C(O)R$^c$, —S(O)$_p$NR$^8$R$^9$, —NR$^8$SO$_2$R$^c$, or —(CF$_2$)$_r$CF$_3$;

R$^a$ is, independently at each occurrence, H, CF$_3$, C$_{1-6}$ alkyl, —(CH$_2$)$_r$—C$_{3-7}$ cycloalkyl, —(CH$_2$)$_r$—C$_{6-10}$ aryl, or —(CH$_2$)$_r$-5- to 10-membered heterocycle comprising carbon atoms and 1-4 heteroatoms selected from N, O, and S(O)$_p$; wherein said alkyl, cycloalkyl, aryl or heterocycle groups are substituted with 0-2 R$^f$;

R$^b$ is, independently at each occurrence, CF$_3$, OH, C$_{1-4}$ alkoxy, C$_{1-6}$ alkyl substituted with 0-2 R$^d$, —(CH$_2$)$_r$—C$_{3-10}$ carbocycle substituted with 0-2 R$^d$, or —(CH$_2$)$_r$-5- to 10-membered heterocycle comprising: carbon atoms and 1-4 heteroatoms selected from N, O, and S(O)$_p$ and substituted with 0-3 R$^d$;

R$^c$ is, independently at each occurrence, CF$_3$, C$_{1-6}$ alkyl substituted with 0-2 R$^f$, C$_{3-6}$ cycloalkyl substituted with 0-2 R$^f$, C$_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl is substituted with 0-3 R$^f$ and said heteroaryl comprises: carbon atoms and 1-4 heteroatoms selected from N, O, and S(O)$_p$ and substituted with 0-3 R$^f$;

R$^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$;

R$^e$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^e$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^f$ is, independently at each occurrence, H, =O, —(CH$_2$)$_r$OR$^g$, F, Cl, Br, I, CN, NO$_2$, —NR$^g$R$^g$, —C(O)R$^g$, —C(O)OR$^g$, —OC(O)R$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, —(CH$_2$)$_p$-phenyl, or —(CH$_2$)$_n$-5- to 10-membered heterocycle comprising carbon atoms and 1-4 heteroatoms selected from N, O, and S(O)$_p$;

R$^g$ is, independently at each occurrence, H, C$_{1-6}$ alkyl, or —(CH$_2$)$_p$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4.
s, at each occurrence, is selected from 1, 2, 3, and 4.

In a second aspect, the present invention includes a compound of Formula (I), or a stereoisomer, a tautomer, a pharmaceutically acceptable salt, a solvate, or a prodrug thereof, within the scope of the first aspect wherein:

R$^2$ is, H, —(CH$_2$)$_r$C(O)R$^a$, —(CH$_2$)$_r$OR$^a$, —(CH$_2$)$_r$NR$^7$R$^8$, C$_{1-6}$ alkyl substituted with 0-1 R$^{2a}$, —(CH$_2$)$_r$—C$_{3-6}$ cycloalkyl substituted with 0-2 R$^{2b}$, —(CH$_2$)$_r$-phenyl substituted with 0-2 R$^{2b}$, or —(CH$_2$)$_r$-5-7 membered heterocycle comprising carbon atoms and 1-4 heteroatoms selected from N, O, and S(O)$_p$, wherein said heterocycle is substituted with 0-2 R$^{2b}$;

R$^3$ is, independently at each occurrence, —(CH$_2$)$_r$-phenyl substituted with 0-2 R$^{3a}$ and 0-1 R$^{3d}$, —(CH$_2$)$_r$-naphthyl substituted with 0-2 R$^{3a}$ and 0-1 R$^{3d}$, —(CH$_2$)$_r$-1,2,3,4-tetrahydronaphthyl substituted with 0-2 R$^{3a}$ and 0-1 R$^{3d}$, or —(CH$_2$)$_r$-5- to 12-membered heterocycle substituted with 0-2 R$^{3a}$ and 0-1 R$^{3d}$, wherein said heterocycle is selected from the group consisting of: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

R$^4$ is, independently at each occurrence, H, F, Cl, Br, OCF$_3$, CF$_3$, CN, NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —(CH$_2$)$_r$NR$^7$R$^8$, —(CH$_2$)$_r$C(O)NR$^8$R$^9$, —(CH$_2$)$_r$S(O)$_2$R$^c$, C$_{1-4}$ alkyl substituted with 0-2 R$^{4a}$, or C$_{2-4}$ alkenyl substituted with 0-2 R$^{4a}$; and R$^{11}$ is —CH$_2$OR$^a$, —CH$_2$CH$_2$OR$^a$, —CH$_2$S(O)$_p$R$^c$, —CH$_2$CH$_2$S(O)$_p$R$^c$, —CH$_2$NR$^7$R$^8$, —CH$_2$CH$_2$NR$^7$R$^8$, —CH$_2$C(O)R$^a$, —CH$_2$CH$_2$C(O)R$^a$, —CH$_2$C(O)OR$^a$, —CH$_2$CH$_2$C(O)OR$^a$, —CH$_2$C(O)NR$^8$R$^9$, —CH$_2$CH$_2$C(O)NR$^8$R$^9$, —CH$_2$NR$^8$C(O)R$^c$, —CH$_2$CH$_2$NR$^8$C(O)R$^c$, —CH$_2$NR$^8$C(O)OR$^c$, —CH$_2$CH$_2$NR$^8$C(O)OR$^c$, —CH$_2$NHS(O)$_2$(3-(pyrazol-1-yl)-Ph), —CH$_2$NHS(O)$_2$(1,3-dimethyl-pyrazol-4-yl), C$_{1-4}$ haloalkyl, C$_{1-6}$ alkyl substituted with 0-2 R$^{11a}$, C$_{2-6}$ alkyl substituted with 0-2 R$^{11a}$, —(CH$_2$)$_s$—C$_{3-6}$ cycloalkyl substituted with 0-2 R$^{11b}$, —(CH$_2$)$_s$-phenyl substituted with 0-3 R$^{11b}$, or —(CH$_2$)$_s$-4- to 10-membered heterocycle comprising: carbon atoms and 1-4 heteroatoms selected from N, O, and S(O)$_p$, wherein said heterocycle is substituted with 0-3 R$^{11b}$.

In a third aspect, the present invention includes a compound of Formula (I) or a stereoisomer, a tautomer, a pharmaceutically acceptable salt, a solvate, or a prodrug thereof, within the scope of the first or second aspects wherein:

L$_1$ is —CH$_2$CH$_2$—, —CH=CH—, —C(Me)=CH—, —C≡C—, —CH$_2$NH—, —CH$_2$O—, —NHNH—, —SCH$_2$—, —SO$_2$CH$_2$— or —OCH$_2$—;

L$_2$ is —CONH— or —NHCO—;

provided that when L$_1$ is —NHNH—, —OCH$_2$—, or —SCH$_2$— then L$_2$ is —CONH—;

R$^3$ is, independently at each occurrence, —(CH$_2$)$_r$-phenyl substituted with 0-3 R$^{3a}$, —(CH$_2$)$_r$-pyridyl substituted with 0-3 R$^{3a}$, —(CH$_2$)$_r$-thiazolyl substituted with 0-2 R$^{3a}$, or

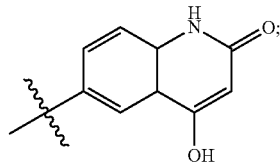

R$^4$ is, independently at each occurrence, H, F, Cl, Br, OCF$_3$, CF$_3$, CN, NO$_2$, —(CH$_2$)$_r$OR$^a$, —CH(OH)CH$_2$OH, —(CH$_2$)$_r$SR$^a$, C(O)R$^a$, C(O)OR$^a$, —(CH$_2$)$_r$NR$^7$R$^8$, —(CH$_2$)$_r$S(O)$_2$R$^c$, C(O)NR$^8$R$^9$, C$_{1-4}$ alkyl substituted with 0-2 R$^{4a}$, or C$_{2-4}$ alkenyl substituted with 0-2 R$^{4a}$; and $R^{11}$ is —CH$_2$OR$^a$, —CH$_2$CH$_2$OR$^a$, —CH$_2$S(O)$_p$R$^c$, —CH$_2$CH$_2$S(O)$_p$R$^c$, —CH$_2$NR$^7$R$^8$, —CH$_2$CH$_2$NR$^7$R$^8$, —CH$_2$C(O)R$^a$, —CH$_2$CH$_2$C(O)R$^a$, —CH$_2$C(O)OR$^a$, —CH$_2$CH$_2$C(O)OR$^a$, —CH$_2$C(O)NR$^8$R$^9$, —CH$_2$CH$_2$C(O)NR$^8$R$^9$, —CH$_2$NR$^8$C(O)R$^c$, —CH$_2$CH$_2$NR$^8$C(O)R$^c$, —CH$_2$NR$^8$C(O)OR$^c$, —CH$_2$CH$_2$NR$^8$C(O)OR$^c$, —CH$_2$NHS(O)$_2$(3-(pyrazol-1-yl)-Ph), —CH$_2$NHS(O)$_2$(1,3-dimethyl-pyrazol-4-yl), C$_{1-6}$ alkyl, C$_{2-6}$ alkenyl, —(CH$_2$)$_s$-phenyl substituted with 0-2 R$^{11b}$, or —(CH$_2$)$_s$-4 to 6-membered heterocycle substituted with 0-2 R$^{11b}$, wherein said heterocycle is selected from the group consisting of: azetidine, oxazolidin-2-one, pyrrolidine, pyrazole, thiazole, thiadiazole, oxazole, oxadiazole, imidazole, piperidine, piperazine, and pyridine;

alternatively, $R^{11}$ is

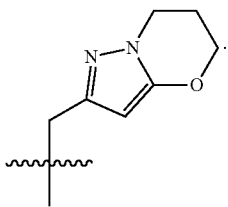

In a fourth aspect, the present invention includes a compound of Formula (II):

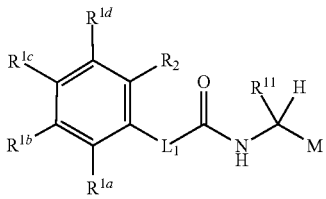

(II)

or a stereoisomer, a tautomer, a pharmaceutically acceptable salt, a solvate, or a prodrug thereof, wherein:

M is selected from the group consisting of:

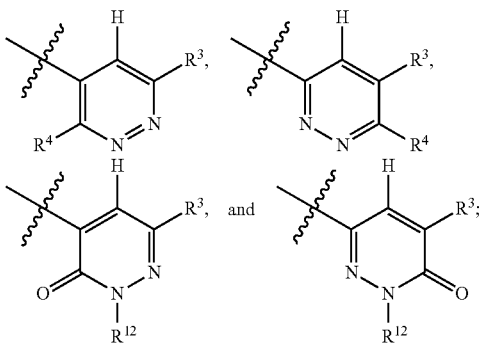

$L_1$ is —CH$_2$CH$_2$—, —CH=CH—, —C≡C—, —OCH$_2$—, —CH$_2$NH—, —CH$_2$O—, or —SCH$_2$—;

$R^{1a}$, $R^{1b}$, $R^{1c}$, and $R^{1d}$ are, are independently at each occurrence, H, F, Cl, Br, CF$_3$, —(CH$_2$)$_r$OR$^a$, CN, —(CH$_2$)$_r$NR$^7$R$^8$, or C$_{1-4}$ alkyl;

$R^2$ is —(CH$_2$)$_r$C(O)R$^a$, —(CH$_2$)$_r$OR$^a$, —(CH$_2$)$_r$NR$^7$R$^8$, or 5-membered heterocycle comprising carbon atoms and 1-4 heteroatoms selected from N, O, and S(O)$_p$, wherein said heterocycle is substituted with 0-2 R$^{2b}$;

$R^{2b}$ is, independently at each occurrence, F, Br, Cl, OCF$_3$, CF$_3$, OR$^a$, SR$^a$, CN, NR$^7$R$^8$, C(O)OR$^a$, or C$_{1-4}$ alkyl;

$R^3$ is, independently at each occurrence, —(CH$_2$)$_r$-phenyl substituted with 0-3 R$^{3a}$, —(CH$_2$)$_r$-pyridyl substituted with 0-3 R$^{3a}$, —(CH$_2$)$_r$-thiazolyl substituted with 0-2 R$^{3a}$, or

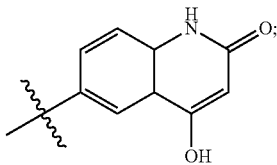

$R^{3a}$ is, independently at each occurrence, F, Cl, Br, I, OCF$_3$, CF$_3$, CN, NO$_2$, ORE, SR$^a$, NR$^7$R$^8$, —NHC(O)NR$^8$R$^9$, —(CH$_2$)$_r$C(O)OR$^a$, —C(O)C$_{1-4}$ alkyl, —(CH$_2$)$_r$NR$^8$C(O)R$^a$, —(CH$_2$)$_r$NR$^8$CO$_2$R$^c$, —C(O)NR$^8$R$^9$, C$_{1-4}$ haloalkyl, C$_{1-4}$ haloalkyloxy-, C$_{1-6}$ alkyl, C$_{3-6}$ cycloalkyl, —(CH$_2$)$_r$-phenyl,

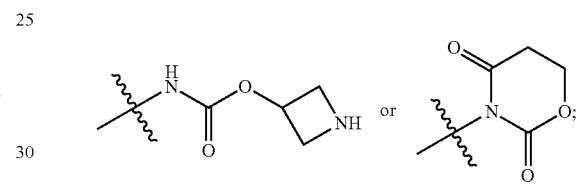

$R^4$ is, independently at each occurrence, H, F, Cl, Br, I, OCF$_3$, CF$_3$, CN, NO$_2$, —(CH$_2$)$_r$OR$^a$, —CH(OH)CH$_2$OH, —(CH$_2$)$_r$SR$^a$, C(O)R$^a$, C(O)OR$^a$, —(CH$_2$)$_r$S(O)$_2$R$^c$, —(CH$_2$)$_r$NR$^7$R$^8$, C(O)NR$^8$R$^9$, C$_{1-4}$ alkyl, or C$_{2-4}$ alkenyl;

$R^7$ is, independently at each occurrence, H, C$_{1-4}$ alkyl substituted with 0-1 OH, or benzyl;

$R^8$ is, independently at each occurrence, H, C$_{1-4}$ alkyl substituted with 0-1 OH, or benzyl;

alternatively, $R^7$ and $R^8$, when attached to the same nitrogen, combine to form a 5- to 6-membered heterocycle comprising: carbon atoms and 0-2 additional heteroatoms selected from N, O, and S(O)$_p$; wherein said heterocycle is substituted with 0-2 R$^f$;

$R^9$ is, independently at each occurrence, H, C$_{1-6}$ alkyl, or benzyl; alternatively, $R^8$ and $R^9$, when attached to the same nitrogen, combine to form a 5- to 6-membered heterocycle comprising: carbon atoms and 0-2 additional heteroatoms selected from N, O, and S(O)$_p$, wherein said heterocycle is substituted with 0-2 R$^d$;

$R^{11}$ is —CH$_2$OR$^a$, —CH$_2$CH$_2$OR$^a$, —CH$_2$S(O)$_p$R$^c$, —CH$_2$CH$_2$S(O)$_p$R$^c$, —CH$_2$NR$^7$R$^8$, —CH$_2$CH$_2$NR$^7$R$^8$, —CH$_2$C(O)R$^a$, —CH$_2$CH$_2$C(O)R$^a$, —CH$_2$C(O)OR$^a$, —CH$_2$CH$_2$C(O)OR$^a$, —CH$_2$C(O)NR$^8$R$^9$, —CH$_2$CH$_2$C(O) NR$^8$R$^9$, —CH$_2$NR$^8$C(O)R$^c$, —CH$_2$CH$_2$NR$^8$C(O)R$^c$, —CH$_2$NR$^8$C(O)OR$^c$, —CH$_2$CH$_2$NR$^8$C(O)OR$^c$, —CH$_2$NHS(O)$_2$(3-(pyrazol-1-yl)-Ph), —CH$_2$NHS(O)$_2$(1,3-dimethyl-pyrazol-4-yl), C$_{1-6}$ alkyl, C$_{2-6}$ alkenyl, —(CH$_2$)$_s$-phenyl substituted with 0-2 R$^{11b}$ or —(CH$_2$)$_s$-4 to 6-membered heterocycle substituted with 0-2 R$^{11b}$, wherein said heterocycle is selected from the group consisting of: azetidine, oxazolidin-2-one, pyrrolidine, pyrazole, thiazole, thiadiazole, oxazole, oxadiazole, imidazole, piperidine, piperazine, and pyridine;

alternatively, $R^{11}$ is

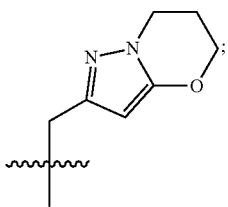

$R^{11b}$ is, independently at each occurrence H, F, $CF_3$, CN, $NO_2$, $NH_2$, $C_{1-4}$ alkyl, OMe, OEt, —C(O)$R^a$, —C(O)O$R^a$, —S(O)$_p R^c$, —C(O)NHMe, —NHCOMe, —NHCONHMe, —NHCOCH$_2$N(Me)$_2$, —NHC(O)OBn, cyclopropyl, or cyclopropylmethyl;

$R^{12}$ is independently at each occurrence, H, $C_{1-4}$ alkyl substituted with 0-2 $R^f$, or benzyl;

$R^a$ is, independently at each occurrence, H, $C_{1-4}$ alkyl substituted with 0-2 $R^f$, $C_{3-6}$ cycloalkyl substituted with 0-2 $R^f$, —(CH$_2$)$_r$-phenyl substituted with 0-2 $R^f$, or —(CH$_2$)$_r$-5- to 6-membered heterocycle comprising carbon atoms and 1-4 heteroatoms selected from N, O, and S(O)$_p$; wherein said heterocycle is substituted with 0-2 $R^f$;

$R^c$ is, independently at each occurrence, $C_{1-6}$ alkyl substituted with 0-2 $R^f$, $C_{3-6}$ cycloalkyl, or phenyl;

$R^d$ is, independently at each occurrence, H, =O, =NR$^8$, ORE, F, Cl, Br, I, CN, $NO_2$, —NR$^7$R$^8$, —C(O)$R^a$, —C(O)O$R^a$, —OC(O)$R^a$, —NR$^8$C(O)$R^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, ORE, F, Cl, Br, I, CN, $NO_2$, —NR$^7$R$^8$, —C(O)$R^a$, —C(O)O$R^a$, —NR$^8$C(O)$R^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

$R^f$ is, independently at each occurrence, H, =O, —(CH$_2$)$_r$OR$^g$, F, Cl, Br, I, CN, $NO_2$, —NR$^g$R$^g$, —C(O)$R^g$, —C(O)OR$^g$, —OC(O)$R^g$, —NR$^g$C(O)$R^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CF$_2$)$_r$CF$_3$, $C_{1-6}$ alkyl, $C_{2-6}$ alkenyl, $C_{2-6}$ alkynyl, —(CH$_2$)$_n$-phenyl, or —(CH$_2$)$_n$-5- to 10-membered heterocycle comprising carbon atoms and 1-4 heteroatoms selected from N, O, and S(O)$_p$;

$R^g$ is, independently at each occurrence, H, $C_{1-6}$ alkyl, or —(CH$_2$)$_n$-phenyl;

p, at each occurrence, is selected from 0, 1, and 2; and
r, at each occurrence, is selected from 0, 1, 2, 3, and 4.

In a fifth aspect, the present invention includes a compound of Formula (II) or a stereoisomer, a tautomer, a pharmaceutically acceptable salt, a solvate, or a prodrug thereof, within the scope of the fourth aspect wherein:

$L_1$ is —CH$_2$CH$_2$—, or —CH=CH—;
$R^{1a}$, $R^{1b}$, $R^{1c}$, and $R^{1d}$ are, independently at each occurrence, H, F, Cl, or Me;
$R^2$ is 5-membered heterocycle selected from the group consisting of imidazole, triazole, and tetrazole; wherein said heterocycle is substituted with 0-2 $R^{2b}$;
$R^3$ is, independently at each occurrence, phenyl substituted with 0-2 $R^{3a}$;

$R^4$ is, independently at each occurrence, H, F, Cl, CN, $C_{1-4}$ alkyl, $C_{2-4}$ alkenyl, OH, —CH$_2$OH, —CH(OH)CH$_2$OH, —O—C$_{1-4}$ alkyl, —CH$_2$O(C$_{1-4}$ alkyl), —NH(C$_{1-4}$ alkyl), —N(C$_{1-4}$ alkyl)$_2$, —CH$_2$NH(C$_{1-4}$ alkyl), —CH$_2$N(C$_{1-4}$ alkyl)$_2$, —S—C$_{1-4}$ alkyl, —CH$_2$S(C$_{1-4}$ alkyl), —S(O)$_2$—C$_{1-4}$ alkyl, —CH$_2$S(O)$_2$—C$_{1-4}$ alkyl, C(O)OH, C(O)NR$^8$R$^9$, or C(O)O(C$_{1-4}$ alkyl); and $R^{11}$ is $C_{1-6}$ alkyl, $C_{2-6}$ alkenyl, benzyl substituted with 0-2 $R^{11b}$, —CH$_2$O(C$_{1-6}$ alkyl), —CH$_2$CH$_2$O(C$_{1-6}$ alkyl), —CH$_2$S(O)$_p$(C$_{1-6}$ alkyl), —CH$_2$CH$_2$S(O)$_p$(C$_{1-6}$ alkyl), —CH$_2$C(O)OH, —CH$_2$C(O)O(C$_{1-4}$ alkyl), —CH$_2$NHC(O)(C$_{1-4}$ alkyl), —CH$_2$NHC(O)O(C$_{1-4}$ alkyl), —CH$_2$NH(C$_{1-4}$ alkyl), —CH$_2$N(C$_{1-4}$ alkyl)$_2$, —CH$_2$C(O)NH(C$_{1-4}$ alkyl substituted with 0-1 OH), —CH$_2$C(O)N(C$_{1-4}$ alkyl)$_2$, —CH$_2$NHC(O)Ph, —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), —CH$_2$NHS(O)$_2$(3-(pyrazol-1-yl)-Ph), —CH$_2$NHS(O)$_2$(1,3-dimethyl-pyrazol-4-yl), or —CH$_2$-4- to 6-membered heterocycle substituted with 0-2 $R^{11b}$, wherein said heterocycle is selected from the group consisting of: azetidine, oxazolidin-2-one, pyrrolidine, pyrazole, thiazole, thiadiazole, oxadiazole, piperidine, and pyridine;

alternatively, $R^{11}$ is

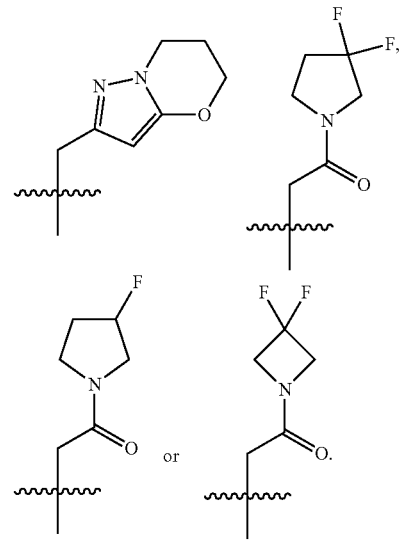

In a sixth aspect, the present invention includes compounds of Formula (III):

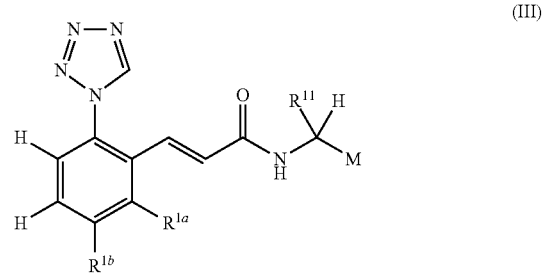

(III)

or a stereoisomer, a tautomer, a pharmaceutically acceptable salt, a solvate, or a prodrug thereof, wherein:

M is selected from the group consisting of:

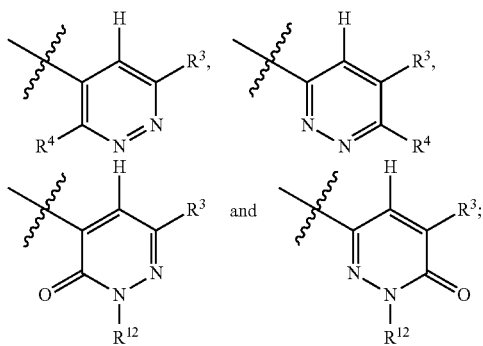

$R^{1a}$ is H or F;
$R^{1b}$ is Cl or Me;
$R^3$ is, independently at each occurrence, —(CH$_2$)$_r$-phenyl substituted with 0-2 $R^{3a}$, —(CH$_2$)$_r$-pyridyl substituted with 0-2 $R^{3a}$, —(CH$_2$)$_r$-thiazolyl substituted with 0-2 $R^{3a}$, or

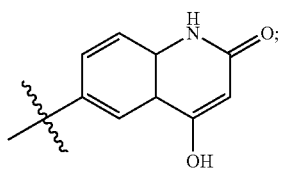

$R^{3a}$ is, independently at each occurrence, F, NH$_2$, —NHC(O)OMe, —NHC(O)OEt, —NHC(O)CH$_2$OH, —NHC(O)O(CH$_2$)$_2$C(O)OH, —NHC(O)OCH$_2$C(O)NH$_2$, —NHC(O)O(CH$_2$)$_2$C(O)NH$_2$, —NHC(O)CH$_2$OC(O)Me, —NHC(O)O(CH$_2$)$_2$OH, —NHC(O)O(CH$_2$)$_2$OMe, —NHC(O)NHC(CH$_2$)$_2$OH, —NHC(O)NHC(Me)$_2$CH$_2$OH,

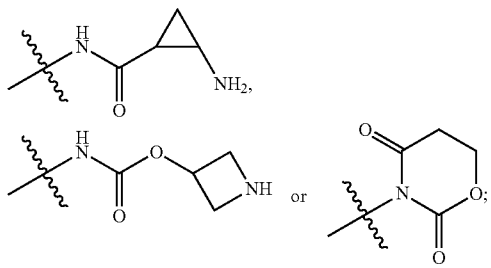

$R^4$ is, independently at each occurrence, H, F, Cl, Me, Et, —CH=CH$_2$, OH, —CH$_2$OH, —CH(OH)CH$_2$OH, OMe, OEt, SMe, —CH$_2$SMe, SEt, SO$_2$Me, —CH$_2$SO$_2$Me, SO$_2$Et, CN, C(O)OH, C(O)OMe, —CH$_2$N(Me)$_2$, C(O)NH$_2$, or C(O)NHMe;
$R^{11}$ is selected from the group consisting of: C$_{1-4}$ alkyl, C$_{2-4}$ alkenyl, benzyl, 3-F-benzyl, 4-F-benzyl, 4-NH$_2$-benzyl, 4-NHCOMe-benzyl, 4-NHCONHMe-benzyl, 4-NHCOCH$_2$N(Me)-2-benzyl, —CH$_2$SMe, —CH$_2$S(neopentyl), —(CH$_2$)$_2$SMe, —(CH$_2$)$_2$S(O)Me, —CH$_2$S(O)$_2$Me, —CH$_2$S(O)$_2$(neopentyl), —(CH$_2$)$_2$S(O)$_2$Me, —CH$_2$C(O)OH, —CH$_2$C(O)OMe, —CH$_2$C(O)O(t-Bu), —CH$_2$NHC(O)Me, —CH$_2$NHC(O)(t-Bu), —CH$_2$NHC(O)Ph, —CH$_2$NHS(O)$_2$(3-(pyrazol-1-yl)-Ph), —CH$_2$NHS(O)$_2$(1,3-dimethyl-pyrazol-4-yl), —CH$_2$NHC(O)O(t-Bu), —CH$_2$NH(i-Pr), —CH$_2$C(O)NH(CH$_2$CH$_2$OH), —CH$_2$C(O)NH(t-Bu), —CH$_2$C(O)N(Me)$_2$, —CH$_2$C(O)NMe(i-Pr), —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), (azetidin-3-yl)methyl, (1-acetyl-azetidin-3-yl)methyl, (1-Et-pyrazol-3-yl)methyl, (4-Me-thiazol-2-yl)methyl, (thiazol-4-yl)methyl, (2-isopropyl-thiazol-4-yl)methyl, (5-methoxy-1-Me-1H-pyrazol-3-yl)methyl, (1-Me-5-(methylsulfinyl)-1H-pyrazol-3-yl)methyl, (1-Me-5-(methylsulfonyl)-1H-pyrazol-3-yl)methyl, (pyrrolidin-3-yl)methyl, (1-Et-pyrrolidin-3-yl)methyl, (1-acetyl-pyrrolidin-3-yl)methyl, (1-(cyclopropylmethyl)-pyrrolidin-3-yl)methyl, (2-(i-Pr)-thiazol-4-yl)methyl, (4,5-dimethylthiazol-2-yl)methyl, (5-cyclopropyl-1,3,4-thiadiazol-2-yl)methyl, (5-(t-Bu)-1,2,4-oxadiazol-3-yl)methyl, (piperidin-3-yl)methyl, (piperidin-4-yl)ethyl, (1-acetyl-piperidin-3-yl)methyl, (1-propionyl-piperidin-3-yl)methyl, (1-isobutyryl-piperidin-3-yl)methyl, (1-(cyclopropanecarbonyl)-piperidin-3-yl)methyl, (pyrid-3-yl)methyl, (6-Me-pyrid-3-yl)methyl, (6-NH$_2$-pyrid-3-yl)methyl, (pyrid-4-yl)methyl,

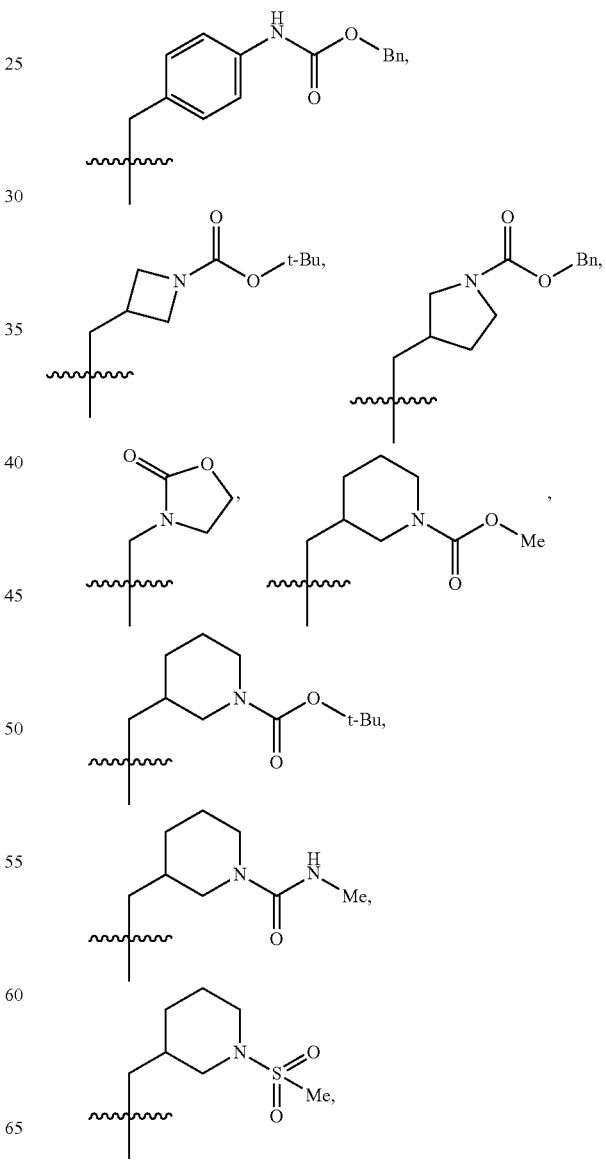

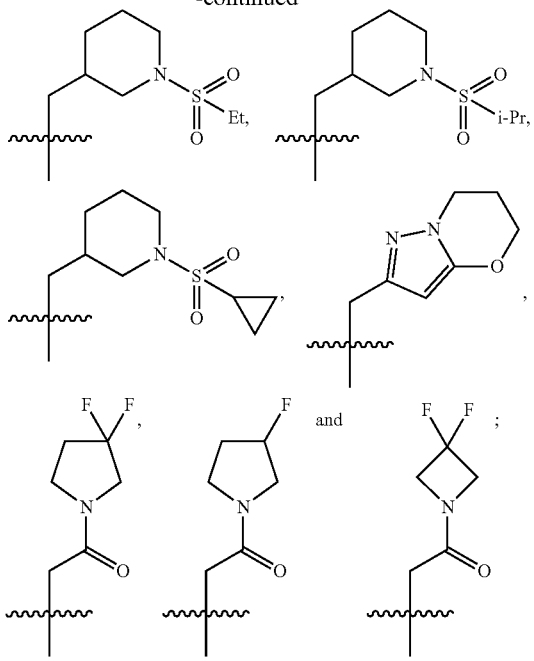

R$^{12}$ is, independently at each occurrence, H, Me, —CH$_2$CH$_2$OH, —CH$_2$C(O)OH, or —CH$_2$C(O)OMe; and r, at each occurrence, is selected from 0, 1, and 2.

In a seventh aspect, the present invention includes a compound of Formula (III) or a stereoisomer, a tautomer, a pharmaceutically acceptable salt, a solvate, or a prodrug thereof, within the scope of the sixth aspect wherein:

R$^3$ is, independently at each occurrence, phenyl substituted with 0-2 R$^{3a}$, pyridyl substituted with 0-2 R$^{1a}$, thiazolyl substituted with 0-2 R$^{1a}$, or

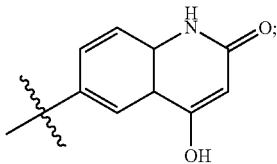

R$^{3a}$ is, independently at each occurrence, NH$_2$, —NHC(O)OMe, —NHC(O)OEt, —NHC(O)CH$_2$OH, —NHC(O)OCH$_2$C(O)NH$_2$, —NHC(O)O(CH$_2$)$_2$C(O)NH$_2$, —NHC(O)CH$_2$OC(O)Me, —NHC(O)O(CH$_2$)$_2$OH, —NHC(O)O(CH$_2$)$_2$OMe, —NHC(O)NHC(CH$_2$)$_2$OH, —NHC(O)NHC(Me)$_2$CH$_2$OH,

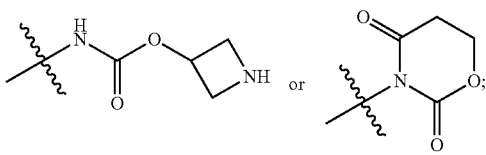

R$^4$ is, independently at each occurrence, H, F, Cl, Me, Et, —CH=CH$_2$, OH, —CH$_2$OH, —CH(OH)CH$_2$OH, OMe, OEt, SMe, —CH$_2$SMe, SEt, SO$_2$Me, —CH$_2$SO$_2$Me, SO$_2$Et, CN, C(O)OH, C(O)OMe, —CH$_2$N(Me)$_2$, C(O)NH$_2$, or C(O)NHMe;

R$^{11}$ is selected from the group consisting of: C$_{1-4}$ alkyl, C$_{2-4}$ alkenyl, benzyl, 3-F-benzyl, 4-F-benzyl, 4-NH$_2$-benzyl, 4-NHCOMe-benzyl, 4-NHCONHMe-benzyl, 4-NHCOCH$_2$N(Me)-2-benzyl, —CH$_2$SMe, —(CH$_2$)$_2$SMe, —(CH$_2$)$_2$S(O)Me, —CH$_2$S(O)$_2$Me, —(CH$_2$)$_2$S(O)$_2$Me, —CH$_2$C(O)OH, —CH$_2$C(O)OMe, —CH$_2$C(O)O(t-Bu), —CH$_2$NHC(O)Me, —CH$_2$NHC(O)(t-Bu), —CH$_2$NHC(O)O(t-Bu), —CH$_2$NH(i-Pr), —CH$_2$C(O)NH(CH$_2$CH$_2$OH), —CH$_2$C(O)NH(t-Bu), —CH$_2$C(O)N(Me)$_2$, —CH$_2$C(O)NMe(i-Pr), —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), (azetidin-3-yl)methyl, (1-acetyl-azetidin-3-yl)methyl, (1-Et-pyrazol-3-yl)methyl, (4-Me-thiazol-2-yl)methyl, (thiazol-4-yl)methyl, (2-isopropyl-thiazol-4-yl)methyl, (5-methoxy-1-Me-1H-pyrazol-3-yl)methyl, (1-Me-5-(methylsulfinyl)-1H-pyrazol-3-yl)methyl, (1-Me-5-(methylsulfonyl)-1H-pyrazol-3-yl)methyl, (pyrrolidin-3-yl)methyl, (1-Et-pyrrolidin-3-yl)methyl, (1-acetyl-pyrrolidin-3-yl)methyl, (1-(cyclopropylmethyl)-pyrrolidin-3-yl)methyl, (2-(i-Pr)-thiazol-4-yl)methyl, (4,5-dimethylthiazol-2-yl)methyl, (5-cyclopropyl-1,3,4-thiadiazol-2-yl)methyl, (5-(t-Bu)-1,2,4-oxadiazol-3-yl)methyl, (piperidin-3-yl)methyl, (piperidin-4-yl)ethyl, (1-acetyl-piperidin-3-yl)methyl, (1-propionyl-piperidin-3-yl)methyl, (1-isobutyryl-piperidin-3-yl)methyl, (1-(cyclopropanecarbonyl)-piperidin-3-yl)methyl, (pyrid-3-yl)methyl, (6-Me-pyrid-3-yl)methyl, (6-NH$_2$-pyrid-3-yl)methyl, (pyrid-4-yl)methyl,

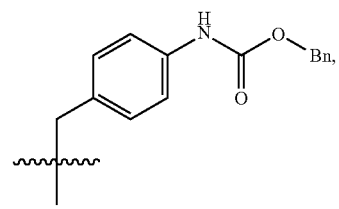

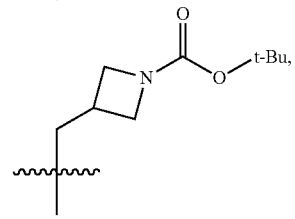

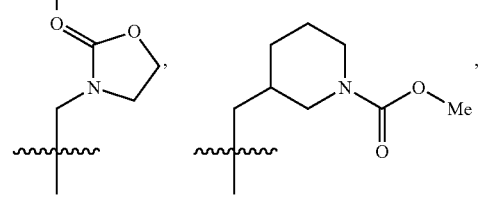

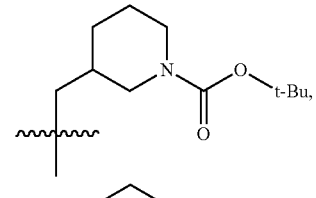

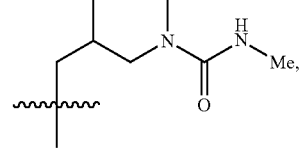

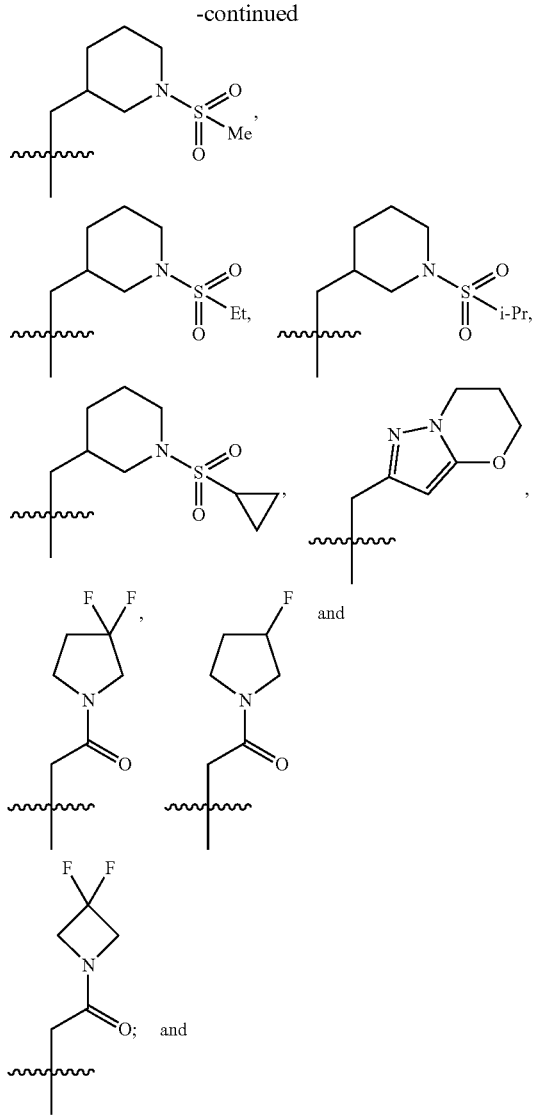

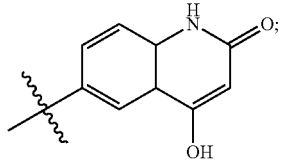

R[12] is, independently at each occurrence, H, Me, —CH$_2$CH$_2$OH, —CH$_2$C(O)OH, or —CH$_2$C(O)OMe.

In an eighth aspect, the present invention includes a compound of Formula (III) or a stereoisomer, a tautomer, a pharmaceutically acceptable salt, a solvate, or a prodrug thereof, within the scope of the sixth or seventh aspect wherein:

R[3] is, independently at each occurrence, phenyl substituted with 0-2 R[3a]

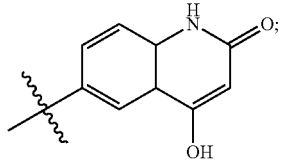

R[3a] is, independently at each occurrence, NH$_2$, —NHC(O)OMe, —NHC(O)OCH$_2$C(O)NH$_2$, —NHC(O)O(CH$_2$)$_2$C(O)NH$_2$, —NHC(O)O(CH$_2$)$_2$OH, —NHC(O)O(CH$_2$)$_2$OMe, or —NHC(O)NHC(CH$_2$)$_2$OH;

R[4] is, independently at each occurrence, H, F, Cl, Me, Et, —CH=CH$_2$, OH, —CH$_2$OH, —CH(OH)CH$_2$OH, OMe, SMe, —CH$_2$SMe, SEt, SO$_2$Me, —CH$_2$SO$_2$Me, SO$_2$Et, CN, C(O)OH, C(O)OMe, —CH$_2$N(Me)$_2$, C(O)NH$_2$, or C(O)NHMe;

R[11] is selected from the group consisting of: benzyl, 3-F-benzyl, 4-F-benzyl, 4-NH$_2$-benzyl, 4-NHCOMe-benzyl, 4-NHCONHMe-benzyl, 4-NHCOCH$_2$N(Me)-2-benzyl, —CH$_2$C(O)OMe, —CH$_2$C(O)O(t-Bu), —CH$_2$NHC(O)Me, —CH$_2$C(O)NH(CH$_2$CH$_2$OH), —CH$_2$C(O)NH(t-Bu), —CH$_2$C(O)N(Me)$_2$, —CH$_2$C(O)NMe(i-Pr), —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), (1-Et-pyrazol-3-yl)methyl, (4-Me-thiazol-2-yl)methyl, (thiazol-4-yl)methyl, (5-methoxy-1-Me-1H-pyrazol-3-yl)methyl, (4,5-dimethylthiazol-2-yl)methyl, (5-cyclopropyl-1,3,4-thiadiazol-2-yl)methyl, (1-acetyl-piperidin-3-yl)methyl, (1-propionyl-piperidin-3-yl)methyl, (1-isobutyryl-piperidin-3-yl)methyl, (pyrid-3-yl)methyl, (6-NH$_2$-pyrid-3-yl)methyl, (pyrid-4-yl)methyl,

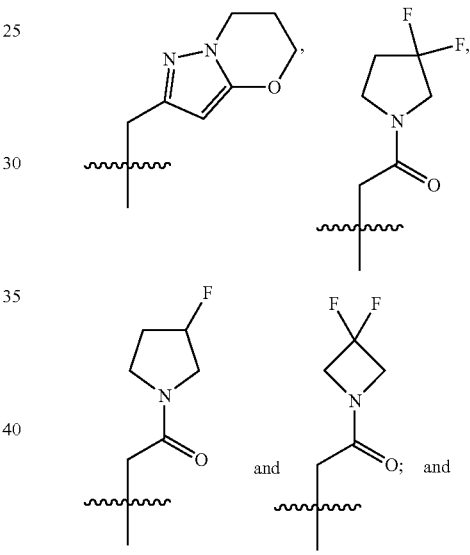

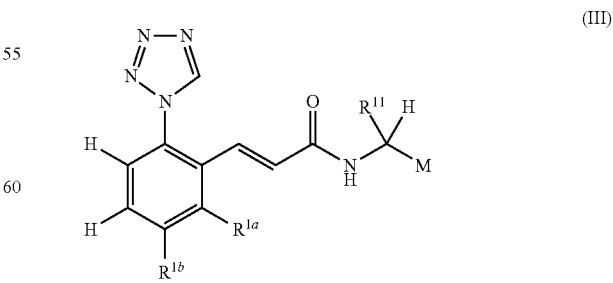

R[12] is, independently at each occurrence, H, Me, —CH$_2$CH$_2$OH, or —CH$_2$C(O)OH.

In another aspect, the present invention includes compounds of Formula (III):

(III)

[Structure of Formula III]

or a stereoisomer, a tautomer, a pharmaceutically acceptable salt, a solvate, or a prodrug thereof, wherein:

M is selected from the group consisting of:

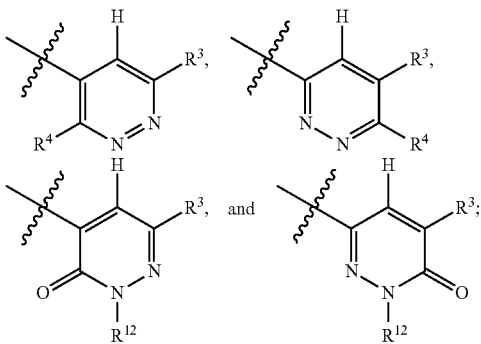

$R^{1a}$ is H or F;
$R^{1b}$ is Cl or Me;
$R^3$ is, independently at each occurrence, —(CH$_2$)$_r$-phenyl substituted with 0-2 $R^{3a}$, or —(CH$_2$)$_r$-pyridyl substituted with 0-2 $R^{1a}$;
$R^{3a}$ is, independently at each occurrence, F, NH$_2$, —NHC(O)OMe, —NHC(O)OEt, —NHC(O)CH$_2$OH, —NHC(O)O(CH$_2$)$_2$C(O)OH, —NHC(O)CH$_2$OC(O)Me, or —NHC(O)O(CH$_2$)$_2$OMe;
$R^4$ is, independently at each occurrence, H, F, Cl, Me, OH, OMe, OEt, SEt, SO$_2$Et, C(O)OH, C(O)OMe, or C(O)NH$_2$;
$R^{11}$ is selected from the group consisting of: C$_{1-4}$ alkyl, benzyl, 3-F-benzyl, 4-F-benzyl, —CH$_2$C(O)OH, —CH$_2$C(O)OMe, —CH$_2$C(O)O(t-Bu), —CH$_2$NHC(O)Me, —CH$_2$NHC(O)O(t-Bu), —CH$_2$NH(i-Pr), —CH$_2$C(O)NH(CH$_2$CH$_2$OH), —CH$_2$C(O)NH(t-Bu), —CH$_2$C(O)N(Me)$_2$, —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), or (1-ethyl-pyrazol-3-yl)methyl; and
$R^{12}$ is, independently at each occurrence, H, Me, —CH$_2$CH$_2$OH, —CH$_2$C(O)OH, or —CH$_2$C(O)OMe.

In another aspect, the present invention includes compounds of Formula (III) or a stereoisomer, a tautomer, a pharmaceutically acceptable salt, a solvate, or a prodrug thereof, wherein:
$R^{1a}$ is H;
$R^3$ is phenyl substituted with 0-2 $R^{1a}$; and
$R^{11}$ is benzyl or 4-F-benzyl.

In another aspect, the present invention provides a compound selected from the group consisting of:
(E)-methyl 4-(6-chloro-5-(1-(3-(5-chloro-2-(1H-tetrazol-1-yl)phenyl)acrylamido)-2-phenylethyl)pyridazin-3-yl)phenylcarbamate;
(E)-methyl 4-(5-(1-(3-(5-chloro-2-(1H-tetrazol-1-yl)phenyl)acrylamido)-2-phenylethyl)-6-oxo-1,6-dihydropyridazin-3-yl)phenylcarbamate;
(E)-methyl 4-(5-(1-(3-(5-chloro-2-(1H-tetrazol-1-yl)phenyl)acrylamido)-2-phenylethyl)pyridazin-3-yl)phenylcarbamate;
(E)-methyl 4-(6-chloro-5-(1-(3-(5-chloro-2-(1H-imidazol-1-yl)phenyl)acrylamido)-2-phenylethyl)pyridazin-3-yl)phenylcarbamate;
(E)-methyl 4-(5-(1-(3-(5-chloro-2-(1H-tetrazol-1-yl)phenyl)acrylamido)-2-phenylethyl)-6-methylpyridazin-3-yl)phenylcarbamate;
(E)-methyl 4-(6-chloro-5-(1-(3-(5-chloro-2-(1H-tetrazol-1-yl)phenyl)acrylamido)ethyl)pyridazin-3-yl)phenylcarbamate;
(E)-methyl 4-(6-chloro-5-(1-(3-(5-chloro-2-(1H-tetrazol-1-yl)phenyl)acrylamido)-3-methylbutyl)pyridazin-3-yl)phenylcarbamate;
[4-(5-{2-tert-butoxycarbonylamino-1-[(E)-3-(5-chloro-2-tetrazol-1-yl-phenyl)-acryloylamino]-ethyl}-6-chloro-pyridazin-3-yl)-phenyl]-carbamic acid methyl ester;
[4-(5-{2-tert-butoxycarbonylamino-1-[(E)-3-(5-chloro-2-tetrazol-1-yl-phenyl)-acryloylamino]-ethyl}-pyridazin-3-yl)-phenyl]-carbamic acid methyl ester;
(E)-methyl 3-(3-(5-chloro-2-(1H-tetrazol-1-yl)phenyl)acrylamido)-3-(3-chloro-6-(4-(methoxycarbonylamino)phenyl)pyridazin-4-yl)propanoate;
(E)-methyl 3-(3-(5-chloro-2-(1H-tetrazol-1-yl)phenyl)acrylamido)-3-(6-(4-(methoxycarbonylamino)phenyl)pyridazin-4-yl)propanoate;
(E)-tert-butyl 3-(3-(5-chloro-2-(1H-tetrazol-1-yl)phenyl)acrylamido)-3-(3-chloro-6-(4-(methoxycarbonylamino)phenyl)pyridazin-4-yl)propanoate;
(E)-methyl 4-(6-chloro-5-(1-(3-(5-chloro-2-(1H-tetrazol-1-yl)phenyl)acrylamido)-3-(dimethylamino)-3-oxopropyl)pyridazin-3-yl)phenylcarbamate;
(E)-methyl 4-(5-(1-(3-(5-chloro-2-(1H-tetrazol-1-yl)phenyl)acrylamido)-3-(dimethylamino)-3-oxopropyl)pyridazin-3-yl)phenylcarbamate;
(E)-methyl 4-(6-chloro-5-(1-(3-(5-chloro-2-(1H-tetrazol-1-yl)phenyl)acrylamido)-3-(4-methylpiperazin-1-yl)-3-oxopropyl)pyridazin-3-yl)phenylcarbamate;
(E)-methyl 4-(6-chloro-5-(1-(3-(5-chloro-2-(1H-tetrazol-1-yl)phenyl)acrylamido)-3-(4-hydroxypiperidin-1-yl)-3-oxopropyl)pyridazin-3-yl)phenylcarbamate;
(E)-methyl 4-(6-chloro-5-(1-(3-(5-chloro-2-(1H-tetrazol-1-yl)phenyl)acrylamido)-3-(4-methylpiperazin-1-yl)-3-oxopropyl)pyridazin-3-yl)phenylcarbamate;
methyl 4-(6-chloro-5-(1-((E)-3-(5-chloro-2-(1H-tetrazol-1-yl)phenyl)acrylamido)-3-(3-hydroxypyrrolidin-1-yl)-3-oxopropyl)pyridazin-3-yl)phenylcarbamate;
(E)-methyl 4-(6-chloro-5-(1-(3-(5-chloro-2-(1H-tetrazol-1-yl)phenyl)acrylamido)-3-(2-hydroxyethylamino)-3-oxopropyl)pyridazin-3-yl)phenylcarbamate;
(E)-methyl 4-(5-(3-(tert-butylamino)-1-(3-(5-chloro-2-(1H-tetrazol-1-yl)phenyl)acrylamido)-3-oxopropyl)-6-chloropyridazin-3-yl)phenylcarbamate;
(E)-methyl 4-(6-chloro-5-(1-(3-(5-chloro-2-(1H-tetrazol-1-yl)phenyl)acrylamido)-3-oxo-3-(pyrrolidin-1-yl)propyl)pyridazin-3-yl)phenylcarbamate;
(E)-methyl 4-(5-(2-acetamido-1-(3-(5-chloro-2-(1H-tetrazol-1-yl)phenyl)acrylamido)ethyl)-6-chloropyridazin-3-yl)phenylcarbamate;
(E)-methyl 4-(6-chloro-5-(1-(3-(5-chloro-2-(1H-tetrazol-1-yl)phenyl)acrylamido)-2-(isopropylamino)ethyl)pyridazin-3-yl)phenylcarbamate;
(E)-N-(1-(6-(6-aminopyridin-3-yl)-3-chloropyridazin-4-yl)-2-phenylethyl)-3-(5-chloro-2-(1H-tetrazol-1-yl)phenyl)acrylamide;
(E)-methyl 4-(6-(1-(3-(5-chloro-2-(1H-tetrazol-1-yl)phenyl)acrylamido)-2-phenylethyl)-3-oxo-2,3-dihydropyridazin-4-yl)phenylcarbamate;
(E)-methyl 4-(3-chloro-6-(1-(3-(5-chloro-2-(1H-tetrazol-1-yl)phenyl)acrylamido)-2-phenylethyl)pyridazin-4-yl)phenylcarbamate;
(E)-methyl 4-(6-(1-(3-(5-chloro-2-(1H-tetrazol-1-yl)phenyl)acrylamido)-2-phenylethyl)-2-(2-hydroxyethyl)-3-oxo-2,3-dihydropyridazin-4-yl)phenylcarbamate;
(E)-methyl 4-(6-(1-(3-(5-chloro-2-(1H-tetrazol-1-yl)phenyl)acrylamido)-2-phenylethyl)-2-methyl-3-oxo-2,3-dihydropyridazin-4-yl)phenylcarbamate;
(E)-methyl 4-(6-(1-(3-(5-chloro-2-(1H-tetrazol-1-yl)phenyl)acrylamido)-2-phenylethyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-methoxypyridazin-4-yl)phenylcarbamate;

(E)-methyl 4-(6-(1-(3-(5-chloro-2-(1H-tetrazol-1-yl)phenyl)acrylamido)-2-(4-fluorophenyl)ethyl)-3-oxo-2,3-dihydropyridazin-4-yl)phenylcarbamate;

(E)-N-(1-(5-(4-aminophenyl)-6-oxo-1,6-dihydropyridazin-3-yl)-2-(4-fluorophenyl)ethyl)-3-(5-chloro-2-(1H-tetrazol-1-yl)phenyl)acrylamide;

(E)-methyl 4-(3-chloro-6-(1-(3-(5-chloro-2-(1H-tetrazol-1-yl)phenyl)acrylamido)-2-(4-fluorophenyl)ethyl)pyridazin-4-yl)phenylcarbamate;

(E)-methyl 4-(6-(1-(3-(5-chloro-2-(1H-tetrazol-1-yl)phenyl)acrylamido)-2-(4-fluorophenyl)ethyl)pyridazin-4-yl)phenylcarbamate;

(E)-3-(3-(5-chloro-2-(1H-tetrazol-1-yl)phenyl)acrylamido)-3-(3-chloro-6-(4-(methoxycarbonylamino)phenyl)pyridazin-4-yl)propanoic acid;

(E)-2-(4-(3-chloro-6-(1-(3-(5-chloro-2-(1H-tetrazol-1-yl)phenyl)acrylamido)-2-phenylethyl)pyridazin-4-yl)phenylamino)-2-oxoethyl acetate;

(E)-3-(5-chloro-2-(1H-tetrazol-1-yl)phenyl)-N-(1-(6-chloro-5-(4-(2-hydroxyacetamido)phenyl)pyridazin-3-yl)-2-phenylethyl)acrylamide;

(E)-3-(4-(3-chloro-6-(1-(3-(5-chloro-2-(1H-tetrazol-1-yl)phenyl)acrylamido)-2-phenylethyl)pyridazin-4-yl)phenylcarbamoyloxy)propanoic acid;

(E)-ethyl 4-(6-(1-(3-(5-chloro-2-(1H-tetrazol-1-yl)phenyl)acrylamido)-2-phenylethyl)-3-ethoxypyridazin-4-yl)phenylcarbamate;

(E)-methyl 2-(3-(1-(3-(5-chloro-2-(1H-tetrazol-1-yl)phenyl)acrylamido)-2-phenylethyl)-5-(4-(methoxycarbonylamino)phenyl)-6-oxopyridazin-1(6H)-yl)acetate;

(E)-methyl 6-(1-(3-(5-chloro-2-(1H-tetrazol-1-yl)phenyl)acrylamido)-2-phenylethyl)-4-(4-(methoxycarbonylamino)phenyl)pyridazine-3-carboxylate;

(E)-methyl 4-(6-(1-(3-(6-acetyl-3-chloro-2-fluorophenyl)acrylamido)-2-phenylethyl)-3-chloropyridazin-4-yl)phenylcarbamate;

(E)-methyl 4-(6-(1-(3-(5-chloro-2-(1H-tetrazol-1-yl)phenyl)acrylamido)-2-phenylethyl)-3-methylpyridazin-4-yl)phenylcarbamate;

(E)-methyl 4-(6-(1-(3-(5-chloro-2-(1H-tetrazol-1-yl)phenyl)acrylamido)-2-phenylethyl)-3-(ethylthio)pyridazin-4-yl)phenylcarbamate;

(E)-2-(3-(1-(3-(5-chloro-2-(1H-tetrazol-1-yl)phenyl)acrylamido)-2-phenylethyl)-5-(4-(methoxycarbonylamino)phenyl)-6-oxopyridazin-1(6H)-yl)acetic acid;

(E)-methyl 4-(6-(1-(3-(5-chloro-2-(1H-tetrazol-1-yl)phenyl)acrylamido)-2-phenylethyl)-3-(ethylsulfonyl)pyridazin-4-yl)phenylcarbamate;

(E)-6-(1-(3-(5-chloro-2-(1H-tetrazol-1-yl)phenyl)acrylamido)-2-phenylethyl)-4-(4-(methoxycarbonylamino)phenyl)pyridazine-3-carboxylic acid;

3-(4-(6-(1-(3-(2-(1H-tetrazol-1-yl)phenyl)propanamido)-2-phenylethyl)pyridazin-4-yl)phenylcarbamoyloxy)propanoic acid;

(E)-methyl 4-(6-(1-(3-(5-chloro-2-(1H-tetrazol-1-yl)phenyl)acrylamido)-2-phenylethyl)-3-oxo-2,3-dihydropyridazin-4-yl)-2-fluorophenylcarbamate;

(E)-methyl 4-(3-chloro-6-(1-(3-(5-chloro-2-(1H-tetrazol-1-yl)phenyl)acrylamido)-2-phenylethyl)pyridazin-4-yl)-2-fluorophenylcarbamate;

(E)-methyl 4-(6-(1-(3-(5-chloro-2-(1H-tetrazol-1-yl)phenyl)acrylamido)-2-phenylethyl)pyridazin-4-yl)-2-fluorophenylcarbamate;

(E)-N-(1-(5-(4-aminophenyl)pyridazin-3-yl)-2-phenylethyl)-3-(5-chloro-2-(1H-tetrazol-1-yl)phenyl)acrylamide;

(E)-methyl 4-(3-carbamoyl-6-(1-(3-(5-chloro-2-(1H-tetrazol-1-yl)phenyl)acrylamido)-2-phenylethyl)pyridazin-4-yl)phenylcarbamate;

(E)-2-methoxyethyl 4-(6-(1-(3-(5-chloro-2-(1H-tetrazol-1-yl)phenyl)acrylamido)-2-phenylethyl)pyridazin-4-yl)phenylcarbamate;

(E)-methyl 4-(6-(1-(3-(5-chloro-2-(1H-tetrazol-1-yl)phenyl)acrylamido)-2-(3-fluorophenyl)ethyl)-3-oxo-2,3-dihydropyridazin-4-yl)phenylcarbamate;

(E)-methyl 4-(3-chloro-6-(1-(3-(5-chloro-2-(1H-tetrazol-1-yl)phenyl)acrylamido)-2-(3-fluorophenyl)ethyl)pyridazin-4-yl)phenylcarbamate;

(E)-methyl 4-(6-(1-(3-(5-chloro-2-(1H-tetrazol-1-yl)phenyl)acrylamido)-2-(3-fluorophenyl)ethyl)pyridazin-4-yl)phenylcarbamate;

(E)-methyl 4-(6-(1-(3-(5-chloro-2-(1H-tetrazol-1-yl)phenyl)acrylamido)-2-(1-ethyl-1H-pyrazol-3-yl)ethyl)-3-oxo-2,3-dihydropyridazin-4-yl)phenylcarbamate;

(E)-methyl 4-(3-chloro-6-(1-(3-(5-chloro-2-(1H-tetrazol-1-yl)phenyl)acrylamido)-2-(1-ethyl-1H-pyrazol-3-yl)ethyl)pyridazin-4-yl)phenylcarbamate;

(E)-methyl 4-(6-(1-(3-(5-chloro-2-(1H-tetrazol-1-yl)phenyl)acrylamido)-2-(1-ethyl-1H-pyrazol-3-yl)ethyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-(hydroxymethyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-(methylcarbamoyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-vinylpyridazin-4-yl)phenylcarbamate;

methyl 4-(6-(1-((E)-3-(5-chloro-2-(1H-tetrazol-1-yl)phenyl)acrylamido)-2-phenylethyl)-3-(1,2-dihydroxyethyl)pyridazin-4-yl)phenylcarbamate;

(E)-3-(5-chloro-2-(1H-tetrazol-1-yl)phenyl)-N-(1-(5-(4-(2,4-dioxo-1,3-oxazinan-3-yl)phenyl)pyridazin-3-yl)-2-phenylethyl)acrylamide;

(E)-3-(5-chloro-2-(1H-tetrazol-1-yl)phenyl)-N-(1-(5-(4-hydroxy-2-oxo-1,2-dihydroquinolin-6-yl)pyridazin-3-yl)-2-phenylethyl)acrylamide;

(E)-3-amino-3-oxopropyl 4-(6-(1-(3-(5-chloro-2-(1H-tetrazol-1-yl)phenyl)acrylamido)-2-phenylethyl)pyridazin-4-yl)phenylcarbamate;

2-amino-N-(4-(6-(1-((E)-3-(5-chloro-2-(1H-tetrazol-1-yl)phenyl)acrylamido)-2-phenylethyl)pyridazin-4-yl)phenyl)cyclopropanecarboxamide;

(E)-3-(5-chloro-2-(1H-tetrazol-1-yl)phenyl)-N-(1-(5-(4-(3-(1-hydroxy-2-methylpropan-2-yl)ureido)phenyl)pyridazin-3-yl)-2-phenylethyl)acrylamide;

(E)-methyl 4-(6-(1-(3-(5-chloro-2-(1H-tetrazol-1-yl)phenyl)acrylamido)-2-phenylethyl)-3-((dimethylamino)methyl)pyridazin-4-yl)phenylcarbamate;

(E)-2-amino-2-oxoethyl 4-(6-(1-(3-(5-chloro-2-(1H-tetrazol-1-yl)phenyl)acrylamido)-2-phenylethyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-(methylthio)pyridazin-4-yl)phenylcarbamate;

(E)-methyl 4-(6-(1-(3-(5-chloro-2-(1H-tetrazol-1-yl)phenyl)acrylamido)-2-phenylethyl)-3-(methylsulfonyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-(methylthiomethyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-ethylpyridazin-4-yl)phenylcarbamate;

(E)-2-hydroxyethyl 4-(6-(1-(3-(5-chloro-2-(1H-tetrazol-1-yl)phenyl)acrylamido)-2-phenylethyl)pyridazin-4-yl)phenylcarbamate;

(E)-azetidin-3-yl 4-(6-(1-(3-(5-chloro-2-(1H-tetrazol-1-yl)phenyl)acrylamido)-2-phenylethyl)pyridazin-4-yl)phenylcarbamate;

(E)-methyl 4-(3-chloro-6-(1-(3-(5-chloro-2-(1H-tetrazol-1-yl)phenyl)acrylamido)-3-(methylthio)propyl)pyridazin-4-yl)phenylcarbamate;

(E)-methyl 4-(3-chloro-6-(1-(3-(5-chloro-2-(1H-tetrazol-1-yl)phenyl)acrylamido)-3-(methylsulfonyl)propyl)pyridazin-4-yl)phenylcarbamate;

methyl 4-(3-chloro-6-(1-((E)-3-(5-chloro-2-(1H-tetrazol-1-yl)phenyl)acrylamido)-3-(methylsulfinyl)propyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-(methylsulfonylmethyl)pyridazin-4-yl)phenylcarbamate;

(E)-methyl 4-(3-chloro-6-(1-(3-(5-chloro-2-(1H-tetrazol-1-yl)phenyl)acrylamido)-2-(pyridin-4-yl)ethyl)pyridazin-4-yl)phenylcarbamate;

(E)-methyl 4-(6-(1-(3-(5-chloro-2-(1H-tetrazol-1-yl)phenyl)acrylamido)-2-phenylethyl)-3-cyanopyridazin-4-yl)phenylcarbamate;

(E)-methyl 4-(3-chloro-6-(1-(3-(5-chloro-2-(1H-tetrazol-1-yl)phenyl)acrylamido)-2-(6,7-dihydro-5H-pyrazolo[5,1-b][1,3]oxazin-2-yl)ethyl)pyridazin-4-yl)phenylcarbamate;

(E)-3-(5-chloro-2-(1H-tetrazol-1-yl)phenyl)-N-(1-(6-chloro-5-(4-(3-(2-hydroxyethyl)ureido)phenyl)pyridazin-3-yl)-2-(3-fluorophenyl)ethyl)acrylamide;

methyl 4-(3-chloro-6-(1-((E)-3-(5-chloro-2-(1H-tetrazol-1-yl)phenyl)acrylamido)-2-(piperidin-3-yl)ethyl)pyridazin-4-yl)phenylcarbamate;

methyl 4-(6-(2-(1-acetylpiperidin-3-yl)-1-((E)-3-(5-chloro-2-(1H-tetrazol-1-yl)phenyl)acrylamido)ethyl)-3-chloropyridazin-4-yl)phenylcarbamate;

(E)-methyl 4-(3-chloro-6-(1-(3-(5-chloro-2-(1H-tetrazol-1-yl)phenyl)acrylamido)-2-(6-methylpyridin-3-yl)ethyl)pyridazin-4-yl)phenylcarbamate;

[4-(6-{2-(4-benzyloxycarbonylamino-phenyl)-1-[(E)-3-(5-chloro-2-tetrazol-1-yl-phenyl)-acryloylamino]-ethyl}-3-chloro-pyridazin-4-yl)-phenyl]-carbamic acid methyl ester;

(E)-methyl 4-(6-(2-(4-aminophenyl)-1-(3-(5-chloro-2-(1H-tetrazol-1-yl)phenyl)acrylamido)ethyl)-3-chloropyridazin-4-yl)phenylcarbamate;

(E)-methyl 4-(6-(2-(4-acetamidophenyl)-1-(3-(5-chloro-2-(1H-tetrazol-1-yl)phenyl)acrylamido)ethyl)-3-chloropyridazin-4-yl)phenylcarbamate;

(E)-methyl 4-(3-chloro-6-(1-(3-(5-chloro-2-(1H-tetrazol-1-yl)phenyl)acrylamido)-2-(4-(3-methylureido)phenyl)ethyl)pyridazin-4-yl)phenylcarbamate;

(E)-methyl 4-(3-chloro-6-(1-(3-(5-chloro-2-(1H-tetrazol-1-yl)phenyl)acrylamido)-2-(4-(2-(dimethylamino)acetamido)phenyl)ethyl)pyridazin-4-yl)phenylcarbamate;

(E)-methyl 4-(3-chloro-6-(1-(3-(5-chloro-2-(1H-tetrazol-1-yl)phenyl)acrylamido)-2-(6-methylpyridin-3-yl)ethyl)pyridazin-4-yl)phenylcarbamate;

(E)-methyl 4-(3-chloro-6-(1-(3-(5-chloro-2-(1H-tetrazol-1-yl)phenyl)acrylamido)-2-(6-methylpyridin-3-yl)ethyl)pyridazin-4-yl)phenylcarbamate;

methyl 4-(6-((1-((E)-3-(5-chloro-2-(1H-tetrazol-1-yl)phenyl)acrylamido)-2-(1-propionylpiperidin-3-yl)ethyl)pyridazin-4-yl)phenylcarbamate;

methyl 4-(3-chloro-6-(1-((E)-3-(5-chloro-2-(1H-tetrazol-1-yl)phenyl)acrylamido)-2-(1-(cyclopropanecarbonyl)piperidin-3-yl)ethyl)pyridazin-4-yl)phenylcarbamate;

benzyl 3-(2-((E)-3-(5-chloro-2-(1H-tetrazol-1-yl)phenyl)acrylamido)-2-(6-chloro-5-(4-(methoxycarbonylamino)phenyl)pyridazin-3-yl)ethyl)pyrrolidine-1-carboxylate;

methyl 4-(3-chloro-6-(1-((E)-3-(5-chloro-2-(1H-tetrazol-1-yl)phenyl)acrylamido)-2-(pyrrolidin-3-yl)ethyl)pyridazin-4-yl)phenylcarbamate;

methyl 4-(6-((2-(1-acetylpyrrolidin-3-yl)-1-((E)-3-(5-chloro-2-(1H-tetrazol-1-yl)phenyl)acrylamido)ethyl)-3-chloropyridazin-4-yl)phenylcarbamate;

methyl 4-(3-chloro-6-(1-((E)-3-(5-chloro-2-(1H-tetrazol-1-yl)phenyl)acrylamido)-2-(1-ethylpyrrolidin-3-yl)ethyl)pyridazin-4-yl)phenylcarbamate;

methyl 4-(3-chloro-6-(1-((E)-3-(5-chloro-2-(1H-tetrazol-1-yl)phenyl)acrylamido)-2-(1-isobutyrylpiperidin-3-yl)ethyl)pyridazin-4-yl)phenylcarbamate;

methyl 4-(3-chloro-6-(1-((E)-3-(5-chloro-2-(1H-tetrazol-1-yl)phenyl)acrylamido)-2-(1-isobutyrylpiperidin-3-yl)ethyl)pyridazin-4-yl)phenylcarbamate;

methyl 4-(3-chloro-6-(1-((E)-3-(5-chloro-2-(1H-tetrazol-1-yl)phenyl)acrylamido)-2-(1-(cyclopropylmethyl)pyrrolidin-3-yl)ethyl)pyridazin-4-yl)phenylcarbamate;

(E)-methyl 3-(3-(5-chloro-2-(1H-tetrazol-1-yl)phenyl)acrylamido)-3-(6-chloro-5-(4-(methoxycarbonylamino)phenyl)pyridazin-3-yl)propanoate;

(E)-methyl 4-(3-chloro-6-(1-(3-(5-chloro-2-(1H-tetrazol-1-yl)phenyl)acrylamido)-3-(isopropyl(methyl)amino)-3-oxopropyl)pyridazin-4-yl)phenylcarbamate;

methyl 4-(3-chloro-6-(1-((E)-3-(5-chloro-2-(1H-tetrazol-1-yl)phenyl)acrylamido)-3-((R)-3-hydroxypyrrolidin-1-yl)-3-oxopropyl)pyridazin-4-yl)phenylcarbamate;

(E)-methyl 4-(3-chloro-6-(1-(3-(5-chloro-2-(1H-tetrazol-1-yl)phenyl)acrylamido)-2-(thiazol-4-yl)ethyl)pyridazin-4-yl)phenylcarbamate;

methyl 4-(3-chloro-6-(1-((E)-3-(5-chloro-2-(1H-tetrazol-1-yl)phenyl)acrylamido)-2-(1-(methylcarbamoyl)piperidin-3-yl)ethyl)pyridazin-4-yl)phenylcarbamate;

(E)-methyl 4-(3-chloro-6-(1-(3-(5-chloro-2-(1H-tetrazol-1-yl)phenyl)acrylamido)-2-(4-methylthiazol-2-yl)ethyl)pyridazin-4-yl)phenylcarbamate;

(E)-methyl 4-(3-chloro-6-(1-(3-(3-chloro-2-fluoro-6-(1H-tetrazol-1-yl)phenyl)acrylamido)-2-(4-methylthiazol-2-yl)ethyl)pyridazin-4-yl)phenylcarbamate;

(E)-methyl 4-(6-(1-(3-(5-chloro-2-(1H-tetrazol-1-yl)phenyl)acrylamido)-3-(piperidin-4-yl)propyl)-3-oxo-2,3-dihydropyridazin-4-yl)phenylcarbamate (E)-N-(1-(5-(2-aminothiazol-4-yl)-6-oxo-1,6-dihydropyridazin-3-yl)-2-phenylethyl)-3-(5-chloro-2-(1H-tetrazol-1-yl)phenyl)acrylamide;

(E)-methyl 4-(6-(1-(3-(5-chloro-2-(1H-tetrazol-1-yl)phenyl)acrylamido)-3-(methylthio)propyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(pyridin-3-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(1-methyl-5-(methylsulfinyl)-1H-pyrazol-3-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(1-methyl-5-(methylsulfonyl)-1H-pyrazol-3-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(5-methoxy-1-methyl-1H-pyrazol-3-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(6,7-dihydro-5H-pyrazolo[5,1-b][1,3]oxazin-2-yl)ethyl)-3-oxo-2,3-dihydropyridazin-4-yl)phenylcarbamate;

(E)-tert-butyl 3-(2-(3-(5-chloro-2-(1H-tetrazol-1-yl)phenyl)acrylamido)-2-(5-(4-(methoxycarbonylamino)phenyl)-6-oxo-1,6-dihydropyridazin-3-yl)ethyl)azetidine-1-carboxylate;

(E)-methyl 4-(6-(2-(azetidin-3-yl)-1-(3-(5-chloro-2-(1H-tetrazol-1-yl)phenyl)acrylamido)ethyl)-3-oxo-2,3-dihydropyridazin-4-yl)phenylcarbamate;

tert-butyl 3-(2-((E)-3-(5-chloro-2-(1H-tetrazol-1-yl)phenyl)acrylamido)-2-(5-(4-(methoxycarbonylamino)phenyl)-6-oxo-1,6-dihydropyridazin-3-yl)ethyl)piperidine-1-carboxylate;

(E)-methyl 4-(6-(1-(3-(5-chloro-2-(1H-tetrazol-1-yl)phenyl)acrylamido)but-3-enyl)-3-oxo-2,3-dihydropyridazin-4-yl)phenylcarbamate;

[4-(6-{2-(4-benzyloxycarbonylamino-phenyl)-1-[(E)-3-(5-chloro-2-tetrazol-1-yl-phenyl)-acryloylamino]-ethyl}-3-oxo-2,3-dihydro-pyridazin-4-yl)-phenyl]-carbamic acid methyl ester;

(E)-methyl 4-(6-(2-(1-acetylazetidin-3-yl)-1-(3-(5-chloro-2-(1H-tetrazol-1-yl)phenyl)acrylamido)ethyl)-3-oxo-2,3-dihydropyridazin-4-yl)phenylcarbamate;

(E)-methyl 4-(6-(2-(4-aminophenyl)-1-(3-(5-chloro-2-(1H-tetrazol-1-yl)phenyl)acrylamido)ethyl)-3-oxo-2,3-dihydropyridazin-4-yl)phenylcarbamate;

(E)-methyl 4-(6-(2-(4-acetamidophenyl)-1-(3-(5-chloro-2-(1H-tetrazol-1-yl)phenyl)acrylamido)ethyl)-3-oxo-2,3-dihydropyridazin-4-yl)phenylcarbamate;

methyl 4-(6-(1-((E)-3-(5-chloro-2-(1H-tetrazol-1-yl)phenyl)acrylamido)-2-(piperidin-3-yl)ethyl)-3-oxo-2,3-dihydropyridazin-4-yl)phenylcarbamate;

(E)-3-(3-(5-chloro-2-(1H-tetrazol-1-yl)phenyl)acrylamido)-3-(5-(4-(methoxycarbonylamino)phenyl)-6-oxo-1,6-dihydropyridazin-3-yl)propanoic acid;

(E)-tert-butyl 3-(3-(5-chloro-2-(1H-tetrazol-1-yl)phenyl)acrylamido)-3-(5-(4-(methoxycarbonylamino)phenyl)-6-oxo-1,6-dihydropyridazin-3-yl)propanoate;

benzyl 3-(2-((E)-3-(5-chloro-2-(1H-tetrazol-1-yl)phenyl)acrylamido)-2-(5-(4-(methoxycarbonylamino)phenyl)-6-oxo-1,6-dihydropyridazin-3-yl)ethyl)pyrrolidine-1-carboxylate;

methyl 4-(6-(1-((E)-3-(5-chloro-2-(1H-tetrazol-1-yl)phenyl)acrylamido)-2-(1-(cyclopropanecarbonyl)piperidin-3-yl)ethyl)-3-oxo-2,3-dihydropyridazin-4-yl)phenylcarbamate;

methyl 3-(2-((E)-3-(5-chloro-2-(1H-tetrazol-1-yl)phenyl)acrylamido)-2-(5-(4-(methoxycarbonylamino)phenyl)-6-oxo-1,6-dihydropyridazin-3-yl)ethyl)piperidine-1-carboxylate;

(E)-methyl 4-(6-(2-(6-aminopyridin-3-yl)-1-(3-(5-chloro-2-(1H-tetrazol-1-yl)phenyl)acrylamido)ethyl)-3-oxo-2,3-dihydropyridazin-4-yl)phenylcarbamate;

methyl 4-(6-(1-((E)-3-(5-chloro-2-(1H-tetrazol-1-yl)phenyl)acrylamido)-2-(pyrrolidin-3-yl)ethyl)-3-oxo-2,3-dihydropyridazin-4-yl)phenylcarbamate;

methyl 4-(6-(2-(1-acetylpyrrolidin-3-yl)-1-((E)-3-(5-chloro-2-(1H-tetrazol-1-yl)phenyl)acrylamido)ethyl)-3-oxo-2,3-dihydropyridazin-4-yl)phenylcarbamate;

methyl 4-(6-(1-((E)-3-(5-chloro-2-(1H-tetrazol-1-yl)phenyl)acrylamido)-2-(1-(ethylsulfonyl)piperidin-3-yl)ethyl)-3-oxo-2,3-dihydropyridazin-4-yl)phenylcarbamate;

methyl 4-(6-(1-((E)-3-(5-chloro-2-(1H-tetrazol-1-yl)phenyl)acrylamido)-2-(1-(methylsulfonyl)piperidin-3-yl)ethyl)-3-oxo-2,3-dihydropyridazin-4-yl)phenylcarbamate;

methyl 4-(6-(1-((E)-3-(5-chloro-2-(1H-tetrazol-1-yl)phenyl)acrylamido)-2-(1-(isopropylsulfonyl)piperidin-3-yl)ethyl)-3-oxo-2,3-dihydropyridazin-4-yl)phenylcarbamate;

methyl 4-(6-(1-((E)-3-(5-chloro-2-(1H-tetrazol-1-yl)phenyl)acrylamido)-2-(1-(methylcarbamoyl)piperidin-3-yl)ethyl)-3-oxo-2,3-dihydropyridazin-4-yl)phenylcarbamate;

methyl 4-(6-(1-((E)-3-(5-chloro-2-(1H-tetrazol-1-yl)phenyl)acrylamido)-2-(1-isobutyrylpiperidin-3-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(thiazol-4-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(4-methylthiazol-2-yl)ethyl)-3-oxo-2,3-dihydropyridazin-4-yl)phenylcarbamate;

(E)-methyl 4-(6-(1-(3-(3-chloro-2-fluoro-6-(1H-tetrazol-1-yl)phenyl)acrylamido)-2-(4-methylthiazol-2-yl)ethyl)-3-oxo-2,3-dihydropyridazin-4-yl)phenylcarbamate;

[4-(6-{2-tert-butoxycarbonylamino-1-[(E)-3-(5-chloro-2-tetrazol-1-yl-phenyl)-acryloylamino]-ethyl}-3-oxo-2,3-dihydro-pyridazin-4-yl)-phenyl]-carbamic acid methyl ester;

(E)-methyl 4-(6-(1-(3-(5-chloro-2-(1H-tetrazol-1-yl)phenyl)acrylamido)-2-pivalamidoethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(2-oxooxazolidin-3-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(2-isopropylthiazol-4-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(5-cyclopropyl-1,3,4-thiadiazol-2-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(methylthio)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(methylsulfonyl)ethyl)-3-oxo-2,3-dihydropyridazin-4-yl)phenylcarbamate;

(E)-methyl 4-(6-(2-(5-tert-butyl-1,2,4-oxadiazol-3-yl)-1-(3-(5-chloro-2-(1H-tetrazol-1-yl)phenyl)acrylamido)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(neopentylthio)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(4,5-dimethylthiazol-2-yl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-2-(neopentylsulfonyl)ethyl)-3-oxo-2,3-dihydropyridazin-4-yl)phenylcarbamate;

(E)-methyl 4-(6-(1-(3-(5-chloro-2-(1H-tetrazol-1-yl)phenyl)acrylamido)-3-(3,3-difluoropyrrolidin-1-yl)-3-oxopropyl)-3-oxo-2,3-dihydropyridazin-4-yl)phenylcarbamate;

methyl 4-(6-(1-((E)-3-(5-chloro-2-(1H-tetrazol-1-yl)phenyl) acrylamido)-3-(3-fluoropyrrolidin-1-yl)-3-oxopropyl)-3-oxo-2,3-dihydropyridazin-4-yl)phenylcarbamate;

(E)-methyl 4-(6-(1-(3-(5-chloro-2-(1H-tetrazol-1-yl)phenyl) acrylamido)-3-(3,3-difluoroazetidin-1-yl)-3-oxopropyl)-3-oxo-2,3-dihydropyridazin-4-yl)phenylcarbamate;

(E)-methyl 4-(6-(2-benzamido-1-(3-(5-chloro-2-(1H-tetrazol-1-yl)phenyl)acrylamido)ethyl)-3-oxo-2,3-dihydropyridazin-4-yl)phenylcarbamate;

(E)-methyl 4-(6-(2-(3-(1H-pyrazol-1-yl)phenylsulfonamido)-1-(3-(5-chloro-2-(1H-tetrazol-1-yl)phenyl)acrylamido)ethyl)-3-oxo-2,3-dihydropyridazin-4-yl)phenylcarbamate;

(E)-methyl 4-(6-(1-(3-(5-chloro-2-(1H-tetrazol-1-yl)phenyl) acrylamido)-2-(1,3-dimethyl-1H-pyrazole-4-sulfonamido)ethyl)-3-oxo-2,3-dihydropyridazin-4-yl)phenylcarbamate;

(E)-methyl 4-(3-chloro-6-(1-(3-(5-chloro-2-(1H-tetrazol-1-yl)phenyl)acrylamido)-2-(2-isopropylthiazol-4-yl)ethyl) pyridazin-4-yl)phenylcarbamate; and (E)-methyl 4-(3-chloro-6-(1-(3-(5-chloro-2-(1H-tetrazol-1-yl)phenyl)acrylamido)-2-(methylsulfonyl)ethyl)pyridazin-4-yl)phenylcarbamate;

or a stereoisomer, a tautomer, a pharmaceutically acceptable salt, a solvate, or a prodrug thereof.

In another aspect, the present invention provides a compound selected from any subset list of compounds within the scope of the seventh aspect.

In another aspect, the present invention provides a compound selected from the exemplified examples or a stereoisomer, a tautomer, a pharmaceutically acceptable salt, a solvate, or a prodrug thereof.

In another embodiment, A is phenyl further substituted with 0-3 $R^1$.

In another embodiment, A is phenyl substituted with $R^2$ and 0-3 $R^1$.

In another embodiment, $L_1$ is —CH$_2$CH$_2$—, —CH=CH—, —C(Me)=CH—, —C≡C—, —CH$_2$NH—, —CH$_2$O—, —NHNH—, —SCH$_2$—, —SO$_2$CH$_2$— or —OCH$_2$—; $L_2$ is —CONH— or —NHCO—; provided that when $L_1$ is —NHNH—, —OCH$_2$—, or —SCH$_2$— then $L_2$ is —CONH—.

In another embodiment, $L_1$ is —CH$_2$CH$_2$—, —CH=CH—, —C≡C—, —OCH$_2$—, —CH$_2$NH—, —CH$_2$O—, or —SCH$_2$—.

In another embodiment, $L_1$ is —CH$_2$CH$_2$—, —CH=CH—, —OCH$_2$—, —CH$_2$NH—, —CH$_2$O—, or —SCH$_2$—.

In another embodiment, $L_1$ is —CH$_2$CH$_2$— or —CH=CH—.

In another embodiment, $L_1$ is —CH$_2$CH$_2$—.

In another embodiment, $L_1$ is —CH=CH—.

In another embodiment, M is selected from the group consisting of:

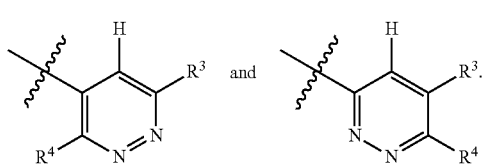

In another embodiment, M is

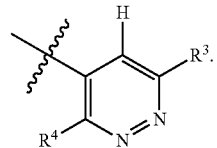

In another embodiment, M is

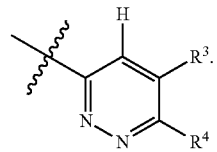

In another embodiment, M is selected from the group consisting of:

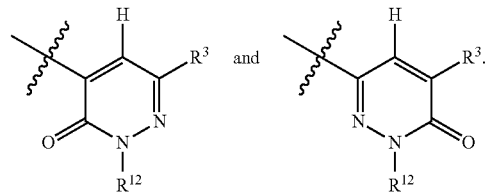

In another embodiment, M is

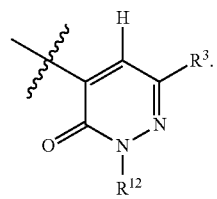

In another embodiment, M is

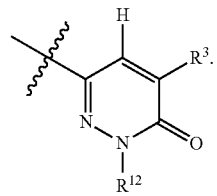

In another embodiment, $R^1$ is, independently at each occurrence, F, Cl, Br, CF$_3$, —(CH$_2$)$_r$OR$^a$, CN, —(CH$_2$)$_r$NR$^7$R$^8$, or C$_{1-4}$ alkyl.

In another embodiment, $R^1$ is, independently at each occurrence, F, Cl or Me.

In another embodiment, $R^2$ is, H, —(CH$_2$)$_r$C(O)R$^a$, —(CH$_2$)$_r$OR$^a$, —(CH$_2$)$_r$NR$^7$R$^8$, C$_{1-6}$ alkyl substituted with 0-1 $R^{2a}$, —(CH$_2$)$_r$-C$_{3-6}$ cycloalkyl substituted with 0-2 $R^{2b}$, —(CH$_2$)$_r$-phenyl substituted with 0-2 $R^{2b}$, or —(CH$_2$)$_r$-5-7 membered heterocycle comprising carbon atoms and 1-4 heteroatoms selected from N, O, and $S(O)_p$, wherein said heterocycle is substituted with 0-2 $R^{2b}$.

In another embodiment, $R^2$ is $-(CH_2)_rC(O)R^a$, $-(CH_2)_rOR^a$, $-(CH_2)_rNR^7R^8$, or 5-membered heterocycle comprising carbon atoms and 1-4 heteroatoms selected from N, O, and $S(O)_p$, wherein said heterocycle is substituted with 0-2 $R^{2b}$.

In another embodiment, $R^2$ is 5-membered heterocycle selected from the group consisting of imidazole, triazole, and tetrazole; wherein said heterocycle is substituted with 0-2 $R^{2b}$.

In another embodiment, $R^2$ is tetrazole substituted with 0-1 $R^{2b}$.

In another embodiment, $R^2$ is tetrazole.

In another embodiment, $R^3$ is, independently at each occurrence, $-(CH_2)_r$-phenyl substituted with 0-2 $R^{1a}$ and 0-1 $R^{3d}$, $-(CH_2)_r$-naphthyl substituted with 0-2 $R^{1a}$ and 0-1 $R^{3d}$, or $-(CH_2)_r$-1,2,3,4-tetrahydronaphthyl substituted with 0-2 $R^{1a}$ and 0-1 $R^{3d}$.

In another embodiment, $R^3$ is, independently at each occurrence, $-(CH_2)_r$-5- to 12-membered heterocycle substituted with 0-2 $R^{1a}$ and 0-1 $R^{3d}$, wherein said heterocycle is selected from the group consisting of: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline.

In another embodiment, $R^3$ is, independently at each occurrence, a 5-6 membered heterocycle substituted with 0-2 $R^{1a}$ and 0-1 $R^{3d}$, wherein said heterocycle is selected from the group consisting of: thiophene, furan, thiazole, tetrazole, pyridine, pyridone, pyrimidine, pyrrole, pyrazole, indole, and 2-oxindole.

In another embodiment, $R^3$ is, independently at each occurrence, $-(CH_2)_r$-phenyl substituted with 0-3 $R^{3a}$, $-(CH_2)_r$-pyridyl substituted with 0-3 $R^{3a}$, $-(CH_2)_r$-thiazolyl substituted with 0-2 $R^{1a}$, or

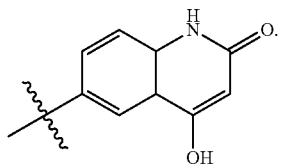

In another embodiment, $R^3$ is, independently at each occurrence, phenyl substituted with 0-2 $R^{3a}$, or

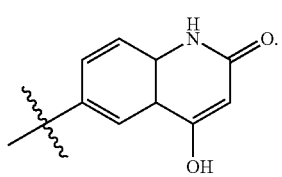

In another embodiment, $R^3$ is, independently at each occurrence, $-(CH_2)_r$-phenyl substituted with 0-2 $R^{3a}$, or $-(CH_2)_r$-pyridyl substituted with 0-2 $R^{3a}$.

In another embodiment, $R^3$ is, independently at each occurrence, phenyl substituted with 0-2 $R^{3a}$.

In another embodiment, $R^3$ is, independently at each occurrence, a 9-10 membered heterocycle substituted with 0-2 $R^{3a}$ and 0-1 $R^{3d}$, wherein said heterocycle is selected from the group consisting of: isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline.

In another embodiment, $R^3$ is, independently at each occurrence, a 9-10 membered heterocycle substituted with 0-2 $R^{3a}$ and 0-1 $R^{3d}$, wherein said heterocycle is selected from the group consisting of: indazole, benzisoxazole, quinazoline, and quinoline.

In another embodiment, $R^3$ is, independently at each occurrence, 3-amino-indazol-5-yl, 3-amino-indazol-6-yl, 3-amino-benzisoxazol-6-yl, 4-amino-quinazolin-7-yl, 4-hydroxy-quinolin-2(1H)-one-6-yl, and 4-carboxy-quinolin-2(1H)-one-6-yl.

In another embodiment, $R^{3a}$ is, independently at each occurrence, F, Cl, Br, I, $OCF_3$, $CF_3$, CN, $NO_2$, $OR^a$, $SR^a$, $NR^7R^8$, $-NHC(O)NR^8R^9$, $-(CH_2)_rC(O)OR^a$, $-C(O)C_{1-4}$ alkyl, $-(CH_2)_rNR^8C(O)R^a$, $-(CH_2)_rNR^8CO_2R^c$, $-C(O)NR^8R^9$, $C_{1-4}$ haloalkyl, $C_{1-4}$ haloalkyloxy-, $C_{1-6}$ alkyl, $C_{3-6}$ cycloalkyl, $-(CH_2)_r$-phenyl,

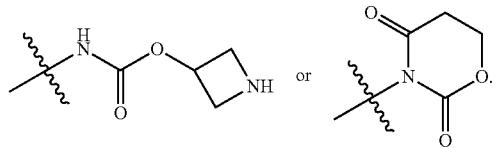

In another embodiment, $R^{3a}$ is, independently at each occurrence, F, Cl, Br, I, $OCF_3$, $CF_3$, CN, $NO_2$, $OR^a$, $SR^a$, $NR^7R^8$, $-NHC(O)NR^8R^9$, $-(CH_2)_rC(O)OR^a$, $-C(O)C_{1-4}$ alkyl, $-(CH_2)_rNR^8C(O)R^a$, $-(CH_2)_rNR^8CO_2R^c$, $-C(O)NR^8R^9$, $C_{1-4}$ haloalkyl, $C_{1-4}$ haloalkyloxy-, $C_{1-6}$ alkyl, $C_{3-6}$ cycloalkyl, $-(CH_2)_r$-phenyl,

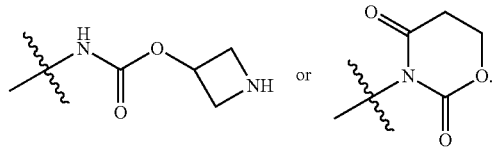

In another embodiment, $R^{3a}$ is, independently at each occurrence, F, $NH_2$, $-NHC(O)OMe$, $-NHC(O)OEt$, $-NHC(O)CH_2OH$, $-NHC(O)O(CH_2)_2C(O)OH$, $-NHC(O)OCH_2C(O)NH_2$, $-NHC(O)O(CH_2)_2C(O)NH_2$, $-NHC(O)CH_2OC(O)Me$, $-NHC(O)O(CH_2)_2OMe$, $-NHC(O)NHC(CH_2)_2OH$, $-NHC(O)NHC(Me)_2CH_2OH$,

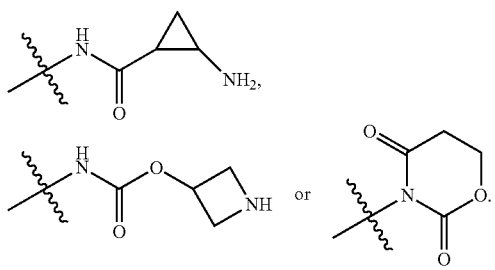

In another embodiment, $R^{3a}$ is, independently at each occurrence, F, $NH_2$, —NHC(O)OMe, —NHC(O)OEt, —NHC(O)CH$_2$OH, —NHC(O)O(CH$_2$)$_2$C(O)OH, —NHC(O)OCH$_2$C(O)NH$_2$, —NHC(O)O(CH$_2$)$_2$C(O)NH$_2$, —NHC(O)CH$_2$OC(O)Me, —NHC(O)O(CH$_2$)$_2$OMe, —NHC(O)NHC(CH$_2$)$_2$OH, —NHC(O)NHC(Me)$_2$CH$_2$OH,

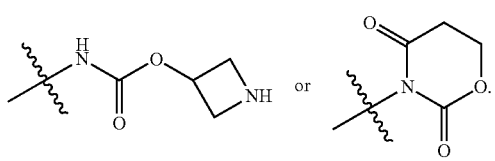

In another embodiment, $R^{3a}$ is, independently at each occurrence, $NH_2$, —NHC(O)OMe, —NHC(O)OCH$_2$C(O)NH$_2$, —NHC(O)O(CH$_2$)$_2$C(O)NH$_2$, —NHC(O)O(CH$_2$)$_2$OH, —NHC(O)O(CH$_2$)$_2$OMe, or —NHC(O)NHC(CH$_2$)$_2$OH.

In another embodiment, $R^4$ is, independently at each occurrence, H, F, Cl, Br, OCF$_3$, CF$_3$, CN, NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —(CH$_2$)$_r$NR$^7$R$^8$, —(CH$_2$)$_r$C(O)NR$^8$R$^9$, —(CH$_2$)$_r$S(O)$_2$R$^c$, $C_{1-4}$ alkyl substituted with 0-2 $R^{4a}$, or $C_{2-4}$ alkenyl substituted with 0-2 $R^{4a}$.

In another embodiment, $R^4$ is, independently at each occurrence, H, F, Cl, Br, OCF$_3$, CF$_3$, CN, NO$_2$, —(CH$_2$)$_r$OR$^a$, —CH(OH)CH$_2$OH, —(CH$_2$)$_r$SR$^a$, C(O)R$^a$, C(O)OR$^a$, —(CH$_2$)$_r$NR$^7$R$^8$, —(CH$_2$)$_r$S(O)$_2$R$^c$, C(O)NR$^8$R$^9$, $C_{1-4}$ alkyl substituted with 0-2 $R^{4a}$, or $C_{2-4}$ alkenyl substituted with 0-2 $R^{4a}$.

In another embodiment, $R^4$ is, independently at each occurrence, H, F, Cl, Br, I, OCF$_3$, CF$_3$, CN, NO$_2$, —(CH$_2$)$_r$OR$^a$, —CH(OH)CH$_2$OH, —(CH$_2$)$_r$SR$^a$, C(O)R$^a$, C(O)OR$^a$, —(CH$_2$)$_r$S(O)$_2$R$^c$, —(CH$_2$)$_r$NR$^7$R$^8$, C(O)NR$^8$R$^9$, $C_{1-4}$ alkyl, or $C_{2-4}$ alkenyl.

In another embodiment, $R^4$ is, independently at each occurrence, H, F, Cl, CN, $C_{1-4}$ alkyl, $C_{2-4}$ alkenyl, OH, —CH$_2$OH, —CH(OH)CH$_2$OH, —O—$C_{1-4}$ alkyl, —CH$_2$O($C_{1-4}$ alkyl), —NH($C_{1-4}$ alkyl), —N($C_{1-4}$ alkyl)$_2$, —CH$_2$NH($C_{1-4}$ alkyl), —CH$_2$N($C_{1-4}$ alkyl)$_2$, —S—$C_{1-4}$ alkyl, —CH$_2$S($C_{1-4}$ alkyl), —S(O)$_2$—$C_{1-4}$ alkyl, —CH$_2$S(O)$_2$—$C_{1-4}$ alkyl, C(O)OH, C(O)NR$^8$R$^9$, or C(O)O($C_{1-4}$ alkyl).

In another embodiment, $R^4$ is, independently at each occurrence, H, F, Cl, Me, Et, —CH=CH$_2$, OH, —CH$_2$OH, —CH(OH)CH$_2$OH, OMe, OEt, SMe, —CH$_2$SMe, SEt, SO$_2$Me, —CH$_2$SO$_2$Me, SO$_2$Et, CN, C(O)OH, C(O)OMe, —CH$_2$N(Me)$_2$, C(O)NH$_2$, or C(O)NHMe.

In another embodiment, $R^4$ is, independently at each occurrence, H, F, Cl, Me, OH, OMe, OEt, SEt, SO$_2$Et, C(O)OH, C(O)OMe, or C(O)NH$_2$.

In another embodiment, $R^{11}$ is —CH$_2$OR$^a$, —CH$_2$CH$_2$OR$^a$, —CH$_2$S(O)$_p$R$^c$, —CH$_2$CH$_2$S(O)$_p$R$^c$, —CH$_2$NR$^7$R$^8$, —CH$_2$CH$_2$NR$^7$R$^8$, —CH$_2$C(O)R$^a$, —CH$_2$CH$_2$C(O)R$^a$, —CH$_2$C(O)OR$^a$, —CH$_2$CH$_2$C(O)OR$^a$, —CH$_2$C(O)NR$^8$R$^9$, —CH$_2$CH$_2$C(O)NR$^8$R$^9$, —CH$_2$NR$^8$C(O)R$^c$, —CH$_2$CH$_2$NR$^8$C(O)R$^c$, —CH$_2$NR$^8$C(O)OR$^c$, —CH$_2$CH$_2$NR$^8$C(O)OR$^c$, $C_{1-4}$ haloalkyl, $C_{1-6}$ alkyl substituted with 0-2 $R^{11a}$, $C_{2-6}$ alkyl substituted with 0-2 $R^{11a}$, —(CH$_2$)$_s$—$C_{3-6}$ cycloalkyl substituted with 0-2 $R^{11b}$, —(CH$_2$)$_s$-phenyl substituted with 0-3 $R^{11b}$, or —(CH$_2$)$_s$-4- to 10-membered heterocycle comprising: carbon atoms and 1-4 heteroatoms selected from N, O, and S(O)$_p$, wherein said heterocycle is substituted with 0-3 $R^{11b}$.

In another embodiment, $R^{11}$ is —CH$_2$OR$^a$, —CH$_2$CH$_2$OR$^a$, —CH$_2$S(O)$_p$R$^c$, —CH$_2$CH$_2$S(O)$_p$R$^c$, —CH$_2$NR$^7$R$^8$, —CH$_2$CH$_2$NR$^7$R$^8$, —CH$_2$C(O)R$^a$, —CH$_2$CH$_2$C(O)R$^a$, —CH$_2$C(O)OR$^a$, —CH$_2$CH$_2$C(O)OR$^a$, —CH$_2$C(O)NR$^8$R$^9$, —CH$_2$CH$_2$C(O)NR$^8$R$^9$, —CH$_2$NR$^8$C(O)R$^c$, —CH$_2$CH$_2$NR$^8$C(O)R$^c$, —CH$_2$NR$^8$C(O)OR$^c$, —CH$_2$CH$_2$NR$^8$C(O)OR$^c$, $C_{1-6}$ alkyl, $C_{2-6}$ alkenyl, —(CH$_2$)$_s$-phenyl substituted with 0-2 $R^{11b}$, or —(CH$_2$)$_s$-4 to 6-membered heterocycle substituted with 0-2 $R^{11b}$, wherein said heterocycle is selected from the group consisting of: azetidine, oxazolidin-2-one, pyrrolidine, pyrazole, thiazole, thiadiazole, oxazole, oxadiazole, imidazole, piperidine, piperazine, and pyridine;

alternatively, $R^{11}$ is

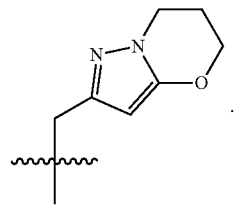

In another embodiment, $R^{11}$ is $C_{1-6}$ alkyl, $C_{2-6}$ alkenyl, benzyl substituted with 0-2 $R^{11b}$, —CH$_2$O($C_{1-6}$ alkyl), —CH$_2$CH$_2$O($C_{1-6}$ alkyl), —CH$_2$S(O)$_p$($C_{1-6}$ alkyl), —CH$_2$CH$_2$S(O)$_p$($C_{1-6}$ alkyl), —CH$_2$C(O)OH, —CH$_2$C(O)O($C_{1-4}$ alkyl), —CH$_2$NHC(O)($C_{1-4}$ alkyl), —CH$_2$NHC(O)O($C_{1-4}$ alkyl), —CH$_2$NH($C_{1-4}$ alkyl), —CH$_2$N($C_{1-4}$ alkyl)$_2$, —CH$_2$C(O)NH($C_{1-4}$ alkyl substituted with 0-1 OH), —CH$_2$C(O)N($C_{1-4}$ alkyl)$_2$, —CH$_2$NHC(O)Ph, —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), —CH$_2$NHS(O)$_2$(3-(pyrazol-1-yl)-Ph), —CH$_2$NHS(O)$_2$(1,3-dimethyl-pyrazol-4-yl), or —CH$_2$-4- to 6-membered heterocycle substituted with 0-2 $R^{11b}$, wherein said heterocycle is selected from the group consisting of: azetidine, oxazolidin-2-one, pyrrolidine, pyrazole, thiazole, thiadiazole, oxadiazole,piperidine, and pyridine;

alternatively, $R^{11}$ is

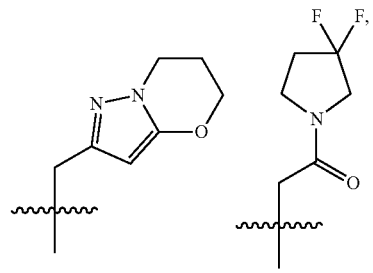

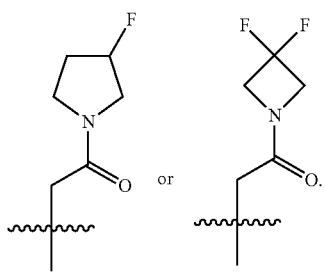

In another embodiment, $R^{11}$ is $C_{1-4}$ haloalkyl, $C_{1-6}$ alkyl substituted with 0-2 $R^{11a}$, —(CH$_2$)$_s$—$C_{3-6}$ cycloalkyl substituted with 0-2 $R^{11b}$, —(CH$_2$)$_s$-phenyl substituted with 0-3 $R^{11b}$, or —(CH$_2$)$_s$-5- to 10-membered heterocycle comprising: carbon atoms and 1-4 heteroatoms selected from N, O, and S(O)$_p$, wherein said heterocycle is substituted with 0-3 $R^{11b}$.

In another embodiment, $R^{11}$ is selected from the group consisting of: $C_{1-4}$ alkyl, $C_{2-4}$ alkenyl, benzyl, 3-F-benzyl, 4-F-benzyl, 4-NH$_2$-benzyl, 4-NHCOMe-benzyl, 4-NHCONHMe-benzyl, 4-NHCOCH$_2$N(Me)$_2$-benzyl, —CH$_2$SMe, —CH$_2$S(neopentyl), —(CH$_2$)$_2$SMe, —(CH$_2$)$_2$S(O)Me, —CH$_2$S(O)$_2$Me, —CH$_2$S(O)$_2$(neopentyl), —(CH$_2$)$_2$S(O)$_2$Me, —CH$_2$C(O)OH, —CH$_2$C(O)OMe, —CH$_2$C(O)O(t-Bu), —CH$_2$NHC(O)Me, —CH$_2$NHC(O)(t-Bu), —CH$_2$NHC(O)Ph, —CH$_2$NHS(O)$_2$(3-(pyrazol-1-yl)-Ph), —CH$_2$NHS(O)$_2$(1,3-dimethyl-pyrazol-4-yl), —CH$_2$NHC(O)O(t-Bu), —CH$_2$NH(i-Pr), —CH$_2$C(O)NH(CH$_2$CH$_2$OH), —CH$_2$C(O)NH(t-Bu), —CH$_2$C(O)N(Me)$_2$, —CH$_2$C(O)NMe(i-Pr), —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), (azetidin-3-yl)methyl, (1-acetyl-azetidin-3-yl)methyl, (1-Et-pyrazol-3-yl)methyl, (4-Me-thiazol-2-yl)methyl, (thiazol-4-yl)methyl, (2-isopropyl-thiazol-4-yl)methyl, (5-methoxy-1-Me-1H-pyrazol-3-yl)methyl, (1-Me-5-(methylsulfinyl)-1H-pyrazol-3-yl)methyl, (1-Me-5-(methylsulfonyl)-1H-pyrazol-3-yl)methyl, (pyrrolidin-3-yl)methyl, (1-Et-pyrrolidin-3-yl)methyl, (1-acetyl-pyrrolidin-3-yl)methyl, (1-(cyclopropylmethyl)-pyrrolidin-3-yl)methyl, (2-(i-Pr)-thiazol-4-yl)methyl, (4,5-dimethylthiazol-2-yl)methyl, (5-cyclopropyl-1,3,4-thiadiazol-2-yl)methyl, (5-(t-Bu)-1,2,4-oxadiazol-3-yl)methyl, (piperidin-3-yl)methyl, (piperidin-3-yl)ethyl, (1-acetyl-piperidin-3-yl)methyl, (1-propionyl-piperidin-3-yl)methyl, (1-isobutyryl-piperidin-3-yl)methyl, (1-(cyclopropanecarbonyl)-piperidin-3-yl)methyl, (pyrid-3-yl)methyl, (6-Me-pyrid-3-yl)methyl, (6-NH$_2$-pyrid-3-yl)methyl, (pyrid-4-yl)methyl,

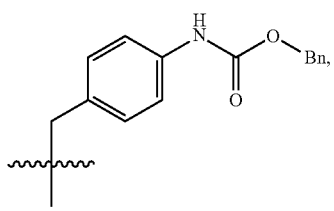

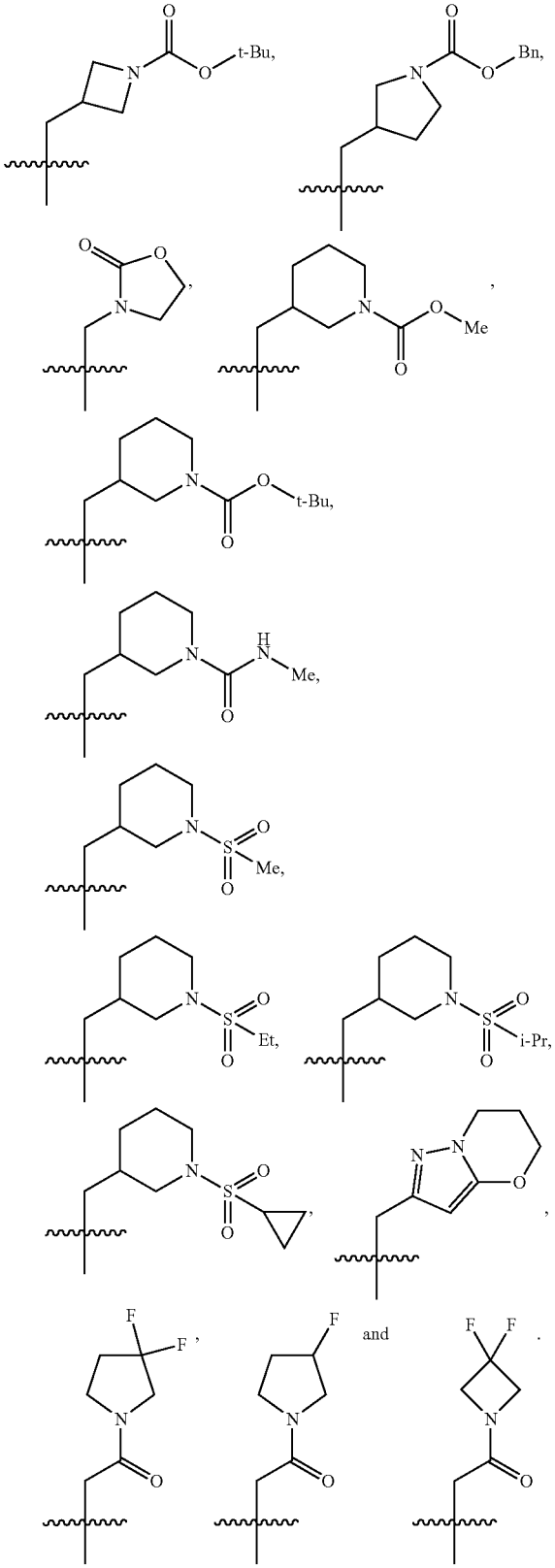

In another embodiment, $R^{11}$ is selected from the group consisting of: $C_{1-4}$ alkyl, $C_{2-4}$ alkenyl, benzyl, 3-F-benzyl, 4-F-benzyl, 4-NH$_2$-benzyl, 4-NHCOMe-benzyl, 4-NHCONHMe-benzyl, 4-NHCOCH$_2$N(Me)$_2$-benzyl, —CH$_2$SMe, —(CH$_2$)$_2$SMe, —(CH$_2$)$_2$S(O)Me, —CH$_2$S(O)$_2$Me, —(CH$_2$)$_2$S(O)$_2$Me, —CH$_2$C(O)OH, —CH$_2$C(O)OMe, —CH$_2$C(O)O(t-Bu), —CH$_2$NHC(O)Me, —CH$_2$NHC(O)(t-Bu), —CH$_2$NHC(O)O(t-Bu), —CH$_2$NH(i-Pr), —CH$_2$C(O)NH(CH$_2$CH$_2$OH), —CH$_2$C(O)NH(t-Bu), —CH$_2$C(O)N(Me)$_2$, —CH$_2$C(O)NMe(i-Pr), —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), (azetidin-3-yl)methyl, (1-acetyl-azetidin-3-yl)methyl, (1-Et-pyrazol-3-yl)methyl, (4-Me-thiazol-2-yl)methyl, (thiazol-4-yl)methyl, (2-isopropyl-thiazol-4-yl)methyl, (5-methoxy-1-Me-1H-pyrazol-3-yl)methyl, (1-Me-5-(methylsulfinyl)-1H-pyrazol-3-yl)methyl, (1-Me-5-(methylsulfonyl)-1H-pyrazol-3-yl)methyl, (pyrrolidin-3-yl)methyl, (1-Et-pyrrolidin-3-yl)methyl, (1-acetyl-pyrrolidin-3-yl)methyl, (1-(cyclopropylmethyl)-pyrrolidin-3-yl)methyl, (2-(i-Pr)-thiazol-4-yl)methyl, (4,5-dimethylthiazol-2-yl)methyl, (5-cyclopropyl-1,3,4-thiadiazol-2-yl)methyl, (5-(t-Bu)-1,2,4-oxadiazol-3-yl)methyl, (piperidin-3-yl)methyl, (piperidin-4-yl)ethyl, (1-acetyl-piperidin-3-yl)methyl, (1-propionyl-piperidin-3-yl)methyl, (1-isobutyryl-piperidin-3-yl)methyl, (1-(cyclopropanecarbonyl)-piperidin-3-yl)methyl, (pyrid-3-yl)methyl, (6-Me-pyrid-3-yl)methyl, (6-NH$_2$-pyrid-3-yl)methyl, (pyrid-4-yl)methyl,

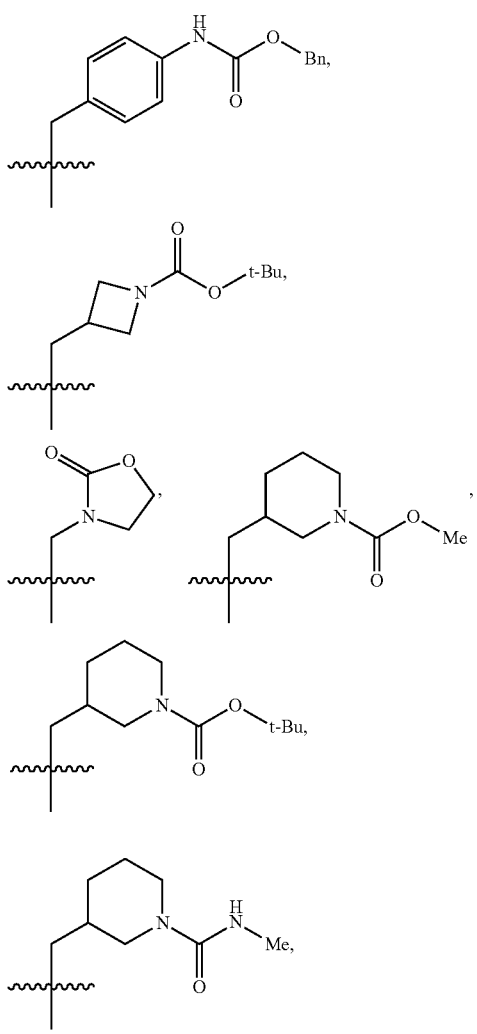

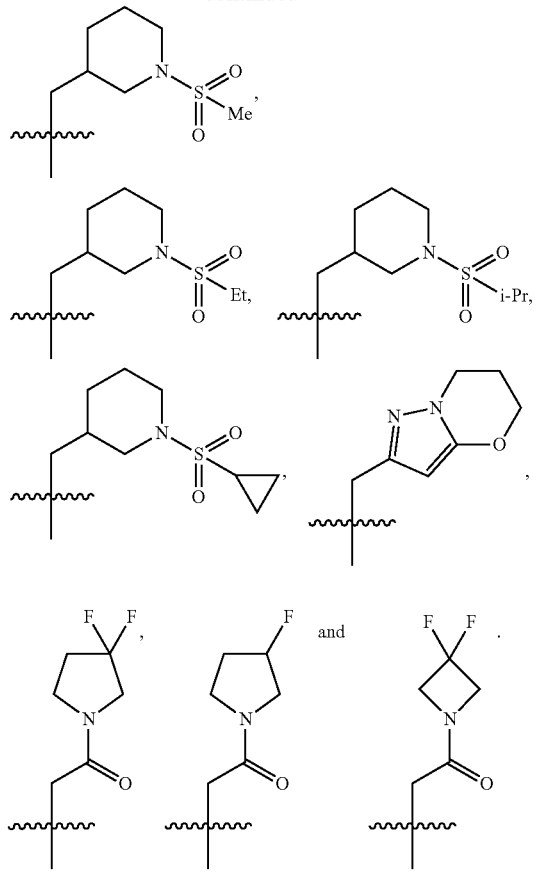

In another embodiment, R$^{11}$ is selected from the group consisting of: benzyl, 3-F-benzyl, 4-F-benzyl, 4-NH$_2$-benzyl, 4-NHCOMe-benzyl, 4-NHCONHMe-benzyl, 4-NHCOCH$_2$N(Me)$_2$-benzyl, —CH$_2$C(O)OMe, —CH$_2$C(O)O(t-Bu), —CH$_2$NHC(O)Me, —CH$_2$C(O)NH(CH$_2$CH$_2$OH), —CH$_2$C(O)NH(t-Bu), —CH$_2$C(O)N(Me)$_2$, —CH$_2$C(O)NMe(i-Pr), —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), (1-Et-pyrazol-3-yl)methyl, (4-Me-thiazol-2-yl)methyl, (thiazol-4-yl)methyl, (5-methoxy-1-Me-1H-pyrazol-3-yl)methyl, (4,5-dimethylthiazol-2-yl)methyl, (5-cyclopropyl-1,3,4-thiadiazol-2-yl)methyl, (1-acetyl-piperidin-3-yl)methyl, (1-propionyl-piperidin-3-yl)methyl, (1-isobutyryl-piperidin-3-yl)methyl, (pyrid-3-yl)methyl, (6-NH$_2$-pyrid-3-yl)methyl, (pyrid-4-yl)methyl,

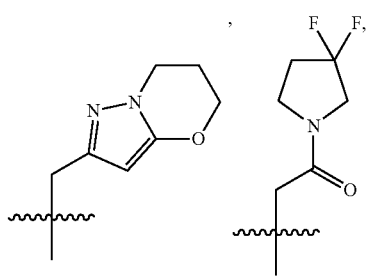

-continued

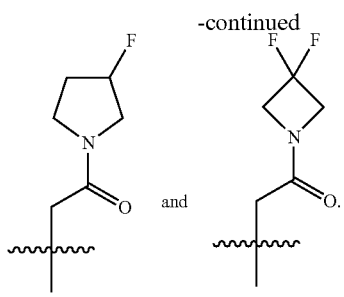

In another embodiment, $R^{11}$ is $C_{1-4}$ alkyl, benzyl substituted with 0-2 F, —$CH_2C(O)OH$, —$CH_2C(O)O(C_{1-4}$ alkyl), —$CH_2NHC(O)(C_{1-4}$ alkyl), —$CH_2NHC(O)O(C_{1-4}$ alkyl), —$CH_2NH(C_{1-4}$ alkyl), —$CH_2N(C_{1-4}$ alkyl)$_2$, —$CH_2C(O)NH(C_{1-4}$ alkyl substituted with 0-1 OH), —$CH_2C(O)N(C_{1-4}$ alkyl)$_2$, —$CH_2C(O)$(pyrrolidin-1-yl), —$CH_2C(O)$(3-OH-pyrrolidin-1-yl), —$CH_2C(O)$(4-OH-piperidin-1-yl), —$CH_2C(O)$(4-Me-piperazin-1-yl), or (1-ethyl-pyrazol-3-yl)methyl.

In another embodiment, $R^{11}$ is $C_{1-4}$ alkyl, benzyl, 3-F-benzyl, 4-F-benzyl, —$CH_2C(O)OH$, —$CH_2C(O)OMe$, —$CH_2C(O)O(t-Bu)$, —$CH_2NHC(O)Me$, —$CH_2NHC(O)O(t-Bu)$, —$CH_2NH(i-Pr)$, —$CH_2C(O)NH(CH_2CH_2OH)$, —$CH_2C(O)NH(t-Bu)$, —$CH_2C(O)N(Me)_2$, —$CH_2C(O)$(pyrrolidin-1-yl), —$CH_2C(O)$(3-OH-pyrrolidin-1-yl), —$CH_2C(O)$(4-OH-piperidin-1-yl), —$CH_2C(O)$(4-Me-piperazin-1-yl), or (1-ethyl-pyrazol-3-yl)methyl.

In another embodiment, $R^{12}$ is, independently at each occurrence, H, $C_{1-4}$ alkyl substituted with 0-2 $R^f$, or benzyl;

In another embodiment, $R^{12}$ is, independently at each occurrence, H, Me, —$CH_2CH_2OH$, —$CH_2C(O)OH$, or —$CH_2C(O)OMe$.

In another embodiment, $R^{12}$ is, independently at each occurrence, H, Me, —$CH_2CH_2OH$, or —$CH_2C(O)OH$.

In another embodiment, r, at each occurrence, is selected from 0, 1, and 2.

II. Other Embodiments of the Invention

In another embodiment, the present invention provides a composition comprising at least one of the compounds of the present invention or a stereoisomer, a tautomer, a pharmaceutically acceptable salt, a solvate, or a prodrug thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, a solvate, or a prodrug thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, a solvate, or a prodrug thereof.

In another embodiment, the present invention provides a process for making a compound of the present invention or a stereoisomer, a tautomer, a pharmaceutically acceptable salt, a solvate, or a prodrug thereof.

In another embodiment, the present invention provides an intermediate for making a compound of the present invention or a stereoisomer, a tautomer, a pharmaceutically acceptable salt, a solvate, or a prodrug thereof.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment or prophylaxis of a thromboembolic disorder comprising administering to a patient in need of such treatment or prophylaxis a therapeutically effective amount of at least one of the compounds of the present invention or stereoisomers, tautomers, pharmaceutically acceptable salts, solvates, or prodrugs thereof. Preferably, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders. Preferably, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a compound of the present invention or a stereoisomer, a tautomer, a pharmaceutically acceptable salt, a solvate, or a prodrug thereof, for use in therapy.

In another embodiment, the present invention provides a compound of the present invention or stereoisomers, tautomers, pharmaceutically acceptable salts, solvates, or prodrugs thereof, for use in therapy for the treatment or prophylaxis of a thromboembolic disorder. Preferably, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders. Preferably, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention also provides the use of a compound of the present invention or stereoisomers, tautomers, pharmaceutically acceptable salts, solvates, or prodrugs thereof, for the manufacture of a medicament for the treatment or prophylaxis of a thromboembolic disorder.

In another embodiment, the present invention provides a method for treating a thromboembolic disorder, comprising: administering to a patient in need thereof a therapeutically effective amount of a first and second therapeutic agent, wherein the first therapeutic agent is a compound of the present invention or a stereoisomer, tautomer, pharmaceutically acceptable salt, solvate or prodrug thereof, and the second therapeutic agent is at least one agent selected from a second factor Xa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

In another embodiment, the present invention provides a method for the treatment or prophylaxis of an inflammatory disorder comprising: administering to a patient in need of such treatment or prophylaxis a therapeutically effective amount of at least one of the compounds of the present invention or a stereoisomer, a tautomer, a pharmaceutically acceptable salt, a solvate, or a prodrug thereof.

In another embodiment, the present invention provides a method for the treatment or prophylaxis of an inflammatory disorder, wherein the inflammatory disorder is selected from the group consisting of sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

Alkenyl" or "alkenylene" is intended to include hydrocarbon chains of either straight or branched configuration having the specified number of carbon atoms and one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9 or 10-membered carbocyclic ring system that contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13th ed.), R. J. Lewis, ed., J. Wiley & Sons, Inc., New York, 1997. "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa., 1990, the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention.

Various forms of prodrugs are well known in the art. For examples of such prodrug derivatives, see:

a) *Design of Prodrugs,* edited by H. Bundgaard (Elsevier, 1985), and *Methods in Enzymology,* Vol. 112, pp. 309-396, edited by K. Widder et al. (Academic Press, 1985);

b) *A Textbook of Drug Design and Development,* edited by Krosgaard-Larsen and H. Bundgaard, Chapter 5, *"Design and Application of Prodrugs,"* by H. Bundgaard, at pp. 113-191 (1991);

c) H. Bundgaard, *Advanced Drug Delivery Reviews,* 8:1-38 (1992);

d) H. Bundgaard et al., *Journal of Pharmaceutical Sciences,* 77:285 (1988); and e) N. Kakeya et al., *Chem. Phar. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g. methoxycarbonyl-oxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of Prodrugs is Well Known in the Art and Described in, for example, *Medicinal Chemistry: Principles and Practice,* ed. F. D. King, The Royal Society of Chemistry, Cambridge, UK, 1994; *Hydrolysis in Drug and Prodrug Metabolism. Chemistry, Biochemistry and Enzymology,* B. Testa, J. M. Mayer, VCHA and Wiley-VCH, Zurich, Switzerland, 2003; *The Practice of Medicinal Chemistry,* C. G. Wermuth, ed., Academic Press, San Diego, Calif., 1999.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| Et$_2$O | diethyl ether |
| i-PrOH or IPA | isopropanol |
| HOAc | acetic acid |
| BOP reagent | benzotriazol-1-yloxytris(dimethylamino) phosphonium hexafluorophosphate |
| BBr$_3$ | boron tribromide |
| Boc | tert-butyloxycarbonyl |
| 2MeS-ADP | 2 methylthio adenosine diphosphate |
| cDNA | complimentary DNA |
| CH$_2$Cl$_2$ | dichloromethane |
| CH$_3$CN | acetonitrile |
| Cs$_2$CO$_3$ | cesium carbonate |
| ACN | acetonitrile |
| CDI | 1,1'-carbonyldiimidazole |
| DCE | 1,2 dichloroethane |
| DCM | dichloromethane |
| DCC | dicyclohexylcarbodiimide |
| DIC or DIPCDI | diisopropylcarbodiimide |
| DIEA or DIPEA | N,N,-diisopropylethylamine |
| DME | 1,2-dimethoxyethane |
| DMF | dimethyl formamide |
| DMSO | dimethyl sulfoxide |
| EDC (or EDC•HCl) or EDCI (or EDCI•HCl) or EDAC | 3-ethyl-3'-(dimethylamino)propyl-carbodiimide hydrochloride (or 1-(3-dimethylaminopropyl)-3-ethylcarbodiimide hydrochloride) |
| EDTA | ethylenediaminetetraacetic acid |
| HCl | hydrochloric acid |
| HEPES | 4-(2-hydroxyethyl)piperazine-1-ethanesulfonic acid |
| Hex | hexane |
| HOBt or HOBT | 1-hydroxybenzotriazole monohydrate |
| Hunig's base | N, N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NBS | N-bromosuccinimide |
| NCS | N-chlorosuccinimide |
| D-PBS | Dulbecco's Phosphate Buffered Saline |
| Pd/C | palladium on carbon |
| PS | polystyrene |
| TEA | triethylamine |
| TFA | trifluoroacetic acid |
| THF | tetrahydrofuran |
| TRIS | tris (hydroxymethyl) aminomethane |
| KOAc | potassium acetate |
| K$_3$PO$_4$ | potassium phosphate |
| MgSO$_4$ | magnesium sulfate |
| NaCl | sodium chloride |
| NaH | sodium hydride |
| NaHCO$_3$ | sodium bicarbonate |
| NaOH | sodium hydroxide |
| Na$_2$SO$_3$ | sodium sulfite |
| Na$_2$SO$_4$ | sodium sulfate |
| NH$_3$ | ammonia |
| NH$_4$Cl | ammonium chloride |
| NH$_4$OH | ammonium hydroxide |
| OTf | tirflate or trifluoromethanesulfonate |
| OTs | tosylate, para-toluenesulfonate |
| PBr$_3$ | phosphorous tribromide |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3rd Edition, 1999).

Synthesis

All references cited herein are hereby incorporated in their entirety herein by reference. Methods for synthesis of a large variety of substituted pyridazines and compounds useful as starting materials for the preparation of compounds of the present invention are well known in the art. (For examples of methods useful for the preparation of pyridazine starting materials see: *Pyridazines in The Chemistry of Heterocyclic Compounds*, Castle, R. N., Ed.; John Wiley and Sons: New York, 1973, Vol. 28.; *The Pyridazines in The Chemistry of Heterocyclic Compounds*, Brown, D. J., Ed.; John Wiley and Sons: New York, 2000; Vol. 57, Supplement 1; *Comprehensive Heterocyclic Chemistry II*, Vol. 6, Boulton, A. J., Ed., Elsevier Science Inc., New York, 1996, pp. 1-93).

Representative pyridazine compounds of this invention can be prepared as shown in Scheme 1. Using a modification of the Minisci reaction described by Cowden (*Org. Lett.* 2003, 5:4497-4499), a Cbz-protected amino acid 1a and 3,6-dichloropyridazine 1b can be coupled at elevated temperature in the presence of silver nitrate, ammonium persulfate, and an acid, such as trifluoroacetic acid, in a solvent, such as water or a water/dimethylformamide mixture, to give 1c. Pyridazinone 1d can also be formed under the reaction conditions as a side product. Suzuki coupling of either 1c or 1d with a suitably substituted aryl or heteroaryl boronic acid or ester 1e in the presence of a base such as potassium phosphate, in a solvent such as dioxane, using a precatalyst system such as bis(dibenzylideneacetone)palladium(0) and tri-t-butylphosphine provides either 1f or 1g. Deprotection of the Cbz group under a hydrogen atmosphere in the presence of a palladium catalyst such as palladium on carbon in a solvent such as methanol can be used to generate either amine 1 h or 1m. Amide coupling between either 1 h or 11 and an appropriately substituted carboxylic acid 1j, employing suitable coupling reagents, such as EDCI, HOBt, and base generates either 1n or 1o (for alternative coupling reagents see: Han, S—Y; Kim, Y-A. *Tetrahedron* 2004, 60:2447). Alternately, amines 1 h or 1m can be coupled with an activated carboxylic ester 1k in the presence of a base such as Hunig's base and in a solvent such as dimethylformamide to give 1n or 1o. Further manipulation of functional groups on R$^3$ using methods known to one skilled in the art of organic synthesis will give additional compounds of the invention.

It should be noted that other suitably protected amino acids can be employed in the Minisci reaction as described in Scheme 1. For instance the Cbz protecting group in 1a can be replaced with a phthalimide protecting group. Deprotection of the phthalimide moiety can be accomplished with hydrazine in ethanol at elevated temperature.

Scheme 1

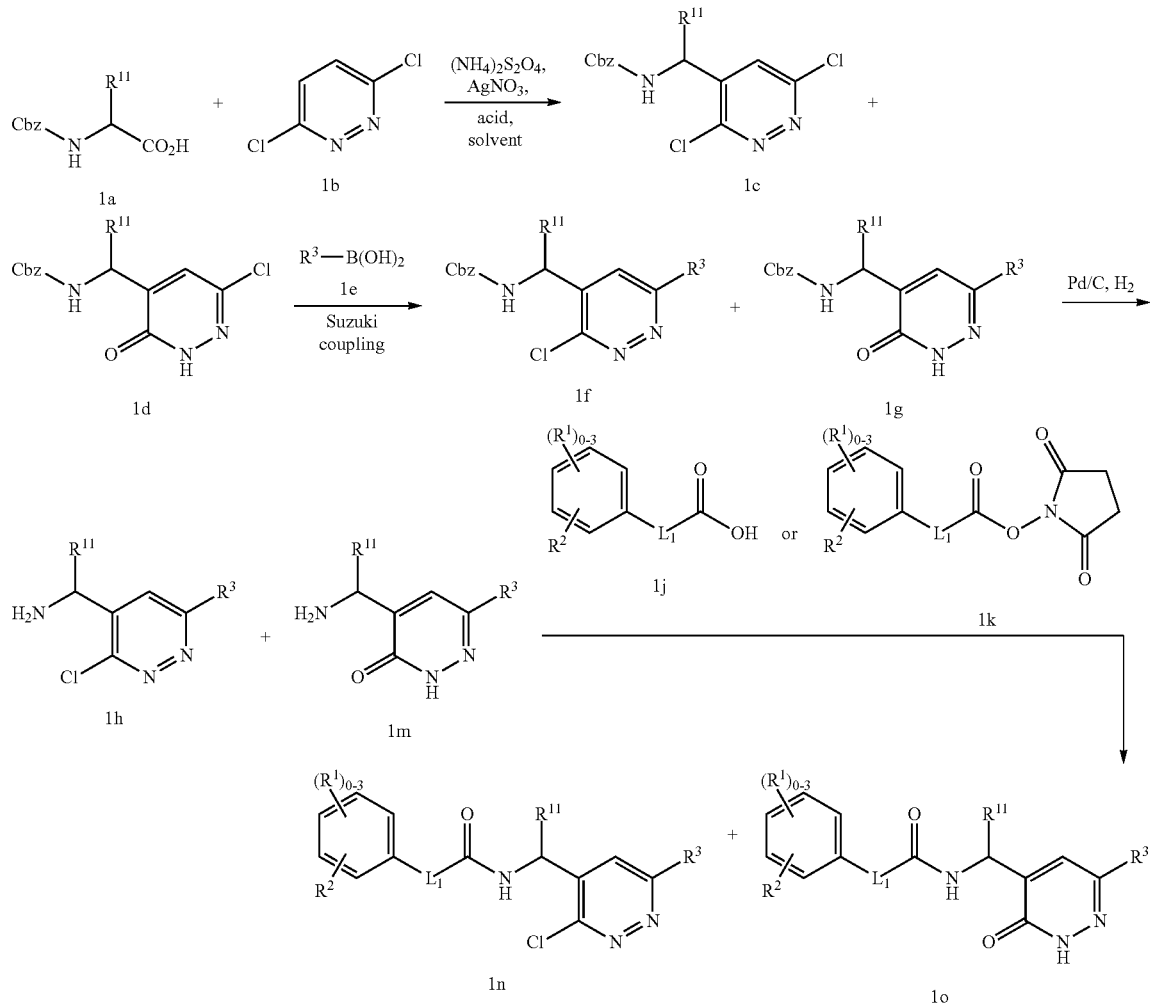

Additional pyridazine compounds of this invention can be prepared as shown in Scheme 1B. When unsymmetrical pyridazines 1p (R⁴≠Cl) are used in the Minisci reaction, regioisomers 1q and 1r are generated in varying ratios. Compounds of the formulae 1q can be converted to 1s according to Scheme 1.

Scheme 1B

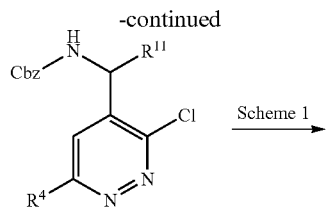

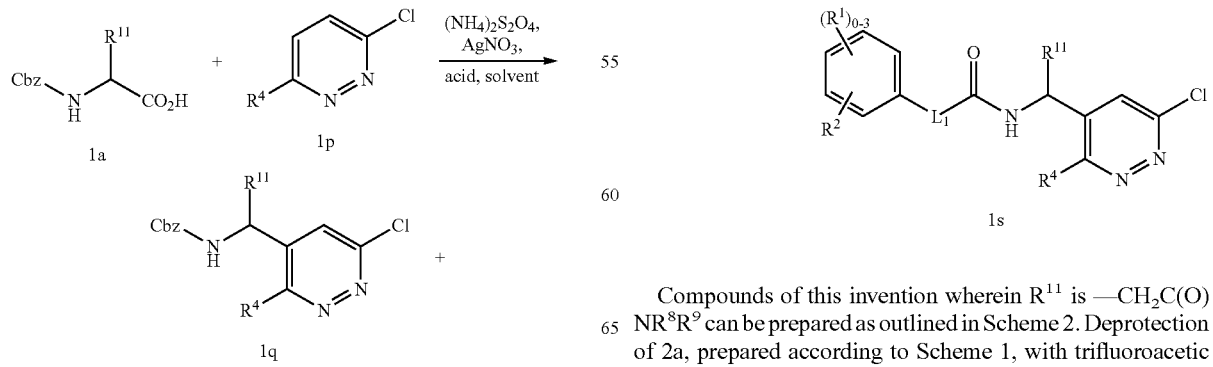

Compounds of this invention wherein $R^{11}$ is —CH$_2$C(O)NR$^8$R$^9$ can be prepared as outlined in Scheme 2. Deprotection of 2a, prepared according to Scheme 1, with trifluoroacetic acid in a solvent such as dichloromethane provides acid 2b.

Amide coupling between 2b and a suitably substituted amine 2c, employing suitable amide coupling reagents as described in Scheme 1, provides 2d.

Scheme 2

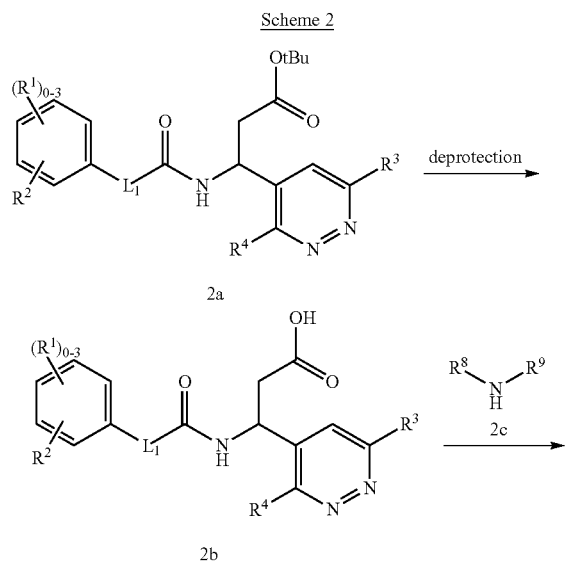

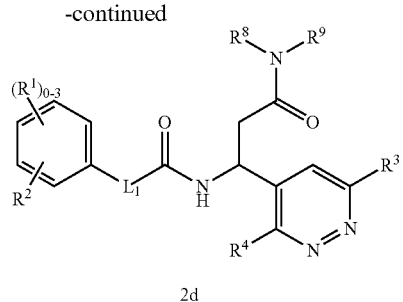

Compounds of this invention wherein $R^{11}$ is —CH$_2$NHC(O)R$^e$ or —CH$_2$NHR$^7$ can be prepared as outlined in Scheme 3. Deprotection of 3a, prepared according to Scheme 1, with trifluoroacetic acid in a solvent such as dichloromethane, provides amine 3b. Amide coupling between 3b and a suitably substituted carboxylic acid 3c, or the corresponding activated carboxylic ester, acid chloride or anhydride, employing suitable amide coupling reagents as described in Scheme 1, provides 3d. Reductive amination of 3b and a suitably substituted aldehyde 3e or ketone with a metal hydride such as sodium triacetoxyborohydride in a solvent mixture such as dichloromethane and dimethylformamide provides 3f.

Scheme 3

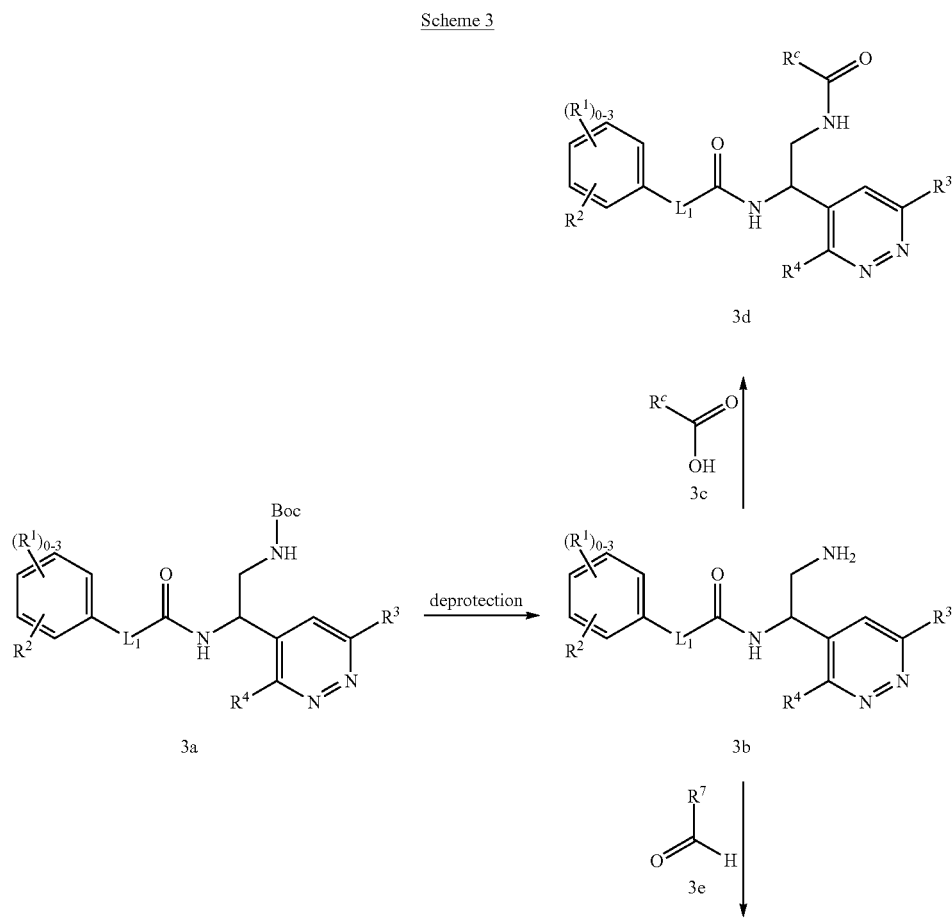

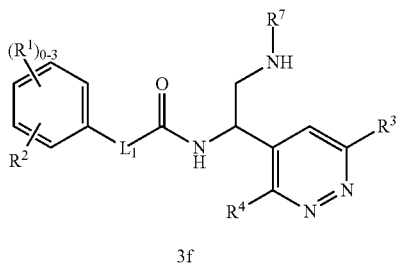

3f

Additional pyridazine compounds of this invention can be prepared as shown in Scheme 4. A suitably protected amino ester 4a can be converted to the corresponding β-ketophosphonate 4b by treatment with lithium dimethylmethylphosphonate. The pyridazinone ring system can then be prepared in a one pot, two-step sequence. Horner-Wadsworth-Emmons reaction of 4b and a suitably substituted α-ketoester 4c, which is either commercially available or prepared using a modified procedure described by Domagala (*Tetrahedron Lett.* 21:4997-5000), in the presence of base such as potassium carbonate in a solvent such as ethanol or tetrahydrofuran gives α,β-unsaturated ketone derivative which can then be condensed with a suitably substituted hydrazine derivative, to give pyridazinone 4d. Deprotection of 4d with trifluoroacetic acid provides the amine which can be coupled with 1j or 1k, according to Scheme 1, to provide 4e. Pyridazinone 4d, when $R^{12}$=H, can be treated with phosphorus oxychloride to give Boc-deprotected chloropyridazine 4f. Amide coupling between amine 4f and 1j or 1k, employing suitable amide coupling reagents as described in Scheme 1, provides 4g.

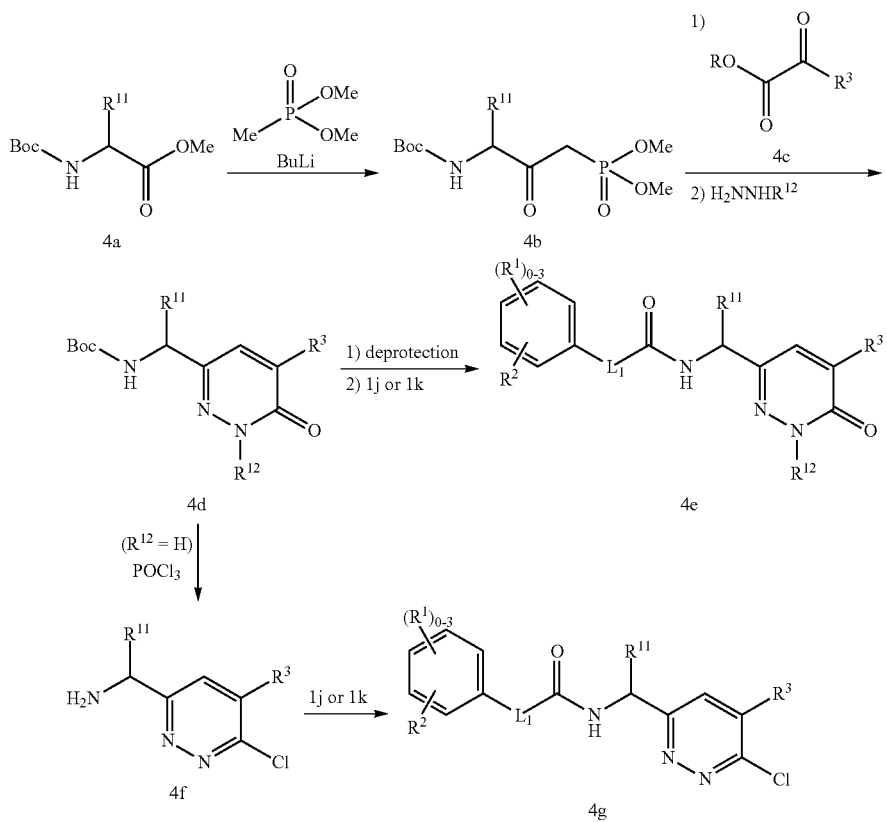

Scheme 4

A variety of $R^4$ groups can be introduced to the pyridazine ring as described in Scheme 5. Hydrogenolysis of 4f, as described in Scheme 1, provides the des-chloro derivative which can be coupled with 1j or 1k to give 5a. The chloro in 4f can be displaced with alcohols and thiols in the presence of a base, such as sodium hydride, in a solvent such as tetrahydrofuran or dimethylformamide to give, after coupling with 1j or 1k, compounds 5b. Alternately, the chloro in 4f can be displaced with amines to give, after coupling with 1j or 1k, additional compounds of 5b. Protection of 4f with $Boc_2O$, followed by Suzuki coupling with boronic acid 5c, employing reagents described in Scheme 1, gives 5d. Deprotection and amide coupling with 1j or 1k, employing suitable amide coupling reagents as described in Scheme 1, provides 5e. Further manipulation of functional groups using methods known to one skilled in the art of organic synthesis will give additional compounds of the invention.

Scheme 5

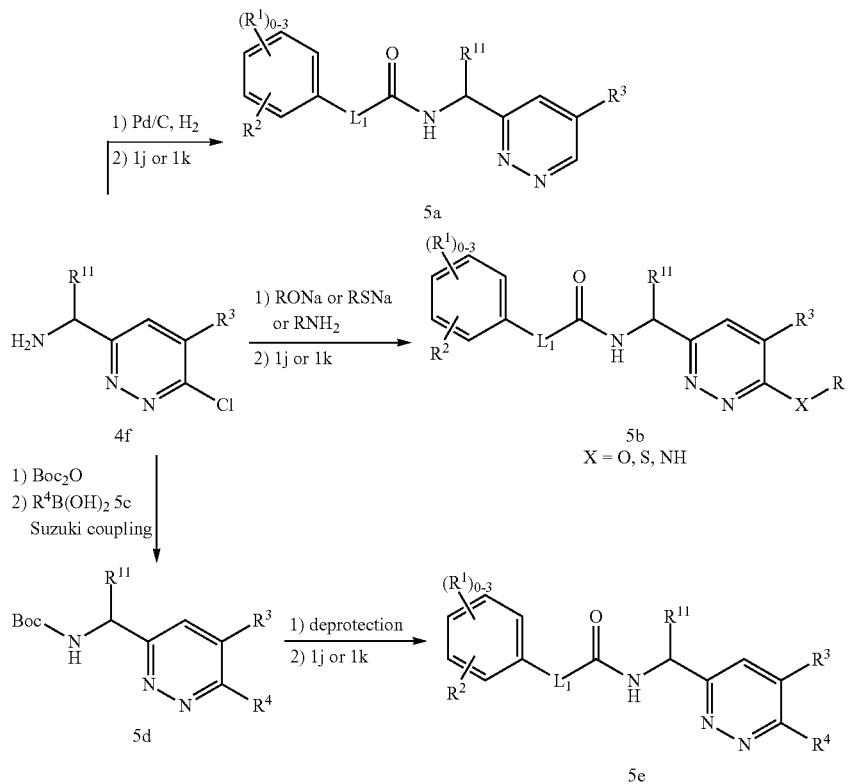

Additional $R^4$ and $R^{12}$ groups can be introduced on the pyridazine ring as described in Scheme 6. Deprotonation of pyridazinone 4d with a base such as sodium hydride in a solvent such as THF or DMF and quenching with an alkyl halide, $R^{12}$—X, gives the N-alkyl derivative and subsequent deprotection provides amine 6a. Amide coupling between amine 6a and 1j or 1k, employing suitable amide coupling reagents as described in Scheme 1, provides 6b. Pyridazinone 4d can be converted to the triflate 6c with trifluoromethane- sulfonic anhydride in the presence of a base such as pyridine and in a solvent such as dichloromethane. Palladium-catalyzed carbonylation of triflate 6c, followed by deprotection, gives amine 6d. Amide coupling between amine 6d and 1j or 1k, employing suitable amide coupling reagents as described in Scheme 1, provides 6e. Further manipulation of functional groups using methods known to one skilled in the art of organic synthesis will give additional compounds of the invention.

Scheme 6

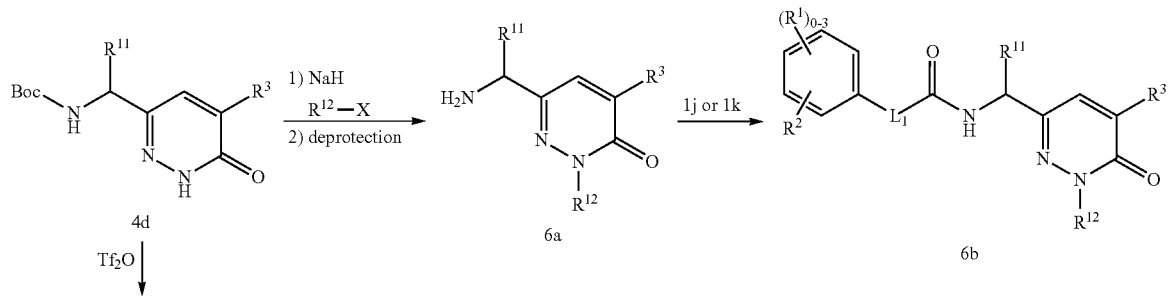

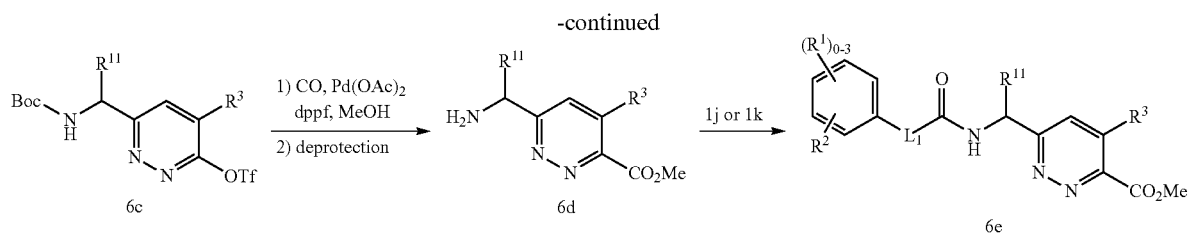
Carboxylic acid intermediates of formulae 1j, where $L_1$=—$CH_2CH_2$— and —CH=CH—, useful for preparation of amide compounds of this invention can be prepared as outlined in Scheme 7.
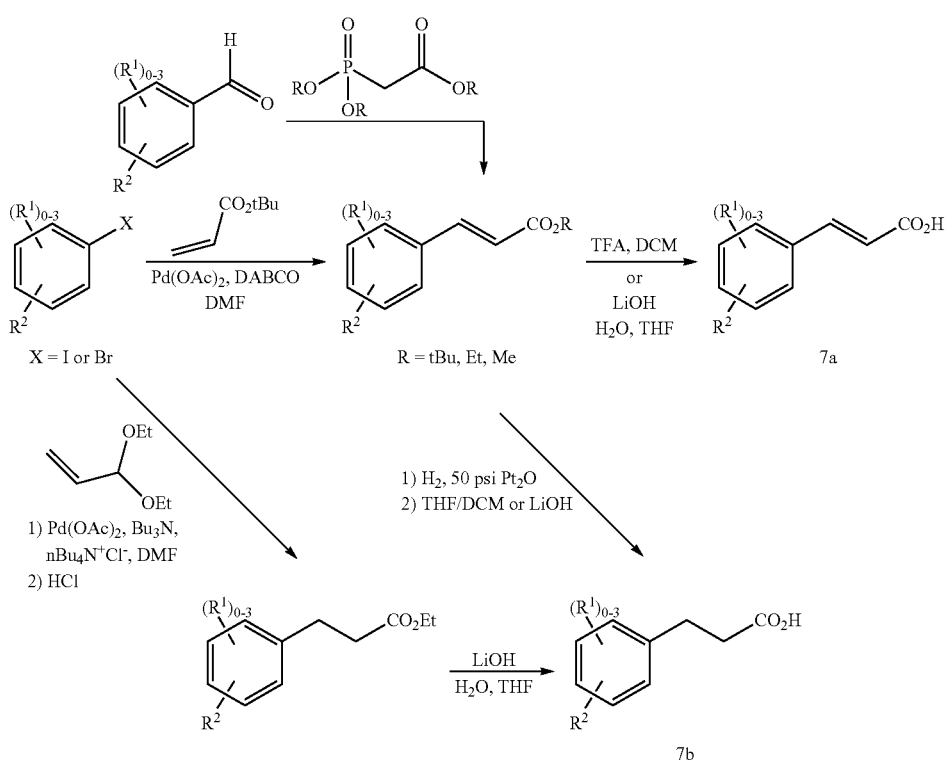
Carboxylic acid intermediates of formulae 1j, where $L_1$=—C≡C—, useful for preparation of amide compounds of this invention can be prepared as outlined in Scheme 8.

Carboxylic acid intermediates of formulae Ij, where $L_1$=—OCH$_2$— and —S(O)$_p$CH$_2$—, useful for preparation of amide compounds of this invention can be prepared as outlined in Scheme 9.

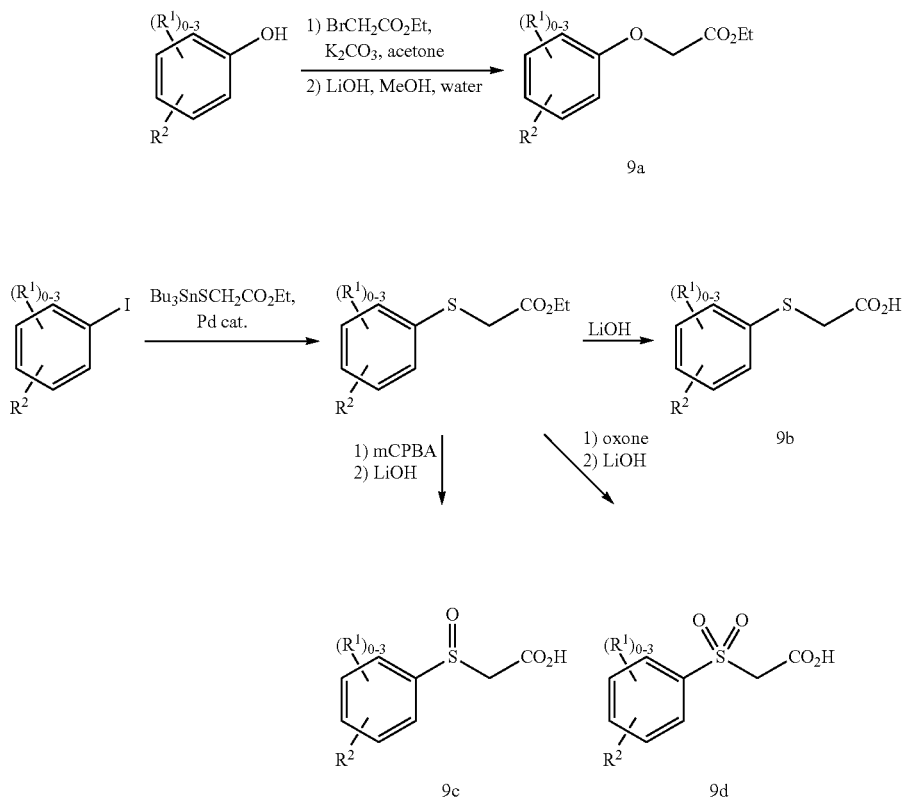

Additional starting materials useful for the preparation of the substituted phenyl acrylic or propanoic acids shown in Schemes 7, 8, and 9, wherein $R^2$ is 1-tetrazolyl, can be prepared from the corresponding anilines by treatment with sodium azide and trimethylorthoformate in acetic acid as shown in Scheme 10.

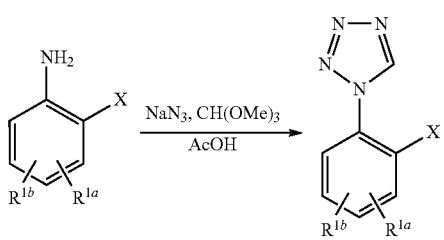

X=Br, I, OH, or CO$_2$H
R$^{1a}$=H or halogen
R$^{1b}$=halogen or alkyl

Compounds of this invention wherein $L_1$ is —CH$_2$NH— may be prepared as outlined in Scheme 11. Condensation of an appropriately functionalized amine 11a, prepared as described above, with a suitably substituted isocyanate 11b in a solvent, such as tetrahydrofuran or methylene chloride, in the presence of a base, such as triethylamine, diisopropylethylamine or potassium carbonate, provides ureas of formula 11c. Alternatively, ureas of formula 11c of this invention can be prepared by condensation of an amine 11a with carbonyldiimidazole in a solvent such as tetrahydrofuran or dimethylformamide followed by treatment in situ with a suitably substituted amine 11d. Urea linked compounds of this invention of formula 11c can also be prepared by condensation of amine intermediate 11a with p-nitrophenylchloroformate in the presence of a suitable base such as triethylamine, followed by treatment of the resulting p-nitrophenylcarbamate with an appropriately substituted amine 11d.

Scheme 11

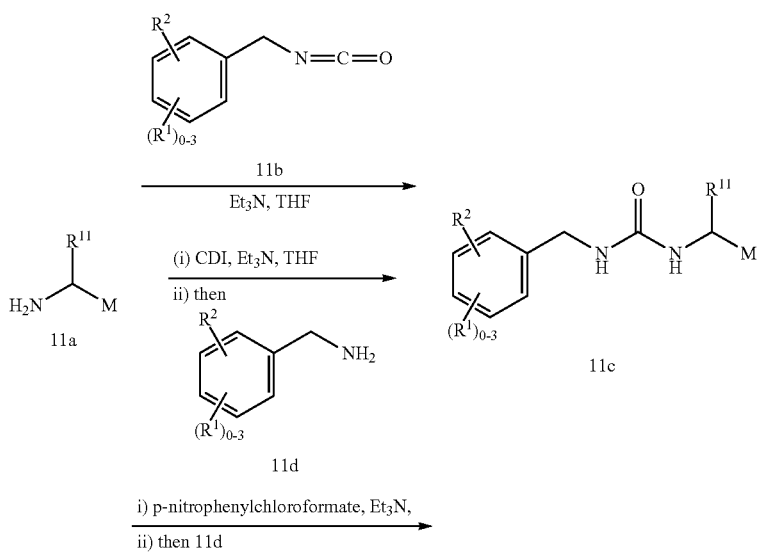

Isocyanates of formula 11b used in Scheme 11 are either commercially available or can be readily prepared from the corresponding amines 11d by treatment with phosgene or by various other methods known in the art (see for example, H. Eckert and B. Forster, *Angew. Chem. Int. Ed.* 1987, 26:894; H. Knolker and T. Braxmeier, *Synlett* 1997, 925; S. Porwanski et al. *Tetrahedron Lett.* 2004, 45:5027). Amines of formula 11d are also available commercially or can be prepared by those knowledgeable in the art from a variety of easily accessible starting materials such as nitriles, aldehydes, alcohols, halides, acids and esters by methods including, but not limited to those outlined in Scheme 12.

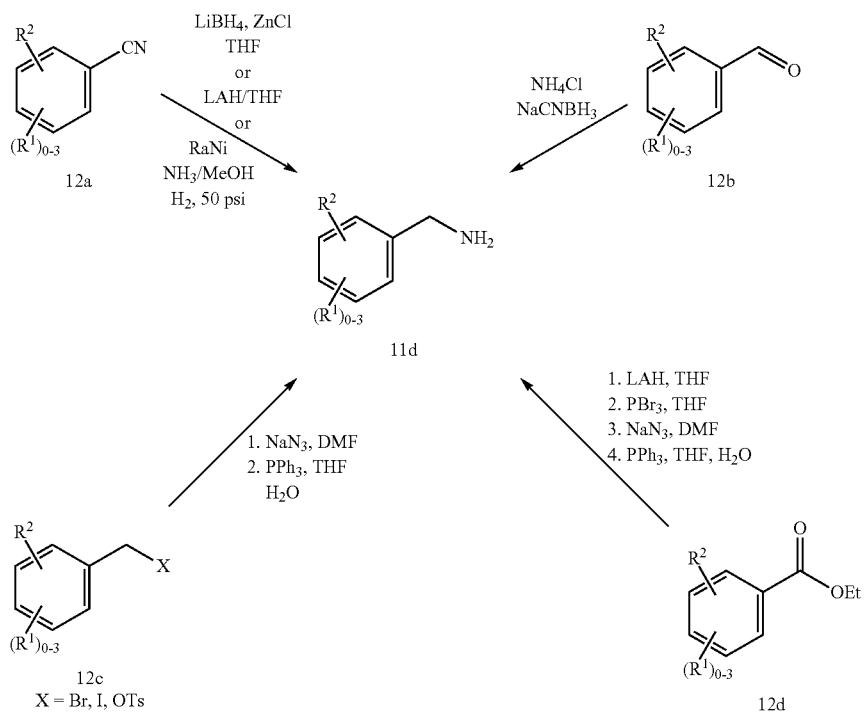

Chiral amino acids useful for the synthesis of pyridazine and pyridazinone compounds of this invention are either commercially available or can be prepared by any of a number of methods known in the art. For example, as shown in Scheme 13, didehydroamino acid derivatives of formula 13c may be reduced to provide protected (S)-amino acids of formula 13d by hydrogenation in the presence of a chiral catalyst such as (S,S)-EtDuPhosRh(I) using a modified procedure of Burk (*J. Am. Chem. Soc.* 1991, 113:8518). Didehydroamino acid derivatives of formula 13c can be prepared via several methods, such as for example, a Heck coupling between an aryl iodide, bromide, or tosylate of formula 13a and Boc didehydroalanine benzyl ester, using a modified procedure of Carlström et al. (*Synthesis* 1989, 414). Alternatively, protected didehydroaminoacids of formula 13c may be prepared by Horner-Emmons type condensation of an aldehyde of formula 13b with Boc-methyl-2-(dimethylphosphono)glycinate, using modifications of literature procedures (Wang et al., *Tetrahedron* 2002, 58:3101). Protected amino acids of formula 13d may also be prepared by alkylation of methyl 2-(diphenylmethyleneamino)acetate with an appropriately substituted benzyl bromide in the presence of a chiral cinchonidinium catalyst in a suitable solvent, such as methylene chloride, using a procedure similar to that described by O'Donnell et al. (*Tetrahedron* 1999, 55:6347), followed by mild acidic workup and reprotection of the amino functionality with a Boc group according to methods known to one skilled in the art. Substitution of heteroaryl bromides or iodides for 13a, heteroaryl, heterocyclic, or alkyl aldehydes for 13b, and heteroarylalkyl or alkylbromides for 13e in Scheme 13 would lead to additional chiral amino acids useful for the synthesis of pyridazine and pyridazinone compounds of this invention. For example, optionally substituted pyrazole carbaldehydes may be used in place of benzaldehydes 13b to give compounds of this invention wherein $R^{11}$ is an optionally substituted pyrazolylmethyl group.

In cases where suitably substituted boronic acids are not commercially available, a modification to this approach may be adopted wherein an aryl halide is subjected to a palladium mediated coupling with a diboron species such as bis(pinacolato) diboron to provide the corresponding 4,4,5,5-tetramethyl-[1,3,2]dioxaborolane intermediate using the method of Ishiyama, T. et al. (*J. Org. Chem.* 1995, 60(23):7508-7510). Alternately, this same intermediate can be prepared by reaction of the intermediate halide with the corresponding dialkoxyhydroborane as described by Murata et al. (*J. Org. Chem.* 1997, 62(19):6458-6459). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N.; Suzuki, A. *Chem. Review* 1995, 95:2457).

For example, Scheme 14 describes the synthesis of a specific example of $R^3$—B(OR)$_2$ (1e) when $R^3$ is a 4-hydroxy quinolinone moiety. Intramolecular Friedel-Craft acylation of 14a in the presence of an acid, such as polyphosphoric acid (PPA), at elevated temperature provides the 4-hydroxy quinolinone derivative 14b. Aryl bromide 14b is then subjected to a palladium mediated coupling with a diboron species such as bis(neopentyl glycolato)diboron to provide the corresponding boronate 14c using the method of Ishiyama, T. et al. (*J. Org. Chem.* 1995, 60(23):7508-7510). The boronate can be

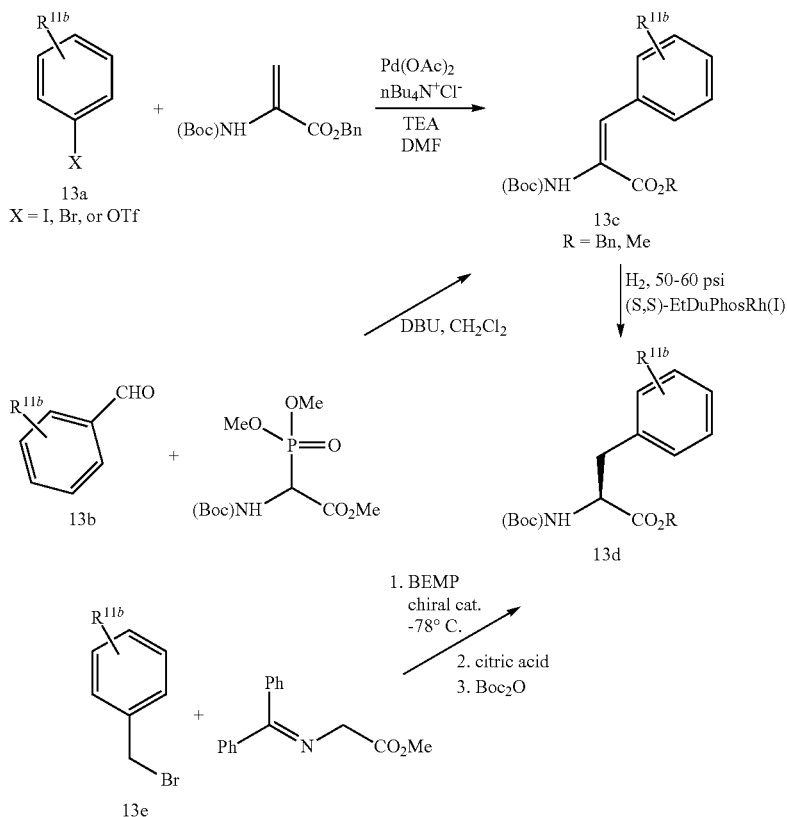

Scheme 13 used in place of boronic acids for coupling to the aryl/heteroaryl halides or triflates or the boronate can be converted to the boronic acid.

Scheme 14

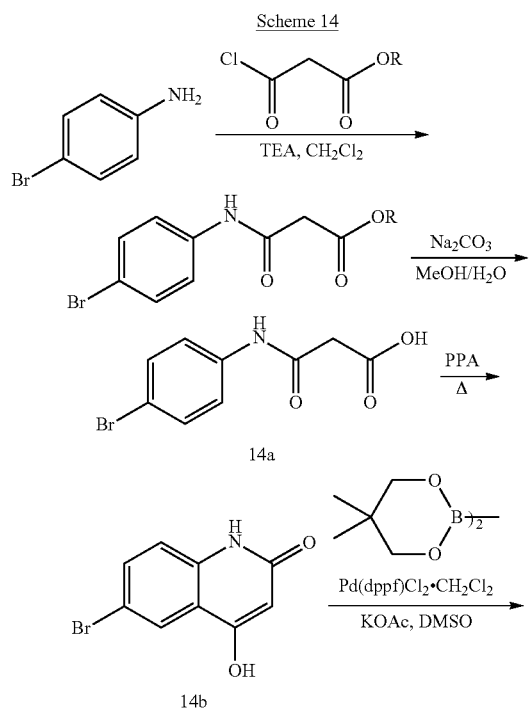

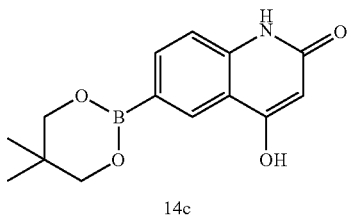

14c

It is also realized that the scope of intermediate synthesis can be further extended outside the use of Suzuki methodology since the precursor aryl halides described above are also precursors for Stille, Negishi, Hiyama, and Kumada-type cross coupling methodologies (Tsuji, J., *Transition Metal Reagents and Catalysts: Innovations in Organic Synthesis*, John Wiley & Sons, 2000; Tsuji, J., *Palladium Reagents and Catalysts: Innovations in Organic Synthesis*, John Wiley & Sons, 1996).

Representative examples of manipulation of functional groups on $R^3$ using methods known to one skilled in the art of organic synthesis are shown in Scheme 15. Heating 15a with hydrazine monohydrate in n-butanol gives the 3-aminoindazole 15b. Reacting 15a with acetohydroxamic acid and potassium tert-butoxide in DMF according to a modified procedure described by Palermo (*Tetrahedron Letters* 1996, 37(17):2885) provides 3-aminobenzisoxazole 15c. Alternately, heating 15a with formamidine acetate in DMA, according to a modified procedure described by Lam (*J. Med. Chem.* 2003, 46:4405) gives 4-amino quinazoline 15d.

Scheme 15

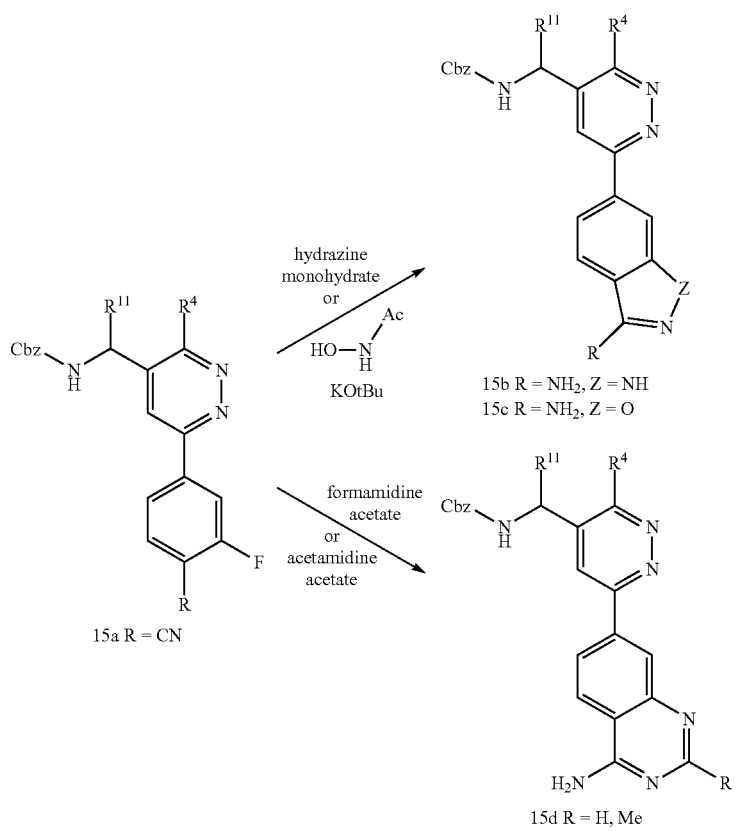

It should be recognized that additional deprotection steps and further functional group manipulations of compounds obtained via Schemes 1-15 above using methods known in the art will then provide additional compounds of this invention.

In the following experimental procedures, solution ratios express a volume relationship, unless stated otherwise. NMR chemical shifts (δ) are reported in parts per million (ppm).

Purification of intermediates and final products was carried out via either normal or reverse phase chromatography. Normal phase chromatography was carried out using prepacked $SiO_2$ cartridges eluting with gradients of hexanes and ethyl acetate unless otherwise indicated. Reverse phase preparative HPLC was carried out using C18 columns eluting with gradients of solvent A (90% water, 10% methanol, 0.1% TFA) and solvent B (10% water, 90% methanol, 0.1% TFA, UV 220 nm) or with gradients of solvent A (90% water, 10% acetonitrile, 0.1% TFA) and solvent B (10% water, 90% acetonitrile, 0.1% TFA, UV 220 nm) or with gradients of solvent A (98% water, 2% acetonitrile, 0.05% TFA) and solvent B (98% acetonitrile, 2% water, 0.05% TFA, UV 254 nm).

Unless otherwise stated, analysis of final products was carried out by reverse phase analytical HPLC using the Waters SUNFIRE™ column (3.5 μm C18, 4.6×150 mm) Gradient elution (1.0 mL/min) from 10-100% solvent B for 10 min and then 100% solvent B for 5 min was used. Solvent A is (95% water, 5% acetonitrile, 0.05% TFA) and solvent B is (5% water, 95% acetonitrile, 0.05% TFA, UV 254 nm). Method B: Agilent Zorbax (3.5 μm C18, 4.6×75 mm) eluted at 2.5 mL/min with an 8 min gradient from 100% A to 100% B (A: 10% methanol, 89.9% water, 0.1% $H_3PO_4$; B: 10% water, 89.9% methanol, 0.1% $H_3PO_4$, UV 220 nm).

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, and artificial heart valves.

Some conditions contribute to the risk of developing thrombosis. For example, alterations of the vessel wall, changes in the flow of blood, and alterations in the composition of the vascular compartment. These risk factors are collectively known as Virchow's triad. (*Hemostasis and Thrombosis, Basic Principles and Clinical Practice,* 5th Edition, p. 853, 2006, edited by Colman, R. W. et al. published by Lippincott Williams & Wilkins)

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood* 2005, 105:453-463).

An alternative way of initiation of coagulation is operative when blood is exposed to artificial surfaces (e.g., during hemodialysis, 'on-pump' cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood* 2006, 108:192-199). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., *Contact Activation Pathway,* pp. 103-122 in *Hemostasis and Thrombosis,* Lippincott Williams & Wilkins, 2001; Schmaier A.H., *Contact Activation,* pp. 105-128 in *Thrombosis and Hemorrhage,* 1998). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Medicine* 2005, 202:271-281; Kleinschmitz et al., *J. Exp. Med.* 2006, 203:513-518). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.* 2000, 10:198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.* 2001, 101:329-354.) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.* 2002, 87:774-777; Wang et al., *J. Thromb. Haemost.* 2005, 3:695-702). Also, factor XI deficiency rescues the perinatal lethal phenotype of complete protein C deficiency (Chan et al., *Amer. J. Pathology* 2001, 158:469-479). Furthermore, baboon cross-reactive, function blocking antibodies to human factor XI protect against baboon arterial—venous shunt thrombosis (Gruber et al., *Blood* 2003, 102:953-955). Evidence for an antithrombotic effect of small molecule inhibitors of factor XIa is also disclosed in published U.S. Patent Application No. US 2004/0180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience* 2001, 6:201-207; Gailani, D. et al., *Blood Coagulation and Fibrinolysis* 1997, 8:134-144.) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.* 2000, 20:2489-2493). A second study establishes a positive correlation between the extent of coronary arteriosclerosis and factor XIa in complex with alpha 1 antitrypsin (Murakami, T. et al., *Arterioscler. Thromb. Vasc. Biol.* 1995, 15:1107-1113.). In another study, Factor XI levels above the 90th percentile in patients were associated with a 2.2-fold increased risk for venous thrombosis (Meijers, J. C. M. et al., *N. Engl. J. Med.* 2000, 342:696-701.)

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., *Contact Activation Pathway*, pp. 103-122 in *Hemostasis and Thrombosis*, Lippincott Williams & Wilkins, 2001; Schmaier A. H., *Contact Activation*, pp. 105-128 in *Thrombosis and Hemorrhage,* 1998).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H., Hathaway, W. E., *Screening Tests of Hemostasis in Disorders of Thrombosis and Hemostasis: A Clinical Guide,* 2nd Edition, McGraw-Hill: New York, 2001, pp. 41-51).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Nov. 12-15, 2006, Abstract No. 6118; Schumacher, W. et al., *Journal of Thrombosis and Haemostasis* 2005, Vol. 3, Supplement 1: P1228; Schumacher, W. A. et al., *European Journal of Pharmacology*, in press). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or 'prevention' cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a 'big baby', hypertension, low HDL cholesterol, and polycystic ovary syndrome.

Risk factor for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore) 1999, 78(5):285-291; Levine M. et al., *N Engl. J. Med.* 1996, 334(11):677-681; Blom, J. W. et al., *JAMA* 2005, 293(6):715-722). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery* 2001, 88:913-930.)

A. In Vitro Assays

The effectiveness of compounds of the present invention as inhibitors of the coagulation factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (S-2288; Chromogenix or BMPM-2; AnaSpec) at a concentration of 0.001-0.0075 M.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate Spectrozyme #312 (pyroGlu-Pro-Arg-pNA; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002-0.00026 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o - v_s)/v_s = I/(K_i(1 + S/K_m)) \text{ for a competitive inhibitor with one binding site;}$$

or $$v_s/v_o = A + ((B-A)/1 + ((IC_{50}/(I)^n))); \text{ and}$$

$$K_i = IC_{50}/(1 + S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5x or IC2x, the inhibitor concentration required to increase the clotting time by 50 or 100 percent, respectively. The IC1.5x or IC2x is found by linear interpolation from relative clotting time versus inhibitor concentration plots using inhibitor concentration that spans the IC1.5x or IC2x.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using Alexin (Trinity Biotech, Ireland) following the directions in the package insert. Plasma (0.05 mL) is warmed to 37° C. for 1 minute. Alexin (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-induced Carotid Artery Thrombosis (ECAT) Model

The rabbit ECAT model, described by Wong et al. (*J. Pharmacol. Exp. Ther.* 2000, 295:212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-venous (AV) Shunt Thrombosis Model

The rabbit AV shunt model, described by Wong et al. (Wong, P. C. et al., *J. Pharmacol. Exp. Ther.* 2000, 292:351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm) The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (Delta-Graph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition, 1990.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intra-musculary, or sub-cutaneously). When administered intra-venous or intra-arterial, the dose can be given continuously or intermittent. Furthermore, formulation can be developed for intramusculary and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-111 (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include clopidogrel, ticlopidine, prasugrel, and AZD-6140, cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

EXAMPLES

The following Examples have been prepared, isolated and characterized using the methods disclosed herein. The following Examples demonstrate a partial scope of the invention and are not meant to be limiting of the scope of the invention.

Intermediate 1

(E)-2,5-Dioxopyrrolidin-1-yl 3-(5-chloro-2-(1H-tetrazol-1-yl)phenyl)acrylate

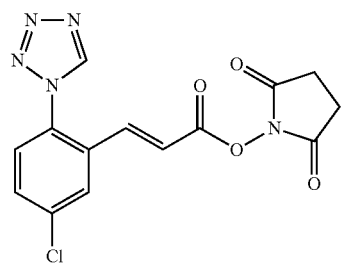

Intermediate 1A. (E)-3-(5-chloro-2-tetrazol-1-yl-phenyl)-acrylic acid methyl ester: To a cooled (0° C.) suspension of NaH (0.262 g, 6.56 mmol) in THF (27.3 mL) was added dropwise methyl 2-(dimethoxyphosphoryl)-acetate (1.150 mL, 7.10 mmol). The resulting thick, white suspension was diluted with additional THF (15 mL) to facilitate mixing. The reaction was allowed to warm to rt and stir for 45 min. Next, a solution of 5-chloro-2-tetrazol-1-yl-benzaldehyde (1.14 g, 5.46 mmol), prepared according to a modification of the procedure described by Howard (*J. Med. Chem.* 2006, 49:1346), in THF (8 mL) was added. The resulting suspension was stirred vigorously. After 30 min, the reaction was poured into cold saturated ammonium chloride and extracted with EtOAc (2×). The combined organic layers were washed with brine, dried over $Na_2SO_4$, filtered, and concentrated to give a green/blue solid weighing 1.76 g. The solid was dissolved in EtOAc and filtered through a plug of silica gel, eluting with EtOAc. The green filtrate was concentrated to give a greenish solid weighing 1.36 g. Recrystallization from EtOAc gave an off-white solid weighing 0.476 g. Additional product was obtained by concentrating the filtrate from the recrystallization, adding methanol, sonicating, and collecting the solid by filtration. A total of 0.829 g (57%) of Intermediate 1A was obtained. $^1$H NMR (500 MHz, $CDCl_3$) δ: 8.80 (s, 1H), 7.78 (d, J=2.2 Hz, 1H), 7.58 (dd, J=8.8, 2.2 Hz, 1H), 7.42 (d, J=8.2 Hz, 1H), 7.25 (d, J=16.0 Hz, 1H), 6.45 (d, J=16.0 Hz, 1H), 3.78 (s, 3H). MS m/z: 265.1 $(M+H)^+$ and 287.2 $(M+Na)^+$.

Intermediate 1B. (E)-3-(5-chloro-2-tetrazol-1-yl-phenyl)-acrylic acid: To a white suspension of Intermediate 1A (0.140 g, 0.529 mmol) in MeOH (3.0 mL) was added 1.0 M sodium hydroxide (1.587 mL, 1.587 mmol). The resulting suspension was stirred vigorously at rt for 2.5 h. The yellow suspension was neutralized with 1.0 N HCl (1.60 mL), and concentrated to give a beige solid. The solid was partitioned between 1.0 N HCl and EtOAc, and the layers were separated. The organic layer was washed with brine, dried over $Na_2SO_4$, filtered and concentrated to give 0.137 g (100%) of Intermediate 1B as a white solid. $^1$H NMR (500 MHz, DMSO-$d_6$) δ: 12.72 (s, 1H), 9.87 (s, 1H), 8.24 (d, J=2.2 Hz, 1H), 7.77 (dd, J=8.8, 2.2 Hz, 1H), 7.73 (d, J=8.2 Hz, 1H), 6.98 (d, J=16.0 Hz, 1H), 6.70 (d, J=16.0 Hz, 1H). MS m/z: 251.1 $(M+H)^+$.

Alternatively, Intermediate 1B can be prepared as follows. To a cold suspension (0-5° C.) of 4-chloro-2-iodoaniline (10.0 g, 39 5 mmol) and sodium azide (7.95 g, 122 mmol) in trimethyl orthoformate (13.08 mL, 118 mmol) was added acetic acid (150 mL). The resulting clear, slightly brown solution was stirred vigorously at 0-5° C. for 30 min and then warmed to rt. A beige precipitate formed overtime and then redissolved to give a clear brown solution. After 22 h, water (400 mL) was added and the suspension was stirred vigorously for 1 h. The solid was collected by filtration, rinsed with water, air-dried, and dried under vacuum to give 11.16 g (92%) of 1-(4-chloro-2-iodo-phenyl)-1H-tetrazole as a beige solid. MS m/z: 307.0. (M+H)$^+$. A flame-dried tube containing this intermediate (0.250 g, 0.816 mmol) and palladium acetate (0.018 g, 0.082 mmol) was purged with argon for several minutes. Next degassed acetonitrile (3.26 mL) was added followed by the addition of ethyl acrylate (0.133 mL, 1.224 mmol) and triethylamine (0.171 mL, 1.224 mmol). The vessel was sealed with a teflon-coated cap and the orange brown solution was warmed to 85° C. to give a brown suspension. After 21 h, the reaction was stopped and cooled to rt. The reaction was filtered through a 0.45 micron glass microfiber filter (GMF), rinsing with acetonitrile, and the filtrate was concentrated to give a brown residue. Purification by normal phase chromatography gave 0.098 g (43%) of (E)-3-(5-chloro-2-tetrazol-1-yl-phenyl)-acrylic acid ethyl ester as a pale yellow solid. MS m/z: 279.1 (M+H)$^+$ and 281 (M+2+H)$^+$. Saponification as described above gave Intermediate 1B.

Intermediate 1. To a solution of Intermediate 1B (5.00 g, 19.95 mmol) in THF (100 mL) and DMF (10 mL) was added 1-hydroxypyrrolidine-2,5-dione (2.53 g, 21.94 mmol) and DIC (3.42 mL, 21.94 mmol). The reaction was stirred overnight. The white precipitate that formed was collected by filtration, washed with methanol and water, and then dried under vacuum to give Intermediate 1 (7.01 g, quantitative) as a white solid. $^1$H NMR (400 MHz, acetone-d$_6$) δ ppm 2.80 (s, 4H) 6.94 (d, J=15.82 Hz, 1 H) 7.45 (d, J=15.82 Hz, 1 H) 7.69-7.76 (m, J=8.85, 2.20 Hz, 2 H) 8.23 (d, J=2.20 Hz, 1 H) 9.52 (s, 1 H). MS (ESI) m/z: 348.0 (M+H)$^+$.

Intermediate 2

(E)-3-(5-Chloro-2-(1H-imidazol-1-yl)phenyl)acrylic acid

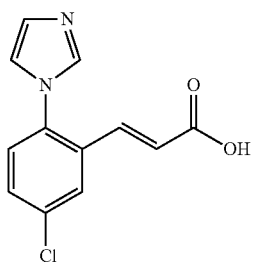

Intermediate 2A. 2-(2-bromo-5-chlorophenyl)-1,3-dioxolane: To a cooled (−60° C.) solution of 2-bromo-5-chlorobenzaldehyde (1.646 g, 7 5 mmol) and 2-chloroethanol (0.762 mL, 11.25 mmol) in DMF (8 mL) and THF (2 mL) was added dropwise over 30 min. a slurry of potassium 2-methylpropan-2-olate (1.329 g, 11.25 mmol) in DMF (8 mL). The resulting mixture was stirred between −78° C. to −30° C. for 2 h. The reaction was quenched with aqueous ammonium chloride and then extracted with EtOAc (2×30 mL). The combined organic layers were washed with brine, dried over Na$_2$SO$_4$, filtered, and concentrated. Purification by normal phase chromatography gave Intermediate 2A (0.92 g, 46.6% yield) as a waxy solid. $^1$H NMR (400 MHz, CDCl$_3$) δ ppm 4.07-4.16 (m, 4 H) 6.04 (s, 1 H) 7.20-7.62 (m, 3 H).

Intermediate 2B. 1-(4-chloro-2-(1,3-dioxolan-2-yl)phenyl)-1H-imidazole: Intermediate 2B was prepared following a modified procedure described by Cozzi (*J. Med. Chem.* 1993, 36(20):2965-2969). To a suspension of sodium hydride (60% mineral oil dispersion, 0.138 g, 3.45 mmol) in DMF (10 mL) was added 1H-imidazole (0.235 g, 3.45 mmol). After hydrogen evolution ceased, Intermediate 2A (0.91 g, 3.45 mmol) and copper powder (0.022 g, 0.345 mmol) were added to the reaction. The reaction was warmed to 150° C. After 8 h, additional copper powder (5-7 mg) was added. After another 2 h at 150° C., the reaction was cooled to rt. Chloroform and water were added and the reaction was stirred for 1 h. The mixture was filtered through CELITE®. The layers were separated and the organic layer was washed with water, brine, dried over Na$_2$SO$_4$, filtered, and concentrated. Purification by normal phase chromatography (DCM/MeOH) gave Intermediate 2B (0.42 g, 48.3% yield) as a yellow oil. MS (ESI) m/z: 251.0/253.0 (M+H)$^+$.

Intermediate 2C. 5-chloro-2-(1H-imidazol-1-yl)benzaldehyde: Intermediate 2B (210 mg, 0.838 mmol) was dissolved in 2 mL of 1N HCl. The reaction was stirred at rt for 6 h and then the reaction was stored at 0° C. overnight. The next day, additional 1N HCl (0.5 mL) was added, and the reaction was stirred at rt for another 7 h. The reaction was neutralized with aqueous NaHCO$_3$ and then extracted with EtOAc. The organic layer was washed with brine, dried over Na$_2$SO$_4$, filtered and concentrated to give Intermediate 2C (170 mg, 98% yield). MS (ESI) m/z: 207.1/209.1 (M+H)$^+$.

Intermediate 2D. (E)-tert-butyl 3-(5-chloro-2-(1H-imidazol-1-yl)phenyl)acrylate: Intermediate 2D was prepared according to the procedure described in Intermediate 1A, by replacing methyl 2-(dimethoxyphosphoryl)-acetate with tert-butyl 2-(dimethoxyphosphoryl)acetate. $^1$H NMR (400 MHz, CDCl$_3$) δ ppm 1.48 (s, 9 H) 6.34 (d, J=16.14 Hz, 1 H) 7.08 (s, 1 H) 7.24 (d, J=1.96 Hz, 2 H) 7.27-7.29 (m, 1 H) 7.44 (dd, J=8.56, 2.20 Hz, 1 H) 7.59 (s, 1 H) 7.70 (d, J=1.96 Hz, 1 H). MS (ESI) m/z: 305.3 (M+H)$^+$.

Intermediate 2. To a solution of Intermediate 2D (202 mg, 0.663 mmol) in DCM (4 mL) was added TFA (4 mL). The reaction mixture was stirred at rt. After 45 min, the reaction was concentrated to give Intermediate 2 (165 mg, 100% yield). MS (ESI) m/z: 249.0/251.0 (M+H)$^+$.

Intermediate 3

(S)-tert-Butyl 4-(diethoxyphosphoryl)-1-(4-fluorophenyl)-3-oxobutan-2-ylcarbamate

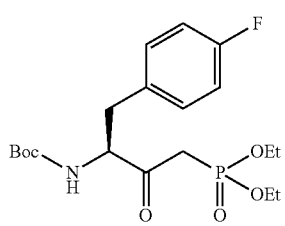

Intermediate 3A. (S)-methyl 2-(tert-butoxycarbonylamino)-3-(4-fluorophenyl)propanoate: Intermediate 3A was prepared following a modified procedure described by Zeggaf (*Tetrahedron* 1989, 45(16):5039-5050). To a cooled (0° C.) solution of (S)-2-(tert-butoxycarbonylamino)-3-(4-fluorophenyl)propanoic acid (6.00 g, 21.18 mmol) and TEA (5.90 mL, 42 4 mmol) in DCM (60 mL) was added dropwise isobutyl chloroformate (3.06 mL, 23.30 mmol). The reaction mixture was stirred at 0° C. for 10 min, and then methanol (1.714 mL, 42.4 mmol) was added. After 30 min, the reaction mixture was diluted with $CH_2Cl_2$ and then washed with 1M HCl (1×50 mL), saturated $NaHCO_3$ (1×50 mL) and brine (1×50 mL). The organic layer was dried over $Na_2SO_4$, filtered and concentrated. Purification by normal phase chromatography gave Intermediate 3A (5.50 g, 87% yield) as a clear, colorless oil. MS (ESI) m/z: 298.1 $(M+H)^+$. $^1$H NMR (400 MHz, $CDCl_3$) δ ppm 1.42 (s, 9 H) 3.01 (dd, J=14.18, 6.36 Hz, 1 H) 3.10 (dd, J=13.69, 5.87 Hz, 1 H) 3.71 (s, 3 H) 4.52-4.60 (m, 1 H) 4.99 (d, br, J=7.34 Hz, 1 H) 6.98 (t, J=8.80 Hz, 2 H) 7.06-7.12 (m, 2 H).

Intermediate 3. To a cooled (−78° C.) solution of diethyl methylphosphonate (12.16 mL, 84 mmol) in THF (60 mL) was added dropwise n-BuLi (33.6 mL, 84 mmol). After 30 min, a solution of Intermediate 3A (5.00 g, 16.82 mmol) in THF (20 mL) was added dropwise. After 1 h, the reaction was quenched with sat. $NH_4Cl$ and then allowed to warm to rt. The reaction mixture was diluted with EtOAc, washed with sat. $NH_4Cl$ (2×25 mL), sat. $NaHCO_3$ (1×25 mL) and brine (1×25 mL). The organic layer was dried over $MgSO_4$, filtered and concentrated to give Intermediate 3 (7.28 g, 100% yield) as a clear oil. $^1$H NMR (400 MHz, $CDCl_3$) δ ppm 1.29-1.36 (m, 6 H) 1.38 (s, 9 H) 2.90 (dd, J=14.43, 8.07 Hz, 1 H) 2.99-3.13 (m, 1 H) 3.19 (dd, J=14.18, 5.38 Hz, 1 H) 3.24-3.38 (m, 1 H) 4.01-4.24 (m, 4 H) 4.46-4.69 (m, 1 H) 5.47 (d, J=8.31 Hz, 1 H) 6.97 (t, J=8.56 Hz, 2 H) 7.15 (dd, J=8.80, 5.38 Hz, 2 H). MS (ESI) m/z: 418.1 $(M+H)^+$.

Intermediate 4

(E)-2,5-Dioxopyrrolidin-1-yl 3-(6-acetyl-3-chloro-2-fluorophenyl)acrylate

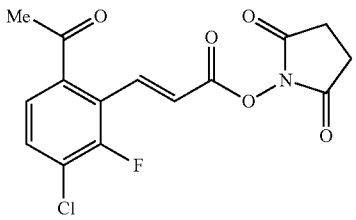

Intermediate 4A. 2-bromo-4-chloro-3-fluorobenzoic acid: To a cooled (78° C.) solution of 4-chloro-3-fluorobenzoic acid (2.0 g, 11.46 mmol) and TMEDA in THF was added dropwise sec-BuLi (90 mL, 2.2 eq, 1.4 M solution). The mixture was stirred at −78° C. for 30 min. Next, a solution of 1,2-dibromo-1,1,2,2-tetrachloroethane (14.92 g, 45.8 mmol) in THF was added. The reaction was stirred at −78° C. for awhile and then the reaction was allowed to warm to rt and stir overnight. The reaction was cooled to −78° C. and then quenched with 4N HCl in dioxane. Purification by reverse phase chromatography gave Intermediate 4A (1.20 g, 41.3% yield) as a white solid. MS (ESI) m/z: 253/255 $(M+H)^+$.

Intermediate 4B. diethyl 2-((2-bromo-4-chloro-3-fluorophenyl)(hydroxy)methylene)malonate: To a suspension of Intermediate 4A (908 mg, 3.58 mmol) in DCM (35 mL) was added thionyl chloride. The mixture was stirred at reflux for 3 h. Solvent was removed and the residue was dried in vacuo to give the acid chloride as a light brown solid. To a cooled (0° C.) suspension of sodium hydride (0.229 g, 5.73 mmol) in THF was added a solution of diethyl malonate (0.612 g, 3.82 mmol) in THF (5 mL). After 10 min, a solution of the acid chloride (1.02 g, 3.58 mmol) in THF (10 mL) was added slowly. Following the addition, the reaction was warmed to rt. After 30 min, the solvent was removed and the residue was treated with cold (0° C.) 1.2 M HCl (10 mL). The mixture was extracted with DCM (5×20 mL) and EtOAc (3×20 mL). The combined organic layers were washed with brine, dried over $Na_2SO_4$, filtered and concentrated to give Intermediate 4B (1.30 g, 86% yield) as a solid. MS (ESI) m/z: 395/397 $(M+H)^+$.

Intermediate 4C. 1-(2-bromo-4-chloro-3-fluorophenyl)ethanone: A solution of Intermediate 4B (1.3 g, 3.29 mmol) in HOAc (12 mL), $H_2O$ (8 mL) and $H_2SO_4$ (0.12 mL) was stirred at 110° C. for 4 h. Most of the solvent was removed and the residue was diluted with EtOAc (80 mL), washed with water (5×20 mL), saturated $NaHCO_3$, 1N NaOH, and brine. The solvent was removed. Purification by reverse phase chromatography gave Intermediate 4C (522 mg, 63.2% yield) as an off-white solid. MS (ESI) m/z: 253/255 $(M+H)^+$.

Intermediate 4D. (E)-tert-butyl 3-(6-acetyl-3-chloro-2-fluorophenyl)acrylate: To the mixture of Intermediate 4C (250 mg, 0.994 mmol), tert-butyl acrylate (255 mg, 1.988 mmol) and TEA (0.277 mL, 1.988 mmol) in DMF was added $Pd(OAc)_2$ (44.6 mg, 0.199 mmol). The resulting mixture was stirred at 90° C. overnight. The reaction was cooled to rt, filtered, and the filtrate was concentrated. Purification by reverse phase chromatography gave Intermediate 4D (168 mg, 56.6%) as a light yellow solid. $^1$H NMR (400 MHz, $CDCl_3$) δ ppm 7.71 (d, J=16.14 Hz, 1H), 7.40-7.48 (m, 2H), 6.38 (dd, J=16.63 Hz, J=1.96 Hz, 1H), 2.57 (s, 3H), 1.53 (s, 9H). MS (ESI) m/z: 243/245 (M+2-tert-Bu)$^+$.

Intermediate 4E. (E)-3-(6-acetyl-3-chloro-2-fluorophenyl)acrylic acid: A solution of Intermediate 4D (150 mg, 0.502 mmol) in DCM (2.0 mL) and TFA (2.0 mL) was stirred at rt. After 1.5 h, the solvent was removed to give Intermediate 4E (121 mg, 99.0% yield) as a white solid. MS (ESI) m/z: 243/245 $(M+H)^+$.

Intermediate 4. To a mixture of Intermediate 4E (468 mg, 2.083 mmol) and 1-hydroxypyrrolidine-2,5-dione (264 mg, 2.292 mmol) in THF was added DIC (0.357 mL, 2.292 mmol). The mixture was stirred overnight. The solvent was removed and the solid obtained was washed with EtOAc to give Intermediate 4 (655 mg, 98.0% yield) as a white solid. $^1$H NMR (400 MHz, $CDCl_3$) δ ppm 8.11 (d, J=16.56 Hz, 1H), 7.51-7.57 (m, 2H), 6.69 (dd, J=16.44 Hz, J=1.63 Hz, 1H), 2.89 (s, 4H), 2.61 (s, 3H). MS (ESI) m/z: 322.1 $(M+H)^+$.

Intermediate 5

(S)-tert-Butyl 4-(diethoxyphosphoryl)-1-(3-fluorophenyl)-3-oxobutan-2-ylcarbamate

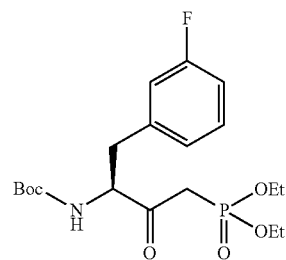

Intermediate 5 was prepared according to the procedures described in Intermediate 3, by replacing (S)-2-(tert-butoxycarbonylamino)-3-(4-fluorophenyl)propanoic acid with (S)-2-(tert-butoxycarbonylamino)-3-(3-fluorophenyl)propanoic acid. $^1$H NMR (400 MHz, $CDCl_3$) δ ppm 7.21-7.29 (m, 1H) 6.87-7.01 (m, 3 H) 4.50-4.63 (m, 1 H) 4.04-4.21 (m, 4 H)

3.25-3.37 (m, 1 H) 3.22 (dd, J=14.18, 5.40 Hz, 1 H) 3.02-3.15 (m, 1 H) 2.93 (dd, J=14.05, 8.03 Hz, 1H) 1.39 (s, 9 H) 1.30-1.37 (m, 6 H). $^{19}$F NMR (376 MHz, CDCl$_3$) δ ppm −113.29 (s, 1 F). MS (ESI) m/z: 418.0 (M+H).

Intermediate 6

(S)-tert-Butyl 4-(dimethoxyphosphoryl)-1-(1-ethyl-1H-pyrazol-3-yl)-3-oxobutan-2-ylcarbamate

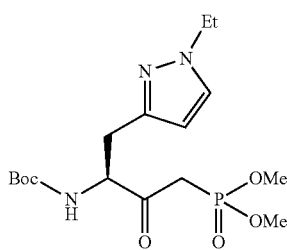

Intermediate 6A. methyl 2-(tert-butoxycarbonylamino)-3-(1-ethyl-1H-pyrazol-3-yl)acrylate: To a solution of Boc-methyl-2-(dimethylphosphono)glycinate (10.7 g, 36.0 mmol) in DCM (60 mL) was added DBU (4.97 mL, 33.0 mmol). The reaction mixture was stirred under argon at rt for 10 min. A solution of 1-ethyl-1H-pyrazole-3-carbaldehyde (3.72 g, 30.0 mmol) in DCM (20 mL) was added dropwise. The reaction was stirred at rt for 24 h. Most of the solvent was removed. The reaction mixture was diluted with EtOAc, washed with citric acid solution (2×25 mL) and brine (1×25 mL). The organic phase was dried over Na$_2$SO$_4$, filtered and concentrated. Purification by normal phase chromatography gave 6A (8.11 g, 27.5 mmol, 92% yield) as a clear colorless oil. LC-MS (ESI) m/z: 296.1 (M+H)$^+$. $^1$H NMR (400 MHz, CHLOROFORM-d) δ ppm 8.67 (br. s., 1 H) 7.36 (d, J=2.26 Hz, 1 H) 6.52 (s, 1 H) 6.28 (d, J=2.51 Hz, 1 H) 4.19 (q, J=7.45 Hz, 2 H) 3.84 (s, 3 H) 1.51 (t, J=7.28 Hz, 3 H) 1.48 (s, 9 H).

Intermediate 6B. (S)-methyl 2-(tert-butoxycarbonylamino)-3-(1-ethyl-1H-pyrazol-3-yl)propanoate: To a solution of methyl 2-(tert-butoxycarbonylamino)-3-(1-ethyl-1H-pyrazol-3-yl)acrylate (8.00 g, 27.1 mmol) in MeOH (100 mL) were added (+)-1,2-bis((2S,5S)-2,5-diethylphospholano)benzene(cyclooctadiene)rhodium (I) trifluoromethanesulfonate (0.196 g, 0.271 mmol). The reaction mixture was stirred under 50 psi hydrogen for 24 hrs. Solvent was removed under reduced pressure and the residue was filtered through a pad of silica gel eluting with EtOAc:hexanes (8:2 v:v) to give 6B (8.06 g, 27.1 mmol, 100% yield) as a clear colorless oil. $^1$H NMR (400 MHz, CDCl$_3$) δ ppm 7.28 (d, J=2.01 Hz, 1 H) 6.00 (d, J=2.26 Hz, 1 H) 5.45 (d, J=8.28 Hz, 1 H) 4.50-4.66 (m, 1 H) 4.11 (q, J=7.19 Hz, 2 H) 3.71 (s, 3 H) 3.11-3.21 (m, J=14.81, 5.77 Hz, 1 H) 3.03-3.11 (m, J=14.56, 5.02 Hz, 1 H) 1.45 (t, J=7.28 Hz, 3 H) 1.43 (s, 9 H). LC-MS (ESI) m/z: 298.1 (M+H)$^+$.

Intermediate 6. Intermediate 6B was converted to the title compound by following the procedure described in Intermediate 3, by replacing diethyl methylphosphonate with dimethylmethylphosphonate. MS (ESI) m/z: 390.0 (M+H)$^+$.

Intermediate 7

(E)-3-(3-Chloro-2-fluoro-6-(1H-tetrazol-1-yl)phenyl)acrylic acid

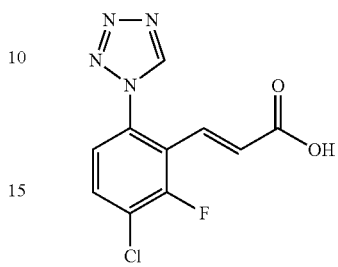

Intermediate 7A. N-(2-bromo-4-chloro-3-fluorophenyl)-2,2,2-trifluoroacetamide: 2,2,2-trifluoroacetic anhydride (5.77 mL, 41.2 mmol) was added dropwise to a stirring mixture of sodium carbonate (6.19 g, 58 4 mmol) and 4-chloro-3-fluoroaniline (5.0 g, 34.3 mmol) in Et$_2$O (50 mL) at −10° C. After 1 h, hexane (30 mL) was added and the reaction mixture filtered. The filtrate was washed with ice-water, 10% aq. NaHCO$_3$ solution, and then brine. The organic phase was treated with activated charcoal, dried over sodium sulfate, filtered through a plug of CELITE®, and concentrated to give N-(4-chloro-3-fluorophenyl)-2,2,2-trifluoroacetamide as a white solid. A solution of tert-butyllithium (1.7M in pentane) (40.4 mL, 68 7 mmol) was added dropwise to N,N,N',N'-tetramethylethylenediamine (10.37 mL, 68.7 mmol) in THF (60 mL) at −78° C. After 1 h, N-(4-chloro-3-fluorophenyl)-2,2,2-trifluoroacetamide in THF (40 mL) was added dropwise to this yellow solution. After stirring for an additional hour, bromine (2.12 mL, 41.2 mmol) was slowly added and the complete mixture stirred for 1.5 h before quenching and neutralized with 1.0N HCl solution (final pH ~6-7). The mixture was brought to rt, treated with brine (100 mL), and THF evaporated. The aqueous layer was extracted with EtOAc (3×). The combined organic extracts were washed with water, saturated NaHCO$_3$ solution, brine, dried over sodium sulfate, filtered and dry-loaded onto silica gel. Purification by flash chromatography (120 g column; (hexane/EtOAc solvent system) gave Intermediate 7A (3.95 g, 36%) as a slowly solidifying tan solid. $^1$H NMR (400 MHz, CDCl$_3$) δ: 8.42 (1 H, br. s.), 8.13 (1 H, dd, J=9.09, 1.77 Hz), 7.43-7.49 (1 H, m) ppm.

Intermediate 7B. (E)-tert-butyl 3-(3-chloro-2-fluoro-6-(2,2,2-trifluoro-acetamido)phenyl)acrylate: Intermediate 7A (1.0 g, 3.12 mmol), tert-butyl acrylate (3.00 mL, 18.72 mmol), DABCO (0.35 g, 3.12 mmol), K$_2$CO$_3$ (1.08 g, 7.80 mmol) were added DMF (10 mL) and degassed 10 min. Palladium (II) acetate (0.035 g, 0.16 mmol) was added and the complete mixture was heated at 110° C. overnight. After cooling to rt, the reaction mixture was filtered through a plug of CELITE® and the filter-cake was rinsed with EtOAc (3×30 mL). The combined filtrate was washed with water, brine, dried over sodium sulfate, filtered, and concentrated onto silica gel. Purification by flash chromatography (40 gram column; hexane/EtOAc solvent system) gave Intermediate 7B (0.84 g, 73.0%) as an off-white solid. $^1$H NMR (400 MHz, CDCl$_3$) δ 8.15 (1 H, br. s.), 7.69 (1 H, dd, J=8.84, 1.52 Hz), 7.43-7.49 (2 H, m), 6.48-6.55 (1 H, m), 1.53 (9 H, s) ppm.

Intermediate 7. (E)-3-(3-chloro-2-fluoro-6-(1H-tetrazol-1-yl)phenyl)acrylic acid: To a solution of Intermediate 7B (0.83 g, 2.25 mmol) in ethanol was added 1.0N NaOH solution (11.29 mL, 11.29 mmol). The resulted mixture was stirred at 80° C. for 1 h before cooling to rt and the organics were concentrated. Both the trifluoroacetamide and t-butyl ester groups were removed under these conditions. The remaining aqueous phase was diluted with water and cooled to 0° C., and neutralized (~6-7) with 1.0M HCl solution. The mixture was extracted with EtOAc (3×50 mL). The combined organic extract was washed with brine, dried over sodium sulfate, filtered, and concentrated to give a yellow solid. AcOH (10 mL) was added to a stirring suspension of (E)-3-(6-amino-3-chloro-2-fluorophenyl)acrylic acid, trimethyl orthoformate (0.73 mL, 6.68 mmol), and sodium azide (0.434 g, 6.68 mmol) at 0° C. The reaction was heated at 75° C. for 4 h. After cooling to rt, the reaction mixture was diluted with water, and extracted with EtOAc (3×75 mL). The combined organic extract was washed with brine, dried over sodium sulfate, filtered, and concentrated. The crude material was purified by reverse phase preparative HPLC (ACN/H$_2$O/TFA). The product fractions were concentrated on a Speedvac to give Intermediate 7 (0.258 g, 43%) as an amber solid. LCMS: m/z 269.1 [M+H]$^+$.

Example 1

(±)-(E)-Methyl 4-(6-chloro-5-(1-(3-(5-chloro-2-(1H-tetrazol-1-yl)phenyl)acrylamido)-2-phenylethyl)pyridazin-3-yl)phenylcarbamate

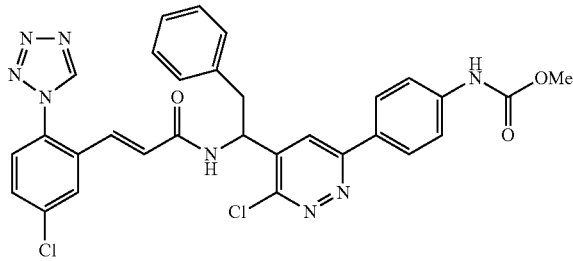

1A. 2-(1-(3,6-dichloropyridazin-4-yl)-2-phenylethyl)isoindoline-1,3-dione: To a mixture of 3,6-dichloropyridazine (5 g, 33 6 mmol), (S)-2-(1,3-dioxoisoindolin-2-yl)-3-phenylpropanoic acid (16.85 g, 57.1 mmol), and silver nitrate (0.570 g, 3.36 mmol) in water (50 mL) was added TFA (0.517 mL, 6.71 mmol). The reaction mixture was warmed up to 70° C. and then a solution of ammonium persulfate (13.79 g, 60.4 mmol) in water (20 mL) was added dropwise over 20 min. The reaction was stirred at 70° C. for an additional 30 min. EtOAc (50 mL) was added and the reaction was cooled to rt Ammonium hydroxide was added to adjust the pH to ~9. The layers were separated and the organic layer was washed with IM HCl (1×25 mL), saturated NaCl (1×25 mL), dried over Na$_2$SO$_4$, filtered and concentrated. Purification by normal phase chromatography gave 1A (3.03 g, 22.7% yield) as a tan solid. MS (ESI) m/z: 398.1/400.1 (M+H)$^+$.

1B. methyl 4-(6-chloro-5-(1-(1,3-dioxoisoindolin-2-yl)-2-phenylethyl)pyridazin-3-yl)phenylcarbamate: To a solution of 1A (100 mg, 0.251 mmol) in dioxane (5 mL) was added 4-(methoxycarbonylamino)phenylboronic acid (50 mg, 0.251 mmol) and potassium phosphate (160 mg, 0.753 mmol). The mixture was purged with nitrogen. Next, tri-tert-butylphosphine (10% in hexane, 200 mg, 0.099 mmol) and bis(dibenzylideneacetone)palladium (0) (14.44 mg, 0.025 mmol) were added. The reaction was stirred at 90° C. for 2 h and then cooled to rt. The solvent was evaporated. Purification by normal phase chromatography gave 1B (52.3 mg, 40.6% yield) as a white solid. MS (ESI) m/z: 513.1 (M+H)$^+$.

1C. methyl 4-(5-(1-amino-2-phenylethyl)-6-chloropyridazin-3-yl)phenylcarbamate, TFA salt: To a solution of 1B (630 mg, 1.228 mmol) in ethanol (25 mL) was added hydrazine (0.3 mL, 9.56 mmol). The reaction was stirred at 80° C. for 4 h. The solid that formed was removed by filtration and the filtrate was concentrated. Purification by reverse phase chromatography gave 1C (444 mg, 72.8% yield) as a light yellow solid. MS (ESI) m/z: 383.2 (M+H)$^+$. The enantiomers were separated by chiral hplc [Chiralcel OD; 80% (1:1) EtOH:MeOH/heptane with 0.1% DEA]: enantiomer A (RT=5.54 min, >98% ee) and enantiomer B (RT=7.46 min, >98% ee).

1D. Example 1: To a solution of 1C (42 mg, 0.110 mmol) in DMF (2 mL) was added Intermediate 1 (38.1 mg, 0.110 mmol) and DIEA (0.038 mL, 0.219 mmol). The reaction was stirred at rt for 24 h. Purification by reverse phase chromatography gave Example 1 (46 mg, 68.1% yield) as a white solid. $^1$H NMR (400 MHz, DMF-d$_7$) δ ppm 3.19 (dd, J=14.18, 9.29 Hz, 1 H) 3.31 (dd, J=13.69, 4.89 Hz, 1 H) 3.76 (s, 3 H) 5.53-5.61 (m, 1 H) 6.91 (d, J=15.65 Hz, 1 H) 7.02 (d, J=15.65 Hz, 1 H) 7.25 (t, J=7.09 Hz, 1 H) 7.30-7.40 (m, J=14.55, 7.21, 7.09 Hz, 4 H) 7.77-7.85 (m, 4 H) 8.15 (d, J=8.31 Hz, 2 H) 8.36 (s, 1 H) 9.17 (d, J=7.83 Hz, 1 H) 9.86 (s, 1 H) 9.97 (s, 1H). MS (ESI) m/z: 615.2/617.2 (M+H)$^+$. Analytical HPLC: RT=12.35 min.

Example 2

(E)-Methyl 4-(6-chloro-5-(1-(3-(5-chloro-2-(1H-tetrazol-1-yl)phenyl)acrylamido)-2-phenylethyl)pyridazin-3-yl)phenylcarbamate (prepared from Enantiomer A of 1C)

The title compound was prepared following the procedure described in 1D, by replacing 1C (racemic) with 1C (enantiomer A). $^1$H NMR (400 MHz, DMF-d$_7$) δ ppm 3.16-3.24 (m, J=14.18, 9.78 Hz, 1H) 3.30 (dd, J=14.18, 4.89 Hz, 1H) 3.76 (s, 3H) 5.53-5.60 (m, 1H) 6.92 (d, J=15.65 Hz, 1H) 7.02 (d, J=15.65 Hz, 1H) 7.25 (t, J=7.09 Hz, 1H) 7.30-7.40 (m, 4H) 7.77-7.85 (m, 4H) 8.15 (d, J=8.31 Hz, 2H) 8.37 (s, 1H) 9.20 (d, J=7.34 Hz, 1H) 9.86 (s, 1H) 9.96 (s, 1H). MS (ESI) m/z: 615.2 (M+H)$^+$. Analytical HPLC: RT=9.12 min.

Example 3

(E)-Methyl 4-(6-chloro-5-(1-(3-(5-chloro-2-(1H-tetrazol-1-yl)phenyl)acrylamido)-2-phenylethyl)pyridazin-3-yl)phenylcarbamate (prepared from Enantiomer B of 1C)

The title compound was prepared following the procedure described in 1D, by replacing 1C (racemic) with 1C (enantiomer B). $^1$H NMR (400 MHz, DMF-D$_7$) δ ppm 3.19 (dd, J=14.18, 9.29 Hz, 1 H) 3.30 (dd, J=14.18, 5.38 Hz, 1 H) 3.76 (s, 3 H) 5.53-5.60 (m, 1 H) 6.92 (d, J=15.65 Hz, 1 H) 7.02 (d, J=15.65 Hz, 1 H) 7.25 (t, J=7.09 Hz, 1 H) 7.35 (dt, J=14.67, 7.34 Hz, 4H) 7.77-7.83 (m, 4 H) 8.15 (d, J=8.80 Hz, 2 H) 8.36

(s, 1 H) 9.19 (d, J=7.82 Hz, 1 H) 9.86 (s, 1 H) 9.96 (s, 1 H). MS (ESI) m/z: 615.3 (M+H)⁺. Analytical HPLC: RT=9.12 min.

Example 4

(±)-(E)-Methyl 4-(5-(1-(3-(5-chloro-2-(1H-tetrazol-1-yl)phenyl)acrylamido)-2-phenylethyl)-6-oxo-1,6-dihydropyridazin-3-yl)phenylcarbamate

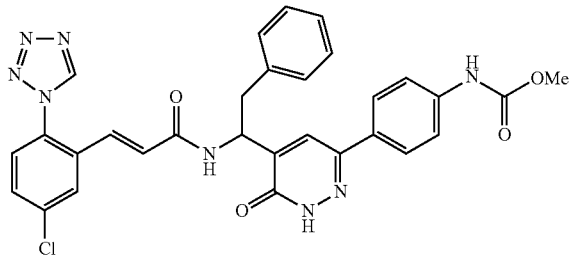

4A. benzyl 1-(3,6-dichloropyridazin-4-yl)-2-phenylethylcarbamate and 4B. benzyl 1-(6-chloro-3-oxo-2,3-dihydropyridazin-4-yl)-2-phenylethylcarbamate: The procedure for Example 1A was followed by replacing (S)-2-(1,3-dioxoisoindolin-2-yl)-3-phenylpropanoic acid with 2-(benzyloxycarbonylamino)-3-phenylpropanoic acid to give 4A (2.5% yield) as a brown solid [MS (ESI): m/z: 402.1 (M+H)⁺] and 4B (4.3% yield) as an off-white solid [MS (ESI): m/z: 384.1 (M+H)⁺].

4C. {4-[5-(1-benzyloxycarbonylamino-2-phenyl-ethyl)-6-oxo-1,6-dihydro-pyridazin-3-yl]-phenyl}-carbamic acid methyl ester: The procedure for Example 1B was followed by replacing 1A with 4B to give 4C (20% yield). MS (ESI) m/z: 499.1 (M+H)⁺.

4D. methyl 4-(5-(1-amino-2-phenylethyl)-6-oxo-1,6-dihydropyridazin-3-yl)phenylcarbamate, TFA salt: To a solution of 4C (20 mg, 0.040 mmol) in MeOH (10 mL) was added a catalytic amount of 5% Pd/C. The reaction mixture was stirred under a hydrogen balloon for 12 h. The reaction was filtered to remove the catalyst and the filtrate was concentrated to give 4D (14.6 mg, 100%) as a solid. MS (ESI): m/z: 365.2 (M+H)⁺.

4E. Example 4 was prepared according to the procedure described in 1D by replacing 1C with 4D. MS (ESI) m/z: 597.2 (M+H)⁺. Analytical HPLC: RT=8.47 min.

Example 5

(±)-(E)-Methyl 4-(5-(1-(3-(5-chloro-2-(1H-tetrazol-1-yl)phenyl)acrylamido)-2-phenylethyl)pyridazin-3-yl)phenylcarbamate

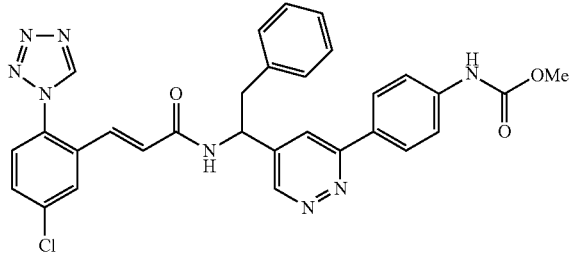

5A. {4-[5-(1-benzyloxycarbonylamino-2-phenyl-ethyl)-6-chloro-pyridazin-3-yl]-phenyl}-carbamic acid methyl ester: The procedure was followed as described in Example 1B, by replacing 1A with 4A. MS (ESI) m/z: 517.2 (M+H)⁺.

5B. methyl 4-(5-(1-amino-2-phenylethyl)pyridazin-3-yl)phenylcarbamate, TFA salt and 1C. Methyl 4-(5-(1-amino-2-phenylethyl)-6-chloropyridazin-3-yl)phenylcarbamate, TFA salt: The procedure was followed as described in Example 4D, replacing 4C with 5A, to give 1C (35% yield) [MS (ESI) m/z: 383.2 (M+H)⁺] and 5B (57% yield) [MS (ESI) m/z: 349.2 (M+H)⁺].

5D. Example 5 was prepared following the procedure described in 1D, replacing 1C with 5B. ¹H NMR (500 MHz, CD₃OD) δ ppm 3.22 (ddd, J=29.14, 13.75, 7.70 Hz, 2 H) 3.77 (s, 3 H) 5.26-5.39 (m, 1 H) 6.70 (d, J=15.40 Hz, 1 H) 7.08 (d, J=15.40 Hz, 1 H) 7.18-7.25 (m, 3 H) 7.25-7.31 (m, 2 H) 7.56 (d, J=8.25 Hz, 1H) 7.62-7.67 (m, 3 H) 7.94 (d, J=8.80 Hz, 2 H) 7.97 (d, J=2.20 Hz, 1 H) 8.01 (d, J=1.65 Hz, 1 H) 9.01 (d, br, J=7.15 Hz, 1 H) 9.05 (d, J=2.20 Hz, 1 H) 9.49 (s, 1 H) 9.57 (s, br, 1 H). MS (ESI) m/z: 581.2/583.2 (M+H)⁺. Analytical HPLC: RT=10.95 min.

Example 6

(E)-Methyl 4-(5-(1-(3-(5-chloro-2-(1H-tetrazol-1-yl)phenyl)acrylamido)-2-phenylethyl)pyridazin-3-yl)phenylcarbamate (Enantiomer A of Example 5)

Chiral separation of Example 5 [Chiralcel OD, 80% (1:1) EtOH:MeOH/heptane) gave Example 6 as enantiomer A. ¹H NMR (400 MHz, CD₃OD) δ ppm 3.17-3.26 (m, 2 H) 3.77 (s, 3 H) 5.32-5.38 (m, 1 H) 6.70 (d, J=15.65 Hz, 1 H) 7.08 (d, J=15.65 Hz, 1 H) 7.20-7.31 (m, 5 H) 7.56 (d, J=8.80 Hz, 1H) 7.65 (d, J=8.81 Hz, 1 H) 7.66 (d, J=8.80 Hz, 2 H) 7.94 (d, J=8.80 Hz, 2 H) 7.97 (d, J=2.45 Hz, 1 H) 8.05 (s, 1 H) 9.00 (d, br, J=7.34 Hz, 1 H) 9.07 (d, J=1.47 Hz, 1 H) 9.48 (s, 1 H) 9.58 (s, br, 1 H). MS (ESI) m/z: 581.3/583.3 (M+H)⁺. Analytical HPLC: RT=7.55 min. Chiral Analytical HPLC: chiralcel OD [(80% (1:1) EtOH:MeOH/heptane)]: RT=5.73 min, 98.5% ee.

Example 7

(E)-Methyl 4-(5-(1-(3-(5-chloro-2-(1H-tetrazol-1-yl)phenyl)acrylamido)-2-phenylethyl)pyridazin-3-yl)phenylcarbamate (Enantiomer B of Example 5)

Chiral separation of Example 5 [Chiralcel OD, 80% (1:1) EtOH-MeOH/heptane) gave Example 7 as enantiomer B. ¹H NMR (400 MHz, CD₃OD) δ ppm 3.17-3.26 (m, 2 H) 3.77 (s, 3 H) 5.31-5.39 (m, 1 H) 6.70 (d, J=15.65 Hz, 1 H) 7.08 (d, J=15.65 Hz, 1 H) 7.20-7.31 (m, 5 H) 7.54-7.58 (m, 1 H) 7.62-7.68 (m, 3H) 7.94 (d, J=8.80 Hz, 2 H) 7.97 (d, J=1.96 Hz, 1 H) 8.07 (s, 1 H) 9.08 (d, J=1.47 Hz, 1 H) 9.48 (s, 1 H). MS (ESI) m/z: 581.3/583.2 (M+H)⁺. Analytical HPLC: RT=7.55 min. Chiral Analytical HPLC: chiralcel OD [(80% (1:1) EtOH:MeOH/heptane)]: RT=6.88 min, 98.0% ee.

Example 8

(±)-(E)-Methyl 4-(6-chloro-5-(1-(3-(5-chloro-2-(1H-imidazol-1-yl)phenyl)acrylamido)-2-phenylethyl)pyridazin-3-yl)phenylcarbamate, TFA salt

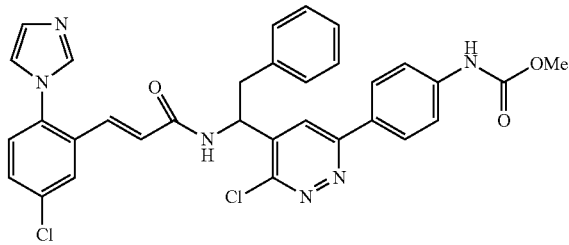

The title compound was prepared following the procedure described in 1D, by replacing Intermediate 1 with Intermediate 2. $^1$H NMR (400 MHz, CD$_3$OD) δ ppm 3.12 (dd, J=13.74, 8.79 Hz, 1 H) 3.25-3.29 (m, 1 H) 3.76 (s, 3 H) 5.46-5.59 (m, 1 H) 6.82 (d, J=15.94 Hz, 1 H) 6.99-7.09 (m, 1 H) 7.18-7.35 (m, 5 H) 7.55-7.60 (m, 1 H) 7.61-7.68 (m, 3 H) 7.71-7.74 (m, 1 H) 7.76 (t, J=1.92 Hz, 1 H) 7.94-8.01 (m, 3 H) 8.03 (s, 1 H) 9.06 (d, br, J=7.15 Hz, 1 H) 9.16 (s, 1 H) 9.55 (s, br, 1 H). MS (ESI) m/z: 613.1/615.1 (M+H)$^+$. Analytical HPLC: RT=6.61 min.

Example 9

(±)-(E)-Methyl 4-(5-(1-(3-(5-chloro-2-(1H-tetrazol-1-yl)phenyl)acrylamido)-2-phenylethyl)-6-methylpyridazin-3-yl)phenylcarbamate

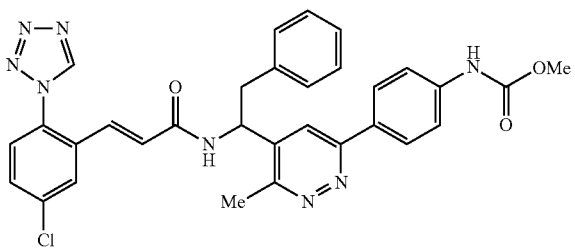

9A. 2-(1-(3-chloro-6-methylpyridazin-4-yl)-2-phenylethyl)isoindoline-1,3-dione and 9B. 2-(1-(6-chloro-3-methylpyridazin-4-yl)-2-phenylethyl)isoindoline-1,3-dione: The procedure was followed as described in 1A, by replacing 3,6-dichloropyridazine with 3-chloro-6-methylpyridazine to give 9A (23.6% yield) as a white solid [MS (ESI) m/z: 378.1/380.0 (M+H)$^+$] and 9B (1.3% yield) as a white solid [MS (ESI) m/z: 378.0/380.0 (M+H)$^+$].

9C. Example 9 was prepared following the procedures described in 1B, 1C, and 1D, by replacing 1A with 9B. $^1$H NMR (400 MHz, CD$_3$OD) δ ppm 2.66 (s, 3 H) 3.15-3.25 (m, 2 H) 3.78 (s, 3 H) 5.40 (t, J=7.58 Hz, 1 H) 6.69 (d, J=15.65 Hz, 1H) 7.06 (d, J=15.65 Hz, 1 H) 7.18-7.24 (m, 2 H) 7.24-7.32 (m, 3 H) 7.53-7.58 (m, 1 H) 7.65 (d, J=2.45 Hz, 1 H) 7.73 (d, J=8.80 Hz, 2 H) 7.97 (s, 1 H) 8.05 (d, J=8.80 Hz, 2 H) 8.55 (s, 1 H) 9.48 (s, 1 H). MS (ESI) m/z: 595.1/597.1 (M+H)$^+$. Analytical HPLC: RT=7.22 min.

Example 11

(±)-(E)-Methyl 4-(6-chloro-5-(1-(3-(5-chloro-2-(1H-tetrazol-1-yl)phenyl)acrylamido)ethyl)pyridazin-3-yl)phenylcarbamate

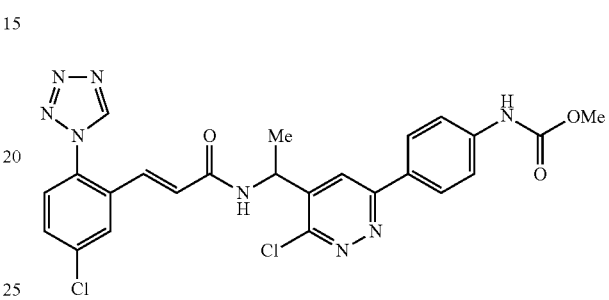

The title compound was prepared following the procedures described in Example 1, by replacing (S)-2-(1,3-dioxoisoindolin-2-yl)-3-phenylpropanoic acid with (S)-2-(1,3-dioxoisoindolin-2-yl)propanoic acid. $^1$H NMR (400 MHz, DMSO-d$_6$) δ ppm 1.46 (d, J=7.34 Hz, 3 H) 3.69 (s, 3 H) 5.11-5.18 (m, J=6.97, 6.97, 6.85, 6.60 Hz, 1 H) 6.76 (d, J=15.65 Hz, 1 H) 6.89 (d, J=15.65 Hz, 1 H) 7.66 (d, J=8.80 Hz, 2 H) 7.72 (d, J=8.31 Hz, 1 H) 7.76 (dd, J=8.31, 1.96 Hz, 1 H) 8.01 (d, J=1.96 Hz, 1 H) 8.04 (d, J=8.80 Hz, 2 H) 8.09 (s, 1 H) 8.93 (d, J=6.85 Hz, 1 H) 9.84 (s, 1 H) 9.98 (s, 1 H). MS (ESI) m/z: 539.2/541.2 (M+H)$^+$. Analytical HPLC: RT=10.82 min.

Example 12

(E)-Methyl 4-(6-chloro-5-(1-(3-(5-chloro-2-(1H-tetrazol-1-yl)phenyl)acrylamido)ethyl)pyridazin-3-yl)phenylcarbamate (Enantiomer A of Example 11)

Chiral separation of Example 11 [Chiralcel OD, (1:1) EtOH-MeOH] gave Example 12 as enantiomer A. MS (ESI) m/z: 539.2/541.2 (M+H)$^+$. Analytical HPLC: RT=10.82 min. Chiral analytical HPLC: chiralcel OD [(80% (1:1) EtOH:MeOH/heptane]: RT=4.71 min, >98% ee.

Example 13

(E)-Methyl 4-(6-chloro-5-(1-(3-(5-chloro-2-(1H-tetrazol-1-yl)phenyl)acrylamido)ethyl)pyridazin-3-yl)phenylcarbamate (Enantiomer B of Example 11)

Chiral separation of Example 11 [Chiralcel OD, (1:1) EtOH:MeOH] gave Example 13 as enantiomer B. MS (ESI) m/z: 539.2/541.2 (M+H)$^+$. Analytical HPLC: RT=10.82 min.

Chiral analytical HPLC: chiralcel OD [(80% (1:1) EtOH: MeOH/heptane]: RT=8.23 min, >98% ee.

Example 14

(±)-(E)-Methyl 4-(6-chloro-5-(1-(3-(5-chloro-2-(1H-tetrazol-1-yl)phenyl)acrylamido)-3-methylbutyl)pyridazin-3-yl)phenylcarbamate

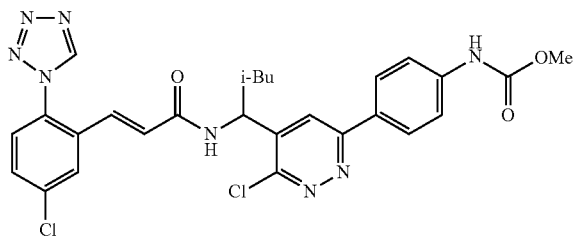

The title compound was prepared following the procedures described in Example 1, by replacing (S)-2-(1,3-dioxoisoindolin-2-yl)-3-phenylpropanoic acid with 2-(1,3-dioxoisoindolin-2-yl)-4-methylpentanoic acid. $^1$H NMR (400 MHz, DMF-$d_7$) δ ppm 0.97 (d, J=6.36 Hz, 3 H) 1.02 (d, J=6.36 Hz, 3 H) 1.58-1.67 (m, 1H) 1.79-1.89 (m, 2 H) 3.75 (s, 3 H) 5.35-5.42 (m, 1 H) 6.98 (d, J=15.65 Hz, 1 H) 7.10 (d, J=15.65 Hz, 1 H) 7.76-7.85 (m, 4 H) 8.08 (d, J=1.96 Hz, 1 H) 8.14 (d, J=8.80 Hz, 2 H) 8.29 (s, 1 H) 9.04 (d, J=7.82 Hz, 1 H) 9.88 (s, 1 H) 9.95 (s, 1 H). MS (ESI) m/z: 581.3 (M+H)$^+$. Analytical HPLC: RT=8.94 min.

Examples 15-18 were prepared according to the procedures described in Example 4 replacing 2-(benzyloxycarbonylamino)-3-phenylpropanoic acid with the appropriately substituted Cbz-protected amino acid.

Example 15

(±)-[4-(5-{2-tert-Butoxycarbonylamino-1-[(E)-3-(5-chloro-2-tetrazol-1-yl-phenyl)-acryloylamino]-ethyl}-6-chloro-pyridazin-3-yl)-phenyl]-carbamic acid methyl ester

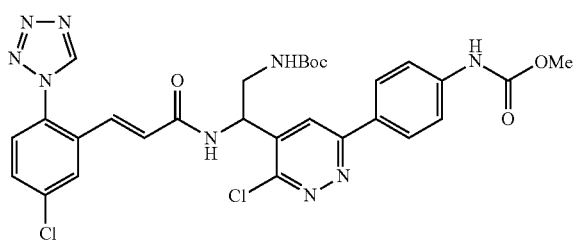

$^1$H NMR (400 MHz, CD$_3$OD) δ ppm 1.29 (s, 9 H) 3.54-3.65 (m, 2 H) 3.76 (s, 3 H) 5.39 (t, J=5.87 Hz, 1 H) 6.75 (d, J=15.65 Hz, 1 H) 7.15 (d, J=15.65 Hz, 1 H) 7.57 (d, J=8.80 Hz, 1 H) 7.61-7.68 (m, 3 H) 7.98-8.08 (m, 4 H) 9.50 (s, 1 H). MS (ESI) m/z: 654.3/656.3 (M+H)$^+$. Analytical HPLC: RT=8.10 min.

Example 16

(±)-[4-(5-{2-tert-Butoxycarbonylamino-1-[(E)-3-(5-chloro-2-tetrazol-1-yl-phenyl)-acryloylamino]-ethyl}-pyridazin-3-yl)-phenyl]-carbamic acid methyl ester

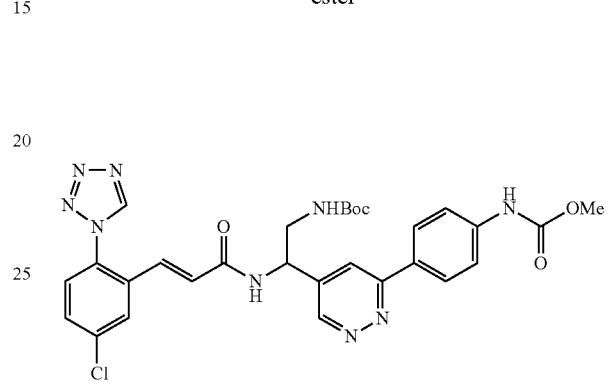

$^1$H NMR (400 MHz, CD$_3$OD) δ ppm 1.31 (s, 9 H) 3.50-3.61 (m, J=7.04, 7.04, 7.04, 7.04, 7.04 Hz, 2 H) 3.77 (s, 3 H) 5.16-5.22 (m, 1 H) 6.76 (d, J=15.65 Hz, 1 H) 7.16 (d, J=15.65 Hz, 1 H) 7.55-7.61 (m, 1 H) 7.63-7.70 (m, J=8.44, 2.20, 2.08 Hz, 3 H) 7.99-8.06 (m, 3 H) 8.23 (s, 1 H) 8.92 (d, br, J=7.34 Hz, 1 H) 9.16 (s, 1 H) 9.51 (s, 1 H) 9.58 (s, br, 1 H). MS (ESI) m/z: 620.3 (M+H)$^+$. Analytical HPLC: RT=7.07 min.

Example 17

(±)-(E)-Methyl 3-(3-(5-chloro-2-(1H-tetrazol-1-yl)phenyl)acrylamido)-3-(3-chloro-6-(4-(methoxycarbonylamino)phenyl)pyridazin-4-yl)propanoate

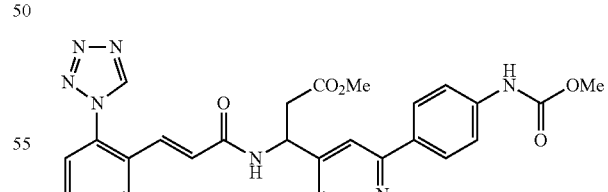

$^1$H NMR (400 MHz, CD$_3$OD) δ ppm 2.92-3.16 (m, 2 H) 3.69 (s, 3 H) 3.76 (s, 3 H) 5.54-5.69 (m, 1 H) 6.72 (d, J=15.65 Hz, 1 H) 7.14 (d, J=15.65 Hz, 1 H) 7.53-7.59 (m, 1 H) 7.61-7.69 (m, 3 H) 7.97-8.05 (m, 3 H) 8.08 (s, 1 H) 9.50 (s, 1H). MS (ESI) m/z: 597.2 (M+H)$^+$. Analytical HPLC: RT=10.96 min.

Example 18

(E)-Methyl 3-(3-(5-chloro-2-(1H-tetrazol-1-yl)phenyl)acrylamido)-3-(6-(4-(methoxycarbonylamino)phenyl)pyridazin-4-yl)propanoate

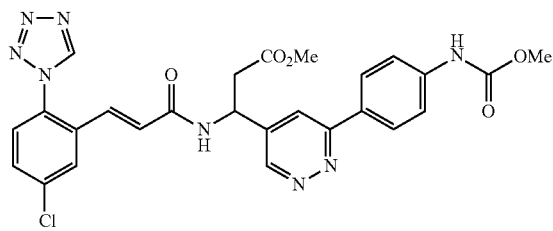

$^1$H NMR (400 MHz, CD$_3$OD) δ ppm 3.09 (d, J=7.34 Hz, 2 H) 3.68 (s, 3 H) 3.77 (s, 3 H) 5.49 (q, J=6.52 Hz, 1 H) 6.72 (d, J=15.65 Hz, 1 H) 7.15 (d, J=15.65 Hz, 1 H) 7.54-7.60 (m, J=8.31, 1.47 Hz, 1 H) 7.66 (dd, J=8.56, 1.71 Hz, 3 H) 7.96-8.07 (m, 3 H) 8.17 (s, 1 H) 9.03 (d, br, J=7.34 Hz, 1 H) 9.16 (s, 1 H) 9.51 (s, 1 H) 9.56 (s, br, 1 H). MS (ESI) m/z: 563.2 (M+H)$^+$. Analytical HPLC: RT=9.63 min.

Example 19

(±)-(E)-tert-Butyl 3-(3-(5-chloro-2-(1H-tetrazol-1-yl)phenyl)acrylamido)-3-(3-chloro-6-(4-(methoxycarbonylamino)phenyl)pyridazin-4-yl)propanoate

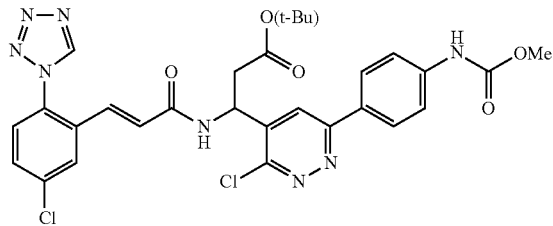

19A. tert-butyl 3-amino-3-(3-chloro-6-(4-(methoxycarbonylamino)phenyl)pyridazin-4-yl)propanoate: The procedures from 4A-C were followed by replacing 2-(benzyloxycarbonylamino)-3-phenylpropanoic acid with 2-(benzyloxycarbonylamino)-4-tert-butoxy-4-oxobutanoic acid to give 19A (57.3% yield) as a light yellow solid. MS (ESI) m/z: 407.2 (M+H)$^+$. The enantiomers were separated by chiral hplc [Chiralcel OD (60% (1:1) EtOH:MeOH/heptane/0.1% DEA] which gave enantiomer A [Chiralcel OD; 80% (1:1) EtOH:MeOH/heptane/0.1% DEA; RT=6.06 min, >99% ee] and enantiomer B [Chiralcel OD; 80% (1:1) EtOH:MeOH/heptane/0.1% DEA; RT=7.35 min, 98% ee).

19B. Example 19 was prepared according to the procedure described in 1D by replacing 1C with 19A (racemic). $^1$H NMR (400 MHz, DMF-d$_7$) δ ppm 1.38 (s, 9 H) 2.93-2.98 (m, 1 H) 3.06-3.13 (m, 1 H) 3.75 (s, 3 H) 5.69 (td, J=8.19, 5.62 Hz, 1 H) 6.92 (d, J=15.65 Hz, 1 H) 7.11 (d, J=15.65 Hz, 1 H) 7.76-7.84 (m, 4 H) 8.07 (d, J=1.96 Hz, 1 H) 8.17 (d, J=8.80 Hz, 2 H) 8.37 (s, 1 H) 9.12 (d, br, J=7.83 Hz, 1 H) 9.88 (s, 1 H) 9.96 (s, br, 1 H). MS (ESI) m/z: 639.2/641.2 (M+H)$^+$. Analytical HPLC: RT=8.66 min.

Example 20

(E)-tert-Butyl 3-(3-(5-chloro-2-(1H-tetrazol-1-yl)phenyl)acrylamido)-3-(3-chloro-6-(4-(methoxycarbonylamino)phenyl)pyridazin-4-yl)propanoate (prepared from Enantiomer A of 19A)

The title compound was prepared following the procedure described in 1D, by replacing 1C (racemic) with 19A (enantiomer A). MS (ESI) m/z: 639.2 (M+H)$^+$. Analytical HPLC: RT=8.58 min.

Example 21

(E)-tert-Butyl 3-(3-(5-chloro-2-(1H-tetrazol-1-yl)phenyl)acrylamido)-3-(3-chloro-6-(4-(methoxycarbonylamino)phenyl)pyridazin-4-yl)propanoate (prepared from Enantiomer B of 19A)

The title compound was prepared following the procedure described in 1D, by replacing 1C (racemic) with 19A (enantiomer B). MS (ESI) m/z: 639.2 (M+H)$^+$. Analytical HPLC: RT=8.58 min.

Example 22

(±)-(E)-Methyl 4-(6-chloro-5-(1-(3-(5-chloro-2-(1H-tetrazol-1-yl)phenyl)acrylamido)-3-(dimethylamino)-3-oxopropyl)pyridazin-3-yl)phenylcarbamate

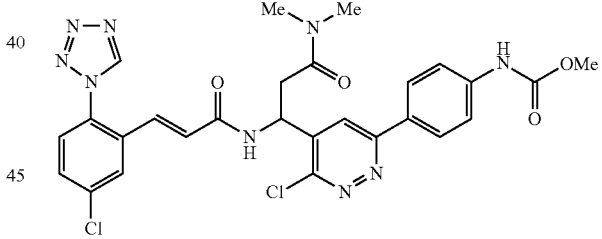

To a solution of Example 19 (30 mg, 0.047 mmol) in DCM (2.0 mL) was added TFA (1.0 mL, 12.98 mmol). After 1 h, the reaction was concentrated. The product was re-dissolved in DMF (2.0 mL) and cooled to 0° C. Next, DIEA (0.082 mL, 0.469 mmol) and isobutyl chloroformate (0.031 mL, 0.235 mmol) were added. After 5 min, dimethylamine HCl salt (38.3 mg, 0.469 mmol) was added. After 10 min, the reaction was quenched with water (0.5 mL). Purification by reverse phase chromatography gave Example 22 (22.2 mg, 73.1% yield) as a light yellow solid. $^1$H NMR (400 MHz, CD$_3$OD) δ ppm 2.91 (s, 3 H) 3.07 (s, 3 H) 3.08-3.18 (m, 2 H) 3.76 (s, 3 H) 5.55-5.70 (m, 1 H) 6.73 (d, J=15.65 Hz, 1 H) 7.12 (d, J=15.65 Hz, 1 H) 7.56 (d, J=8.80 Hz, 1 H) 7.60-7.68 (m, 3 H) 7.94-8.05 (m, 3 H) 8.11 (s, 1 H) 8.92 (d, br, J=6.85 Hz, 1 H) 9.50 (s, 1 H) 9.52 (s, br, 1 H). MS (ESI) m/z: 610.2 (M+H)$^+$. Analytical HPLC: RT=6.87 min.

Examples 23-33 were synthesized according to the procedure described in Example 22.

Example 23

(E)-Methyl 4-(6-chloro-5-(1-(3-(5-chloro-2-(1H-tetrazol-1-yl)phenyl)acrylamido)-3-(dimethylamino)-3-oxopropyl)pyridazin-3-yl)phenylcarbamate (Enantiomer A)

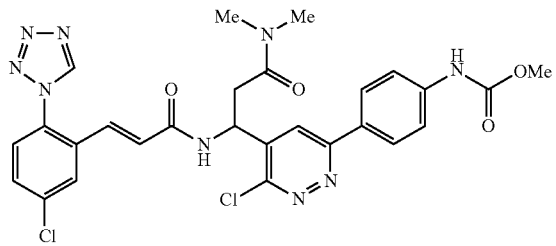

Prepared from Example 20. $^1$H NMR (400 MHz, CD$_3$OD) δ ppm 2.91 (s, 3 H) 3.07 (s, 3 H) 3.08-3.16 (m, 2 H) 3.76 (s, 3 H) 5.57-5.68 (m, 1 H) 6.73 (d, J=15.65 Hz, 1 H) 7.13 (d, J=15.65 Hz, 1 H) 7.56 (d, J=8.80 Hz, 1 H) 7.60-7.70 (m, 3H) 7.99 (d, J=1.96 Hz, 1 H) 8.02 (d, J=8.80 Hz, 2 H) 8.11 (s, 1 H) 8.91 (d, br, J=6.36 Hz, 1 H) 9.50 (s, 1 H) 9.53 (s, br, 1 H). MS (ESI) m/z: 610.2 (M+H)$^+$. Analytical HPLC: RT=7.24 min.

Example 24

(±)-(E)-Methyl 4-(5-(1-(3-(5-chloro-2-(1H-tetrazol-1-yl)phenyl)acrylamido)-3-(dimethylamino)-3-oxopropyl)pyridazin-3-yl)phenylcarbamate

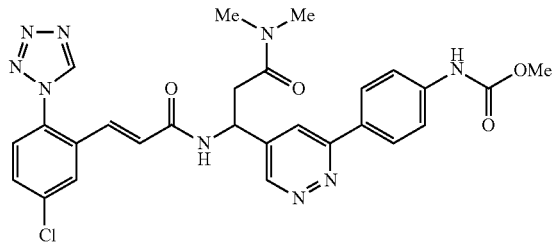

Prepared from Example 19. $^1$H NMR (400 MHz, CD$_3$OD) δ ppm 2.89 (s, 3 H) 3.06 (s, 3 H) 3.10-3.25 (m, 2 H) 3.76 (s, 3 H) 5.41-5.57 (m, 1 H) 6.75 (d, J=15.65 Hz, 1 H) 7.14 (d, J=15.65 Hz, 1 H) 7.53-7.60 (m, 1 H) 7.60-7.71 (m, 3 H) 7.94-8.06 (m, 3 H) 8.13 (s, 1 H) 9.14 (s, 1 H) 9.51 (s, 1 H) 9.52 (s, br, 1 H). MS (ESI) m/z: 576.2 (M+H)$^+$. Analytical HPLC: RT=5.83 min.

Example 25

(±)-(E)-Methyl 4-(6-chloro-5-(1-(3-(5-chloro-2-(1H-tetrazol-1-yl)phenyl)acrylamido)-3-(4-methylpiperazin-1-yl)-3-oxopropyl)pyridazin-3-yl)phenylcarbamate, TFA salt

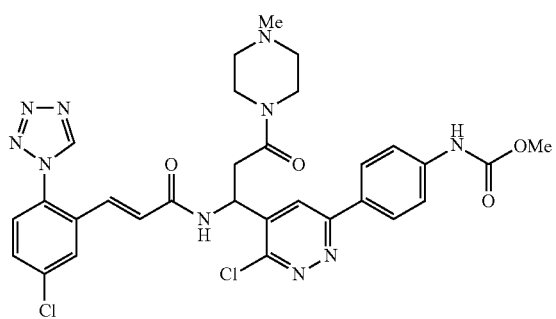

Prepared from Example 19. $^1$H NMR (500 MHz, CD$_3$OD) δ ppm 2.94 (s, 3 H) 2.95-3.57 (m, br, 10 H) 3.76 (s, 3 H) 5.66 (t, J=6.87 Hz, 1 H) 6.71 (d, J=15.40 Hz, 1 H) 7.12 (d, J=15.40 Hz, 1 H) 7.58 (d, J=8.25 Hz, 1 H) 7.62-7.67 (m, 3 H) 7.96 (d, J=2.20 Hz, 1 H) 8.02 (d, J=8.80 Hz, 2 H) 8.20 (s, 1 H) 9.53 (s, 1 H). MS (ESI) m/z: 665.2 (M+H)$^+$. Analytical HPLC: RT=4.92 min.

Example 26

(±)-(E)-Methyl 4-(6-chloro-5-(1-(3-(5-chloro-2-(1H-tetrazol-1-yl)phenyl)acrylamido)-3-(4-hydroxypiperidin-1-yl)-3-oxopropyl)pyridazin-3-yl)phenylcarbamate

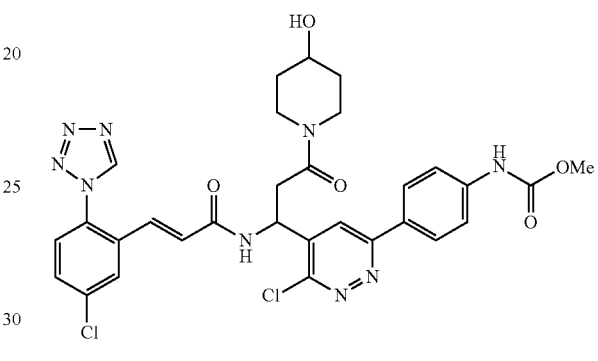

Prepared from Example 19. MS (ESI) m/z: 666.2 (M+H)$^+$. Analytical HPLC: RT=6.15 min.

Example 27

(E)-Methyl 4-(6-chloro-5-(1-(3-(5-chloro-2-(1H-tetrazol-1-yl)phenyl)acrylamido)-3-(4-methylpiperazin-1-yl)-3-oxopropyl)pyridazin-3-yl)phenylcarbamate, TFA salt (Enantiomer of Example 25)

Prepared from Example 20. $^1$H NMR (500 MHz, CD$_3$OD) δ ppm 2.94 (s, 3 H) 2.97-3.69 (m, br, 10 H) 3.76 (s, 3 H) 5.67 (t, J=6.60 Hz, 1 H) 6.70 (d, J=15.40 Hz, 1 H) 7.13 (d, J=15.95 Hz, 1 H) 7.58 (d, J=8.25 Hz, 1 H) 7.62-7.70 (m, 3 H) 7.97 (d, J=2.20 Hz, 1 H) 8.03 (d, J=8.80 Hz, 2 H) 8.20 (s, 1 H) 9.53 (s, 1 H). MS (ESI) m/z: 665.3 (M+H)$^+$. Analytical HPLC: RT=4.81 min.

Example 28

(E)-Methyl 4-(6-chloro-5-(1-(3-(5-chloro-2-(1H-tetrazol-1-yl)phenyl)acrylamido)-3-(4-methylpiperazin-1-yl)-3-oxopropyl)pyridazin-3-yl)phenylcarbamate, TFA salt (Enantiomer of Example 25)

Prepared from Example 21. $^1$H NMR (500 MHz, CD$_3$OD) δ ppm 2.94 (s, 3 H) 3.10-3.47 (m, br, 10 H) 3.77 (s, 3 H) 5.67 (t, J=6.60 Hz, 1 H) 6.70 (d, J=15.40 Hz, 1 H) 7.14 (d, J=15.95 Hz, 1 H) 7.55-7.61 (m, 1 H) 7.63-7.69 (m, 3 H) 7.97 (d, J=2.20 Hz, 1H) 8.04 (d, J=8.80 Hz, 2 H) 8.21 (s, 1 H) 9.53 (s, 1 H). MS (ESI) m/z: 665.3 (M+H)$^+$. Analytical HPLC: RT=4.81 min.

Example 29

Methyl 4-(6-chloro-5-(1-((E)-3-(5-chloro-2-(1H-tetrazol-1-yl)phenyl)acrylamido)-3-((R)-3-hydroxypyrrolidin-1-yl)-3-oxopropyl)pyridazin-3-yl)phenylcarbamate

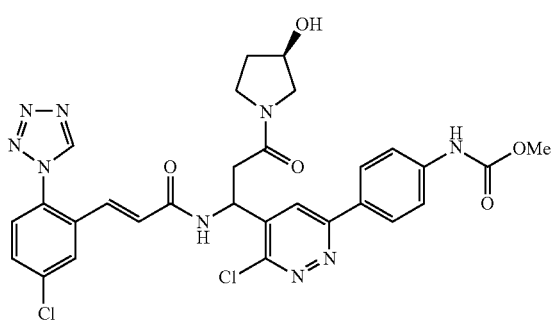

Prepared from Example 20. $^1$H NMR (500 MHz, CD$_3$OD) δ ppm 3.02-3.11 (m, 2 H) 3.34 (s, 2 H) 3.38-3.47 (m, 2 H) 3.47-3.56 (m, 1H) 3.60-3.68 (m, 1H) 3.76 (s, 3 H) 4.29-4.52 (m, 1 H) 5.59-5.67 (m, 1 H) 6.71-6.79 (m, 1 H) 7.13 (d, J=14.85 Hz, 1 H) 7.56 (d, J=8.25 Hz, 1 H) 7.62-7.67 (m, 3 H) 7.98-8.03 (m, 3 H) 8.12 (s, 1 H) 9.50 (s, 1 H). MS (ESI) m/z: 652.1 (M+H)$^+$. Analytical HPLC: RT=6.52 min.

Example 30

(E)-Methyl 4-(6-chloro-5-(1-(3-(5-chloro-2-(1H-tetrazol-1-yl)phenyl)acrylamido)-3-(2-hydroxyethylamino)-3-oxopropyl)pyridazin-3-yl)phenylcarbamate (Enantiomer A)

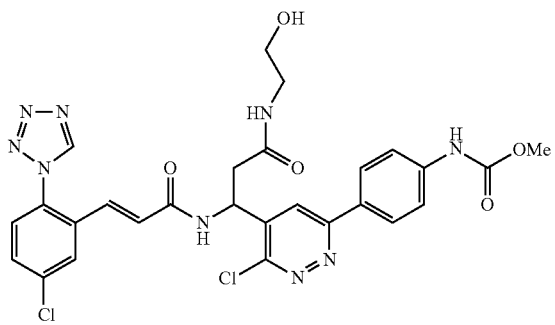

Prepared from Example 20. $^1$H NMR (500 MHz, DMF-d$_7$) δ ppm 2.94-2.99 (m, 2 H) 3.20 (q, J=5.68 Hz, 2 H) 3.73 (s, 3 H) 4.66 (t, J=4.12 Hz, 1 H) 5.66 (q, J=6.78 Hz, 1 H) 6.97 (d, J=15.40 Hz, 1 H) 7.04 (d, J=15.40 Hz, 1 H) 7.74-7.82 (m, 4 H) 8.06-8.09 (m, 2H) 8.11 (d, J=8.80 Hz, 2 H) 8.28 (s, 1 H) 9.03 (d, J=7.15 Hz, 1H) 9.86 (s, 1H) 9.92 (s, 1 H). MS (ESI) m/z: 626.1 (M+H)$^+$. Analytical HPLC: RT=6.38 min.

Example 31

(E)-Methyl 4-(5-(3-(tert-butylamino)-1-(3-(5-chloro-2-(1H-tetrazol-1-yl)phenyl)acrylamido)-3-oxopropyl)-6-chloropyridazin-3-yl)phenylcarbamate (Enantiomer A)

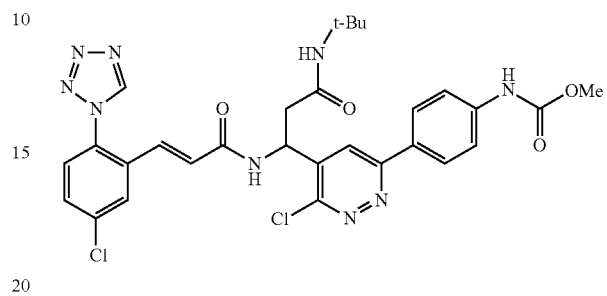

Prepared from Example 20. $^1$H NMR (500 MHz, DMF-d$_7$) δ ppm 1.17 (s, 9 H) 2.81-2.87 (m, 2 H) 3.73 (s, 3 H) 5.61 (q, J=7.15 Hz, 1 H) 6.99 (d, J=15.40 Hz, 1 H) 7.05 (d, J=15.40 Hz, 1 H) 7.72 (s, 1 H) 7.75-7.82 (m, 4 H) 8.08 (d, J=2.20 Hz, 1 H) 8.13 (d, J=8.80 Hz, 2 H) 8.26 (s, 1 H) 9.03 (d, J=7.15 Hz, 1 H) 9.86 (s, 1 H) 9.93 (s, 1 H). MS (ESI) m/z: 638.2 (M+H)$^+$. Analytical HPLC: RT=8.17 min.

Example 32

(±)-(E)-Methyl 4-(6-chloro-5-(1-(3-(5-chloro-2-(1H-tetrazol-1-yl)phenyl)acrylamido)-3-oxo-3-(pyrrolidin-1-yl)propyl)pyridazin-3-yl)phenylcarbamate

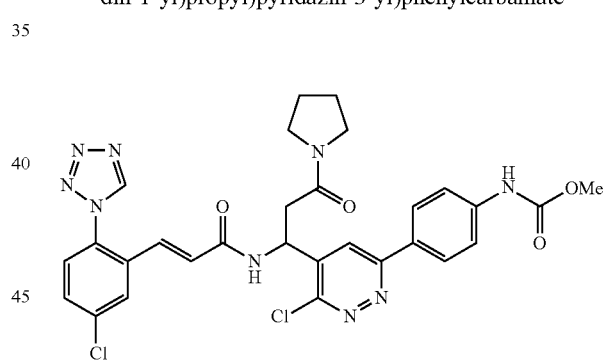

Prepared from Example 19. MS (ESI) m/z: 636.2 (M+H)$^+$. Analytical HPLC: RT=7.13 min.

Example 33

(S,E)-Methyl 4-(6-chloro-5-(1-(3-(5-chloro-2-(1H-tetrazol-1-yl)phenyl)acrylamido)-3-oxo-3-(pyrrolidin-1-yl)propyl)pyridazin-3-yl)phenylcarbamate (Enantiomer of Example 32)

Prepared from Example 20. $^1$H NMR (500 MHz, DMF-d$_7$) δ ppm 1.56-1.85 (m, 4 H) 2.90-3.03 (m, 2 H) 3.10-3.24 (m, 2 H) 3.31-3.43 (m, 2 H) 3.63 (s, 3H) 5.60 (q, J=6.96 Hz, 1 H) 6.83 (d, J=15.40 Hz, 1 H) 6.94 (d, J=15.95 Hz, 1 H) 7.55-7.75 (m, 4 H) 7.94 (d, J=2.20 Hz, 1 H) 8.03 (d, J=8.80 Hz, 2 H) 8.24 (s, 1 H) 8.92 (d, J=7.15 Hz, 1 H) 9.76 (s, 1 H) 9.82 (s, 1 H). MS (ESI) m/z: 636.1 (M+H)$^+$. Analytical HPLC: RT=7.70 min.

Example 34

(±)-(E)-Methyl 4-(5-(2-acetamido-1-(3-(5-chloro-2-(1H-tetrazol-1-yl)phenyl)acrylamido)ethyl)-6-chloropyridazin-3-yl)phenylcarbamate

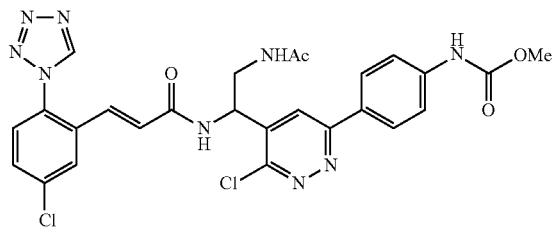

To a solution of Example 15 (5.5 mg, 8.40 mmol) in DCM (2 mL) was added TFA (0.5 mL, 6.49 mmol). After 1 h, the reaction was concentrated to give a residue. To a cooled (0° C.) solution of the residue in DCM (2 mL) and DMF (0.5 mL) was added TEA (0.05 mL) and acetic anhydride (3.96 µL, 0.042 mmol). After 1 h at 0° C., the reaction was concentrated. Purification by reverse phase chromatography gave Example 34 (4.1 mg, 79% yield) as a white solid. $^1$H NMR (400 MHz, CD$_3$OD) δ ppm 1.91 (s, 3 H) 3.64-3.74 (m, 2 H) 3.76 (s, 3 H) 5.40 (t, J=6.60 Hz, 1 H) 6.74 (d, J=15.65 Hz, 1 H) 7.14 (d, J=15.65 Hz, 1 H) 7.55-7.59 (m, 1H) 7.62-7.68 (m, 3 H) 8.00-8.05 (m, 3 H) 8.11 (s, 1 H) 9.51 (s, 1 H). MS (ESI) m/z: 596.2/598.2 (M+H)$^+$. Analytical HPLC: RT=6.53 min.

Example 35

(±)-(E)-Methyl 4-(6-chloro-5-(1-(3-(5-chloro-2-(1H-tetrazol-1-yl)phenyl)acrylamido)-2-(isopropylamino)ethyl)pyridazin-3-yl)phenylcarbamate, TFA salt

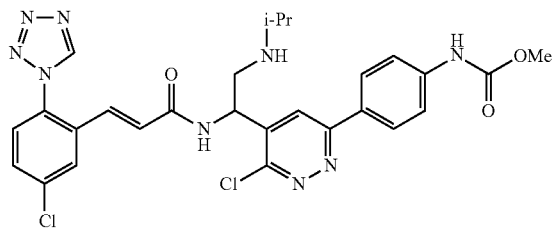

To a solution of Example 15 (8 mg, 0.012 mmol) in DCM (2 mL) was added TFA (0.5 mL). After 1 h, the reaction was concentrated to give a residue. To a solution of the residue in DCM (1 mL) and DMF (0.5 mL) was added acetone (one drop) and NaBH(OAc)$_3$ (10 mg). The reaction was stirred at rt for 1.5 h. Then HCl (1.0 N, 0.5 mL) was added to the reaction. The solvent was evaporated and purification by reverse phase chromatography gave Example 35 (5.1 mg, 58.3% yield) as a white solid. $^1$H NMR (400 MHz, CD$_3$OD) δ ppm 1.39 (d, J=6.36 Hz, 6 H) 3.46-3.55 (m, 1 H) 3.55-3.65 (m, 2 H) 3.77 (s, 3 H) 5.70 (dd, J=8.80, 4.89 Hz, 1 H) 6.75 (d, J=15.65 Hz, 1 H) 7.23 (d, J=15.65 Hz, 1 H) 7.57-7.62 (m, 1 H) 7.64-7.70 (m, 3 H) 7.97-8.01 (m, 1 H) 8.09 (d, J=8.80 Hz, 2 H) 8.25 (s, 1 H) 9.53 (s, 1 H) 9.57 (s, br, 1 H). MS (ESI) m/z: 596.2 (M+H)$^+$. Analytical HPLC: RT=5.32 min.

Example 36

(±)-(E)-N-(1-(6-(6-Aminopyridin-3-yl)-3-chloropyridazin-4-yl)-2-phenylethyl)-3-(5-chloro-2-(1H-tetrazol-1-yl)phenyl)acrylamide, TFA salt

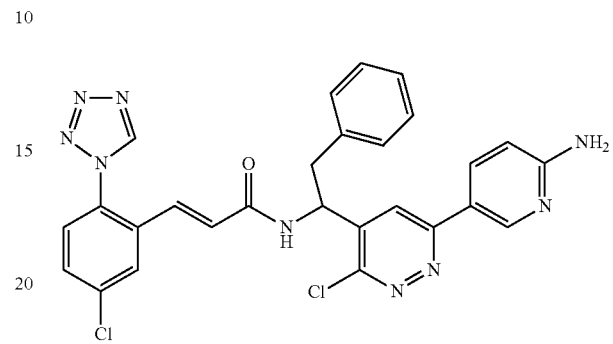

The title compound was prepared following the procedures described in Example 1, by replacing 4-(methoxycarbonylamino)phenylboronic acid with 5-(4,4,5,5-tetramethyl-1,3,2-dioxaborolan-2-yl)pyridin-2-amine $^1$H NMR (400 MHz, CD$_3$OD) δ ppm 2.98-3.42 (m, 2 H) 5.35 (dd, J=9.29, 4.89 Hz, 1 H) 6.73 (d, J=15.65 Hz, 1 H) 7.07 (d, J=15.65 Hz, 1 H) 7.18-7.35 (m, 7 H) 7.45 (d, J=8.31 Hz, 1 H) 7.56 (d, J=8.31 Hz, 1 H) 7.63-7.69 (m, 1 H) 8.34 (d, J=5.87 Hz, 1 H) 9.48 (s, 1 H). MS (ESI) m/z: 558.2 (M+H)$^+$. Analytical HPLC: RT=7.11 min.

Example 37

(S,E)-Methyl 4-(6-(1-(3-(5-chloro-2-(1H-tetrazol-1-yl)phenyl)acrylamido)-2-phenylethyl)-3-oxo-2,3-dihydropyridazin-4-yl)phenylcarbamate

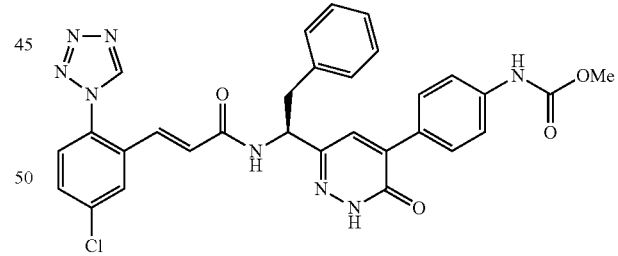

37A. (S)-tert-butyl 1-(5-(4-nitrophenyl)-6-oxo-1,6-dihydropyridazin-3-yl)-2-phenylethylcarbamate: To a cooled (0° C.) solution of (S)-tert-butyl 4-(dimethoxyphosphoryl)-3-oxo-1-phenylbutan-2-ylcarbamate (0.53 g, 1.427 mmol), prepared according to a modification of the procedure described by Resmini (*Tetrahedron Asymmetry* 2004, 15:1847), in ethanol (10 mL) was added ethyl 2-(4-nitrophenyl)-2-oxoacetate (0.319 g, 1.427 mmol) and potassium carbonate (0.296 g, 2.141 mmol). After 1 h, hydrazine (0.224 mL, 7.14 mmol) was added dropwise. After 10 min, the reaction was diluted with EtOAc and washed with 1M HCl (1×20 mL) and saturated NaCl (1×20 mL). The organic layer was dried over MgSO$_4$, filtered, and concentrated. Purification by normal phase chromatography gave 37A (515 mg, 83% yield) as an off-white solid. MS (ESI) m/z: 437.1 (M+H)⁺.

37B. (S)-tert-butyl 1-(5-(4-aminophenyl)-6-oxo-1,6-dihydropyridazin-3-yl)-2-phenylethylcarbamate: A suspension of 37A (0.39 g, 0.894 mmol) and 10% Pd/C (catalytic amount) in MeOH (40 mL) was stirred under a hydrogen balloon overnight. The reaction was filtered to remove the catalyst and the filtrate was concentrated to give 37B (364 mg, 100% yield) as a tan solid. MS (ESI) m/z: 407.2 (M+H)⁺.

37C. {4-[6-((S)-1-tert-butoxycarbonylamino-2-phenyl-ethyl)-3-oxo-2,3-dihydro-pyridazin-4-yl]-phenyl}-carbamic acid methyl ester: To a cooled (0° C.) solution of 37B (300 mg, 0.738 mmol) in dichloromethane (15 mL) was added TEA (0.154 mL, 1.107 mmol) and methyl chloroformate (0.057 mL, 0.738 mmol). After 1 h, the reaction was diluted with CH₂Cl₂, washed with IM HCl (1×5 mL), saturated NaHCO₃ (1×5 mL) and saturated NaCl (1×5 mL). The organic layer was dried over MgSO₄, filtered, and concentrated to give 37C (335 mg, 98% yield) as a tan solid. MS (ESI) m/z: 465.2 (M+H)⁺.

37D. (S)-methyl 4-(6-(1-amino-2-phenylethyl)-3-oxo-2,3-dihydropyridazin-4-yl)phenylcarbamate, TFA salt: To a solution of 37C (30 mg, 0.065 mmol) in DCM (3 mL) was added TFA (1 mL). After 30 min, the reaction was concentrated to give 37D. MS (ESI) m/z: 365.1 (M+H)⁺.

37E. Example 37 was prepared by following the procedure described in 1D, by replacing 1C with 37D. ¹H NMR (500 MHz, CD₃OD) δ ppm 3.19 (ddd, J=24.74, 13.75, 7.70 Hz, 2 H) 3.74 (s, 3 H) 5.26 (q, J=7.70 Hz, 1 H) 6.70 (d, J=15.40 Hz, 1 H) 7.08 (d, J=15.40 Hz, 1 H) 7.16-7.24 (m, 3 H) 7.23-7.31 (m, 2 H) 7.37 (s, 1H) 7.51 (d, J=8.80 Hz, 2 H) 7.55 (d, J=8.25 Hz, 1 H) 7.64 (dd, J=8.80, 2.20 Hz, 1 H) 7.70 (d, J=8.80 Hz, 2 H) 7.95 (d, J=2.20 Hz, 1 H) 8.82 (d, J=8.25 Hz, 1 H) 9.44 (s, 1H) 9.49 (s, 1 H). MS (ESI) m/z: 597.2 (M+H)⁺. Analytical HPLC: RT=7.73 min.

Example 38

(S,E)-Methyl 4-(3-chloro-6-(1-(3-(5-chloro-2-(1H-tetrazol-1-yl)phenyl)acrylamido)-2-phenylethyl)pyridazin-4-yl)phenylcarbamate

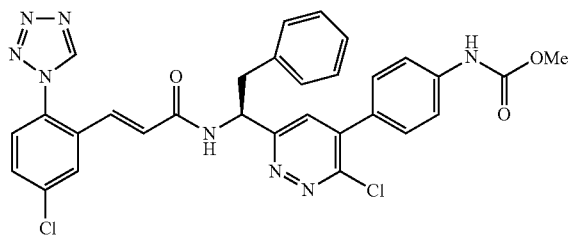

38A. {4-[6-((S)-1-amino-2-phenyl-ethyl)-3-chloro-pyridazin-4-yl]-phenyl}-carbamic acid methyl ester TFA salt: To a solution of 37C (150 mg, 0.323 mmol) in acetonitrile (5 mL) and chloroform (5 mL) was added POCl₃ (0.4 mL, 4.29 mmol). The reaction was warmed to 60° C. After 3 h, the reaction was cooled to rt and concentrated. Purification by reverse phase chromatography gave 38A (80.8 mg, 50.4% yield) as a tan solid. MS (ESI) m/z: 383.1 (M+H)⁺.

38B. Example 38 was prepared by following the procedure described in 1D, replacing 1C with 38A. ¹H NMR (500 MHz, CD₃OD) δ ppm 3.26-3.34 (m, 2H) 3.75 (s, 3 H) 5.48 (t, J=7.70 Hz, 1 H) 6.75 (d, J=15.40 Hz, 1 H) 7.06 (d, J=15.95 Hz, 1 H) 7.16-7.19 (m, 2 H) 7.21 (d, J=7.15 Hz, 1 H) 7.26 (t, J=7.15 Hz, 2 H) 7.36-7.40 (m, 3 H) 7.55 (d, J=8.25 Hz, 1 H) 7.57 (d, J=8.80 Hz, 2 H) 7.64 (dd, J=8.80, 2.20 Hz, 1 H) 7.95 (d, J=2.20 Hz, 1 H) 9.48 (s, 1 H). MS (ESI) m/z: 615.2 (M+H)⁺.

Analytical HPLC: RT=8.76 min.

Example 39

(S,E)-Methyl 4-(6-(1-(3-(5-chloro-2-(1H-tetrazol-1-yl)phenyl)acrylamido)-2-phenylethyl)-2-(2-hydroxyethyl)-3-oxo-2,3-dihydropyridazin-4-yl)phenylcarbamate

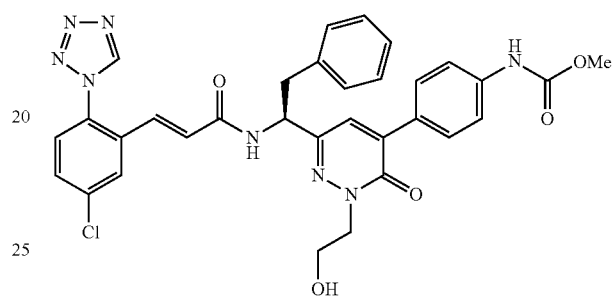

The title compound was prepared following the procedures described in Example 37, by replacing hydrazine with 2-hydrazinylethanol. ¹H NMR (500 MHz, CD₃OD) δ ppm 3.15-3.23 (m, 2 H) 3.74 (s, 3 H) 3.92 (t, J=5.77 Hz, 2 H) 4.34 (t, J=5.77 Hz, 2 H) 5.25 (t, J=7.42 Hz, 1 H) 6.71 (d, J=15.40 Hz, 1 H) 7.08 (d, J=15.95 Hz, 1 H) 7.18-7.24 (m, 3 H) 7.25-7.29 (m, 2 H) 7.32 (s, 1 H) 7.51 (d, J=8.25 Hz, 2 H) 7.56 (d, J=8.80 Hz, 1 H) 7.63-7.68 (m, 3 H) 7.96 (d, J=2.20 Hz, 1 H) 9.49 (s, 1H). MS (ESI) m/z: 641.3 (M+H)⁺. Analytical HPLC: RT=7.42 min.

Example 40

(S,E)-Methyl 4-(6-(1-(3-(5-chloro-2-(1H-tetrazol-1-yl)phenyl)acrylamido)-2-phenylethyl)-2-methyl-3-oxo-2,3-dihydropyridazin-4-yl)phenylcarbamate

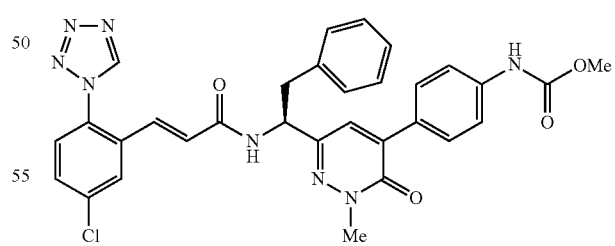

The title compound was prepared following the procedure described in Example 37, by replacing hydrazine with methylhydrazine. ¹H NMR (400 MHz, DMF-d₇) δ ppm 3.20 (dd, J=13.69, 8.31 Hz, 1 H) 3.28 (dd, J=13.69, 6.85 Hz, 1 H) 3.74 (s, 6 H) 5.25-5.32 (m, 1 H) 6.93 (d, J=15.65 Hz, 1 H) 7.04 (d, J=15.16 Hz, 1 H) 7.21 (t, J=7.09 Hz, 1 H) 7.28-7.35 (m, 4 H) 7.68 (d, J=8.80 Hz, 2 H) 7.73-7.76 (m, 1 H) 7.78 (dd, J=8.80, 1.96 Hz, 1 H) 7.81 (d, J=8.80 Hz, 1 H) 7.95 (d, J=8.31 Hz, 2H)

8.02 (d, J=1.96 Hz, 1 H) 8.87 (d, br, J=8.31 Hz, 1 H) 9.87 (s, br, 1 H) 9.88 (s, 1H). MS (ESI) m/z: 611.3 (M+H)⁺. Analytical HPLC: RT=8.20 min.

Example 41

(S,E)-Methyl 4-(6-(1-(3-(5-chloro-2-(1H-tetrazol-1-yl)phenyl)acrylamido)-2-phenylethyl)pyridazin-4-yl)phenylcarbamate

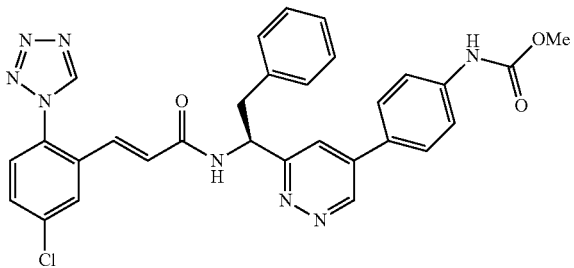

41A. (S)-methyl 4-(6-(1-amino-2-phenylethyl)pyridazin-4-yl)phenylcarbamate, TFA salt and 41B. (S)-methyl 4-(6-(1-amino-2-phenylethyl)-3-methoxypyridazin-4-yl)phenylcarbamate, TFA salt: To 38A (98 mg, 0.197 mmol) in MeOH (10 mL) was added 10% Pd/C (catalytic amount). The reaction mixture was stirred under a hydrogen balloon for 3 h. The catalyst was removed by filtration and the filtrate was concentrated. Purification by reverse phase chromatography gave 41A (40.1 mg, 44.0% yield) as a light brown solid [MS (ESI) m/z: 349.1 (M+H)⁺] and 41B (25.6 mg, 26.4%) as light brown solid [MS (ESI) m/z: 379.0 (M+H)⁺].

41C. Example 41 was prepared following the procedure described in 1D, by replacing 1C with 41A. ¹H NMR (400 MHz, CD₃OD) δ ppm 3.23-3.44 (m, 2 H) 3.76 (s, 3 H) 5.51 (t, J=7.70 Hz, 1 H) 6.76 (d, J=15.39 Hz, 1 H) 7.07 (d, J=15.39 Hz, 1 H) 7.15-7.22 (m, 3 H) 7.22-7.30 (m, 2 H) 7.51-7.59 (m, 1 H) 7.65 (d, J=8.25 Hz, 3 H) 7.74 (d, J=8.79 Hz, 2 H) 7.83 (d, J=1.65 Hz, 1 H) 7.97 (d, J=2.20 Hz, 1 H) 9.47 (d, J=1.65 Hz, 1 H) 9.48 (s, 1 H) 9.58 (s, br, 1 H). MS (ESI) m/z: 581.0/583.0 (M+H)⁺. Analytical HPLC: RT=8.18 min.

Example 42

(S,E)-Methyl 4-(6-(1-(3-(5-chloro-2-(1H-tetrazol-1-yl)phenyl)acrylamido)-2-phenylethyl)-3-methoxypyridazin-4-yl)phenylcarbamate

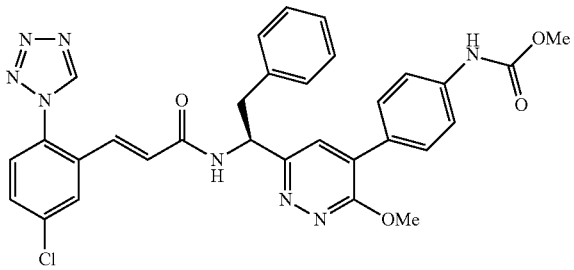

The title compound was prepared following the procedure described in 1D, by replacing 1C with 41B. ¹H NMR (400 MHz, CD₃OD) δ ppm 3.24-3.29 (m, 2 H) 3.75 (s, 3 H) 4.13 (s, 3 H) 5.43 (t, J=7.70 Hz, 1 H) 6.74 (d, J=15.39 Hz, 1 H) 7.07 (d, J=15.94 Hz, 1 H) 7.15-7.23 (m, 3 H) 7.24-7.31 (m, 2 H) 7.52-7.62 (m, 6H) 7.62-7.68 (m, 1 H) 7.96 (d, J=2.20 Hz, 1 H) 9.48 (s, 1 H). MS (ESI) m/z: 611.1/613.1 (M+H)⁺. Analytical HPLC: RT=8.70 min.

Example 43

(S,E)-Methyl 4-(6-(1-(3-(5-chloro-2-(1H-tetrazol-1-yl)phenyl)acrylamido)-2-(4-fluorophenyl)ethyl)-3-oxo-2,3-dihydropyridazin-4-yl)phenylcarbamate

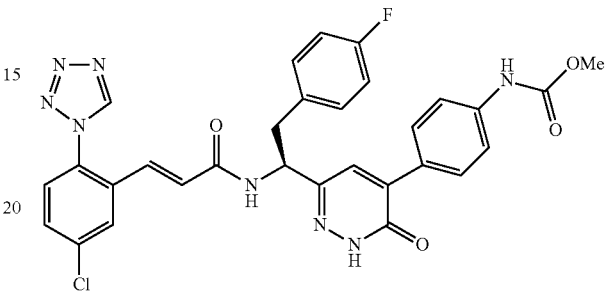

43A. (S)-tert-butyl 2-(4-fluorophenyl)-1-(5-(4-nitrophenyl)-6-oxo-1,6-dihydropyridazin-3-yl)ethylcarbamate: This compound was prepared following the procedure described in Example 37A, by replacing (S)-tert-butyl 4-(dimethoxyphosphoryl)-3-oxo-1-phenylbutan-2-ylcarbamate with Intermediate 3. MS (ESI) m/z: 455.0 (M+H)⁺.

43B. (4-{6-[(S)-1-tert-butoxycarbonylamino-2-(4-fluorophenyl)-ethyl]-3-oxo-2,3-dihydro-pyridazin-4-yl}-phenyl)-carbamic acid methyl ester: This compound was prepared following the procedures described in Examples 37B and 37C, by replacing 37A with 43A. MS (ESI) m/z: 483.0 (M+H)⁺.

43C. Example 43 was prepared following the procedures described in 37D and 37E, by replacing 37C with 43B. ¹H NMR (400 MHz, CD₃OD) δ ppm 3.13 (dd, J=14.29, 8.25 Hz, 1 H) 3.23 (dd, J=13.74, 6.60 Hz, 1 H) 3.74 (s, 3 H) 5.17-5.31 (m, 1 H) 6.67 (d, J=15.94 Hz, 1 H) 6.99 (t, J=8.79 Hz, 2 H) 7.09 (d, J=15.39 Hz, 1 H) 7.23 (dd, J=8.79, 5.50 Hz, 2 H) 7.44 (s, 1 H) 7.52 (d, J=8.25 Hz, 2 H) 7.55 (d, J=8.79 Hz, 1H) 7.64 (dd, J=8.24, 2.20 Hz, 1 H) 7.74 (d, J=8.79 Hz, 2 H) 7.94 (d, J=2.20 Hz, 1 H) 9.49 (s, 1 H). MS (ESI) m/z: 615.0 (M+H)⁺. Analytical HPLC: RT=8.19 min.

Example 44

(S,E)-N-(1-(5-(4-Aminophenyl)-6-oxo-1,6-dihydropyridazin-3-yl)-2-(4-fluorophenyl)ethyl)-3-(5-chloro-2-(1H-tetrazol-1-yl)phenyl)acrylamide

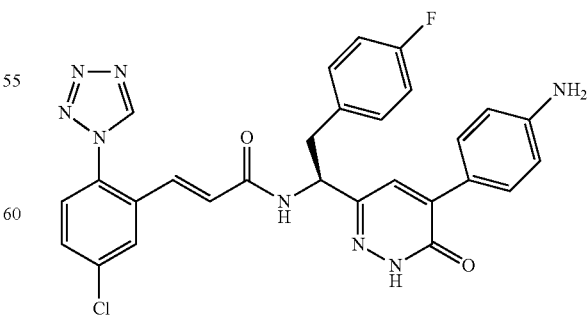

44A. (S,E)-3-(5-chloro-2-(1H-tetrazol-1-yl)phenyl)-N-(2-(4-fluorophenyl)-1-(5-(4-nitrophenyl)-6-oxo-1,6-dihydropyridazin-3-yl)ethyl)acrylamide: This compound was prepared following the procedures described in Examples 37D and 37E, by replacing 37C with 43A. MS (ESI) m/z: 587.0 (M+H)+.

44B. Example 44: To a solution of 44A (17 mg, 0.029 mmol) in methanol (5 mL) was added tin (II) chloride dihydrate (32.7 mg, 0.145 mmol). The reaction mixture was stirred overnight. The reaction was filtered and the filtrate was concentrated. Purification by reverse phase chromatography gave the Example 44 (15.5 mg, 96% yield) as a light yellow solid. $^1$H NMR (400 MHz, CD$_3$OD) δ ppm 3.08-3.26 (m, 2 H) 5.24 (t, J=7.70 Hz, 1 H) 6.68 (d, J=15.39 Hz, 1 H) 7.00 (t, J=8.79 Hz, 2 H) 7.08 (d, J=15.39 Hz, 1 H) 7.25 (dd, J=8.79, 5.50 Hz, 2 H) 7.41 (d, J=8.79 Hz, 2 H) 7.49 (s, 1 H) 7.52-7.60 (m, 1 H) 7.61-7.69 (m, 1 H) 7.89 (d, J=8.25 Hz, 2H) 7.95 (d, J=2.20 Hz, 1 H) 9.50 (s, 1 H). MS (ESI) m/z: 557.0/559.0 (M+H)+.
Analytical HPLC: RT=6.52 min.

Example 45

(S,E)-Methyl 4-(3-chloro-6-(1-(3-(5-chloro-2-(1H-tetrazol-1-yl)phenyl)acrylamido)-2-(4-fluorophenyl)ethyl)pyridazin-4-yl)phenylcarbamate

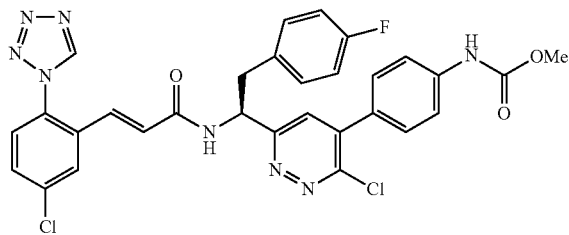

The title compound was prepared following the procedures described in Example 38, by replacing 37C with 43B. $^1$H NMR (400 MHz, CD$_3$OD) δ ppm 9.49 (s, 1 H) 7.96 (d, J=2.20 Hz, 1 H) 7.64 (dd, J=8.52, 2.47 Hz, 1 H) 7.60 (d, J=8.79 Hz, 2 H) 7.55 (d, J=8.25 Hz, 1 H) 7.49 (s, 1 H) 7.43 (d, J=8.79 Hz, 2 H) 7.21 (dd, J=8.24, 5.50 Hz, 2 H) 7.07 (d, J=15.39 Hz, 1 H) 6.99 (t, J=8.52 Hz, 2 H) 6.73 (d, J=15.94 Hz, 1 H) 5.42-5.53 (m, 1 H) 3.76 (s, 3 H) 3.23-3.29 (m, 2 H). MS (ESI) m/z: 633.0 (M+H)+. Analytical HPLC: RT=9.21 min.

Example 46

(S,E)-Methyl 4-(6-(1-(3-(5-chloro-2-(1H-tetrazol-1-yl)phenyl)acrylamido)-2-(4-fluorophenyl)ethyl)pyridazin-4-yl)phenylcarbamate

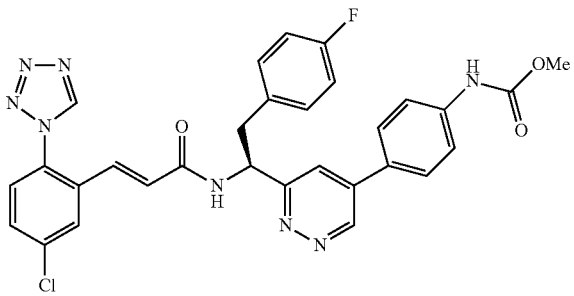

The title compound was prepared following the procedure described in 38A, by replacing 37C with 43B, and then following the procedure described in Example 41. $^1$H NMR (400 MHz, CD$_3$OD) δ ppm 9.48 (s, 1 H) 9.47 (d, J=2.27 Hz, 1H) 7.97 (d, J=2.27 Hz, 1 H) 7.87 (d, J=2.27 Hz, 1 H) 7.74-7.80 (m, 2 H) 7.61-7.69 (m, 3 H) 7.55 (d, J=8.34 Hz, 1 H) 7.21 (dd, J=8.59, 5.31 Hz, 2 H) 7.08 (d, J=15.41 Hz, 1 H) 6.98 (t, J=8.72 Hz, 2 H) 6.75 (d, J=15.66 Hz, 1 H) 5.50 (t, J=7.58 Hz, 1 H) 3.76 (s, 3 H) 3.23-3.42 (m, 2 H). MS (ESI) m/z: 599.2 (M+H)+. Analytical HPLC: RT=8.42 min.

Example 47

(±)-(E)-3-(3-(5-Chloro-2-(1H-tetrazol-1-yl)phenyl)acrylamido)-3-(3-chloro-6-(4-(methoxycarbonylamino)phenyl)pyridazin-4-yl)propanoic acid

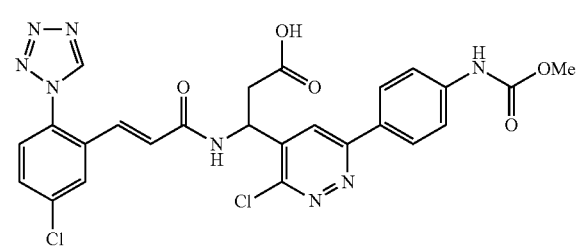

Deprotection of Example 19 according to the procedure described in Example 22 gave Example 47. $^1$H NMR (400 MHz, CD$_3$OD) δ ppm 2.90-2.99 (m, 1 H) 3.01-3.08 (m, 1 H) 3.76 (s, 3 H) 5.60 (dd, J=8.56, 5.14 Hz, 1 H) 6.75 (d, J=15.65 Hz, 1 H) 7.14 (d, J=15.16 Hz, 1 H) 7.56 (d, J=8.31 Hz, 1 H) 7.61-7.67 (m, 3H) 7.97-8.03 (m, 3 H) 8.08 (s, 1 H) 9.50 (s, 1 H). MS (ESI) m/z: 583.1 (M+H)+. Analytical HPLC: RT=6.65 min.

Example 48

(S,E)-2-(4-(3-Chloro-6-(1-(3-(5-chloro-2-(1H-tetrazol-1-yl)phenyl)acrylamido)-2-phenylethyl)pyridazin-4-yl)phenylamino)-2-oxoethyl acetate

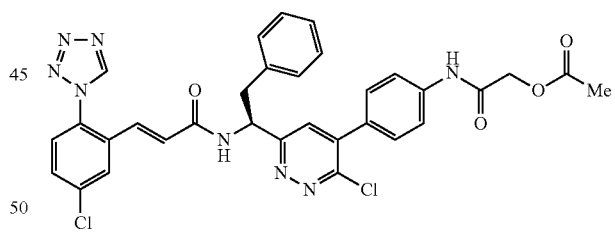

48A. (S)-2-(4-(6-(1-(tert-butoxycarbonylamino)-2-phenylethyl)-3-oxo-2,3-dihydropyridazin-4-yl)phenylamino)-2-oxoethyl acetate: The compound was prepared by following the procedure described in Example 37C, by replacing methyl chloroformate with 2-chloro-2-oxoethyl acetate to give 48A. MS (ESI) m/z: 507.2 (M+H)+.

48B. (S)-2-(4-(6-(1-amino-2-phenylethyl)-3-chloropyridazin-4-yl)phenylamino)-2-oxoethyl acetate: The compound was prepared by following the procedure described in Example 38A, by replacing 37C with 48A to give 48B. MS (ESI) m/z: 425.1 (M+H)+.

48C. Example 48: To a solution of Intermediate 1B (50.1 mg, 0.200 mmol) in THF (3 mL) was added BOP (88 mg, 0.200 mmol) and TEA (0.139 mL, 1.000 mmol). The resulting reaction was stirred for 10 min. Next a solution of 48B (53.9 mg, 0.1 mmol) in THF (1 mL) was added. The resulting reaction was stirred for 10 min. Purification by reverse phase chromatography gave Example 48 (50 mg, 76% yield) as a yellow solid. $^1$H NMR (400 MHz, CD$_3$OD) δ ppm 2.17 (s, 3 H) 3.28-3.33 (m, 2 H) 4.71 (s, 2 H) 5.45-5.52 (m, 1 H) 6.75 (d, J=15.65 Hz, 1 H) 7.06 (d, J=15.65 Hz, 1 H) 7.16-7.22 (m, 3 H) 7.23-7.28 (m, 2 H) 7.40-7.44 (m, 3 H) 7.52-7.56 (m, 1 H) 7.61-7.66 (m, 1 H) 7.69-7.74 (m, 2 H) 7.95 (s, 1 H) 9.48 (s, 1 H). MS (ESI) m/z: 657.1 (M+H)$^+$. Analytical HPLC: RT=8.24 min.

Example 49

(S,E)-3-(5-Chloro-2-(1H-tetrazol-1-yl)phenyl)-N-(1-(6-chloro-5-(4-(2-hydroxyacetamido)phenyl)pyridazin-3-yl)-2-phenylethyl)acrylamide

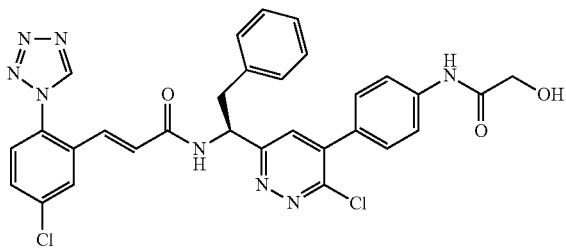

49A. (S)-N-(4-(6-(1-amino-2-phenylethyl)-3-chloropyridazin-4-yl)phenyl)-2-hydroxyacetamide: To a solution of 48B (42 mg, 0.099 mmol) in MeOH (1.5 mL) was added sodium hydroxide (297 μL, 0.297 mmol). The mixture was stirred for 0.5 h. Purification by reverse phase chromatography gave 49A (28 mg, 57.0% yield) as a white solid. MS (ESI) m/z: 383.1/385.1 (M+H)$^+$.

49B. Example 49 was prepared following the procedure described in 48C, by replacing 48B with 49A. $^1$H NMR (400 MHz, CD$_3$OD) δ ppm 3.27-3.35 (m, 2H) 4.14 (s, 2 H) 5.49 (t, J=7.58 Hz, 1 H) 6.75 (d, J=15.65 Hz, 1 H) 7.07 (d, J=15.65 Hz, 1 H) 7.16-7.22 (m, 3 H) 7.24-7.28 (m, 2 H) 7.42 (d, J=9.29 Hz, 3 H) 7.52-7.57 (m, 1 H) 7.62-7.66 (m, 1 H) 7.78 (d, J=8.31 Hz, 2 H) 7.95 (s, 1 H) 9.49 (s, 1 H). MS (ESI) m/z: 615.1 (M+H)$^+$. Analytical HPLC: RT=7.54 min.

Example 50

(S,E)-3-(4-(3-Chloro-6-(1-(3-(5-chloro-2-(1H-tetrazol-1-yl)phenyl)acrylamido)-2-phenylethyl)pyridazin-4-yl)phenylcarbamoyloxy)propanoic acid

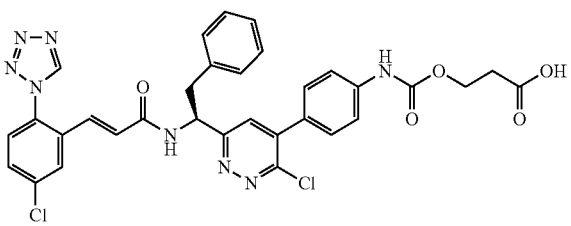

50A. (S)-N-(4-(6-(1-amino-2-phenylethyl)-3-chloropyridazin-4-yl)phenyl)-2,2,2-trifluoroacetamide: To a suspension of 37B (98 mg, 0.188 mmol) in acetonitrile (2.5 mL)/CHCl$_3$ (1.25 mL) was added POCl$_3$ (0.757 mL, 8.27 mmol). The reaction mixture was stirred at 60° C. overnight. The solvent was removed under reduced pressure. Purification by reverse phase chromatography gave 50A (57 mg, 68.3% yield) as a white solid. MS (ESI) m/z: 421.0/423.0 (M+H)$^+$.

50B. (S)-4-(6-(1-amino-2-phenylethyl)-3-chloropyridazin-4-yl)aniline: To a solution of 50A (57 mg, 0.107 mmol) in MeOH (2 mL) was added potassium carbonate (1.066 mL, 1.066 mmol). The resulting mixture was stirred at rt overnight. Purification by reverse phase chromatography gave 50B (68 mg, 96.0% yield) as a white solid. MS (ESI) m/z: 325.0 (M+H)$^+$.

50C. (S,E)-N-(1-(5-(4-aminophenyl)-6-chloropyridazin-3-yl)-2-phenylethyl)-3-(5-chloro-2-(1H-tetrazol-1-yl)phenyl)acrylamide: The compound was prepared following the procedures described in Example 48C, by replacing 48B with 50B. MS (ESI) m/z: 557.0 (M+H)$^+$.

50D. (S,E)-tert-butyl 3-(4-(3-chloro-6-(1-(3-(5-chloro-2-(1H-tetrazol-1-yl)phenyl)acrylamido)-2-phenylethyl)pyridazin-4-yl)phenylcarbamoyloxy)propanoate: To a solution of 50C (49.2 mg, 0.066 mmol) in DCM (2.5 mL) and acetonitrile (2.5 mL) was added sodium bicarbonate (16.62 mg, 0.198 mmol). The reaction was cooled to 0° C., and then a phosgene solution (20% in toluene) (0.104 mL, 0.198 mmol) was added. The reaction was stirred at 0° C. for 30 min and then concentrated to give a residue. To a cooled (0° C.) solution of the residue in DCM (4 mL) was added tert-butyl 3-hydroxypropanoate (10.60 mg, 0.073 mmol) and TEA (0.018 mL, 0.132 mmol). The resulting mixture was stirred at 0° C. for 40 min, and then at rt for 2 h. Purification by normal phase chromatography (DCM/MeOH) gave 50D (33.8 mg, 70.2% yield) as a white solid. MS (ESI) m/z: 729.1 (M+H)$^+$.

50E. Example 50: To a suspension of 50D (17 mg, 0.016 mmol) in DCM (1.0 mL) was added TFA (1.0 mL). The resulting solution was stirred at rt for 45 min and then concentrated. Purification by reverse phase chromatography gave Example 50 (8.96 mg, 77% yield) as a yellow solid. $^1$H NMR (400 MHz, CD$_3$OD) δ ppm 2.61 (t, J=6.05 Hz, 2 H) 3.20-3.25 (m, 2 H) 4.30 (t, J=6.05 Hz, 2 H) 5.38 (t, J=7.70 Hz, 1 H) 6.65 (d, J=15.94 Hz, 1 H) 6.97 (d, J=15.39 Hz, 1 H) 7.06-7.18 (m, 5 H) 7.26-7.34 (m, 3 H) 7.46 (ddd, J=18.28, 9.34, 9.21 Hz, 3 H) 7.52-7.57 (m, 1 H) 7.86 (d, J=2.20 Hz, 1 H) 9.39 (s, 1 H). MS (ESI) m/z: 673.0 (M+H)$^+$. Analytical HPLC: RT=6.86 min.

Example 51

(S,E)-Ethyl 4-(6-(1-(3-(5-chloro-2-(1H-tetrazol-1-yl)phenyl)acrylamido)-2-phenylethyl)-3-ethoxypyridazin-4-yl)phenylcarbamate

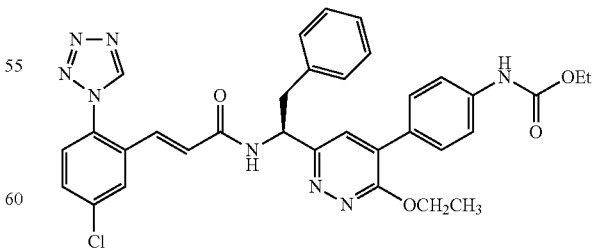

51A. (S)-ethyl 4-(6-(1-amino-2-phenylethyl)-3-ethoxypyridazin-4-yl)phenylcarbamate: To a solution of 38A (41 mg, 0.083 mmol) in THF (3.0 mL) was added sodium hydride (16.50 mg, 0.413 mmol) and ethanol (0.019 mL, 0.330 mmol). The reaction mixture was stirred at rt for 20 min, and then at reflux for 4 h. Additional EtOH (0.1 mL) was added. The resulting mixture was stirred at reflux for 1 h, and then cooled to rt. Purification by reverse phase chromatography gave 51A (18 mg, 41.9% yield) as a white solid. MS (ESI) m/z: 407.0 (M+H)+.

51B. Example 51 was prepared following the procedure described in 48C, by replacing 48B with 51A. $^1$H NMR (400 MHz, CD$_3$OD) δ ppm 1.32 (t, J=7.15 Hz, 3 H) 1.45 (t, J=6.87 Hz, 3 H) 3.32-3.36 (m, 2 H) 4.20 (q, J=7.15 Hz, 2 H) 4.56 (q, J=7.15 Hz, 2 H) 5.42 (t, J=7.97 Hz, 1 H) 6.73 (d, J=15.94 Hz, 1 H) 7.07 (d, J=15.94 Hz, 1 H) 7.17-7.23 (m, 3 H) 7.25-7.29 (m, 2 H) 7.53-7.60 (m, 3 H) 7.64 (td, J=8.52, 2.75 Hz, 4 H) 7.96 (d, J=2.20 Hz, 1 H) 9.48 (s, 1 H). MS (ESI) m/z: 639.4 (M+H)+. Analytical HPLC: RT=8.59 min.

Example 52

(S,E)-Methyl 2-(3-(1-(3-(5-chloro-2-(1H-tetrazol-1-yl)phenyl)acrylamido)-2-phenylethyl)-5-(4-(methoxycarbonylamino)phenyl)-6-oxopyridazin-1(6H)-yl)acetate

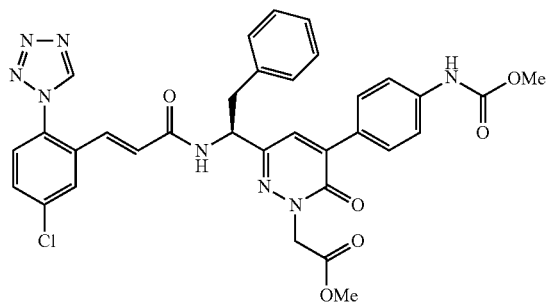

52A. (S)-methyl 2-(3-(1-(tert-butoxycarbonylamino)-2-phenylethyl)-5-(4-(methoxycarbonylamino)phenyl)-6-oxopyridazin-1(6H)-yl)acetate: A modification of the procedure described by Russell was used (*J. Med. Chem.*, 2005, 48(5), 1367-1383). To a solution of 37C (170 mg, 0.366 mmol) in DMF (5 mL) was added sodium hydride (17.57 mg, 0.439 mmol). The mixture was heated at 80° C. for 30 min. Next, methyl 2-bromoacetate (0.049 mL, 0.512 mmol) was added and the reaction was heated at 80° C. for another 35 min. The mixture was cooled to rt and partitioned between water and EtOAc. The layers were separated and the organic layer was washed with water (2×10 mL), brine (15 mL), dried (Na$_2$SO$_4$), filtered, and concentrated to give 52A (137 mg, 64.7%) as a yellow solid. MS (ESI) m/z: 537.3 (M+H)+.

52B. (S)-methyl 2-(3-(1-amino-2-phenylethyl)-5-(4-(methoxycarbonyl amino)phenyl)-6-oxopyridazin-1(6H)-yl)acetate: The compound was prepared following the procedure described in 37D, by replacing 37C with 52A. MS (ESI) m/z: 437.2 (M+H)+.

52C. Example 52 was prepared following the procedure described in 48C, by replacing 48B with 52B. $^1$H NMR (400 MHz, DMSO-d$_6$) δ ppm 2.99-3.08 (m, 1H) 3.08-3.17 (m, 1 H) 3.67 (s, 3 H) 3.68 (s, 3 H) 4.81-4.93 (m, 2 H) 5.06-5.17 (m, 1 H) 6.69-6.77 (m, 1 H) 6.80-6.87 (m, 1 H) 7.16-7.28 (m, 4 H) 7.55 (d, J=8.79 Hz, 2 H) 7.66-7.75 (m, 3 H) 7.80 (d, J=8.79 Hz, 2 H) 7.96 (d, J=2.20 Hz, 1 H) 8.74 (d, J=8.79 Hz, 1 H) 9.84 (s, 1 H) 9.89 (s, 1 H). MS (ESI) m/z: 669.0 (M+H)+. Analytical HPLC: RT=9.08 min.

Example 53

(S,E)-Methyl 6-(1-(3-(5-chloro-2-(1H-tetrazol-1-yl)phenyl)acrylamido)-2-phenylethyl)-4-(4-(methoxycarbonylamino)phenyl)pyridazine-3-carboxylate

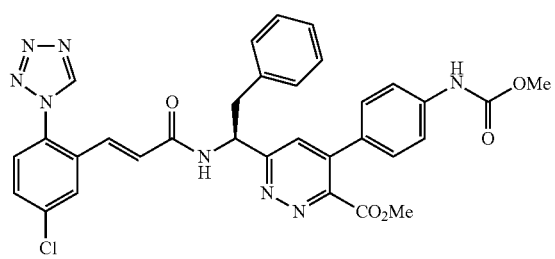

53A. (S)-6-(1-(tert-butoxycarbonylamino)-2-phenylethyl)-4-(4-(methoxycarbonylamino)phenyl)pyridazin-3-yl-trifluoromethanesulfonate: A modification of the procedure described by Rohr was used (*Heterocycles*, 1996, 43(7): 1459-1461). To a cooled (0° C.) solution of 37C (635 mg, 1.162 mmol) in pyridine (7 mL) was added dropwise over 15 min trifluoromethanesulfonic anhydride (0.326 mL, 1.917 mmol). The resulting reaction mixture was allowed to warm to rt over 5 h. Water (20 mL) was added and the mixture was extracted with DCM (3×20 mL). The combined organic layers were washed with brine, dried over Na$_2$SO$_4$, filtered and concentrated to give a red oil. Purification by normal phase chromatography gave 53A (440 mg, 75% purity, 47.6% yield) as a yellow solid. MS (ESI) m/z: 597.0 (M+H)+.

53B. (S)-methyl 6-(1-(tert-butoxycarbonylamino)-2-phenylethyl)-4-(4-(methoxycarbonylamino)phenyl)pyridazine-3-carboxylate: A mixture of 53A (101 mg, 0.127 mmol), palladium(II) acetate (1.140 mg, 5.08 μmol), 1,1'-bis(diphenylphosphino)ferrocene (DPPF) (5.63 mg, 10.16 μmol), methanol (0.360 ml, 8.89 mmol), and N-ethyl-N-isopropylpropan-2-amine (0.049 ml, 0.279 mmol) in DMF (0.8 mL) was purged with carbon monoxide. The reaction mixture was stirred under a carbon monoxide balloon at 55° C. for 4 h. The reaction was cooled to rt and then partitioned between water and EtOAc. The layers were separated and the organic layer was washed with brine, dried over Na$_2$SO$_4$, filtered and concentrated to give a solid. Purification by normal phase chromatography gave 53B (31 mg, 85% purity, 41.0% yield) as a yellow solid. MS (ESI) m/z: 507.3 (M+H)+.

53C. (S)-methyl 6-(1-amino-2-phenylethyl)-4-(4-(methoxycarbonylamino) phenyl)pyridazine-3-carboxylate: This compound was prepared following the procedure described in Example 37D, by replacing 37C with 53B. MS (ESI) m/z: 407.0 (M+H)+.

53D. Example 53 was prepared following the procedure described in 48C, by replacing 48B with 53C. $^1$H NMR (400 MHz, CD$_3$OD) ppm 3.30-3.33 (m, 2 H) 3.75 (s, 3 H) 3.83 (s, 3 H) 5.54 (t, J=7.70 Hz, 1 H) 6.76 (d, J=15.39 Hz, 1 H) 7.07 (d, J=15.39 Hz, 1 H) 7.16-7.28 (m, 7 H) 7.49-7.60 (m, 4 H)

7.64 (dd, J=8.79, 2.20 Hz, 1 H) 7.96 (d, J=2.20 Hz, 1 H) 9.48 s, 1 H). MS (ESI) m/z: 639.1/641.1 (M+H)⁺. Analytical HPLC: RT=8.92 min.

Example 54

(S,E)-Methyl 4-(6-(1-(3-(6-acetyl-3-chloro-2-fluorophenyl)acrylamido)-2-phenylethyl)-3-chloropyridazin-4-yl)phenylcarbamate

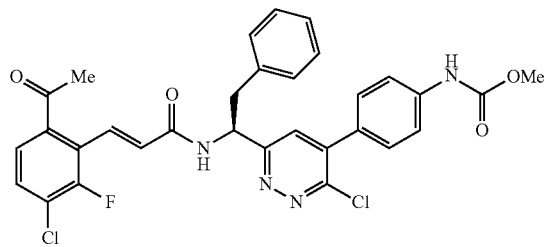

The title compound was prepared following the procedure described in 1D, by replacing 1C with 38A and by replacing Intermediate 1 with Intermediate 4. ¹H NMR (400 MHz, CD₃OD) δ ppm 7.55-7.66 (m, 5H) 7.37-7.47 (m, 3 H) 7.16-7.32 (m, 6 H) 6.63 (dd, J=16.04, 1.89 Hz, 1 H) 5.54 (t, J=7.83 Hz, 1 H) 3.76 (s, 3 H) 3.27-3.37 (m, 2 H) 2.54 (s, 3 H). MS (ESI) m/z: 608.9 (M+H)⁺. Analytical HPLC: RT=9.90 min.

Example 55

(S,E)-Methyl 4-(6-(1-(3-(5-chloro-2-(1H-tetrazol-1-yl)phenyl)acrylamido)-2-phenylethyl)-3-methylpyridazin-4-yl)phenylcarbamate

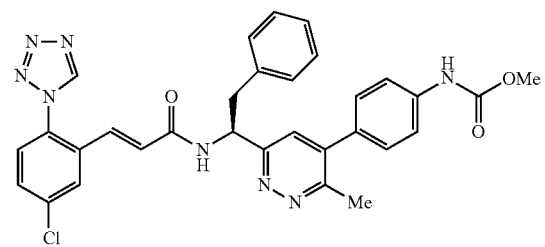

55A. {4-[6-((S)-1-tert-butoxycarbonylamino-2-phenylethyl)-3-chloro-pyridazin-4-yl]-phenyl}-carbamic acid methyl ester: To a solution of 38A (340 mg, 0.684 mmol) in acetonitrile (10 mL) was added BOC₂O (0.191 mL, 0.821 mmol) and TEA (0.191 mL, 1.369 mmol). The reaction mixture was stirred at 60° C. for 3 h. The reaction was cooled to rt and then concentrated. Purification by normal phase chromatography gave 55A (278 mg, 84% yield) as a solid. ¹H NMR (400 MHz, CDCl₃) δ ppm 7.47 (d, J=8.53 Hz, 2 H) 7.17-7.31 (m, 4 H) 7.00-7.11 (m, 2 H) 6.72-6.86 (m, 2 H) 5.85 (d, br, 1 H) 5.05-5.20 (m, 1 H) 3.81 (s, 3 H) 3.40 (dd, J=12.80, 5.27 Hz, 1 H) 3.09 (dd, J=12.67, 9.16 Hz, 1 H) 1.42 (s, 9 H). MS (ESI) m/z: 483.0 (M+H)⁺.

55B. {4-[6-((S)-1-tert-butoxycarbonylamino-2-phenylethyl)-3-methyl-pyridazin-4-yl]-phenyl}-carbamic acid methyl ester: To a solution of 55A (80 mg, 0.166 mmol) in dioxane (10 mL) was added methylboronic acid (49.6 mg, 0.828 mmol), potassium phosphate tribasic (176 mg, 0.828 mmol) and bis(tri-tert-butylphosphine)palladium(0) (16.93 mg, 0.033 mmol). The reaction mixture was stirred at 90° C. for 3 h. The reaction was cooled to rt and the solid was removed by filtration. The filtrate was concentrated and purified. Purification by normal phase chromatography gave 55B (4.1 mg, 53.5% yield) as a solid. MS (ESI) m/z: 463.0 (M+H)⁺.

55C. (S)-methyl 4-(6-(1-amino-2-phenylethyl)-3-methylpyridazin-4-yl)phenylcarbamate TFA salt: To a solution of 55B (40 mg, 0.086 mmol) in DCM (3 mL) was added TFA (1 mL, 12.98 mmol). After 1 h, the reaction was concentrated to give 55C (41 mg, 100% yield). MS (ESI) m/z: 363.1 (M+H)⁺.

55D. Example 55 was prepared following the procedure described in 1D, by replacing 1C with 55C. ¹H NMR (400 MHz, CD₃OD) δ ppm 9.48 (s, 1 H) 7.95 (d, J=2.26 Hz, 1 H) 7.79 (s, 1 H) 7.59-7.70 (m, 3 H) 7.50-7.59 (m, 1 H) 7.37 (d, J=8.53 Hz, 2 H) 7.25-7.32 (m, 2 H) 7.16-7.25 (m, 3 H) 7.06 (d, J=15.56 Hz, 1 H) 6.72 (d, J=15.56 Hz, 1 H) 5.50 (t, J=7.53 Hz, 1 H) 3.76 (s, 3 H) 3.20-3.32 (m, 2 H) 2.77 (s, 3 H). MS (ESI) m/z: 595.0/597.0 (M+H)⁺. Analytical HPLC: RT=7.89 min.

Example 56

(S,E)-Methyl 4-(6-(1-(3-(5-chloro-2-(1H-tetrazol-1-yl)phenyl)acrylamido)-2-phenylethyl)-3-(ethylthio)pyridazin-4-yl)phenylcarbamate

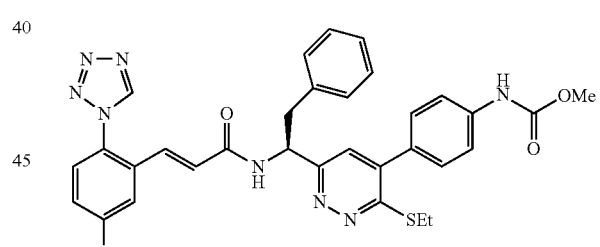

56A. (S)-methyl 4-(6-(1-amino-2-phenylethyl)-3-(ethylthio)pyridazin-4-yl)phenylcarbamate: To a mixture of 38A (45 mg, 0.082 mmol) in THF (1 mL) was added sodium ethanethiolate (14.57 mg, 0.139 mmol). After the addition, the mixture was stirred at 140° C. in a microwave for 5 min. Purification by reverse phase chromatography gave 56A (31 mg, 0.059 mmol, 72.8% yield) as a yellow solid. MS (ESI) m/z: 409.3 (M+H)⁺.

56B. Example 56 was prepared following the procedure described in 48C, by replacing 48B with 56A. ¹H NMR (400 MHz, CDCl₃) δ ppm 1.42 (t, J=7.40 Hz, 3 H) 3.25-3.36 (m, 3 H) 3.55 (dd, J=13.55, 7.03 Hz, 1 H) 3.83 (s, 3 H) 5.44 (d, J=8.53 Hz, 1 H) 6.65 (d, J=15.56 Hz, 1 H) 6.91 (s, 1 H) 7.03 (s, 1 H) 7.13 (s, 1 H) 7.14-7.17 (m, 2 H) 7.25-7.33 (m, 5 H) 7.41 (d, J=8.28 Hz, 1 H) 7.50-7.58 (m, 3 H) 7.80 (d, J=2.26

Hz, 1 H) 8.83 (s, 1 H) 9.31 (d, J=7.28 Hz, 1 H). MS (ESI) m/z: 641.6 (M+H)+. Analytical HPLC: RT=9.50 min.

Example 57

(S,E)-2-(3-(1-(3-(5-Chloro-2-(1H-tetrazol-1-yl)phenyl)acrylamido)-2-phenylethyl)-5-(4-(methoxycarbonylamino)phenyl)-6-oxopyridazin-1(6H)-yl)acetic acid

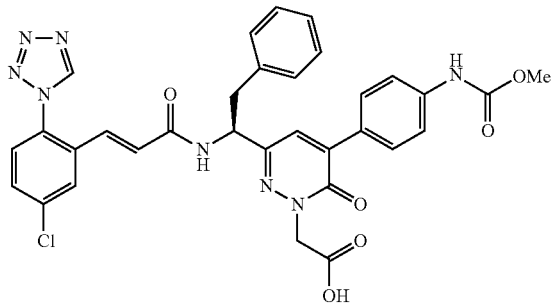

57A. (S)-2-(3-(1-(tert-butoxycarbonylamino)-2-phenylethyl)-5-(4-(methoxycarbonylamino)phenyl)-6-oxopyridazin-1(6H)-yl)acetic acid: This compound was prepared following the procedure described in Example 49A, by replacing 48B with 52A, and by replacing sodium hydroxide with potassium hydroxide. MS (ESI) m/z: 523.1 (M+H)+.

57B. (S)-2-(3-(1-amino-2-phenylethyl)-5-(4-(methoxycarbonyl amino)phenyl)-6-oxopyridazin-1(6H)-yl)acetic acid: This compound was prepared following the procedure described in 37D, by replacing 37C with 57A. MS (ESI) m/z: 423.0 (M+H)+.

57C. Example 57 was prepared following the procedure described in 48C, by replacing 48B with 57B. $^1$H NMR (400 MHz, CD$_3$OD) ppm 3.15-3.26 (m, 2 H) 3.74 (s, 3 H) 4.84-4.95 (m, 2 H) 5.26 (d, J=7.78 Hz, 1 H) 6.71 (d, J=15.56 Hz, 1 H) 7.06 (d, J=15.56 Hz, 1 H) 7.18-7.29 (m, 5 H) 7.37 (s, 1 H) 7.49-7.58 (m, 3 H) 7.62-7.71 (m, 3 H) 7.96 (d, J=2.26 Hz, 1 H) 9.50 (s, 1 H). MS (ESI) m/z: 655.0 (M+H)+. Analytical HPLC: RT=8.06 min.

Example 58

(S,E)-Methyl 4-(6-(1-(3-(5-chloro-2-(1H-tetrazol-1-yl)phenyl)acrylamido)-2-phenylethyl)-3-(ethylsulfonyl)pyridazin-4-yl)phenylcarbamate

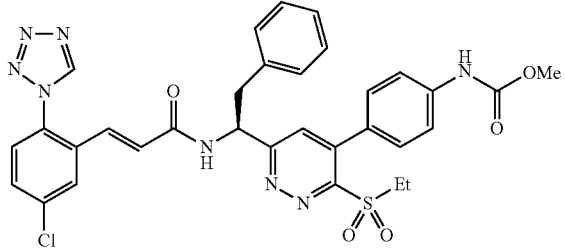

To a mixture of 56B (14 mg, 0.022 mmol) in CHCl$_3$ (2 mL) was added mCPBA (7.34 mg, 0.033 mmol). The resulting solution was stirred at rt for 3.5 h. The reaction was diluted with DCM, washed with saturated sodium sulfite, saturated NaHCO$_3$, brine, and concentrated. Purification by reverse phase chromatography gave Example 58 (4.2 mg, 28.1% yield) as a yellow solid. $^1$H NMR (400 MHz, CD$_3$OD) δ ppm 1.35 (t, J=7.40 Hz, 3 H) 3.36 (m, 2 H) 3.69 (ddd, J=15.87, 7.34, 7.15 Hz, 2 H) 3.77 (s, 3 H) 5.52-5.58 (m, 1 H) 6.73 (d, J=15.56 Hz, 1 H) 7.09-7.17 (m, 3H) 7.19-7.29 (m, 3 H) 7.38-7.42 (m, 3 H) 7.53 (dd, J=19.32, 8.53 Hz, 3 H) 7.61 (dd, J=8.53, 2.26 Hz, 1 H) 7.73 (s, 1 H) 7.92 (d, J=2.26 Hz, 1 H) 9.38 (s, 1 H). MS (ESI) m/z: 673.0/675.1 (M+H)+. Analytical HPLC: RT=8.81 min.

Example 59

(S,E)-6-(1-(3-(5-Chloro-2-(1H-tetrazol-1-yl)phenyl)acrylamido)-2-phenylethyl)-4-(4-(methoxycarbonylamino)phenyl)pyridazine-3-carboxylic acid

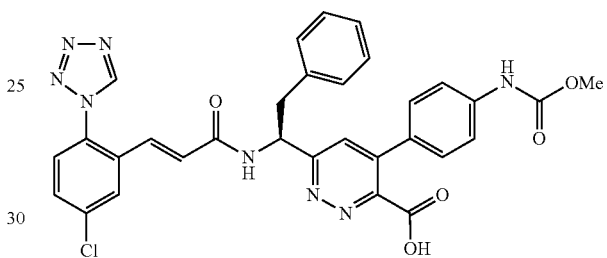

Compound 53B was converted to Example 59 by following the procedures described in 49A, 37D, and 48C. $^1$H NMR (400 MHz, CD$_3$OD) δ ppm 9.48 (1 H, s), 7.96 (1 H, d, J=2.26 Hz), 7.64 (1 H, dd, J=8.53, 2.26 Hz), 7.55 (3 H, dd, J=8.53, 4.02 Hz), 7.49 (1 H, s), 7.33 (2 H, d, J=8.53 Hz), 7.23-7.28 (2 H, m), 7.16-7.22 (3 H, m), 7.07 (1 H, d, J=15.56 Hz), 6.76 (1 H, d, J=15.56 Hz), 5.54 (1 H, t, J=7.65 Hz), 3.75 (3 H, s), 3.33 (2 H, d, J=7.53 Hz). MS (ESI) m/z: 625.1 (M+H)+. Analytical HPLC: RT=7.90 min.

Example 60

(S)-3-(4-(6-(1-(3-(2-(1H-Tetrazol-1-yl)phenyl)propanamido)-2-phenylethyl)pyridazin-4-yl)phenylcarbamoyloxy)propanoic acid

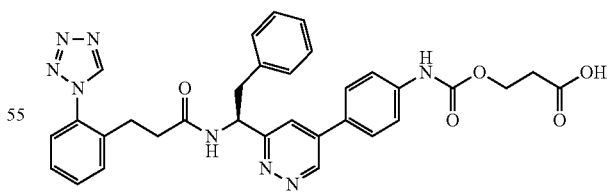

To a solution of 50E (8.5 mg, 0.013 mmol) in MeOH (1.5 mL) was added two drops of aq. NH$_3$ and 10% Pd/C (1.612 mg, 1.514 μmol). The resulting mixture was flushed with hydrogen, and then stirred under a hydrogen balloon for 4 h. The mixture was filtered to remove the catalyst and the filtrate was concentrated. Purification by reverse phase chromatography gave Example 60 (3.7 mg, 6.10 μmol, 48.3%). $^1$H NMR (400 MHz, CD$_3$OD) δ ppm 9.33-9.37 (2 H, m), 7.71 (1 H, s), 7.64 (3 H, s), 7.55 (1 H, d, J=2.01 Hz), 7.37-7.42 (2 H, m), 7.28-7.36 (2 H, m), 7.16-7.26 (3 H, m), 7.10-7.15 (2 H, m), 5.39 (1 H, t, J=7.78 Hz), 4.44 (2 H, t, J=6.27 Hz), 3.21 (2 H, t, J=7.15 Hz), 2.73 (2 H, t, J=6.27 Hz), 2.65-2.71 (2 H, m), 2.49 (2 H, t, J=7.15 Hz). MS (ESI) m/z: 607.1 (M+H)$^+$. Analytical HPLC: RT=6.78 min.

Example 61

(S,E)-Methyl 4-(6-(1-(3-(5-chloro-2-(1H-tetrazol-1-yl)phenyl)acrylamido)-2-phenylethyl)-3-oxo-2,3-dihydropyridazin-4-yl)-2-fluorophenylcarbamate

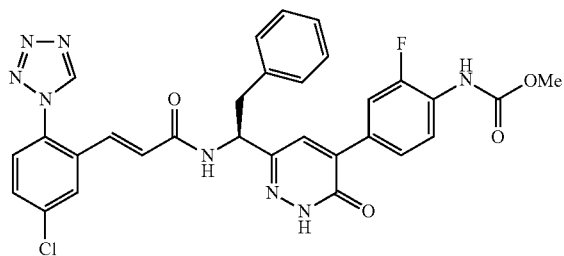

61A. tert-butyl 4-acetyl-2-fluorophenylcarbamate: To a solution of tert-butyl 2-fluoro-4-iodophenylcarbamate (5.5 g, 16.31 mmol) in dioxane (50 mL) was added tributyl(1-ethoxyvinyl)stannane (5.51 mL, 16.31 mmol) and tetrakis(triphenylphosphine)palladium(0) (0.377 g, 0.326 mmol). The reaction mixture was stirred under argon at 100° C. for 12 h. The reaction was cooled to rt, diluted with EtOAc, and washed with saturated NaCl (2×25 mL). The organic layer was dried over MgSO$_4$, filtered, and concentrated. Purification by normal phase chromatography gave 61A (3.29 g, 80% yield) as an off-white solid. MS (ESI) m/z: 254.1 (M+H)$^+$.

61B. 1-(4-amino-3-fluorophenyl)ethanone, HCl salt: A solution of 61A (2.0 g, 7.90 mmol) in HCl (4M in dioxane, 15 mL, 60.0 mmol) was stirred at rt for 4 h. The reaction was concentrated to give 61B (1.21 g, 100% yield) as a brown solid. MS (ESI) m/z: 154.1 (M+H)$^+$.

61C. methyl 4-acetyl-2-fluorophenylcarbamate: This compound was prepared according to the procedure described in Example 37C, by replacing 37B with 61B. MS (ESI) m/z: 212.1 (M+H)$^+$.

61D. 2-(3-fluoro-4-(methoxycarbonylamino)phenyl)-2-oxoacetic acid: To a solution of 61C (1.61 g, 7.62 mmol) in pyridine (20 mL) was added SeO$_2$ (1.269 g, 11.44 mmol). The reaction mixture was stirred under argon at 100° C. for 5 h. The reaction was cooled to rt and most of the pyridine was removed in vacuo. The reaction mixture was diluted with CH$_2$Cl$_2$, washed with 1M HCl (1×25 mL) and saturated NaCl (1×25 mL). The organic layer was dried over Na$_2$SO$_4$, filtered, and concentrated to give 61D (1.747 g, 95% yield) as a tan solid. MS (ESI) m/z: 242.0 (M+H)$^+$.

61E. methyl 2-(3-fluoro-4-(methoxycarbonylamino)phenyl)-2-oxoacetate: To a solution of 61D (1.75 g, 7.26 mmol) in DCM (30 mL) was added TEA (1.011 mL, 7.26 mmol) and methyl chloroformate (0.558 mL, 7.26 mmol). After 30 min, the reaction mixture was diluted with CH$_2$Cl$_2$, washed with 1M HCl (1×20 mL) and saturated NaCl (1×20 mL). The organic layer was dried over Na$_2$SO$_4$, filtered, and concentrated to give 61E (1.60 g, 86% yield) as a tan solid. MS (ESI) m/z: 256.0 (M+H)$^+$.

61F. {4-[6-((S)-1-tert-butoxycarbonylamino-2-phenylethyl)-3-oxo-2,3-dihydro-pyridazin-4-yl]-2-fluoro-phenyl}-carbamic acid methyl ester: This compound was prepared according to the procedure described in Example 37A, by replacing ethyl-2-(4-nitrophenyl)-2-oxoacetate with 61E. MS (ESI) m/z: 482.9 (M+H)$^+$.

61G. Example 61: Compound 61F was converted to Example 61 by following the procedures described in 37D and 1D. $^1$H NMR (400 MHz, DMF-d$_7$) δ ppm 13.19 (s, 1 H) 9.89 (s, 1 H) 9.61 (s, 1 H) 8.87 (d, J=8.28 Hz, 1 H) 7.97-8.03 (m, 3 H) 7.86 (s, 1 H) 7.75-7.85 (m, 3 H) 7.26-7.37 (m, 4 H) 7.17-7.25 (m, 1 H) 7.05 (d, J=15.56 Hz, 1 H) 6.95 (d, J=15.56 Hz, 1 H) 5.25-5.37 (m, 1 H) 3.77 (s, 3 H) 3.29 (dd, J=13.80, 6.53 Hz, 1 H) 3.20 (dd, J=13.80, 8.53 Hz, 1 H). MS (ESI) m/z: 615.0 (M+H)$^+$. Analytical HPLC: RT=8.68 min.

Example 62

(S,E)-Methyl 4-(3-chloro-6-(1-(3-(5-chloro-2-(1H-tetrazol-1-yl)phenyl)acrylamido)-2-phenylethyl)pyridazin-4-yl)-2-fluorophenylcarbamate

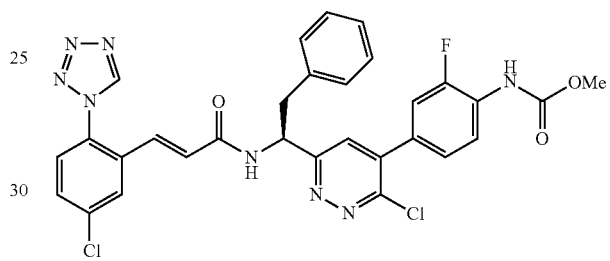

62A. (S)-methyl 4-(6-(1-amino-2-phenylethyl)-3-chloropyridazin-4-yl)-2-fluorophenylcarbamate TFA salt: This compound was prepared according to the procedure described in Example 38A, by replacing 37C with 61F. MS (ESI) m/z: 400.9 (M+H)$^+$.

62B. Example 62 was prepared following the procedure described in 1D, by replacing 1C with 62A. $^1$H NMR (400 MHz, DMF-d$_7$) δ ppm 10.04 (s, 1 H) 9.87 (s, 1 H) 9.20 (d, J=8.03 Hz, 1 H) 8.25-8.31 (m, 1 H) 8.04 (s, 1 H) 7.90-8.02 (m, 2H) 7.76 (dd, J=11.92, 1.88 Hz, 1 H) 7.62 (d, J=8.53 Hz, 1 H) 7.44-7.54 (m, 4 H) 7.35-7.43 (m, 1 H) 7.10-7.25 (m, 2 H) 5.74-5.87 (m, 1 H) 3.95 (s, 3 H) 3.43-3.61 (m, 2 H). MS (ESI) m/z: 633.0 (M+H)$^+$. Analytical HPLC: RT=9.69 min.

Example 63

(S,E)-Methyl 4-(6-(1-(3-(5-chloro-2-(1H-tetrazol-1-yl)phenyl)acrylamido)-2-phenylethyl)pyridazin-4-yl)-2-fluorophenylcarbamate

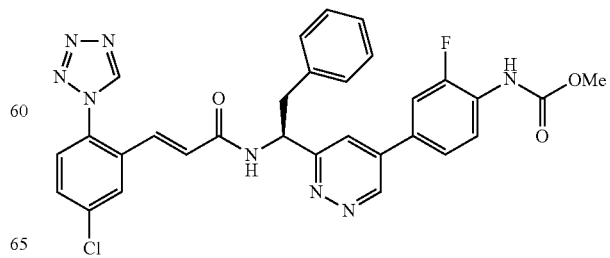

The title compound was prepared following the procedures described in Example 41, by replacing 38A with 62A. $^1$H NMR (400 MHz, DMF-d$_7$) δ ppm 10.05 (s, 1 H) 9.81 (d, J=2.26 Hz, 1 H) 8.31 (t, J=8.41 Hz, 1 H) 8.09 (dd, J=12.30, 2.01 Hz, 1 H) 7.92-8.02 (m, 3 H) 7.42-7.50 (m, 4 H) 7.34-7.42 (m, 1 H) 7.20 (s, 2H) 5.81 (dd, J=8.53, 6.27 Hz, 1 H) 3.95 (s, 3 H) 3.53-3.60 (m, 1 H) 3.45-3.53 (m, 1H). MS (ESI) m/z: 599.1 (M+H)$^+$. Analytical HPLC: RT=8.89 min.

Example 64

(S,E)-N-(1-(5-(4-Aminophenyl)pyridazin-3-yl)-2-phenylethyl)-3-(5-chloro-2-(1H-tetrazol-1-yl)phenyl)acrylamide

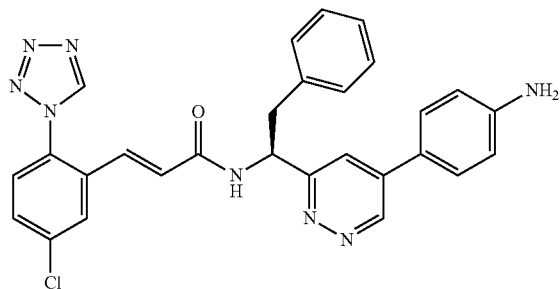

Compound 37B was converted to Example 64 by following the procedures described in 38A, 37B, and 48C. $^1$H NMR (400 MHz, CD$_3$OD) δ ppm 9.49 (1 H, s), 9.47 (1 H, d, J=2.26 Hz), 8.02 (1 H, d, J=2.26 Hz), 7.97 (1 H, d, J=2.26 Hz), 7.76-7.81 (2 H, m), 7.66 (1 H, dd, J=8.53, 2.26 Hz), 7.54-7.58 (1 H, m), 7.24-7.30 (2 H, m), 7.17-7.23 (3 H, m), 7.08 (1 H, d, J=15.56 Hz), 6.91 (2 H, d, J=8.78 Hz), 6.75 (1H, d, J=15.56 Hz), 5.42 (1 H, t, J=7.78 Hz), 3.32-3.40 (2 H, m). MS (ESI) m/z: 523.0 (M+H)$^+$. Analytical HPLC: RT=6.61 min.

Example 65

(S,E)-Methyl 4-(3-carbamoyl-6-(1-(3-(5-chloro-2-(1H-tetrazol-1-yl)phenyl)acrylamido)-2-phenylethyl)pyridazin-4-yl)phenylcarbamate

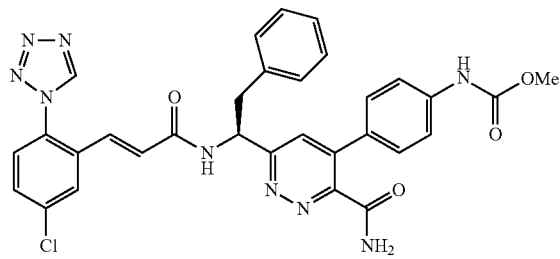

The title compound was prepared according to the procedure described in 48C, by replacing Intermediate 1B with Example 59 and by replacing 48B with ammonium chloride. $^1$H NMR (400 MHz, CD$_3$OD) δ ppm 9.49 (1 H, s), 7.96 (1 H, d, J=2.26 Hz), 7.62-7.67 (1 H, m), 7.52-7.57 (3 H, m), 7.49 (1 H, s), 7.37-7.42 (2 H, m), 7.23-7.29 (2 H, m), 7.17-7.22 (3 H, m), 7.06 (1 H, d, J=15.56 Hz), 6.75 (1 H, d, J=15.56 Hz), 5.52 (1 H, t, J=7.65 Hz), 3.75 (3 H, s), 3.33-3.37 (2 H, m). MS (ESI) m/z: 624.0 (M+H)$^+$. Analytical HPLC: RT=8.31 min.

Example 66

(S,E)-2-Methoxyethyl 4-(6-(1-(3-(5-chloro-2-(1H-tetrazol-1-yl)phenyl)acrylamido)-2-phenylethyl)pyridazin-4-yl)phenylcarbamate

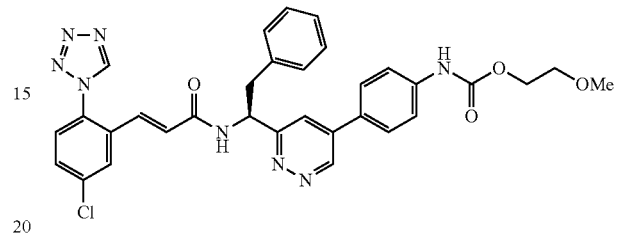

Example 64 was converted to the title compound by following the procedure described in 50D. $^1$H NMR (400 MHz, CD$_3$OD) δ ppm 9.52 (1 H, d, J=2.01 Hz), 9.48 (1 H, s), 7.95 (2 H, dd, J=13.18, 2.13 Hz), 7.77 (2 H, d, J=8.78 Hz), 7.65 (3 H, td, J=5.71, 2.89 Hz), 7.53-7.58 (1 H, m), 7.23-7.28 (2 H, m), 7.17-7.22 (3 H, m), 7.07 (1 H, d, J=15.56 Hz), 6.76 (1 H, d, J=15.56 Hz), 5.51 (1 H, t, J=7.78 Hz), 4.27-4.33 (2 H, m), 3.65 (2 H, dd, J=5.40, 3.89 Hz), 3.39 (3 H, s), 3.34 (2 H, d, J=2.26 Hz). MS (ESI) m/z: 625.1 (M+H)$^+$. Analytical HPLC: RT=8.67 min.

Example 67

(S,E)-Methyl 4-(6-(1-(3-(5-chloro-2-(1H-tetrazol-1-yl)phenyl)acrylamido)-2-(3-fluorophenyl)ethyl)-3-oxo-2,3-dihydropyridazin-4-yl)phenylcarbamate

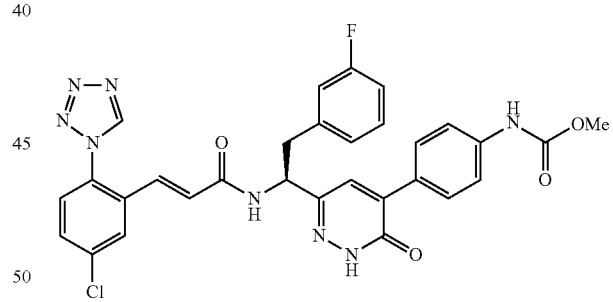

67A. (S)-tert-butyl 2-(3-fluorophenyl)-1-(5-(4-nitrophenyl)-6-oxo-1,6-dihydropyridazin-3-yl)ethylcarbamate: This compound was prepared following the procedure described in 37A, by replacing (S)-tert-butyl 4-(dimethoxyphosphoryl)-3-oxo-1-phenylbutan-2-ylcarbamate with Intermediate 5. MS (ESI) m/z: 455.0 (M+H)$^+$.

67B. (4-{6-[(S)-1-tert-butoxycarbonylamino-2-(3-fluorophenyl)-ethyl]-3-oxo-2,3-dihydro-pyridazin-4-yl}-phenyl)-carbamic acid methyl ester: This compound was prepared following the procedures described in 37B and 37C, by replacing 37A with 67A. MS (ESI) m/z: 483.0 (M+H)$^+$.

67C. Example 67 was prepared following the procedures described in 37D and 37E, by replacing 37C with 67B. $^1$H NMR (400 MHz, DMF-d$_7$) δ ppm 13.08 (s, 1 H) 9.88 (s, 1 H) 9.88 (s, 1 H) 8.86 (d, J=8.28 Hz, 1 H) 8.00-8.02 (m, 2 H) 7.99

(s, 1 H) 7.76-7.86 (m, 3 H) 7.69 (d, J=9.03 Hz, 2 H) 7.36 (td, J=7.91, 6.27 Hz, 1 H) 7.15-7.24 (m, 2 H) 7.00-7.09 (m, 2 H) 6.93 (d, J=15.56 Hz, 1 H) 5.33 (td, J=8.41, 6.27 Hz, 1 H) 3.74 (s, 3 H) 3.34 (dd, J=13.55, 6.02 Hz, 1 H) 3.22 (dd, J=13.55, 8.78 Hz, 1 H). MS (ESI) m/z: 615.0 (M+H)+. Analytical HPLC: RT=8.88 min.

Example 68

(S,E)-Methyl 4-(3-chloro-6-(1-(3-(5-chloro-2-(1H-tetrazol-1-yl)phenyl)acrylamido)-2-(3-fluorophenyl)ethyl)pyridazin-4-yl)phenylcarbamate

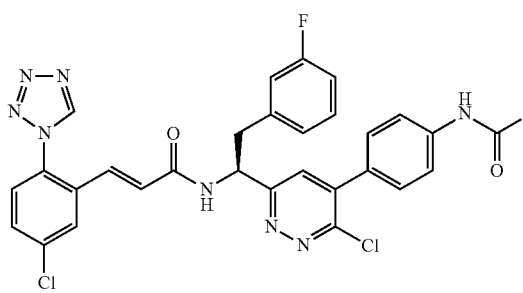

The title compound was prepared following the procedures described in Example 38, by replacing 37C with 67B. ¹H NMR (400 MHz, DMF-d₇) δ ppm 10.14 (s, 1 H) 10.04 (s, 1 H) 9.21 (d, J=8.28 Hz, 1 H) 8.19 (m, 1 H) 8.05 (s, 1 H) 7.92-8.01 (m, 4 H) 7.76-7.82 (m, 2 H) 7.53 (td, J=7.91, 6.27 Hz, 1 H) 7.31-7.43 (m, 2 H) 7.17-7.26 (m, 2 H) 7.11-7.17 (m, J=15.56 Hz, 1 H) 5.83 (td, J=8.60, 5.90 Hz, 1 H) 3.93 (s, 3 H) 3.61 (dd, J=13.68, 5.90 Hz, 1 H) 3.47-3.56 (m, J=13.80, 9.03 Hz, 1 H). MS (ESI) m/z: 632.9 (M+H)+. Analytical HPLC: RT=9.73 min.

Example 69

(S,E)-Methyl 4-(6-(1-(3-(5-chloro-2-(1H-tetrazol-1-yl)phenyl)acrylamido)-2-(3-fluorophenyl)ethyl)pyridazin-4-yl)phenylcarbamate

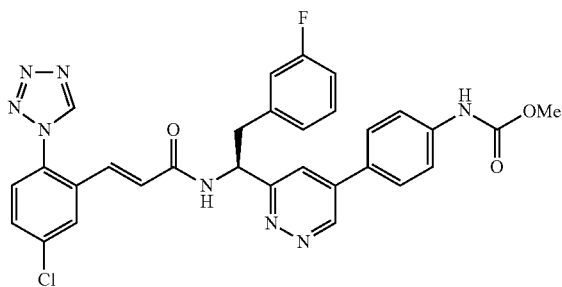

The title compound was prepared following the procedure described in 38A, by replacing 37C with 67B, and then following the procedure described in Example 41. ¹H NMR (400 MHz, CD₃OD) δ ppm 9.51 (d, J=1.51 Hz, 1 H) 9.49 (s, 1 H) 7.97 (s, 2 H) 7.79 (d, J=8.78 Hz, 2 H) 7.66 (d, J=8.03 Hz, 3 H) 7.51-7.58 (m, 1H) 7.22-7.32 (m, 1 H) 7.08 (d, J=15.81 Hz, 1 H) 6.98-7.05 (m, 2 H) 6.94 (t, J=8.53 Hz, 1 H) 6.75 (d, J=15.56 Hz, 1 H) 5.55 (t, J=7.65 Hz, 1 H) 3.77 (s, 3 H) 3.33-3.42 (m, 2 H). MS (ESI) m/z: 599.0 (M+H)+. Analytical HPLC: RT=8.85 min.

Example 70

(S,E)-Methyl 4-(6-(1-(3-(5-chloro-2-(1H-tetrazol-1-yl)phenyl)acrylamido)-2-(1-ethyl-1H-pyrazol-3-yl)ethyl)-3-oxo-2,3-dihydropyridazin-4-yl)phenylcarbamate

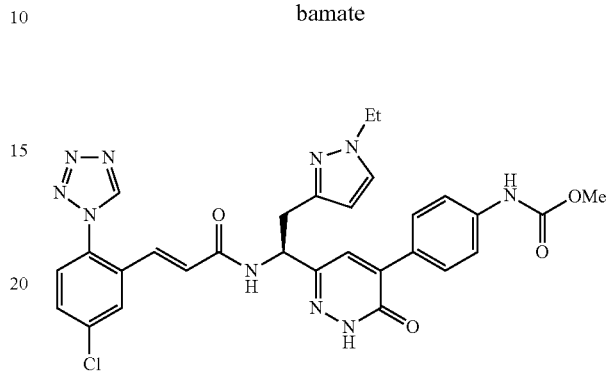

70A. (4-{6-[(S)-1-tert-butoxycarbonylamino-2-(1-ethyl-1H-pyrazol-3-yl)-ethyl]-3-oxo-2,3-dihydro-pyridazin-4-yl}-phenyl)-carbamic acid methyl ester: The compound was prepared according to the procedures described in 37A, 37B, and 37C, by replacing (S)-tert-butyl 4-(dimethoxyphosphoryl)-3-oxo-1-phenylbutan-2-ylcarbamate with Intermediate 6. MS (ESI) m/z: 483.3 (M+H)+.

70B. Example 70 was prepared according to the procedures described in 37D and 37E, by replacing 37C with 70A. ¹H NMR (400 MHz, CD₃OD) δ ppm 9.51 (s, 1 H) 7.96 (d, J=2.26 Hz, 1 H) 7.75 (d, J=8.78 Hz, 2 H) 7.62-7.68 (m, J=8.53, 2.26 Hz, 1 H) 7.56 (d, J=8.53 Hz, 1 H) 7.54 (s, 1 H) 7.49-7.53 (m, 2 H) 7.42 (s, 1 H) 7.10 (d, J=15.81 Hz, 1 H) 6.72 (d, J=15.81 Hz, 1 H) 6.13 (d, J=2.26 Hz, 1 H) 5.29 (t, J=7.40 Hz, 1 H) 4.08 (q, J=7.28 Hz, 2 H) 3.75 (s, 3 H) 3.13-3.26 (m, 2 H) 1.33 (t, J=7.28 Hz, 3 H). MS (ESI) m/z: 615.3 (M+H)+. Analytical HPLC: RT=7.69 min.

Example 71

(S,E)-Methyl 4-(3-chloro-6-(1-(3-(5-chloro-2-(1H-tetrazol-1-yl)phenyl)acrylamido)-2-(1-ethyl-1H-pyrazol-3-yl)ethyl)pyridazin-4-yl)phenylcarbamate

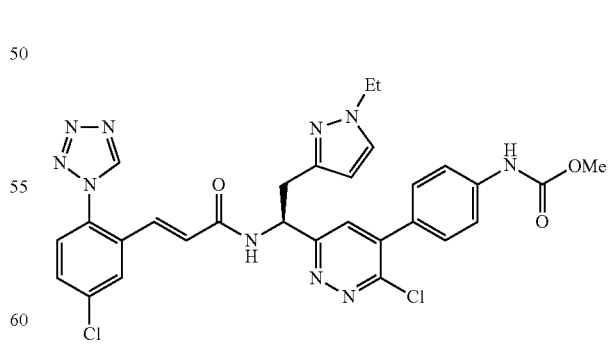

The title compound was prepared using the procedure described in Example 38, by replacing 37C with 70A. ¹H NMR (400 MHz, CD₃OD) δ ppm 9.50 (s, 1 H) 7.98 (d, J=2.01 Hz, 1 H) 7.63-7.67 (m, J=8.53, 2.26 Hz, 1 H) 7.61 (d, J=8.78 Hz, 2 H) 7.54-7.58 (m, J=8.53 Hz, 1 H) 7.49-7.52 (m, 2 H)

7.46 (d, J=8.78 Hz, 2 H) 7.09 (d, J=15.81 Hz, 1 H) 6.77 (d, J=15.56 Hz, 1 H) 6.08 (d, J=2.26 Hz, 1 H) 5.53 (t, J=7.53 Hz, 1 H) 4.07 (q, J=7.28 Hz, 2 H) 3.76 (s, 3 H) 3.24-3.37 (m, 2 H) 1.32 (t, J=7.28 Hz, 3 H). MS (ESI) m/z: 633.0 (M+H)⁺. Analytical HPLC: RT=10.70 min.

Example 72

(S,E)-Methyl 4-(6-(1-(3-(5-chloro-2-(1H-tetrazol-1-yl)phenyl)acrylamido)-2-(1-ethyl-1H-pyrazol-3-yl)ethyl)pyridazin-4-yl)phenylcarbamate

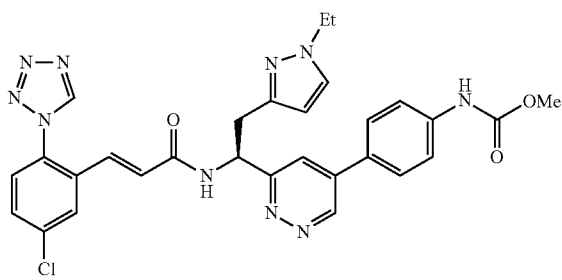

The title compound was prepared using the procedures described in 3 8A and Example 41, by replacing 37C with 70A. ¹H NMR (400 MHz, CD₃OD) δ ppm 9.55 (d, J=2.26 Hz, 1 H) 9.50 (s, 1 H) 8.04 (d, J=2.26 Hz, 1 H) 7.99 (d, J=2.26 Hz, 1H) 7.84 (d, J=8.78 Hz, 2 H) 7.68 (d, J=9.03 Hz, 2 H) 7.65 (dd, J=8.53, 2.26 Hz, 1 H) 7.56 (d, J=8.53 Hz, 1 H) 7.50 (d, J=2.26 Hz, 1 H) 7.10 (d, J=15.56 Hz, 1 H) 6.78 (d, J=15.81 Hz, 1 H) 6.11 (d, J=2.26 Hz, 1 H) 5.54 (t, J=7.53 Hz, 1 H) 4.05 (q, J=7.28 Hz, 2 H) 3.77 (s, 3 H) 3.34-3.36 (m, 2 H) 1.30 (t, J=7.28 Hz, 3 H). MS (ESI) m/z: 599.0 (M+H)⁺. Analytical HPLC: RT=9.46 min.

Example 73

(S,E)-Methyl 4-(6-(1-(3-(5-chloro-2-(1H-tetrazol-1-yl)phenyl)acrylamido)-2-phenylethyl)-3-(hydroxymethyl)pyridazin-4-yl)phenylcarbamate

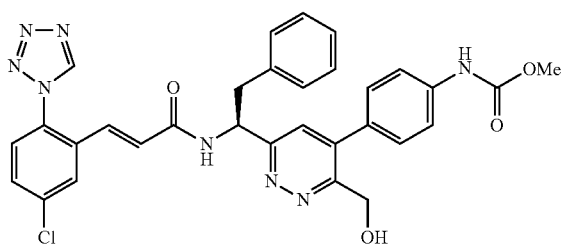

73A. {4-[6-((S)-1-tert-butoxycarbonylamino-2-phenylethyl)-3-hydroxymethyl-pyridazin-4-yl]-phenyl}-carbamic acid methyl ester: To a slurry of 53B (30.3 mg, 0.060 mmol) in EtOH (1 mL) was added calcium chloride (1.992 mg, 0.018 mmol). The resulting mixture was cooled to −10° C. and sodium borohydride (5.66 mg, 0.150 mmol) in ethanol (0.5 mL) was slowly added. The mixture was then allowed to warm to rt and stand at rt for 40 min. The mixture was concentrated to remove the solvent. The residue was dissolved in EtOAc and then washed with water. The aqueous layer was extracted with EtOAc. The combined organic layers were washed with brine, dried (Na₂SO₄), filtered, and concentrated to give 73A (31 mg, 0.060 mmol, 100% yield) as a colorless solid. MS (ESI) m/z: 479.1 (M+H)⁺.

73B. Example 73 was prepared following the procedures described in 37D and 48C, by replacing 37C with 73A. ¹H NMR (400 MHz, CD₃OD) ppm 9.49 (1 H, s), 7.95 (1 H, d, J=2.26 Hz), 7.81 (1 H, s), 7.61-7.67 (3 H, m), 7.54-7.58 (1 H, m), 7.41 (2 H, d, J=8.78 Hz), 7.20-7.30 (5 H, m), 7.06 (1 H, d, J=15.56 Hz), 6.73 (1 H, d, J=15.56 Hz), 5.51-5.57 (1 H, m), 4.96 (2 H, s), 3.76 (3 H, s), 3.34 (2 H, d, J=7.78 Hz). MS (ESI) m/z: 611.1 (M+H)⁺. Analytical HPLC: RT=7.06 min.

Example 74

(S,E)-Methyl 4-(6-(1-(3-(5-chloro-2-(1H-tetrazol-1-yl)phenyl)acrylamido)-2-phenylethyl)-3-(methylcarbamoyl)pyridazin-4-yl)phenylcarbamate

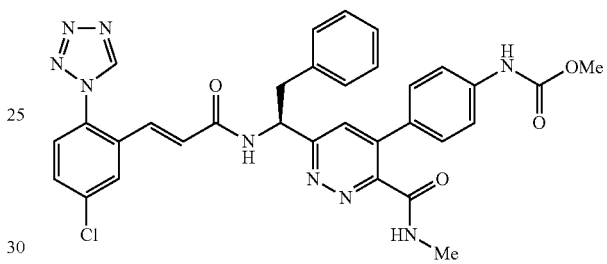

The title compound was prepared using the procedure described in 48C, by replacing Intermediate 1B with Example 59 and by replacing 48B with methanamine ¹H NMR (400 MHz, DMSO-D₆) δ ppm 9.91 (1 H, s), 9.83 (1 H, s), 9.00 (1 H, d, J=8.28 Hz), 8.81 (1 H, t, J=4.52 Hz), 7.96 (1 H, d, J=2.01 Hz), 7.69-7.77 (3 H, m), 7.56 (2 H, d, J=8.78 Hz), 7.39 (2 H, d, J=8.78 Hz), 7.25-7.31 (4 H, m), 7.17-7.23 (1 H, m), 6.80 (2 H, s), 5.45 (1 H, td, J=8.72, 6.15 Hz), 3.69 (3 H, s), 3.20 (2 H, ddd, J=19.32, 13.93, 5.14 Hz), 2.73 (3 H, d, J=4.77 Hz). MS (ESI) m/z: 638.1 (M+H)⁺. Analytical HPLC: RT=7.55 min.

Example 75

(S,E)-Methyl 4-(6-(1-(3-(5-chloro-2-(1H-tetrazol-1-yl)phenyl)acrylamido)-2-phenylethyl)-3-vinylpyridazin-4-yl)phenylcarbamate

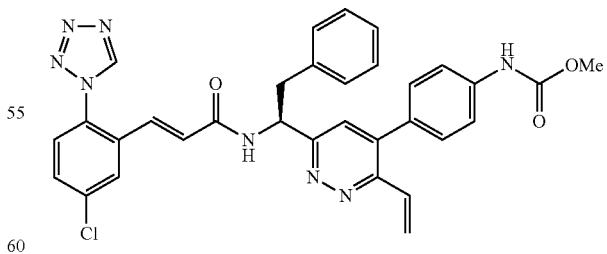

75A. {4-[6-((S)-1-tert-butoxycarbonylamino-2-phenylethyl)-3-vinyl-pyridazin-4-yl]-phenyl}-carbamic acid methyl ester: The compound was prepared using the procedure described in Example 55B, by replacing methylboronic acid with potassium vinyltrifluoroborate. LC-MS (ESI) m/z: 475.1 (M+H)⁺.

75B. Example 75 was prepared following the procedures described in 37D-E, by replacing 37C with 75A. $^1$H NMR (400 MHz, CD$_3$OD) δ ppm 9.49 (s, 1H) 7.96 (d, J=2.26 Hz, 1 H) 7.64 (dd, J=8.53, 2.26 Hz, 1 H) 7.59 (d, J=8.53 Hz, 2 H) 7.54-7.57 (m, 1 H) 7.41 (s, 1 H) 7.29 (d, J=8.78 Hz, 2 H) 7.25 (d, J=7.28 Hz, 2 H) 7.17-7.22 (m, 3 H) 7.07 (d, J=15.56 Hz, 1 H) 6.87 (dd, J=17.32, 11.04 Hz, 1 H) 6.75 (d, J=15.56 Hz, 1 H) 6.45 (dd, J=17.32, 1.51 Hz, 1 H) 5.66 (dd, J=11.04, 1.51 Hz, 1H) 5.49 (t, J=7.65 Hz, 1 H) 3.76 (s, 3 H) 3.29-3.34 (m, 2 H). MS (ESI) m/z: 607.1/609.1 (M+H)$^+$. Analytical HPLC: RT=8.52 min.

Example 76

Methyl 4-(6-((S)-1-((E)-3-(5-chloro-2-(1H-tetrazol-1-yl)phenyl)acrylamido)-2-phenylethyl)-3-(1,2-dihydroxyethyl)pyridazin-4-yl)phenylcarbamate (diastereomer mixture)

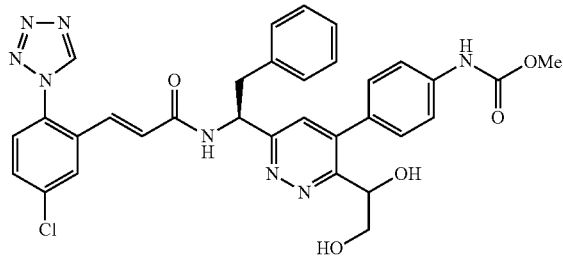

76A. {4-[6-((S)-1-tert-butoxycarbonylamino-2-phenylethyl)-3-(1,2-dihydroxy-ethyl)-pyridazin-4-yl]-phenyl}-carbamic acid methyl ester: To a cooled solution (0° C.) of 75A (25 mg, 0.053 mmol) in acetonitrile (3 mL) were added osmium tetraoxide (0.033 mL, 2.63 μmol) and NMO (9.26 mg, 0.079 mmol). The reaction mixture was stirred under argon at 0° C. for 4 hrs. Purification by reverse phase chromatography gave 76A (21.1 mg, 0.041 mmol, 79% yield) as a solid. LC-MS (ESI) m/z: 509.1 (M+H)$^+$.

76B. Example 76 was prepared following the procedures described in 37D-E, by replacing 37C with 76A. $^1$H NMR (400 MHz, CD$_3$OD) δ ppm 9.49 (s, 1H) 7.96 (d, J=1.76 Hz, 1 H) 7.65 (dd, J=8.53, 2.26 Hz, 1 H) 7.61 (d, J=8.78 Hz, 2 H) 7.55 (d, J=8.78 Hz, 1 H) 7.50 (s, 1 H) 7.33-7.41 (m, 2 H) 7.22-7.30 (m, 2 H) 7.15-7.22 (m, 3 H) 7.06 (d, J=15.56 Hz, 1 H) 6.74 (d, J=15.56 Hz, 1 H) 5.45-5.57 (m, 1H) 5.15 (td, J=5.65, 3.01 Hz, 1 H) 3.88 (m, 1 H) 3.77-3.82 (m, 1 H) 3.76 (s, 3 H) 3.29-3.34 (m, 2 H). MS (ESI) m/z: 641.2 (M+H)$^+$. Analytical HPLC: RT=6.93 min.

Example 77

(S,E)-3-(5-Chloro-2-(1H-tetrazol-1-yl)phenyl)-N-(1-(5-(4-(2,4-dioxo-1,3-oxazinan-3-yl)phenyl)pyridazin-3-yl)-2-phenylethyl)acrylamide

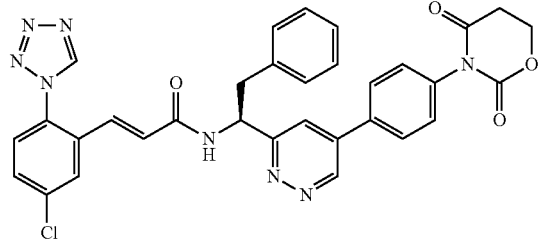

The title compound was prepared using the procedure described in 48C, by replacing 1B with des-Cl of Example 50, and by replacing 48B with ammonium chloride. $^1$H NMR (400 MHz, CD$_3$OD) δ ppm 9.47-9.50 (2 H, m), 7.97 (1 H, d, J=2.01 Hz), 7.83 (1 H, s), 7.79-7.82 (2 H, m), 7.62-7.66 (1 H, m), 7.53-7.57 (1 H, m), 7.45 (2 H, d, J=8.53 Hz), 7.22-7.28 (2 H, m), 7.16-7.21 (3 H, m), 7.08 (1 H, d, J=15.81 Hz), 6.77 (1 H, d, J=15.56 Hz), 5.55 (1 H, t, J=7.65 Hz), 4.63 (2 H, t, J=6.27 Hz), 3.34 (2 H, d, J=7.53 Hz), 3.03 (2 H, t, J=6.27 Hz). MS (ESI) m/z: 621.0 (M+H)$^+$. Analytical HPLC: RT=7.63 min.

Example 78

(S,E)-3-(5-Chloro-2-(1H-tetrazol-1-yl)phenyl)-N-(1-(5-(4-hydroxy-2-oxo-1,2-dihydroquinolin-6-yl)pyridazin-3-yl)-2-phenylethyl)acrylamide

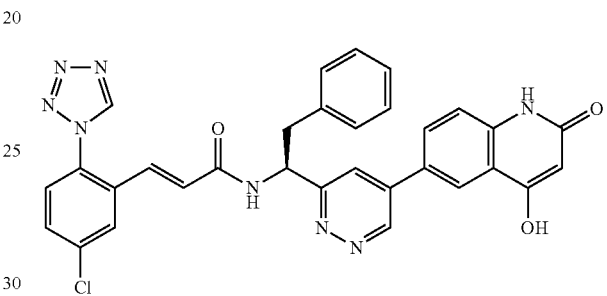

78A. {4-[6-((S)-1-tert-butoxycarbonylamino-2-phenylethyl)-3-oxo-2,3-dihydro-pyridazin-4-yl]-phenyl}-carbamic acid benzyl ester: To a cooled solution (0° C.) of 37B (340 mg, 0.836 mmol) in dichloromethane (20 mL) were added pyridine (0.081 mL, 1.004 mmol) and CBZ-Cl (0.119 mL, 0.836 mmol). The reaction mixture was stirred under argon at 0° C. for 1 h. The reaction mixture was diluted with CH$_2$Cl$_2$, washed with IM HCl (1×5 mL) and brine (1×10 mL). The organic phase was dried over Na$_2$SO$_4$, filtered and concentrated to give 78A (0.45 g, 0.832 mmol, 100% yield) as a light yellow solid. LC-MS (ESI) m/z: 541.1 (M+H)$^+$.

78B. (S)-tert-butyl 1-(5-(4-aminophenyl)pyridazin-3-yl)-2-phenylethylcarbamate: The compound was prepared using the procedures described in 38A, 55A, and 37B, by replacing 37C with 78A. LC-MS (ESI) m/z: 391.1 (M+H)$^+$.

78C. (S)-tert-butyl 3-(4-(6-(1-(tert-butoxycarbonylamino)-2-phenylethyl)pyridazin-4-yl)phenylamino)-3-oxopropanoate: To a solution of 78B (58 mg, 0.149 mmol) in DMF (5.0 mL) were added 3-tert-butoxy-3-oxopropanoic acid (28.5 mg, 0.178 mmol), PyBOP (93 mg, 0.178 mmol) and DIEA (0.052 mL, 0.297 mmol). The reaction mixture was stirred over night. The reaction mixture was diluted with EtOAc, washed with IM HCl (1×5 mL), saturated NaHCO$_3$ (1×5 mL) and brine (1×5 mL). The organic phase was dried over MgSO$_4$, filtered and concentrated. Purification by normal phase chromatography gave 78C (70 mg, 0.131 mmol, 88% yield) as a solid. LC-MS (ESI) m/z: 533.1 (M+H)$^+$.

78D. (S)-6-(6-(1-amino-2-phenylethyl)pyridazin-4-yl)-4-hydroxyquinolin-2(1H)-one, TFA salt: To a powder of 78C (70 mg, 0.131 mmol) was added PPA (2.427 ml, 0.131 mmol) at rt. The reaction mixture was stirred under argon at 130° C. for 1 h. The reaction was cooled to rt and ice was added cautiously. Purification by reverse phase chromatography gave 78D (28.5 mg, 0.060 mmol, 45.9% yield) as a white solid. LC-MS (ESI) m/z: 359.1 (M+H)$^+$.

78E. Example 78 was prepared by following the procedure described in 1D, by replacing 1C with 78D. ¹H NMR (400 MHz, CD₃OD) δ ppm 9.49 (s, 1 H) 9.48 (s, 1 H) 8.30 (d, J=2.01 Hz, 1 H) 7.98 (d, J=2.26 Hz, 1 H) 7.94 (dd, J=8.78, 2.01 Hz, 1 H) 7.75 (d, J=2.01 Hz, 1 H) 7.65 (dd, J=8.53, 2.51 Hz, 1 H) 7.55 (d, J=8.28 Hz, 1 H) 7.48 (d, J=8.78 Hz, 1 H) 7.23-7.29 (m, 2 H) 7.16-7.22 (m, 3 H) 7.08 (d, J=15.56 Hz, 1 H) 6.79 (d, J=15.56 Hz, 1 H) 5.94 (s, 1 H) 5.54 (t, J=7.65 Hz, 1 H) 3.21-3.39 (m, 2 H). LC-MS (ESI) m/z: 591.2 (M+H)⁺. Analytical HPLC: RT=6.71 min.

Example 79

(S,E)-3-Amino-3-oxopropyl 4-(6-(1-(3-(5-chloro-2-(1H-tetrazol-1-yl)phenyl)acrylamido)-2-phenylethyl)pyridazin-4-yl)phenylcarbamate

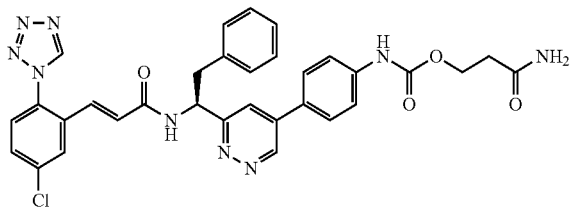

The title compound was prepared using the procedure described in 50D, by replacing 50C with Example 64, and by replacing tert-butyl 3-hydroxypropanoate with 3-hydroxypropanamide. ¹H NMR (400 MHz, CD₃OD) δ ppm 9.64 (1 H, s), 9.48-9.53 (2 H, m), 7.97 (1 H, d, J=2.26 Hz), 7.90 (1 H, s), 7.75 (2 H, d, J=8.28 Hz), 7.62-7.68 (3 H, m), 7.54-7.58 (1 H, m), 7.22-7.28 (2 H, m), 7.17-7.22 (3 H, m), 7.07 (1 H, d, J=15.56 Hz), 6.76 (1 H, d, J=15.56 Hz), 5.51 (1 H, t, J=7.65 Hz), 4.42 (2H, t, J=6.15 Hz), 3.34 (2 H, m), 2.61 (2 H, t, J=6.15 Hz). MS (ESI) m/z: 638.1 (M+H)⁺. Analytical HPLC: RT=6.59 min.

Example 80

2-Amino-N-(4-(6-((S)-1-((E)-3-(5-chloro-2-(1H-tetrazol-1-yl)phenyl)acrylamido)-2-phenylethyl)pyridazin-4-yl)phenyl)cyclopropanecarboxamide

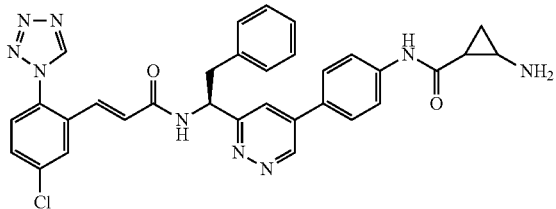

The title compound was prepared using the procedures described in 48C and 37D, by replacing 48B with Example 64 and by replacing Intermediate 1B with 2-(tert-butoxycarbonylamino)cyclopropanecarboxylic acid. ¹H NMR (400 MHz, CD₃OD) δ ppm 9.58 (1 H, s), 9.44 (1 H, s), 7.96 (1 H, s), 7.77 (5 H, m), 7.63 (1 H, d), 7.52-7.60 (1 H, m), 7.15-7.27 (5 H, m), 7.07 (1 H, d, J=15.56 Hz), 6.77 (1 H, d, J=15.56 Hz), 5.50 (1 H, m), 3.34 (2 H, m), 1.78 (2 H, m), 1.48 (2 H, m). MS (ESI) m/z: 606.1 (M+H)⁺. Analytical HPLC: RT=5.62 min.

Example 81

(S,E)-3-(5-Chloro-2-(1H-tetrazol-1-yl)phenyl)-N-(1-(5-(4-(3-(1-hydroxy-2-methylpropan-2-yl)ureido)phenyl)pyridazin-3-yl)-2-phenylethyl)acrylamide

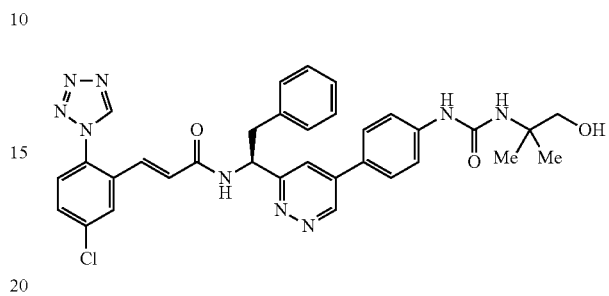

The title compound was prepared using the procedure described in 50D, by replacing 50C with Example 64, and by replacing tert-butyl 3-hydroxypropanoate with 2-amino-2-methylpropan-1-ol. ¹H NMR (400 MHz, DMSO-D₆) δ ppm 9.84 (1H, s), 9.50 (1 H, d, J=2.26 Hz), 8.94 (1 H, d, J=8.53 Hz), 8.83 (1 H, s), 7.96 (1 H, d, J=2.01 Hz), 7.85 (1 H, d, J=2.26 Hz), 7.74 (4 H, ddd, J=15.62, 13.36, 8.66 Hz), 7.53 (2 H, d, J=8.78 Hz), 7.23 (4 H, dq, J=7.03, 6.78 Hz), 7.15-7.20 (1 H, m), 6.79-6.88 (2 H, m), 6.03 (1 H, s), 5.39-5.48 (1 H, m), 3.38 (2 H, s), 3.16-3.26 (2 H, m), 1.23 (6 H, s). MS (ESI) m/z: 638.2 (M+H)⁺. Analytical HPLC: RT=7.09 min.

Example 82

(S,E)-Methyl 4-(6-(1-(3-(5-chloro-2-(1H-tetrazol-1-yl)phenyl)acrylamido)-2-phenylethyl)-3-((dimethylamino)methyl)pyridazin-4-yl)phenylcarbamate

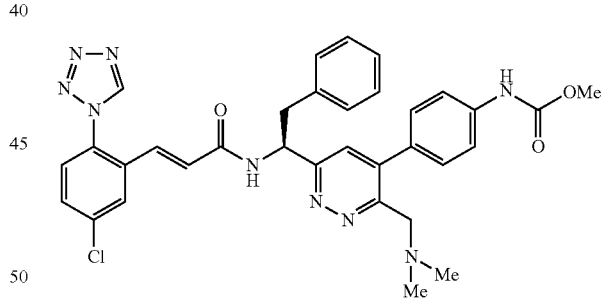

82A. {4-[6-((S)-1-tert-butoxycarbonylamino-2-phenyl-ethyl)-3-chloromethyl-pyridazin-4-yl]-phenyl}-carbamic acid methyl ester: To a cooled (0° C.), clear, colorless solution of 73A (154 mg, 0.322 mmol) in anhydrous CHCl₃ (2 mL) was added sulfurous dichloride (0.031 mL, 0.419 mmol). After 1 min, the cooling bath was removed, and the resulting yellow solution was stirred at rt for 70 min. The mixture was concentrated to remove the solvent. The residue was partitioned between EtOAc/aq.NaHCO₃, and the layers were separated. The organic layer was washed with brine (2×), dried (Na₂SO₄), filtered, and concentrated to give 82A (98% yield) as a solid. MS (ESI) m/z: 497.0 (M+H)⁺.

82B. {4-[6-((S)-1-tert-butoxycarbonylamino-2-phenyl-ethyl)-3-dimethylaminomethyl-pyridazin-4-yl]-phenyl}-carbamic acid methyl ester: To a mixture of 82A (28 mg, 0.056 mmol) and potassium hydroxide (31.6 mg, 0.563 mmol) in Dioxane (1 mL) was added dimethylamine (0.141 mL, 0.282 mmol). The resulted suspension was stirred at rt under argon for 1.5 hr. The reaction mixture was concentrated. Purification by reverse phase chromatography gave 82B (13.4 mg, 0.027 mmol, 47.0% yield) as a yellow solid. MS (ESI) m/z: 506.1 (M+H)+.

82C. Example 82 was prepared using the procedures described in 37D and 48C, by replacing 37C with 82B. $^1$H NMR (400 MHz, CD$_3$OD) ppm 9.49 (1 H, s), 7.96 (1 H, d, J=2.26 Hz), 7.61-7.68 (3 H, m), 7.53-7.59 (1 H, m), 7.46 (1 H, s), 7.23-7.31 (4 H, m), 7.17-7.21 (3 H, m), 7.05 (1 H, d, J=15.56 Hz), 6.75 (1 H, d, J=15.56 Hz), 5.48-5.57 (1 H, m), 4.75 (2 H, d, J=2.26 Hz), 3.76 (3 H, s), 3.34 (2 H, m), 2.95 (6 H, s). MS (ESI) m/z: 638.1 (M+H)+. Analytical HPLC: RT=6.07 min.

Example 83

(S,E)-2-Amino-2-oxoethyl 4-(6-(1-(3-(5-chloro-2-(1H-tetrazol-1-yl)phenyl)acrylamido)-2-phenylethyl)pyridazin-4-yl)phenylcarbamate

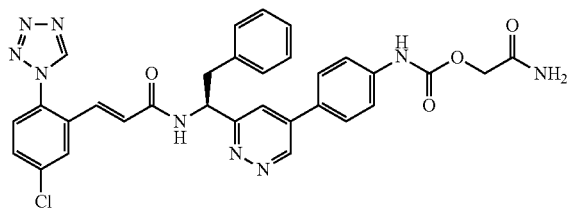

The title compound was prepared using the procedure described in 50D, by replacing 50C with Example 64 and by replacing tert-butyl 3-hydroxypropanoate with 2-hydroxyacetamide (Glycolamide). $^1$H NMR (400 MHz, DMSO-D$_6$) δ ppm 10.11 (1 H, s), 9.83 (1 H, s), 9.52 (1 H, d, J=2.26 Hz), 8.95 (1 H, d, J=8.53 Hz), 7.96 (1 H, d, J=2.01 Hz), 7.89 (1 H, d, J=2.01 Hz), 7.86 (2 H, d, J=8.78 Hz), 7.64-7.75 (4H, m), 7.48 (1 H, s), 7.15-7.27 (6 H, m), 6.79-6.89 (2 H, m), 5.41-5.50 (1 H, m), 4.49 (2 H, s), 3.21 (2 H, ddd, J=19.64, 13.87, 5.65 Hz). MS (ESI) m/z: 624.0 (M+H)+. Analytical HPLC: RT=6.65 min.

Example 84

(S,E)-Methyl 4-(6-(1-(3-(5-chloro-2-(1H-tetrazol-1-yl)phenyl)acrylamido)-2-phenylethyl)-3-(methylthio)pyridazin-4-yl)phenylcarbamate

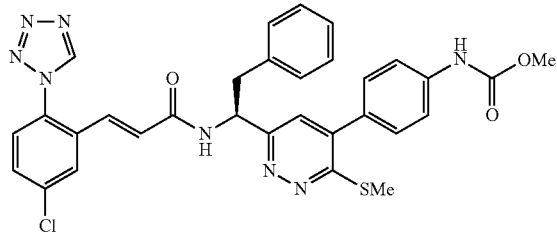

84A. (S)-methyl 4-(6-(1-amino-2-phenylethyl)-3-(methylthio)pyridazin-4-yl)phenylcarbamate: To a mixture of 38A in THF (1 mL) was added sodium methanethiolate (10.22 mg, 0.139 mmol). After addition, the mixture was stirred at 120° C. in a microwave for 30 min. The mixture was purified by reverse phase chromatography to give 84A (25 mg, 0.049 mmol, 60.3% yield) as a yellow solid. MS (ESI) m/z: 395.5 (M+H)+.

84B. Example 84 was prepared using the procedure described in 48C, by replacing 48B with 84A. $^1$H NMR (400 MHz, CD$_3$OD) δ ppm 9.49 (1 H, s), 7.96 (1 H, d, J=2.26 Hz), 7.62-7.66 (1 H, m), 7.52-7.58 (3 H, m), 7.32-7.37 (2 H, m), 7.24-7.29 (2 H, m), 7.16-7.22 (3 H, m), 7.13 (1 H, s), 7.07 (1 H, d, J=15.81 Hz), 6.74 (1H, d, J=15.56 Hz), 5.42 (1 H, t, J=7.78 Hz), 3.75 (3 H, s), 3.18-3.25 (1 H, m), 3.11-3.15 (1 H, m), 2.62 (3 H, s). MS (ESI) m/z: 627.0 (M+H)+. Analytical HPLC: RT=8.85 min.

Example 85

(S,E)-Methyl 4-(6-(1-(3-(5-chloro-2-(1H-tetrazol-1-yl)phenyl)acrylamido)-2-phenylethyl)-3-(methylsulfonyl)pyridazin-4-yl)phenylcarbamate

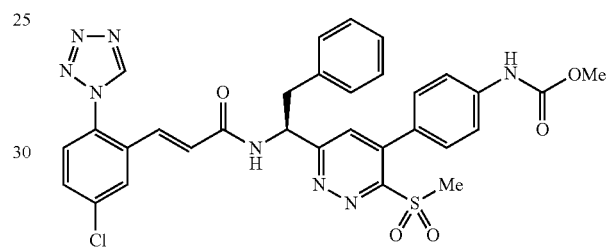

The title compound was prepared using the procedure described in Example 58, by replacing 56B with 84B. $^1$H NMR (400 MHz, CD$_3$OD-THF-D$_8$) δ ppm 9.47 (1 H, s), 7.95 (1 H, d, J=2.26 Hz), 7.62-7.67 (1 H, m), 7.51-7.59 (4 H, m), 7.44 (2 H, d, J=8.78 Hz), 7.23-7.29 (2 H, m), 7.17-7.22 (3 H, m), 7.08 (1 H, d, J=15.56 Hz), 6.74 (1 H, d, J=15.56 Hz), 5.53-5.61 (1 H, m), 3.74 (3 H, s), 3.43 (3 H, s), 3.32-3.36 (2 H, m). MS (ESI) m/z: 659.0 (M+H)+. Analytical HPLC: RT=8.37 min.

Example 86

(S,E)-Methyl 4-(6-(1-(3-(5-chloro-2-(1H-tetrazol-1-yl)phenyl)acrylamido)-2-phenylethyl)-3-(methylthiomethyl)pyridazin-4-yl)phenylcarbamate

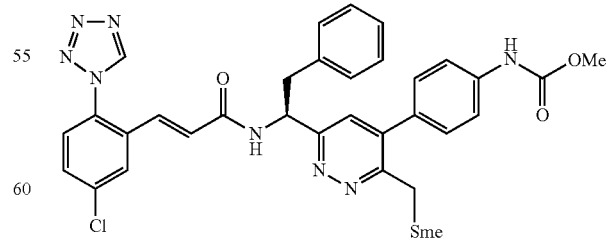

The title compound was prepared using the procedures described in 84A, 37D, and 48C, by replacing 38A with 82A. $^1$H NMR (400 MHz, DMSO-D$_6$) δ ppm 9.91 (1 H, s), 9.84 (1 H, s), 8.93 (1 H, d, J=8.53 Hz), 7.96 (1 H, d, J=2.01 Hz), 7.69-7.76 (2 H, m), 7.60 (2 H, d, J=8.78 Hz), 7.39-7.47 (3 H, m), 7.17-7.28 (5 H, m), 6.82 (2 H, s), 5.39-5.47 (1 H, m), 3.97 (2 H, s), 3.70 (3 H, s), 3.15-3.25 (2 H, m), 1.98 (3 H, s). MS (ESI) m/z: 641.1 (M+H)+. Analytical HPLC: RT=8.41 min.

Example 87

(S,E)-Methyl 4-(6-(1-(3-(5-chloro-2-(1H-tetrazol-1-yl)phenyl)acrylamido)-2-phenylethyl)-3-ethylpyridazin-4-yl)phenylcarbamate

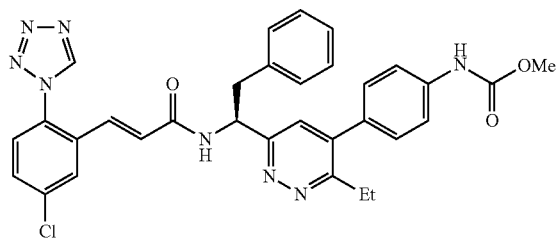

The title compound was prepared using the procedures described in 37B and 37D-E, by replacing 37A with 75A. ¹H NMR (400 MHz, CD₃OD) δ ppm 9.49 (s, 1 H) 7.96 (d, J=2.01 Hz, 1 H) 7.59-7.68 (m, 4 H) 7.55 (d, 1 H) 7.16-7.34 (m, 7 H) 7.06 (d, J=15.81 Hz, 1 H) 6.73 (d, J=15.56 Hz, 1 H) 5.48 (t, J=7.78 Hz, 1 H) 3.76 (s, 3 H) 3.08-3.32 (m, 2 H) 3.09 (q, J=7.53 Hz, 2 H) 1.21 (t, J=7.53 Hz, 3 H). LC-MS (ESI) m/z: 609.2 (M+H)+. Analytical HPLC: RT=7.628 min.

Example 88

(S,E)-2-Hydroxyethyl 4-(6-(1-(3-(5-chloro-2-(1H-tetrazol-1-yl)phenyl)acrylamido)-2-phenylethyl)pyridazin-4-yl)phenylcarbamate

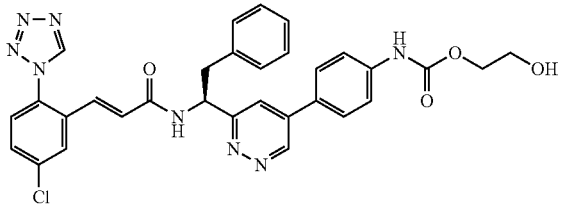

The title compound was prepared using the procedure described in 50D, by replacing 50C with Example 64 and by replacing tert-butyl 3-hydroxypropanoate with ethane-1,2-diol. ¹H NMR (400 MHz, DMSO-D₆) δ ppm 10.03 (1 H, s), 9.84 (1H, s), 9.52 (1 H, d, J=2.26 Hz), 8.96 (1 H, d, J=8.28 Hz), 7.97 (1 H, d, J=2.01 Hz), 7.82-7.89 (3 H, m), 7.65-7.76 (4 H, m), 7.16-7.27 (5 H, m), 6.79-6.89 (2 H, m), 5.41-5.48 (1 H, m), 4.10-4.17 (2 H, m), 3.60-3.68 (2 H, m), 3.22 (2 H, ddd, J=19.70, 13.93, 5.52 Hz). MS (ESI) m/z: 611.1 (M+H)+. Analytical HPLC: RT=6.93 min.

Example 89

(S,E)-Azetidin-3-yl 4-(6-(1-(3-(5-chloro-2-(1H-tetrazol-1-yl)phenyl)acrylamido)-2-phenylethyl)pyridazin-4-yl)phenylcarbamate

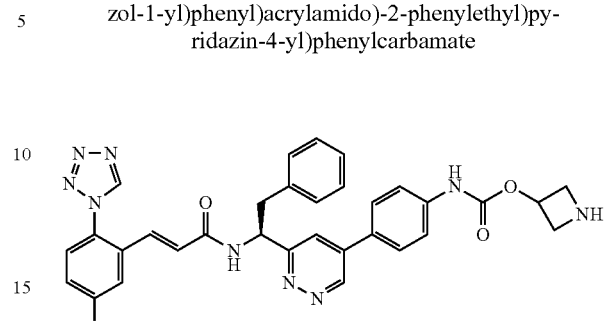

The title compound was prepared using the procedures described in 50D and 37D, by replacing 50C with Example 64 and by replacing tert-butyl 3-hydroxypropanoate with tert-butyl 3-hydroxyazetidine-1-carboxylate. ¹H NMR (400 MHz, CD₃OD) δ ppm 9.49 (1 H, s), 9.44 (1 H, d, J=2.01 Hz), 7.96 (1 H, d, J=2.26 Hz), 7.73-7.80 (2 H, m), 7.73 (1 H, s), 7.61-7.67 (3 H, m), 7.53-7.57 (1 H, m), 7.16-7.27 (5 H, m), 7.07 (1 H, d, J=15.56 Hz), 6.77 (1 H, d, J=15.56 Hz), 5.50 (1 H, t, J=7.78 Hz), 5.31-5.40 (1 H, m), 4.46 (2 H, dd, J=12.80, 7.03 Hz), 4.21 (2 H, dd, J=12.67, 5.14 Hz), 3.30-3.43 (2 H, m). MS (ESI) m/z: 622.2 (M+H)+. Analytical HPLC: RT=5.55 min.

Example 90

(S,E)-Methyl 4-(3-chloro-6-(1-(3-(5-chloro-2-(1H-tetrazol-1-yl)phenyl)acrylamido)-3-(methylthio)propyl)pyridazin-4-yl)phenylcarbamate

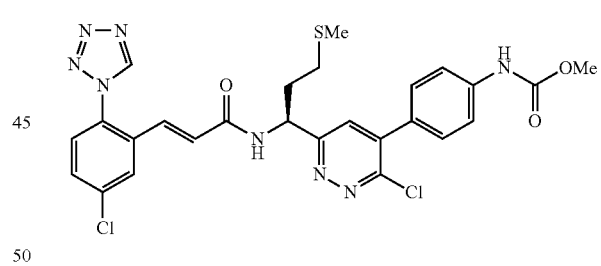

90A. (S)-methyl 2-(tert-butoxycarbonylamino)-4-(methylthio)butanoate: To a colorless solution of (S)-2-(tert-butoxycarbonylamino)-4-(methylthio)butanoic acid (0.997 g, 4.0 mmol) in toluene (5 mL)/methanol (2.0 mL, 49 4 mmol) was added dropwise (diazomethyl)trimethylsilane (2M/ether) (3.40 mL, 6.80 mmol). Gas evolution was observed. The reaction mixture was stirred under argon at rt for 40 min. The solvent was removed under reduced pressure to give 90A (1.053 g, 4.00 mmol, 100% yield) as a colorless oil. MS (ESI) m/z: 164.1 (M+H-Boc)+.

90B. (5)-tert-butyl 1-(dimethoxyphosphoryl)-5-(methylthio)-2-oxopentan-3-ylcarbamate: The compound was prepared using the procedure described in Intermediate 3, by replacing Intermediate 3A with 90A and by replacing diethyl methylphosphonate with dimethyl methylphosphonate. MS (ESI) m/z: 256.1 (M+H-Boc)+.

90C. Example 90 was prepared using the procedures described in 37A-C, 38A, and 48C, by replacing (S)-tert-butyl 4-(dimethoxyphosphoryl)-3-oxo-1-phenylbutan-2-yl-carbamate with 90B. $^1$H NMR (400 MHz, CD$_3$OD) δ ppm 9.50 (1 H, s), 7.98 (1 H, d, J=2.01 Hz), 7.60-7.69 (4 H, m), 7.51-7.58 (3 H, m), 7.12 (1 H, d, J=15.56 Hz), 6.76 (1 H, d, J=15.81 Hz), 5.39 (1 H, dd, J=8.53, 6.02 Hz), 3.76 (3 H, s), 2.54-2.65 (2 H, m), 2.24-2.36 (2 H, m), 2.10 (3 H, s). MS (ESI) m/z: 599.0 (M+H)$^+$. Analytical HPLC: RT=8.4 min.

Example 91

(S,E)-Methyl 4-(3-chloro-6-(1-(3-(5-chloro-2-(1H-tetrazol-1-yl)phenyl)acrylamido)-3-(methylsulfonyl)propyl)pyridazin-4-yl)phenylcarbamate

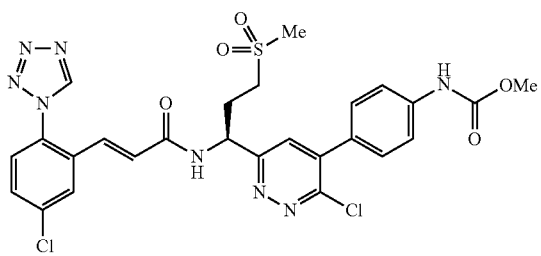

The title compound was prepared using the procedure described in Example 58, by replacing 56B with Example 90. $^1$H NMR (400 MHz, CD$_3$OD) δ ppm 9.51 (1 H, s), 7.98 (1 H, s), 7.72 (1 H, s), 7.60-7.67 (3 H, m), 7.55 (3 H, t, J=8.78 Hz), 7.14 (1 H, d, J=15.56 Hz), 6.75 (1 H, d, J=15.56 Hz), 5.45 (1 H, m), 3.76 (3 H, s), 3.24-3.28 (2 H, m), 3.00 (3 H, s), 2.58-2.49 (2 H, m). MS (ESI) m/z: 631.1 (M+H)$^+$. Analytical HPLC: RT=7.36 min.

Example 92

Methyl 4-(3-chloro-6-((1S)-1-((E)-3-(5-chloro-2-(1H-tetrazol-1-yl)phenyl)acrylamido)-3-(methylsulfinyl)propyl)pyridazin-4-yl)phenylcarbamate

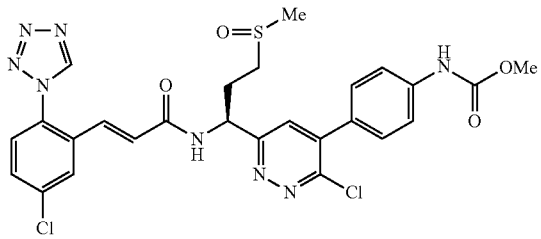

The title compound was prepared using the procedure described in Example 91. $^1$H NMR (400 MHz, CD$_3$OD) δ ppm 9.51 (1 H, s), 7.99 (1 H, d, J=2.01 Hz), 7.74 (1 H, s), 7.59-7.67 (3 H, m), 7.56 (3 H, t, J=8.41 Hz), 7.14 (1 H, d, J=15.56 Hz), 6.76 (1 H, d, J=15.56 Hz), 5.43 (1 H, m), 3.76 (3 H, s), 2.86-2.96 (2 H, m), 2.66 (3 H, s), 2.51-2.44 (2 H, m). MS (ESI) m/z: 615.0 (M+H)$^+$. Analytical HPLC: RT=6.65 min.

Example 93

(S,E)-Methyl 4-(6-(1-(3-(5-chloro-2-(1H-tetrazol-1-yl)phenyl)acrylamido)-2-phenylethyl)-3-(methylsulfonylmethyl)pyridazin-4-yl)phenylcarbamate

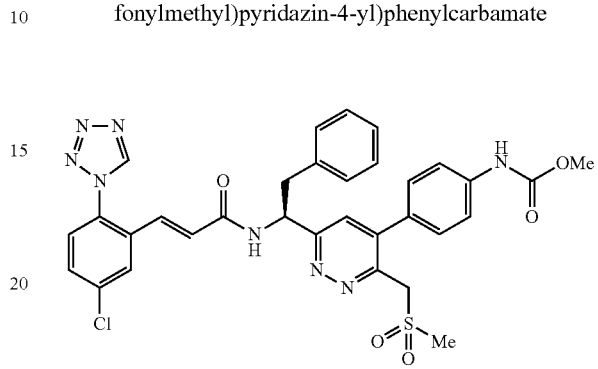

The title compound was prepared using the procedure described in Example 58, by replacing 56B with Example 86. $^1$H NMR (400 MHz, DMSO-D$_6$) δ ppm 9.84 (1 H, s), 7.97 (1 H, s), 7.68-7.76 (2 H, m), 7.58-7.67 (3 H, m), 7.43 (2 H, d, J=8.28 Hz), 7.23 (5 H, dd, J=15.43, 6.40 Hz), 6.82 (2 H, s), 5.47 (1 H, m), 4.81 (2H, s), 3.70 (3 H, s), 3.22-3.32 (2 H, m), 3.14 (3 H, s). MS (ESI) m/z: 673.2 (M+H)$^+$. Analytical HPLC: RT=7.99 min.

Example 94

(S,E)-Methyl 4-(3-chloro-6-(1-(3-(5-chloro-2-(1H-tetrazol-1-yl)phenyl)acrylamido)-2-(pyridin-4-yl)ethyl)pyridazin-4-yl)phenylcarbamate

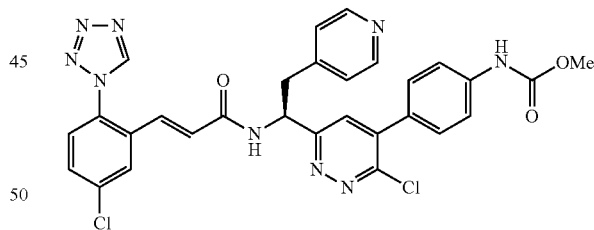

94A. (S)-tert-butyl 4-(dimethoxyphosphoryl)-3-oxo-1-(pyridin-4-yl)butan-2-ylcarbamate: The compound was prepared according to the procedures described in 90A-B, by replacing (S)-2-(tert-butoxycarbonylamino)-4-(methylthio)butanoic acid with (S)-2-(tert-butoxycarbonylamino)-3-(pyridin-4-yl)propanoic acid. MS (ESI) m/z: 373.0 (M+H)$^+$.

94B. Example 94 was prepared using the procedures described in 37A-C, 38A, and 48C, by replacing (S)-tert-butyl 4-(dimethoxyphosphoryl)-3-oxo-1-phenylbutan-2-yl-carbamate with 94A. $^1$H NMR (400 MHz, DMSO-D$_6$) δ ppm 9.99 (1 H, s), 9.84 (1 H, s), 9.08 (1 H, d, J=8.53 Hz), 8.72 (2 H, d, J=5.77 Hz), 7.96 (1 H, d, J=1.76 Hz), 7.88 (1 H, s), 7.70-7.79 (4 H, m), 7.62-7.68 (2 H, m), 7.56 (2 H, d, J=8.53 Hz), 6.79-6.86 (1 H, d), 6.70-6.77 (1 H, d), 5.63 (1 H, m), 3.70

(3 H, s), 3.50 (1 H, m), 3.37 (1 H, m). MS (ESI) m/z: 616.1 (M+H)⁺. Analytical HPLC: RT=5.6 min.

Example 95

(S,E)-Methyl 4-(3-chloro-6-(1-(3-(5-chloro-2-(1H-tetrazol-1-yl)phenyl)acrylamido)-2-(pyridin-3-yl)ethyl)pyridazin-4-yl)phenylcarbamate

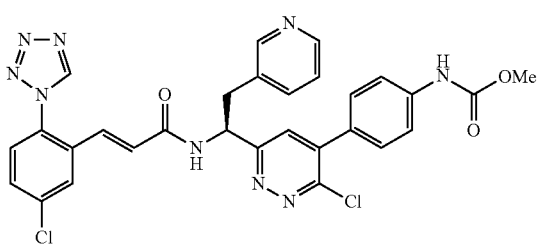

95A. (S)-tert-butyl 4-(dimethoxyphosphoryl)-3-oxo-1-(pyridin-3-yl)butan-2-ylcarbamate: The compound was prepared according to the procedures described in Examples 90A-B, by replacing (S)-2-(tert-butoxycarbonylamino)-4-(methylthio)butanoic acid with (S)-2-(tert-butoxycarbonylamino)-3-(pyridin-3-yl)propanoic acid. MS (ESI) m/z: 373.1 (M+H)⁺.

95B. Example 95 was prepared using the procedures described in 37A-C, 38A, and 48C, by replacing (S)-tert-butyl 4-(dimethoxyphosphoryl)-3-oxo-1-phenylbutan-2-ylcarbamate with 95A. ¹H NMR (400 MHz, CD₃OD) δ ppm 9.51 (1H, s), 8.85 (1 H, s), 8.75 (1 H, d, J=5.27 Hz), 8.52 (1 H, d, J=8.03 Hz), 7.93-8.02 (2H, m), 7.78 (1 H, s), 7.61-7.69 (3 H, m), 7.53-7.60 (3 H, m), 7.03 (1 H, d, J=15.56 Hz), 6.66 (1 H, d, J=15.56 Hz), 5.75 (1 H, dd, J=9.16, 5.65 Hz), 3.78 (3 H, s), 3.72-3.77 (1 H, m), 3.50 (1 H, dd, J=14.18, 9.41 Hz). MS (ESI) m/z: 616.1 (M+H)⁺. Analytical HPLC: RT=5.72 min.

Example 96

(S,E)-Methyl 4-(6-(1-(3-(5-chloro-2-(1H-tetrazol-1-yl)phenyl)acrylamido)-2-phenylethyl)-3-cyanopyridazin-4-yl)phenylcarbamate

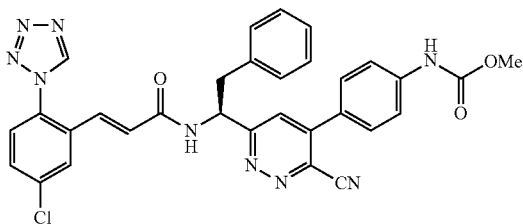

96A. (S)-methyl 4-(6-(1-amino-2-phenylethyl)-3-cyanopyridazin-4-yl)phenylcarbamate: To a mixture of 38A (120 mg, 0.242 mmol) and dicyanozinc (48.2 mg, 0.411 mmol) in DMF (2.5 mL) was added Pd(PPh₃)₄ (27.9 mg, 0.024 mmol). The mixture was stirred at 200° C. in a microwave for 5 min, and the reaction was purified by reverse phase chromatography to give 96A (30 mg, 0.062 mmol, 25.5% yield) as a pale yellow solid. MS (ESI) m/z: 374.0 (M+H)⁺

96B. Example 96 was prepared using the procedure described in 48C, by replacing 48B with 96A. ¹H NMR (400 MHz, DMSO-D₆) δ ppm 10.07 (1 H, s), 9.86 (1 H, s), 9.06 (1 H, d, J=7.78 Hz), 7.98 (2 H, s), 7.68-7.76 (5 H, m), 7.56-7.61 (1 H, m), 7.18-7.30 (5 H, m), 6.81 (2 H, s), 5.5 (1 H, m), 3.71 (3 H, s), 3.21 (2 H, m). MS (ESI) m/z: 606.1 (M+H)⁺. Analytical HPLC: RT=8.9 min.

Example 97

(S,E)-Methyl 4-(3-chloro-6-(1-(3-(5-chloro-2-(1H-tetrazol-1-yl)phenyl)acrylamido)-2-(6,7-dihydro-5H-pyrazolo[5,1-b][1,3]oxazin-2-yl)ethyl)pyridazin-4-yl)phenylcarbamate

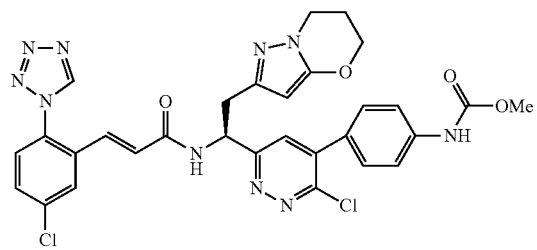

97A. (5)-tert-butyl 1-(6,7-dihydro-5H-pyrazolo[5,1-b][1,3]oxazin-2-yl)-4-(dimethoxyphosphoryl)-3-oxobutan-2-ylcarbamate: The compound was prepared by following the procedure described in Intermediate 6, by replacing 1-ethyl-1H-pyrazole-4-carbaldehyde with 6,7-dihydro-5H-pyrazolo[5,1-b][1,3]oxazine-2-carbaldehyde (prepared by a modified procedure described by Venkatesan, A. R. et al., *J. Med. Chem.* 2006, 49:4623-4637) to give 97A as a tan oil. LC-MS (ESI) m/z: 418.3 (M+H)⁺.

97B. Example 97 was prepared by following the procedures described in 37A-C and Example 38, by replacing (S)-tert-butyl 4-(dimethoxyphosphoryl)-3-oxo-1-phenylbutan-2-ylcarbamate with 97A. ¹H NMR (400 MHz, CD₃OD) δ ppm 9.50 (s, 1 H) 7.97 (d, J=2.01 Hz, 1 H) 7.64 (dd, J=8.53, 2.26 Hz, 1 H) 7.61 (d, J=8.53 Hz, 2H) 7.57 (s, 1 H) 7.55 (d, J=8.53 Hz, 1 H) 7.49 (d, J=8.78 Hz, 2 H) 7.10 (d, J=15.56 Hz, 1 H) 6.74 (d, J=15.56 Hz, 1 H) 5.54 (t, J=7.28 Hz, 1 H) 5.50 (s, 1 H) 4.30 (t, J=4.77 Hz, 2 H) 4.08 (td, J=6.15, 1.25 Hz, 2 H) 3.76 (s, 3 H) 3.20-3.29 (m, 2 H) 2.15-2.30 (m, 2 H). LC-MS (ESI) m/z: 661.3 (M+H)⁺. Analytical HPLC: RT=6.96 min.

Example 98

(S,E)-3-(5-Chloro-2-(1H-tetrazol-1-yl)phenyl)-N-(1-(6-chloro-5-(4-(3-(2-hydroxyethyl)ureido)phenyl)pyridazin-3-yl)-2-(3-fluorophenyl)ethyl)acrylamide

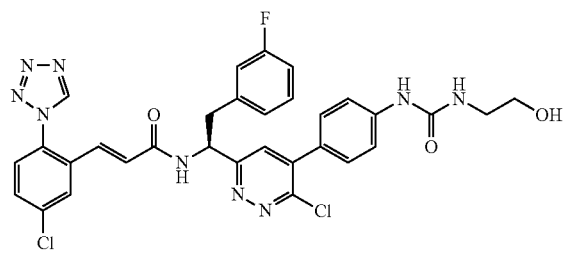

98A. (S)-tert-butyl 1-(6-chloro-5-(4-(3-(2-hydroxyethyl)ureido)phenyl)pyridazin-3-yl)-2-(3-fluorophenyl)ethylcarbamate: A solution of (4-{6-[(S)-1-tert-Butoxycarbonylamino-2-(3-fluoro-phenyl)-ethyl]-3-chloro-pyridazin-4-yl}-phenyl)-carbamic acid methyl ester (110 mg, 0.220 mmol) (prepared from starting material 67B following the procedures described in 38A and 55A) in DMF (1.5 mL) in a microwave vial was added 2-aminoethanol (67.1 mg, 1.098 mmol). The reaction mixture was heated in a microwave at 150° C. for 35 min. Purification by reverse phase chromatography gave 98A (50 mg, 0.094 mmol, 43.0% yield) as a white solid. LC-MS (ESI) m/z: 530.2/532.2 (M+H)$^+$.

98B. Example 98 was prepared by following the procedures described in 37D-E, by replacing 37C with 98A. $^1$H NMR (400 MHz, CD$_3$OD) δ ppm 9.38 (s, 1H) 7.86 (d, J=2.26 Hz, 1 H) 7.51-7.58 (m, 1 H) 7.40-7.47 (m, 4 H) 7.32 (d, J=8.78 Hz, 2 H) 7.18 (td, J=7.97, 6.15 Hz, 1 H) 6.97 (d, J=15.81 Hz, 1 H) 6.87-6.94 (m, 2 H) 6.84 (td, J=8.53, 2.51 Hz, 1 H) 6.63 (d, J=15.56 Hz, 1 H) 5.42 (t, J=7.65 Hz, 1 H) 3.54 (t, J=5.52 Hz, 2 H), 3.20-3.25 (m, 4 H). $^{19}$F NMR (376 MHz, CD$_3$OD) δ ppm −115.30 (s, 1 F). LC-MS (ESI) m/z: 662.3 (M+H)$^+$. Analytical HPLC: RT=7.708 min.

Example 99

Methyl 4-(3-chloro-6-((1S)-1-((E)-3-(5-chloro-2-(1H-tetrazol-1-yl)phenyl)acrylamido)-2-(piperidin-3-yl)ethyl)pyridazin-4-yl)phenylcarbamate (Diastereomer A)

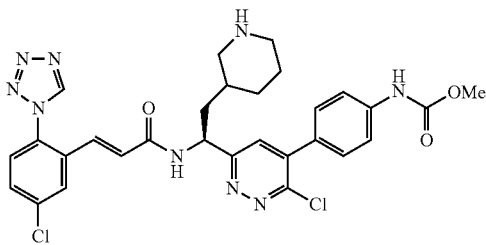

99A. tert-butyl 3-((S)-2-(benzyloxycarbonylamino)-4-(dimethoxyphosphoryl)-3-oxobutyl)piperidine-1-carboxylate: The compound, as a mixture of diastereomers, was prepared according to the procedure described in Intermediate 6 by replacing 1-ethyl-1H-pyrazole-4-carbaldehyde with tert-butyl 3-formylpiperidine-1-carboxylate and by replacing Boc-methyl-2-(dimethylphosphono)glycinate with methyl 2-(benzyloxycarbonylamino)-2-(dimethoxyphosphoryl)acetate. MS (ESI) m/z: 413.5 (M+H-Boc)$^+$.

99B. tert-butyl 3-((S)-2-(benzyloxycarbonylamino)-2-(5-(4-nitrophenyl)-6-oxo-1,6-dihydropyridazin-3-yl)ethyl)piperidine-1-carboxylate: The compound, as a mixture of diastereomers, was prepared according to the procedure described in 37A by replacing (5)-tert-butyl 4-(dimethoxyphosphoryl)-3-oxo-1-phenylbutan-2-ylcarbamate with 99A. MS (ESI) m/z: 478.4 (M+H-Boc)$^+$.

99C. tert-butyl 3-((S)-2-(5-(4-aminophenyl)-6-oxo-1,6-dihydropyridazin-3-yl)-2-((E)-3-(5-chloro-2-(1H-tetrazol-1-yl)phenyl)acrylamido)ethyl)piperidine-1-carboxylate: The compound, as a mixture of diastereomers, was prepared according to the procedures described in 37B and 37E, by replacing 37A with 99B. MS (ESI) m/z: 646.4 (M+H)$^+$.

99D. Example 99 was prepared using the procedures described in 37C and 38A, by replacing 37B with 99C. Purification by reverse phase chromatography gave Example 99 as diastereomer A and Example 100 as diastereomer B. $^1$H NMR (400 MHz, CD$_3$OD) δ ppm 9.52-9.56 (1 H, m), 7.95-7.98 (1 H, m), 7.72 (1 H, s), 7.61-7.68 (3 H, m), 7.52-7.59 (3 H, m), 7.15 (1 H, d, J=15.56 Hz), 6.71 (1 H, d, J=15.56 Hz), 5.40-5.46 (1 H, m), 3.76 (3 H, s), 3.44 (1 H, m), 3.35 (1 H, m), 2.90 (1 H, m), 2.72-2.81 (1 H, m), 1.95-2.04 (3 H, m), 1.68-1.80 (2 H, m), 1.37 (2 H, dd, J=6.90, 3.39 Hz). MS (ESI) m/z: 622.3 (M+H)$^+$. Analytical HPLC: RT=5.4 min.

Example 100

Methyl 4-(3-chloro-6-((1S)-1-((E)-3-(5-chloro-2-(1H-tetrazol-1-yl)phenyl)acrylamido)-2-(piperidin-3-yl)ethyl)pyridazin-4-yl)phenylcarbamate (Diastereomer B)

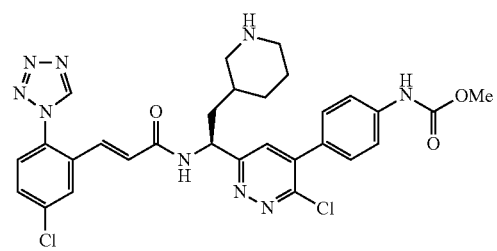

The title compound was obtained from 99D (diastereomer B). $^1$H NMR (400 MHz, CD$_3$OD) δ ppm 9.52-9.56 (1 H, m), 7.95-7.98 (1 H, m), 7.72 (1 H, s), 7.61-7.68 (3 H, m), 7.52-7.59 (3 H, m), 7.15 (1 H, d, J=15.56 Hz), 6.71 (1 H, d, J=15.56 Hz), 5.40-5.46 (1 H, m), 3.76 (3 H, s), 3.44 (1 H, m), 3.35 (1 H, m), 2.90 (1 H, m), 2.72-2.81 (1 H, m), 1.95-2.04 (3 H, m), 1.68-1.80 (2 H, m), 1.37 (2 H, dd, J=6.90, 3.39 Hz). MS (ESI) m/z: 622.3 (M+H)$^+$. Analytical HPLC: RT=5.4 min.

Example 101

Methyl 4-(6-((1S)-2-(1-acetylpiperidin-3-yl)-1-((E)-3-(5-chloro-2-(1H-tetrazol-1-yl)phenyl)acrylamido)ethyl)-3-chloropyridazin-4-yl)phenylcarbamate

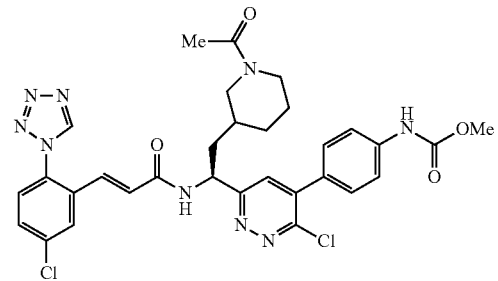

To a cooled solution (0-5° C.) of Example 99 (diastereomer A) (25 mg, 0.034 mmol) in DCM (2 mL)/Pyridine (600 mL) was added acetyl chloride (44.82 mL, 0.63 mmol). After 1 h, the mixture was concentrated, and purified by reverse phase chromatography to give Example 101 (17 mg, 0.023 mmol, 66.5% yield) as a yellow fluffy solid. $^1$H NMR (400 MHz, CD$_3$OD) δ ppm 9.41 (1 H, s), 7.89 (1 H, d, J=1.76 Hz), 7.60 (1 H, d, J=4.02 Hz), 7.51-7.58 (3 H, m), 7.42-7.48 (3 H, m), 7.00-7.06 (1 H, m), 6.62-6.68 (1 H, m), 5.29 (1 H, m), 3.66 (3 H, s), 3.23-3.26 (1 H, m), 3.18-3.19 (1 H, m), 2.86-2.95 (1 H, m), 2.76 (1 H, m), 2.06 (1 H, m), 1.90-2.00 (3 H, m), 1.78-1.90 (2 H, m), 1.70 (1 H, m). MS (ESI) m/z: 664.3 (M+H)+. Analytical HPLC: RT=7.0 min.

Example 102

Methyl 4-(6-((1S)-2-(1-acetylpiperidin-3-yl)-1-((E)-3-(5-chloro-2-(1H-tetrazol-1-yl)phenyl)acrylamido) ethyl)-3-chloropyridazin-4-yl)phenylcarbamate

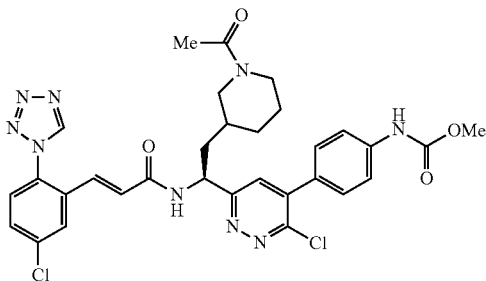

The title compound was prepared using the procedure described in Example 101, by replacing Example 99 with Example 100 (diastereomer B). ¹H NMR (400 MHz, CD₃OD) δ ppm 9.41 (1 H, s), 7.89 (1 H, d, J=1.76 Hz), 7.60 (1 H, d, J=4.02 Hz), 7.51-7.58 (3 H, m), 7.42-7.48 (3 H, m), 7.00-7.06 (1 H, m), 6.62-6.68 (1 H, m), 5.29 (1 H, m), 3.66 (3 H, s), 3.23-3.26 (1 H, m), 3.18-3.19 (1 H, m), 2.86-2.95 (1 H, m), 2.76 (1 H, m), 2.06 (1 H, m), 1.90-2.00 (3 H, m), 1.78-1.90 (2H, m), 1.70 (1 H, m). MS (ESI) m/z: 664.3 (M+H)+. Analytical HPLC: RT=7.1 min.

Example 103

(E)-Methyl 4-(3-chloro-6-(1-(3-(5-chloro-2-(1H-tetrazol-1-yl)phenyl)acrylamido)-2-(6-methylpyridin-3-yl)ethyl)pyridazin-4-yl)phenylcarbamate

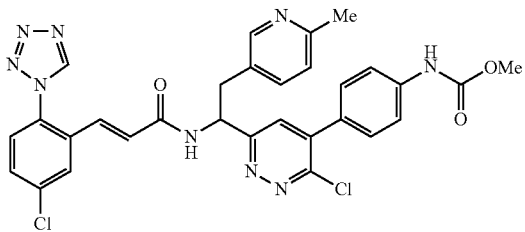

103A. tert-butyl 4-(dimethoxyphosphoryl)-1-(6-methylpyridin-3-yl)-3-oxobutan-2-ylcarbamate: The compound was prepared according to the procedures described in Intermediate 6, by replacing 1-ethyl-1H-pyrazole-4-carbaldehyde with 6-methylnicotinaldehyde. In procedure Intermediate 6B, (S,S)-EtDuPhosRh(I) was replaced with 10% Pd/C. MS (ESI) m/z: 387.2 (M+H)+.

103B. Example 103 (racemate) was prepared using the procedures described in 37A-C and Example 38, by replacing (S)-tert-butyl 4-(dimethoxyphosphoryl)-3-oxo-1-phenylbutan-2-ylcarbamate with 103A. ¹H NMR (400 MHz, CD₃OD) δ ppm 9.51 (1 H, s), 8.70 (1 H, d, J=1.76 Hz), 8.43 (1 H, dd, J=8.28, 2.01 Hz), 7.95 (1 H, d, J=2.26 Hz), 7.87 (1 H, d, J=8.28 Hz), 7.80 (1 H, s), 7.61-7.69 (3 H, m), 7.53-7.61 (3 H, m), 7.02 (1 H, d, J=15.56 Hz), 6.65 (1 H, d, J=15.56 Hz), 5.73 (1 H, dd, J=9.54, 5.52 Hz), 3.78 (3 H, s), 3.71 (1 H, dd, J=14.18, 5.65 Hz), 3.44 (1 H, dd, J=14.31, 9.54 Hz), 2.80 (3 H, s). MS (ESI) m/z: 630.4 (M+H)+. Analytical HPLC: RT=5.7 min.

Example 104

[4-(6-{2-(S)-(4-Benzyloxycarbonylamino-phenyl)-1-[(E)-3-(5-chloro-2-tetrazol-1-yl-phenyl)-acryloylamino]-ethyl}-3-chloro-pyridazin-4-yl)-phenyl]-carbamic acid methyl ester

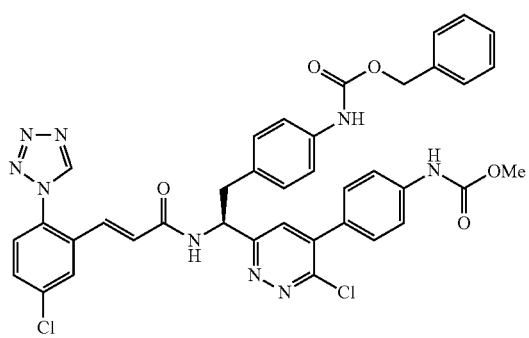

The title compound was prepared using the procedures described in 37A-C and Example 38, by replacing (S)-tert-butyl 4-(dimethoxyphosphoryl)-3-oxo-1-phenylbutan-2-ylcarbamate with [(S)-4-(4-Benzyloxycarbonylamino-phenyl)-3-tert-butoxycarbonylamino-2-oxo-butyl]-phosphonic acid dimethyl ester (which was synthesized according to the procedure described in Intermediate 3). ¹H NMR (400 MHz, CD₃OD) δ ppm 9.39 (s, 1 H) 7.87 (d, J=2.26 Hz, 1 H) 7.55 (dd, J=8.53, 2.26 Hz, 1 H) 7.43-7.50 (m, 3 H) 7.17-7.34 (m, 10 H) 6.93-7.02 (m, 3 H) 6.67 (d, J=15.56 Hz, 1 H) 5.29-5.39 (m, 1 H) 5.08 (s, 2 H) 3.65 (s, 3 H) 3.07-3.19 (m, 2 H). LC-MS (ESI) m/z: 764.2 (M+H)+. Analytical HPLC: RT=9.159 min.

Example 105

(S,E)-Methyl 4-(6-(2-(4-aminophenyl)-1-(3-(5-chloro-2-(1 H-tetrazol-1-yl)phenyl)acrylamido) ethyl)-3-chloropyridazin-4-yl)phenylcarbamate, TFA salt

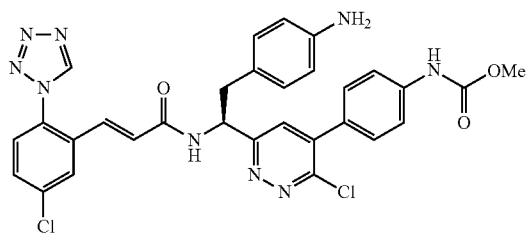

To a cooled solution (0° C.) of Example 104 (98 mg, 0.128 mmol) in acetonitrile (5 mL) was added dropwise iodotrimethylsilane (0.087 mL, 0.641 mmol). The reaction mixture was stirred under argon at 0° C. for 1.5 H. Water was added to quench the reaction. Purification by reverse phase chromatography gave the title compound (77 mg, 0.095 mmol, 73.9% yield) as a light yellow solid. $^1$H NMR (400 MHz, CD$_3$OD) δ ppm 9.40 (s, 1 H) 7.84 (d, J=2.01 Hz, 1 H) 7.56 (dd, J=8.53, 2.26 Hz, 1 H) 7.49-7.54 (m, 3 H) 7.47 (d, J=8.53 Hz, 1 H) 7.38 (d, J=8.78 Hz, 2 H) 7.31 (d, J=8.28 Hz, 2 H) 7.19 (d, J=8.28 Hz, 2 H) 6.93 (d, J=15.81 Hz, 1 H) 6.58 (d, J=15.56 Hz, 1 H) 5.39-5.51 (m, 1 H) 3.67 (s, 3 H) 3.30-3.38 (m, 1 H) 3.19-3.34 (m, 1 H). LC-MS (ESI) m/z: 630.2 (M+H)$^+$. Analytical HPLC: RT=5.363 min.

Example 106

(S,E)-Methyl 4-(6-(2-(4-acetamidophenyl)-1-(3-(5-chloro-2-(1 H-tetrazol-1-yl)phenyl)acrylamido)ethyl)-3-chloropyridazin-4-yl)phenylcarbamate

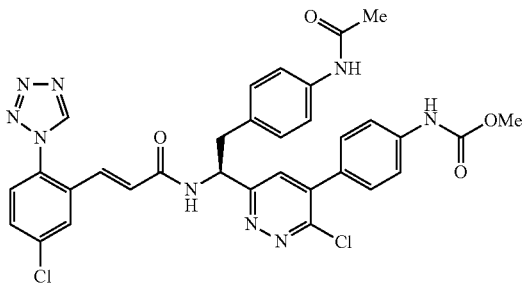

A cooled solution (0° C.) of Example 105 (10 mg, 0.013 mmol) in acetonitrile (1 mL) were added TEA (0.05 mL, 0.359 mmol) and Ac$_2$O (0.013 mL, 0.134 mmol). The reaction mixture was stirred under argon at 0° C. for 30 min. Water (5 drops) was added. Purification by reverse phase chromatography gave the title compound (8.95 mg, 0.013 mmol, 96% yield) as a light yellow solid. $^1$H NMR (400 MHz, CD$_3$OD) δ ppm 9.39 (s, 1 H) 7.87 (d, J=2.01 Hz, 1 H) 7.55 (dd, J=8.53, 2.26 Hz, 1 H) 7.43-7.51 (m, 3 H) 7.35 (d, J=8.53 Hz, 2 H) 7.28 (d, J=8.78 Hz, 2 H) 7.26 (s, 1 H) 7.02 (d, J=8.53 Hz, 2 H) 6.98 (d, J=15.81 Hz, 1 H) 6.67 (d, J=15.56 Hz, 1 H) 5.36 (t, J=7.53 Hz, 1 H) 3.66 (s, 3 H) 3.10-3.18 (m, 2 H) 2.02 (s, 3 H). LC-MS (ESI) m/z: 672.3 (M+H)$^+$. Analytical HPLC: RT=7.376 min.

Example 107

(S,E)-Methyl 4-(3-chloro-6-(1-(3-(5-chloro-2-(1 H-tetrazol-1-yl)phenyl)acrylamido)-2-(4-(3-methylureido)phenyl)ethyl)pyridazin-4-yl)phenylcarbamate

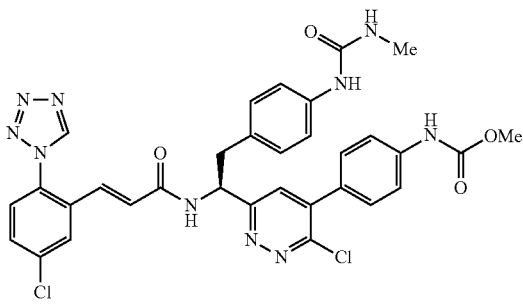

The title compound was prepared by following the procedure described in Example 106, by replacing Ac$_2$O with methyl isocyanate. $^1$H NMR (400 MHz, CD$_3$OD) δ ppm 9.49 (s, 1 H) 7.97 (d, J=2.26 Hz, 1 H) 7.64 (dd, J=8.53, 2.26 Hz, 1 H) 7.53-7.60 (m, 3 H) 7.38 (d, J=8.78 Hz, 2 H) 7.34 (s, 1 H) 7.26 (d, J=8.53 Hz, 2 H) 7.07 (d, J=15.56, 1 H) 7.05 (d, J=8.53 Hz, 2 H) 6.77 (d, J=15.56 Hz, 1 H) 5.36-5.49 (m, 1 H) 3.75 (s, 3 H) 3.17-3.27 (m, 2 H) 2.76 (s, 3 H). LC-MS (ESI) m/z: 687.3 (M+H)$^+$. Analytical HPLC: RT=7.181 min.

Example 108

(S,E)-Methyl 4-(3-chloro-6-(1-(3-(5-chloro-2-(1 H-tetrazol-1-yl)phenyl)acrylamido)-2-(4-(2-(dimethylamino)acetamido)phenyl)ethyl)pyridazin-4-yl)phenylcarbamate, TFA salt

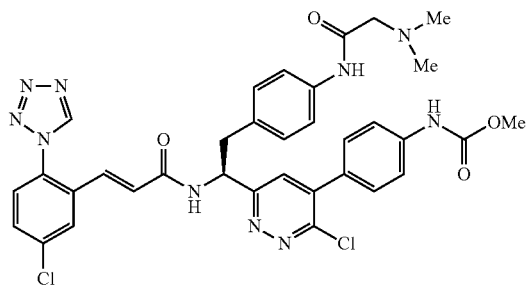

The title compound was prepared following the procedure described in 78C, by replacing 78B with Example 105 and by replacing 3-tert-butoxy-3-oxopropanoic acid with 2-(dimethylamino)acetic acid. $^1$H NMR (400 MHz, CD$_3$OD) δ ppm 9.47 (s, 1 H) 7.65 (dd, J=8.53, 2.26 Hz, 1 H) 7.53-7.60 (m, 3 H) 7.51 (d, J=8.53 Hz, 2 H) 7.37 (d, J=8.78 Hz, 2 H) 7.34 (s, 1 H) 7.16 (d, J=8.53 Hz, 2 H) 7.05 (d, J=15.56 Hz, 1 H) 6.75 (d, J=15.56 Hz, 1 H) 5.42-5.53 (m, 1 H) 4.12 (s, 2H) 3.76 (s, 3 H) 3.21-3.34 (m, 2 H) 3.01 (s, 6 H). LC-MS (ESI) m/z: 715.3 (M+H)$^+$. Analytical: RT=5.435 min.

Example 109

(E)-Methyl 4-(3-chloro-6-(1-(3-(5-chloro-2-(1 H-tetrazol-1-yl)phenyl)acrylamido)-2-(6-methylpyridin-3-yl)ethyl)pyridazin-4-yl)phenylcarbamate

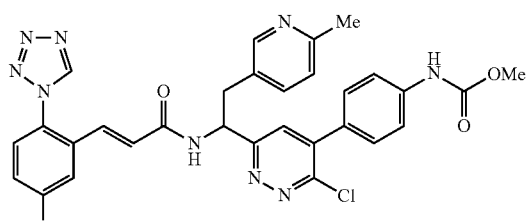

The title compound was prepared by chiral hplc of Example 103 [Chiral OD (21 mm×250 mm); 100% (1:1) EtOH/MeOH with 0.1% DEA] gave Example 109 as enantiomer A (>99% ee) and Example 110 as enantiomer B (>99% ee). $^1$H NMR (400 MHz, CD$_3$OD) δ ppm 9.38 (1 H, s), 8.15 (1 H, d, J=1.76 Hz), 7.85 (1 H, d, J=2.26 Hz), 7.50-7.61 (5 H, m), 7.44-7.48 (1 H, m), 7.36-7.40 (2 H, m), 7.18 (1 H, d, J=8.03 Hz), 6.96 (1 H, d, J=15.81 Hz), 6.61 (1 H, d, J=15.81 Hz), 5.44 (1 H, dd, J=8.78, 6.53 Hz), 3.67 (3 H, s), 3.26-3.35 (1 H, m), 3.18-3.20 (1 H, m), 2.40 (3 H, s). MS (ESI) m/z: 630.3 (M+H)⁺. Analytical HPLC: RT=6.0 min.

Example 110

(E)-Methyl 4-(3-chloro-6-(1-(3-(5-chloro-2-(1 H-tetrazol-1-yl)phenyl)acrylamido)-2-(6-methylpyridin-3-yl)ethyl)pyridazin-4-yl)phenylcarbamate

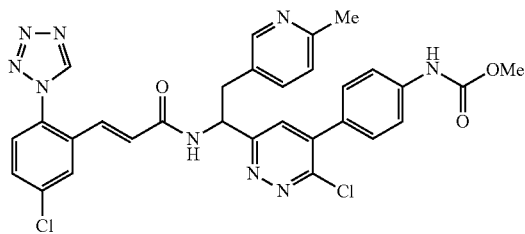

The title compound was prepared by chiral HPLC of Example 103 [Chiral OD (21 mm×250 mm); 100% (1:1) EtOH/MeOH with 0.1% DEA] gave Example 110 as enantiomer B (>99% ee). ¹ H NMR (400 MHz, CD₃OD) δ ppm 9.38 (1 H, s), 8.15 (1 H, d, J=1.76 Hz), 7.85 (1 H, d, J=2.26 Hz), 7.50-7.61 (5 H, m), 7.44-7.48 (1 H, m), 7.36-7.40 (2 H, m), 7.18 (1 H, d, J=8.03 Hz), 6.96 (1 H, d, J=15.81 Hz), 6.61 (1H, d, J=15.81 Hz), 5.44 (1 H, dd, J=8.78, 6.53 Hz), 3.67 (3 H, s), 3.26-3.35 (1 H, m), 3.18-3.20 (1 H, m), 2.40 (3 H, s). MS (ESI) m/z: 630.2 (M+H)⁺. Analytical HPLC: RT=6.0 min.

Example 111

Methyl 4-(6-((1S)-1-((E)-3-(5-chloro-2-(1 H-tetrazol-1-yl)phenyl)acrylamido)-2-(1-propionylpiperidin-3-yl)ethyl)pyridazin-4-yl)phenylcarbamate (diastereomer mixture)

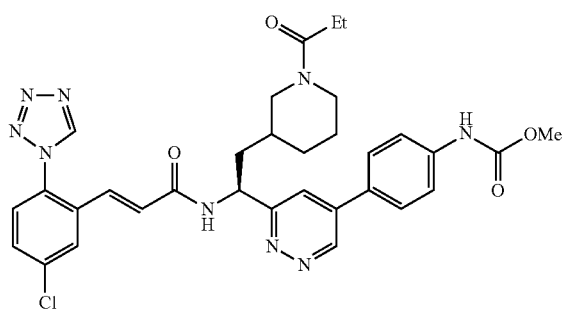

111A. tert-butyl 3-((S)-2-(5-(4-aminophenyl)-6-oxo-1,6-dihydropyridazin-3-yl)-2-(benzyloxycarbonylamino)ethyl)piperidine-1-carboxylate: To a solution of 99B (280 mg, 0.485 mmol) in MeOH (3 mL) and EtOAc (1.5 mL) was added ammonium chloride (259 mg, 4.85 mmol) and zinc (317 mg, 4.85 mmol) portionally. The reaction mixture was stirred at rt for 1 Hr and filtered through CELITE®. The filtrate was evaporated under reduced pressure to give 111A (265 mg, 0.485 mmol, 100% yield) as a yellow solid. MS (ESI) m/z: 548.5 (M+H)⁺.

111B. tert-butyl 3-((S)-2-(benzyloxycarbonylamino)-2-(5-(4-(methoxycarbonylamino) phenyl)-6-oxo-1,6-dihydropyridazin-3-yl)ethyl)piperidine-1-carboxylate: The compound was prepared according to the procedure described in 37C by replacing 37B with 111A. MS (ESI) m/z: 606.3 (M+H)⁺.

111C. {4-[6-((S)-1-benzyloxycarbonylamino-2-piperidin-3-yl-ethyl)-3-chloro-pyridazin-4-yl]-phenyl}-carbamic acid methyl ester: The compound was prepared according to the procedure described in 38A by replacing 37C with 111B. MS (ESI) m/z: 524.3 (M+H)⁺.

111D. methyl 4-(6-((1S)-1-amino-2-(1-propionylpiperidin-3-yl)ethyl)pyridazin-4-yl)phenylcarbamate: The compound was prepared according to the procedures described in Example 101 and 37B, by replacing acetyl chloride with propionyl chloride and by replacing Example 99 with 111C. MS (ESI) m/z: 412.4 (M+H)⁺.

111E. Example 111 was prepared using the procedure described in 37E, by replacing 37D with 111D. ¹ H NMR (400 MHz, CD₃OD) δ ppm 9.41-9.40 (2 H, d), 7.89 (1 H, d, J=1.76 Hz), 7.60 (1 H, d, J=4.02 Hz), 7.51-7.58 (3 H, m), 7.42-7.48 (3H, m), 7.00-7.06 (1 H, m), 6.62-6.6 8(1 H, m), 5.31 (1 H, m), 3.67 (3 H, s), 3.23-3.26 (1 H, m), 3.18-3.19 (1 H, m), 2.86-2.95 (1 H, m), 2.76 (1 H, m), 2.28 (3 H, m), 1.80-2.00 (3 H, m), 1.35-1.65 (3 H, m), 1.01 (3 H, m). MS (ESI) m/z: 644.4 (M+H)⁺. Analytical HPLC: RT=6.5 min.

Example 112

Methyl 4-(3-chloro-6-((1S)-1-((E)-3-(5-chloro-2-(1 H-tetrazol-1-yl)phenyl)acrylamido)-2-(1-(cyclopropanecarbonyl)piperidin-3-yl)ethyl)pyridazin-4-yl)phenylcarbamate

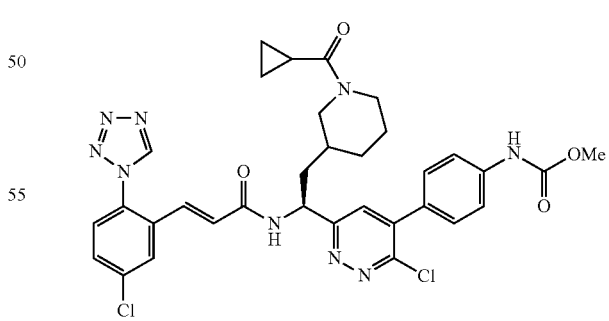

The title compound was prepared using the procedure described in Example 101, by replacing acetyl chloride with cyclopropanecarbonyl chloride. ¹ H NMR (400 MHz, CD₃OD) ppm 9.48-9.55 (1 H, m), 7.99 (1 H, s), 7.68-7.64 (4 H, m), 7.53-7.61 (3 H, m), 7.12 (1 H, s), 6.80 (1 H, s), 5.41 (1 H, m), 4.31 (1 H, m), 3.78 (3 H, s),3.5-3.3 (2 H, m), 3.03 (1 H, s), 2.79 (1 H, m), 1.99 (4 H, m), 1.71 (1 H, m), 1.44 (2 H, m), 0.75-0.87 (4 H, m). MS (ESI) m/z: 690.3 (M+H)⁺. Analytical HPLC: RT=7.6 min.

Example 113

Benzyl 3-((S)-2-((E)-3-(5-chloro-2-(1 H-tetrazol-1-yl)phenyl)acrylamido)-2-(6-chloro-5-(4-(methoxycarbonylamino)phenyl)pyridazin-3-yl)ethyl)pyrrolidine-1-carboxylate (diastereomer mixture)

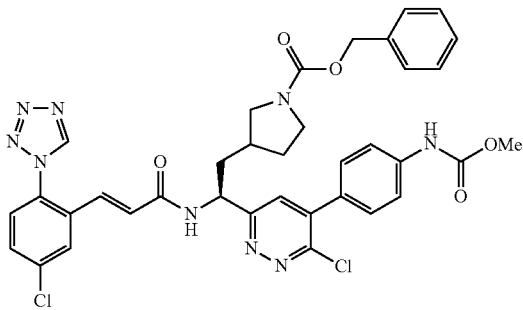

113A. benzyl 3-((S)-2-(tert-butoxycarbonylamino)-4-(dimethoxyphosphoryl)-3-oxobutyl)pyrrolidine-1-carboxylate: This compound was prepared following the procedures described in Intermediate 6, by replacing 1-ethyl-1 H-pyrzole-4-carbaldehyde with (±)-benzyl 3-formylpyrrolidine-1-carboxylate. LC-MS (ESI) m/z: 499.2 (M+H)⁺.

113B. Example 113 was prepared following the procedures described in 37A-C and Example 38, by replacing (S)-tert-butyl 4-(dimethoxyphosphoryl)-3-oxo-1-phenylbutan-2-ylcarbamate with 113A. ¹H NMR (400 MHz, CD₃OD) δ ppm 9.45-9.53 (m, 1 H) 7.92-8.00 (m, 1 H) 7.68-7.73 (m, 1 H) 7.48-7.68 (m, 6 H) 7.25-7.36 (m, 5 H) 7.13 (d, J=15.56 Hz, 1 H) 6.69-6.79 (m, 1 H) 5.22-5.39 (m, 1 H) 5.08 (s, 2 H) 3.76 (s, 3 H) 3.47-3.69 (m, 2 H) 3.23-3.29 (m, 1 H) 2.96-3.10 (m, 1 H) 2.19-2.41 (m, 1 H) 2.02-2.19 (m, 3 H) 1.56-1.79 (m, 1 H). LC-MS (ESI) m/z: 742.2 (M+H)⁺. Analytical HPLC: RT=8.609 min.

Example 114

Methyl 4-(3-chloro-6-((1S)-1-((E)-3-(5-chloro-2-(1 H-tetrazol-1-yl)phenyl)acrylamido)-2-(pyrrolidin-3-yl)ethyl)pyridazin-4-yl)phenylcarbamate, TFA salt (diastereomer mixture)

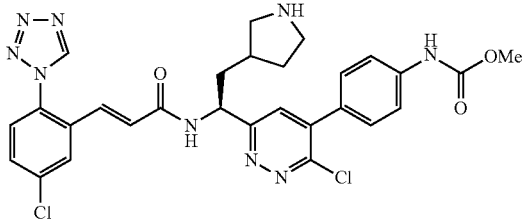

The title compound was prepared following the procedure described in Example 105, by replacing Example 104 with 113B. ¹H NMR (400 MHz, CD₃OD) δ ppm 9.52 (s, 1 H) 8.95 (t, J=7.03 Hz, 1 H) 7.97 (t, J=1.63 Hz, 1 H) 7.73 (s, 1 H) 7.65-7.69 (m, 1 H) 7.60-7.64 (m, 2 H) 7.58 (d, J=8.53 Hz, 1 H) 7.51-7.56 (m, 2 H) 7.15 (d, J=15.56 Hz, 1 H) 6.74 (dd, J=15.56, 7.53 Hz, 1 H) 5.31-5.44 (m, 1 H) 3.76 (s, 3H) 3.46-3.56 (m, 1 H) 3.36-3.45 (m, 1 H) 3.18-3.27 (m, 1 H) 2.89-3.02 (m, 1 H) 2.33-2.49 (m, 1 H) 2.10-2.32 (m, 3 H) 1.68-1.83 (m, 1 H) LC-MS (ESI) m/z: 608.1 (M+H)⁺. Analytical HPLC: RT=5.185 min.

Example 115

Methyl 4-(6-((1S)-2-(1-acetylpyrrolidin-3-yl)-1-((E)-3-(5-chloro-2-(1 H-tetrazol-1-yl)phenyl)acrylamido)ethyl)-3-chloropyridazin-4-yl)phenylcarbamate (diastereomer mixture)

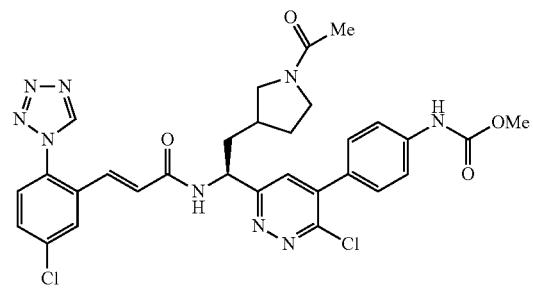

The title compound was prepared following the procedure described in Example 106 by replacing Example 105 with Example 114. ¹H NMR (400 MHz, CD₃OD) δ ppm 9.49-9.51 (m, 1 H) 7.94-8.01 (m, 1 H) 7.69-7.74 (m, 1 H) 7.59-7.67 (m, 3 H) 7.51-7.58 (m, 3 H) 7.09-7.18 (m, 1 H) 6.68-6.80 (m, 1 H) 5.20-5.43 (m, 1 H) 3.76 (s, 3 H) 3.72 (dd, J=11.04, 7.53 Hz, 1 H) 3.55-3.67 (m, 1 H) 3.36-3.53 (m, 1 H) 3.16-3.27 (m, 1 H) 2.91-3.15 (m, 1 H) 2.07-2.24 (m, 3 H) 2.00-2.07 (m, 3 H) 1.60-1.81 (m, 1 H). LC-MS (ESI) m/z: 650.1 (M+H)⁺. Analytical HPLC: RT=6.738 min.

Example 116

Methyl 4-(3-chloro-6-((1S)-1-((E)-3-(5-chloro-2-(1 H-tetrazol-1-yl)phenyl)acrylamido)-2-(1-ethylpyrrolidin-3-yl)ethyl)pyridazin-4-yl)phenylcarbamate, TFA salt (diastereomer mixture)

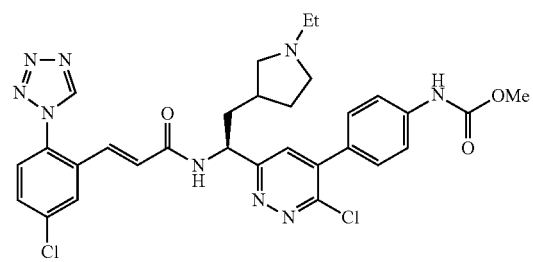

To a solution of Example 114 (20 mg, 0.028 mmol) in MeOH (2 mL) were added acetaldehyde (12.19 mg, 0.277 mmol) and sodium triacetoxyborohydride (20 mg, 0.094 mmol). The reaction mixture was stirred under argon at rt for 1 H. HCl (1.0N, 1.0 mL) was added to quench the reaction. Purification by reverse phase chromatography gave the title compound (17.23 mg, 0.023 mmol, 81% yield) as a yellow solid. ¹H NMR (400 MHz, CD₃OD) δ ppm 9.52 (d, 1 H) 7.90-8.01 (m, 1 H) 7.69-7.75 (m, 1 H) 7.64-7.68 (m, 1 H) 7.60-7.64 (m, 2 H) 7.56-7.60 (m, 1 H) 7.51-7.56 (m, 2 H) 7.15 (d, J=15.81 Hz, 1 H) 6.68-6.78 (m, 1 H) 5.30-5.42 (m, 1H) 3.55-3.91 (m, 2 H) 3.76 (s, 3 H) 3.34-3.49 (m, 1 H) 3.00-3.28 (m, 3 H) 2.08-2.67 (m, 4 H) 1.65-2.00 (m, 1 H) 1.33 (t, J=7.15 Hz, 3 H). LC-MS (ESI) m/z: 636.2 (M+H)⁺. Analytical HPLC: RT=5.333 min.

Example 117

Methyl 4-(3-chloro-6-((1S)-1-((E)-3-(5-chloro-2-(1 H-tetrazol-1-yl)phenyl)acrylamido)-2-(1-isobutyrylpiperidin-3-yl)ethyl)pyridazin-4-yl) phenylcarbamate

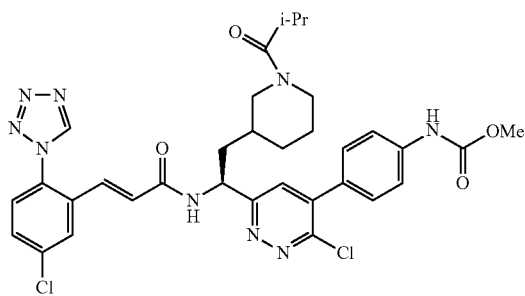

To a cooled suspension (0° C.) of Example 99 (diastereomer A) (15 mg, 0.024 mmol) in acetonitrile (1.7 mL) were added TEA (0.024 mL, 0.169 mmol) and isobutyric anhydride (0.016 mL, 0.096 mmol). The reaction mixture was stirred under argon at 0° C. for 20 min. Water (3 drops) was added. The mixture was warmed to rt and purified by reverse phase chromatography to give Example 117 as diastereomer A. ¹H NMR (400 MHz, CD₃OD) δ ppm 9.48 (1 H, s), 7.96-8.00 (1 H, m), 7.68-7.73 (1 H, m), 7.60-7.66 (3 H, m), 7.51-7.58 (3 H, m), 7.09-7.16 (1 H, m), 6.71-6.79 (1 H, m), 5.34-5.43 (1 H, m), 4.32 (1 H, dd, J=12.30 Hz), 3.85-4.02 (1 H, dd, J=12.30 Hz), 3.78 (3 H, s), 3.12-3.22 (1 H, m), 2.86-2.98 (2 H, m), 2.60-2.70 (1H, m), 1.92-2.01 (2 H, m), 1.81 (1 H, m), 1.61 (1 H, d, J=8.03 Hz), 1.46 (1 H, m), 1.33 (1 H, t, J=7.28 Hz), 1.01-1.10 (6 H, m). MS (ESI) m/z: 692.3 (M+H)⁺. Analytical HPLC: RT=7.84 min.

Example 118

Methyl 4-(3-chloro-6-((1S)-1-((E)-3-(5-chloro-2-(1 H-tetrazol-1-yl)phenyl)acrylamido)-2-(1-isobutyrylpiperidin-3-yl)ethyl)pyridazin-4-yl)phenylcarbamate

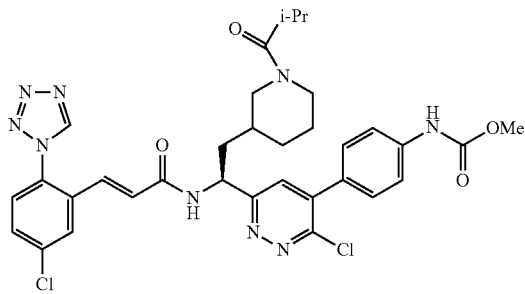

The title compound was prepared using the procedure described in Example 117, by replacing Example 99 (diastereomer A) with Example 100 (diastereomer B). ¹H NMR (400 MHz, CD₃OD) δ ppm 9.48 (1 H, s), 7.97 (1 H, s), 7.68-7.73 (1 H, m), 7.59-7.67 (3 H, m), 7.51-7.58 (3 H, m), 7.14 (1 H, dd, J=18.07, 15.81 Hz), 6.75 (1 H, dd, J=15.56, 5.02 Hz), 5.34-5.53 (1 H, m), 4.32 (1 H, dd, J=12.30 Hz), 3.85-4.02 (1 H, dd, J=12.30 Hz), 3.76 (3 H, s), 3.12-3.22 (1 H, m), 2.85-2.96 (2 H, m), 1.96 (2 H, m), 1.86 (1 H, m), 1.74 (1 H, m), 1.64 (1 H, m), 1.46 (1 H, m), 1.30-1.42 (1 H, m), 0.94-1.10 (6 H, m). MS (ESI) m/z: 692.4 (M+H)⁺. Analytical HPLC: RT=7.88 min.

Example 119

Methyl 4-(3-chloro-6-((1S)-1-((E)-3-(5-chloro-2-(1 H-tetrazol-1-yl)phenyl)acrylamido)-2-(1-(cyclopropylmethyl)pyrrolidin-3-yl)ethyl)pyridazin-4-yl)phenylcarbamate, TFA salt (diastereomer mixture)

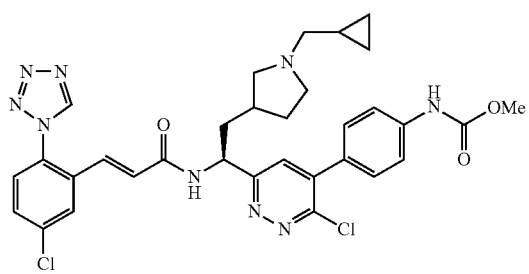

The title compound was prepared following the procedure described in Example 116 by replacing acetaldehyde with cyclopropanecarbaldehyde. ¹H NMR (400 MHz, METHANOL-d₃) δ ppm 9.53 (s, 1 H) 7.97 (t, J=2.20 Hz, 1 H) 7.71-7.75 (m, 1 H) 7.67 (dd, J=8.25, 2.20 Hz, 1 H) 7.63 (d, J=8.24 Hz, 2 H) 7.56-7.60 (m, 1 H) 7.54 (d, J=8.79 Hz, 2 H) 7.15 (d, J=15.39 Hz, 1 H) 6.69-6.79 (m, 1 H) 5.29-5.43 (m, 1 H) 3.78-3.91 (m, 1 H) 3.76 (s, 3 H) 3.62-3.74 (m, 1 H) 3.37-3.49 (m, 1 H) 3.32-3.37 (m, 1 H) 3.21-3.28 (m, 1 H) 3.05-3.14 (m, 2 H) 2.10-2.47 (m, 3 H) 1.65-2.03 (m, 1 H) 1.02-1.19 (m, 1 H) 0.68-0.78 (m, 2 H) 0.36-0.49 (m, 2 H). LC-MS (ESI) m/z: 662.2 (M+H)⁺. Analytical HPLC: RT=5.583 min.

Example 120

(S,E)-Methyl 3-(3-(5-chloro-2-(1 H-tetrazol-1-yl)phenyl)acrylamido)-3-(6-chloro-5-(4-(methoxycarbonylamino)phenyl)pyridazin-3-yl)propanoate

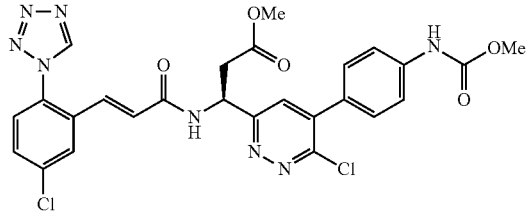

120A. (S)-tert-butyl 3-(tert-butoxycarbonylamino)-3-(5-(4-nitrophenyl)-6-oxo-1,6-dihydropyridazin-3-yl)propanoate: The compound was prepared following the procedure described in 37A by replacing (S)-tert-butyl 4-(dimethoxyphosphoryl)-3-oxo-1-phenylbutan-2-ylcarbamate with (S)-tert-butyl 3-(tert-butoxycarbonylamino)-5-

(dimethoxyphosphoryl)-4-oxopentanoate, which was prepared according to a modification of the procedure described in Intermediate 3. LC-MS (ESI) m/z: 461.1 (M+H).

120B. (S)-3-amino-3-(5-(4-(methoxycarbonylamino)phenyl)-6-oxo-1,6-dihydropyridazin-3-yl)propanoic acid, TFA salt: The compound was prepared following the procedures described in 111A, 37C, and 37D, by replacing 99B with 120A. In procedure 37C, pyridine was used instead of TEA. LC-MS (ESI) m/z: 333.1 (M+H)⁺.

120C. (S)-methyl 3-amino-3-(6-chloro-5-(4-(methoxycarbonylamino)phenyl)pyridazin-3-yl)propanoate: The compound was prepared following the procedures described in 55A, 90A, and 38A, by replacing 38A with 120B. LC-MS (ESI) m/z: 365.1 (M+H)⁺.

120D. Example 120 was prepared following the procedure described in 37E, by replacing 37D with 120C. $^1$H NMR (400 MHz, METHANOL-d$_3$) δ ppm 9.51 (s, 1 H) 7.97 (d, J=2.20 Hz, 1 H) 7.72 (s, 1 H) 7.62-7.67 (m, 2 H) 7.61 (s, 1 H) 7.55-7.58 (m, 1 H) 7.53-7.55 (m, 1 H) 7.50-7.53 (m, 1 H) 7.14 (d, J=15.39 Hz, 1H) 6.72 (d, J=15.39 Hz, 1 H) 5.66 (t, J=6.87 Hz, 1 H) 3.76 (s, 3 H) 3.67 (s, 3 H) 3.25 (dd, J=16.49, 7.15 Hz, 1 H) 3.12 (dd, J=16.49, 7.15 Hz, 1 H). LC-MS (ESI) m/z: 597.0 (M+H)⁺. Analytical HPLC: RT=7.635 min.

Example 121

(S,E)-Methyl 4-(3-chloro-6-(1-(3-(5-chloro-2-(1H-tetrazol-1-yl)phenyl)acrylamido)-3-(isopropyl(methyl)amino)-3-oxopropyl)pyridazin-4-yl)phenylcarbamate

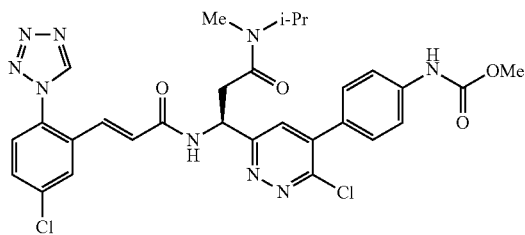

121A. (S)-methyl 3-(tert-butoxycarbonylamino)-3-(6-chloro-5-(4-(methoxycarbonylamino)phenyl)pyridazin-3-yl)propanoate: The compound was prepared following the procedure described in 55A, by replacing 38A with 120C. LC-MS (ESI) m/z: 465.1 (M+H)⁺.

121B. (S)-3-(tert-butoxycarbonylamino)-3-(6-chloro-5-(4-(methoxycarbonylamino)phenyl)pyridazin-3-yl)propanoic acid: To a solution of 121A (91 mg, 0.196 mmol) in MeOH (1 mL), THF (1.000 mL) and water (1.000 mL) was added LiOH (23.44 mg, 0.979 mmol). The reaction mixture was stirred under argon at rt for 1 h. HCl (1.0N) was added to neutralize the reaction mixture. The solvent was removed to give 121B as a crude product, which was used without further purification. LC-MS (ESI) m/z: 451.1 (M+H)⁺.

121C. (4-{6-[(S)-1-tert-butoxycarbonylamino-2-(isopropyl-methyl-carbamoyl)-ethyl]-3-chloro-pyridazin-4-yl}-phenyl)-carbamic acid methyl ester: The compound was prepared following the procedure for amide formation described in Example 22, by replacing dimethylamine HCl salt with N-methylpropan-2-amine LC-MS (ESI) m/z: 506.1 (M+H)⁺.

121D. Example 121 was prepared following the procedures described in 37D-E by replacing 37C with 121C. $^1$H NMR (400 MHz, METHANOL-d$_3$) δ ppm 9.50 (s, 1 H) 7.97 (d, J=2.20 Hz, 1 H) 7.73 (s, 1 H) 7.62-7.67 (m, 2 H) 7.61 (s, 1 H) 7.52-7.57 (m, 3 H) 7.13 (d, J=15.94 Hz, 1 H) 6.74 (dd, J=15.39, 1.10 Hz, 1 H) 5.67 (ddd, J=7.56, 5.63, 2.20 Hz, 1 H) 3.76 (s, 3 H) 3.38-3.46 (m, 1 H) 3.18 (dd, J=16.49, 6.05 Hz, 1 H) 2.92, 2.71 (two singlets, 3 H) 1.22 (t, J=6.87 Hz, 3 H) 1.06 (dd, J=12.92, 6.87 Hz, 3 H). LC-MS (ESI) m/z: 638.1 (M+H)⁺. Analytical HPLC: RT=8.049 min.

Example 122

Methyl 4-(3-chloro-6-((S)-1-((E)-3-(5-chloro-2-(1H-tetrazol-1-yl)phenyl)acrylamido)-3-((R)-3-hydroxypyrrolidin-1-yl)-3-oxopropyl)pyridazin-4-yl)phenylcarbamate

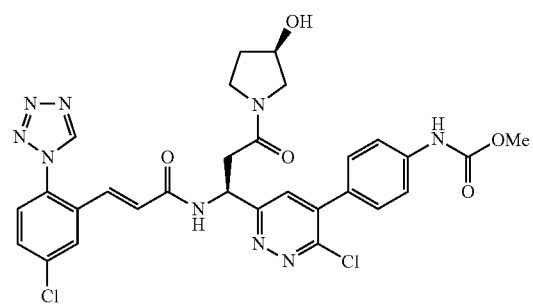

The title compound was prepared following the procedures described in 121C-D, by replacing N-methylpropan-2-amine with (R)-pyrrolidin-3-ol. $^1$H NMR (400 MHz, CD$_3$OD) δ ppm 9.49 (s, 1 H) 7.95 (d, J=2.27 Hz, 1 H) 7.73 (d, J=1.26 Hz, 1 H) 7.62-7.66 (m, 1 H) 7.58-7.62 (m, 2 H) 7.49-7.58 (m, 3 H) 7.13 (d, J=15.66 Hz, 1 H) 6.73 (dd, J=15.66, 3.79 Hz, 1 H) 5.61-5.76 (m, 1 H) 4.31-4.52 (m, 1 H) 3.76 (s, 3 H) 3.60-3.73 (m, 2 H) 3.45-3.51 (m, 1 H) 3.37-3.41 (m, 1 H) 3.21-3.28 (m, 1 H) 3.10-3.21 (m, 1 H) 1.85-2.02 (m, 2 H). LC-MS (ESI) m/z: 652.1 (M+H)⁺. Analytical HPLC: RT=6.231 min.

Example 123

(S,E)-Methyl 4-(3-chloro-6-(1-(3-(5-chloro-2-(1H-tetrazol-1-yl)phenyl)acrylamido)-2-(thiazol-4-yl)ethyl)pyridazin-4-yl)phenylcarbamate

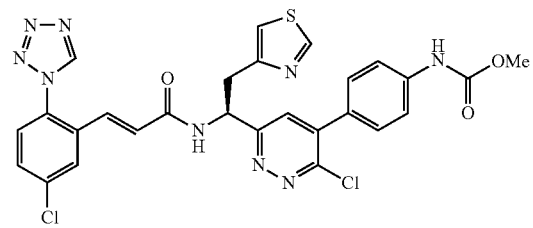

123A. (S)-tert-butyl 4-(dimethoxyphosphoryl)-3-oxo-1-(thiazol-4-yl)butan-2-ylcarbamate: The compound was prepared using the procedures described in 90A-B, by replacing (S)-2-(tert-butoxycarbonylamino)-4-(methylthio)butanoic acid with (S)-2-(tert-butoxycarbonylamino)-3-(thiazol-4-yl)propanoic acid. MS (ESI) m/z: 278.8 (M+H-Boc)⁺.

123B. Example 123 was prepared using the procedures described in 37A-C and Example 38, by replacing (S)-tert-butyl 4-(dimethoxyphosphoryl)-3-oxo-1-phenylbutan-2-ylcarbamate with 123A. ¹H NMR (400 MHz, CD₃OD) δ ppm 9.49 (1H, s), 9.00 (1 H, d, J=2.01 Hz), 7.96 (1 H, d, J=2.26 Hz), 7.54-7.66 (5 H, m), 7.45-7.50 (2 H, m), 7.33 (1 H, d, J=2.01 Hz), 7.07 (1 H, d, J=15.56 Hz), 6.74 (1 H, d, J=15.56 Hz), 5.69 (1 H, dd, J=7.91, 6.65 Hz), 3.76 (3 H, s), 3.55 (2 H, dd, J=9.91, 7.40 Hz). MS (ESI) m/z: 622.0 (M+H)⁺. Analytical HPLC: RT=7.26 min.

Example 124

Methyl 4-(3-chloro-6-((1S)-1-((E)-3-(5-chloro-2-(1H-tetrazol-1-yl)phenyl)acrylamido)-2-(1-(methylcarbamoyl)piperidin-3-yl)ethyl)pyridazin-4-yl)phenylcarbamate

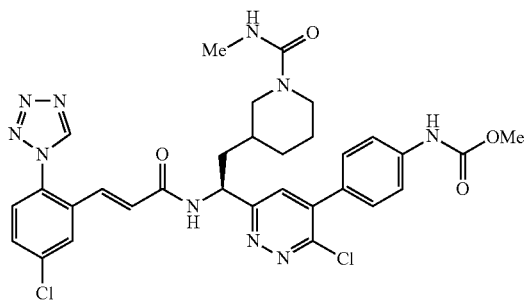

124A. (4-{6-[(S)-1-benzyloxycarbonylamino-2-(1-methylcarbamoyl-piperidin-3-yl)-ethyl]-3-chloro-pyridazin-4-yl}-phenyl)-carbamic acid methyl ester: The compound was prepared using the procedure described in Example 107, by replacing Example 106 with 111C. MS (ESI) m/z: 581.2 (M+H)⁺.

124B. methyl 4-(6-((1S)-1-amino-2-(1-(methylcarbamoyl)piperidin-3-yl)ethyl)-3-chloropyridazin-4-yl)phenylcarbamate: A solution of 124A (85 mg, 0.146 mmol) in TFA (2 mL) was heated at reflux under for 1.5 h. The mixture was concentrated and purified by reverse phase chromatography to give 124B as diastereomer A (25 mg, 0.045 mmol, 30.5% yield) [MS (ESI) m/z: 447.1 (M+H)⁺] and 124C as diastereomer B (12 mg, 0.021 mmol, 14.62% yield) [MS (ESI) m/z: 447.2 (M+H)⁺]

124D. Example 124 (diastereomer A) was prepared using the procedure described in 37E by replacing 37D with 124B (diastereomer A). ¹H NMR (400 MHz, CD₃OD) δ ppm 9.52 (1 H, s), 7.99 (1 H, d, J=2.01 Hz), 7.69-7.73 (1 H, m), 7.59-7.67 (3 H, m), 7.52-7.58 (3 H, m), 7.14 (1 H, d, J=15.56 Hz), 6.75-6.82 (1 H, m), 5.46 (1 H, dd, J=9.79, 5.52 Hz), 3.94 (1 H, d, J=2.51 Hz), 3.85 (1 H, m), 3.76 (3 H, s), 2.78-2.87 (1 H, m), 2.73 (1 H, dd, J=13.30, 10.04 Hz), 2.64 (3 H, s), 1.83-1.94 (3 H, m), 1.61-1.70 (1 H, m), 1.55 (1 H, s), 1.44 (1 H, s), 1.28-1.39 (1 H, m). MS (ESI) m/z: 679.2 (M+H)⁺. Analytical HPLC: RT=7.09 min.

Example 125

Methyl 4-(3-chloro-6-((1S)-1-((E)-3-(5-chloro-2-(1H-tetrazol-1-yl)phenyl)acrylamido)-2-(1-(methylcarbamoyl)piperidin-3-yl)ethyl)pyridazin-4-yl)phenylcarbamate

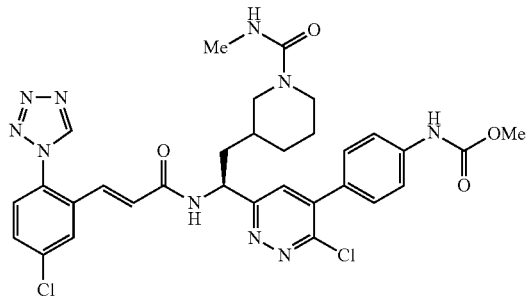

The title compound (diastereomer B) was prepared using the procedure described in 37E, by replacing 37D with 124C (diastereomer B). ¹H NMR (400 MHz, CD₃OD) δ ppm 9.50 (1 H, s), 7.98 (1 H, d, J=2.26 Hz), 7.68-7.72 (1 H, m), 7.59-7.66 (3 H, m), 7.51-7.58 (3 H, m), 7.11 (1 H, d, J=15.81 Hz), 6.76 (1 H, d, J=15.56 Hz), 5.36 (1 H, dd, J=9.54, 6.02 Hz), 3.95 (1 H, dd, J=13.05, 3.76 Hz), 3.79 (1 H, s), 3.76 (3 H, s), 2.80-2.90 (1 H, m), 2.70 (3 H, s), 2.61-2.67 (1 H, m), 1.85-1.97 (3H, m), 1.63-1.71 (1 H, m), 1.53 (1 H, d, J=6.02 Hz), 1.35-1.46 (1 H, m), 1.21-1.32 (1 H, m). MS (ESI) m/z: 679.2 (M+H)⁺. Analytical HPLC: RT=6.88 min.

Example 126

(S,E)-Methyl 4-(3-chloro-6-(1-(3-(5-chloro-2-(1H-tetrazol-1-yl)phenyl)acrylamido)-2-(4-methylthiazol-2-yl)ethyl)pyridazin-4-yl)phenylcarbamate

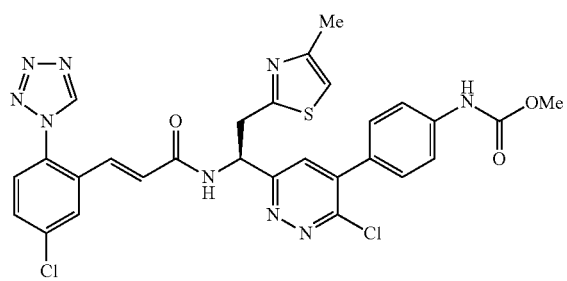

126A. (S)-tert-butyl 4-(dimethoxyphosphoryl)-1-(4-methylthiazol-2-yl)-3-oxobutan-2-ylcarbamate: The compound was prepared according to the procedures described in Intermediate 6 by replacing 1-ethyl-1H-pyrazole-4-carbaldehyde with 4-methylthiazole-2-carbaldehyde. MS (ESI) m/z: 393.1 (M+H)⁺.

126B. Example 126 was prepared using the procedures described in 37A-C and Example 38, by replacing (S)-tert-butyl 4-(dimethoxyphosphoryl)-3-oxo-1-phenylbutan-2-ylcarbamate with 126A. ¹H NMR (400 MHz, CD₃OD) δ ppm 9.48 (1H, s), 7.95 (1 H, d, J=2.27 Hz), 7.59-7.68 (4 H, m), 7.54-7.58 (1 H, m), 7.47-7.52 (2 H, m), 7.08-7.15 (2 H, m), 6.72 (1 H, d, J=15.66 Hz), 5.73 (1 H, dd, J=7.96, 6.19 Hz), 3.80-3.89 (1 H, m), 3.76-3.79 (3 H, s), 3.71-3.76 (1 H, m), 2.39 (3 H, d, J=1.01 Hz). MS (ESI) m/z: 636.1 (M+H)+. Analytical HPLC: RT=7.3 min.

Example 127

(S,E)-Methyl 4-(3-chloro-6-(1-(3-(3-chloro-2-fluoro-6-(1H-tetrazol-1-yl)phenyl)acrylamido)-2-(4-methylthiazol-2-yl)ethyl)pyridazin-4-yl)phenylcarbamate

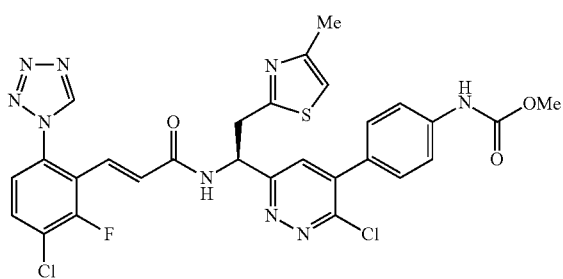

The title compound was prepared using the procedures described in 37A-C, Example 38A, and 48C, by replacing (S)-tert-butyl 4-(dimethoxyphosphoryl)-3-oxo-1-phenylbutan-2-ylcarbamate with 126A. In addition, in procedure 48C, Intermediate 1B was replaced with Intermediate 7. ¹H NMR (400 MHz, CD₃OD) δ ppm 9.51 (1 H, s), 7.73-7.80 (1 H, m), 7.67 (1 H, s), 7.62 (2 H, d, J=8.78 Hz), 7.49-7.53 (2 H, m), 7.45 (1 H, dd, J=8.53, 1.51 Hz), 7.14 (1 H, d, J=1.00 Hz), 7.00 (1 H, d, J=16.06 Hz), 6.71 (1 H, d, J=16.56 Hz), 5.72 (1 H, dd, J=8.16, 6.15 Hz), 3.81-3.87 (1 H, m), 3.76 (3 H, s), 3.69-3.75 (1 H, m), 2.40 (3 H, s). MS (ESI) m/z: 654.2 (M+H)+. Analytical HPLC: RT=7.47 min.

Example 128

(S,E)-Methyl 4-(6-(1-(3-(5-chloro-2-(1H-tetrazol-1-yl)phenyl)acrylamido)-3-(piperidin-4-yl)propyl)-3-oxo-2,3-dihydropyridazin-4-yl)phenylcarbamate, TFA salt

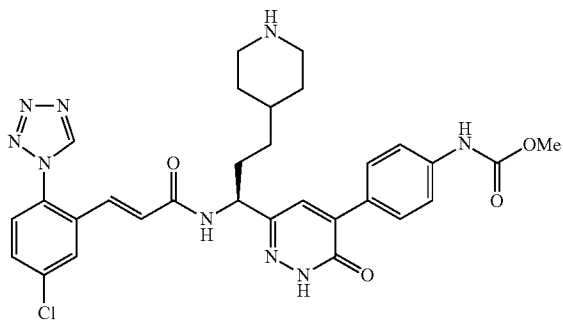

128A. (S)-tert-butyl 4-(3-(benzyloxycarbonylamino)-5-(dimethoxyphosphoryl)-4-oxopentyl)piperidine-1-carboxylate: The compound was prepared following the procedures described in Intermediate 6, by replacing tert-butyl 4-(2-oxoethyl)piperidine-1-carboxylate with 1-ethyl-1H-pyrazole-4-carbaldehyde and by replacing methyl 2-(benzyloxycarbonylamino)-2-(dimethoxyphosphoryl)acetate with Boc-methyl-2-(dimethylphosphono)glycinate. MS (ESI) m/z: 527.4 (M+H)+.

128B. (S)-tert-butyl 4-(3-(benzyloxycarbonylamino)-3-(5-(4-(methoxycarbonylamino)phenyl)-6-oxo-1,6-dihydropyridazin-3-yl)propyl)piperidine-1-carboxylate: To 128A (0.7 g, 1.329 mmol) and ethyl 2-(4-(methoxycarbonylamino)phenyl)-2-oxoacetate (0.334 g, 1.329 mmol) in EtOH (25 mL), cooled to 0° C., was added K₂CO₃ (0.551 g, 3.99 mmol). After 4 h, hydrazine hydrate (0.083 mL, 2.66 mmol) was added dropwise to the cold reaction mixture. After 0.5 h, an additional 0.3 mL of hydrazine hydrate was added and the reaction was stirred 18 h. The reaction was concentrated partially and dilute HCl was added. A yellow solid was filtered off. The filtrate was extracted (3×25 mL) EtOAc, organic layer washed with brine (25 mL) and dried (MgSO₄). The solid and extract were purified by HPLC to afford two fractions of 0.161 g and 0.114 g with the desired mass. MS (ESI) m/z: 620.5 (M+H)+.

128C. (S)-tert-butyl 4-(3-amino-3-(5-(4-(methoxycarbonylamino)phenyl)-6-oxo-1,6-dihydropyridazin-3-yl)propyl)piperidine-1-carboxylate: The products of 128B were each separately hydrogenated at 50 psi in presence of 10% Pd/C in EtOH(25 mL). Each was purified by HPLC freeze-dried and afforded two fractions of white solids 15 mg and 48 mg, both MS (ESI) m/z: 430.3 (M+H-t-butyl)+.

128D. Example 128: To Intermediate 1 (0.036 g, 0.103 mmol) and 128C (0.05 g, 0.103 mmol) was added DMF (1 mL) and Hunig's Base (0.054 mL, 0.309 mmol). After stirring 18 h, the reaction was concentrated and treated with 30% TFA/DCM for 1 h. Purification by reverse phase chromatography and freeze-drying afforded 1.8 mg (2.1%) white solid. ¹H NMR (400 MHz, CD₃OD) δ: 9.50-9.56 (1H, m), 8.73 (1 H, d, J=8.25 Hz), 7.96 (1 H, d, J=2.20 Hz), 7.76-7.86 (2 H, m), 7.62-7.69 (1 H, m), 7.49-7.60 (3 H, m), 7.14 (1 H, d, J=15.39 Hz), 6.70 (1 H, d, J=15.39 Hz), 4.95-5.04 (1 H, m), 3.74 (3 H, s), 3.33-3.40 (2 H, m), 2.88-3.06 (2 H, m), 1.83-2.06 (4 H, m), 1.57-1.69 (1 H, m), 1.26-1.47 (4 H, m) ppm. MS (ESI) m/z: 618.4 (M+H)+. Analytical HPLC: RT=4.49 min. (Method B).

Example 129

(S,E)-N-(1-(5-(2-Aminothiazol-4-yl)-6-oxo-1,6-dihydropyridazin-3-yl)-2-phenylethyl)-3-(5-chloro-2-(1H-tetrazol-1-yl)phenyl)acrylamide, TFA salt

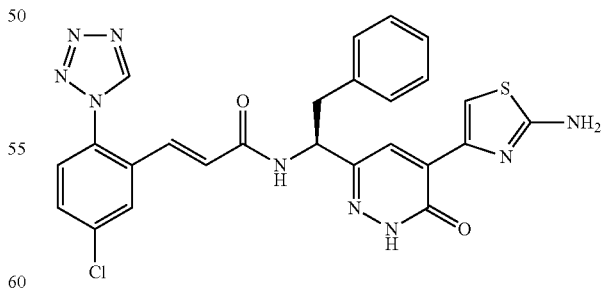

The title compound was prepared following the procedure described in Example 37 by replacing ethyl 2-(4-nitrophenyl)-2-oxoacetate with ethyl 2-(2-aminothiazol-4-yl)-2-oxoacetate. ¹H NMR (400 MHz, CD₃OD) δ ppm 9.50 (s, 1 H) 7.94 (d, J=2.01 Hz, 1 H) 7.88 (s, 1 H) 7.84 (s, 1 H) 7.64 (dd, J=8.53, 2.26 Hz, 1 H) 7.56 (d, J=8.53 Hz, 1 H) 7.14-7.29 (m, 5 H) 7.07 (d, J=15.56 Hz, 1 H) 6.67 (d, J=15.56 Hz, 1 H) 5.11-5.33 (m, 1 H) 3.25-3.27 (m, 1 H) 3.10-3.18 (m, 1 H). LC-MS (ESI) m/z: 546.0/548.0 (M+H)$^+$. Analytical HPLC: RT=6.156 min.

Example 130

(S,E)-Methyl 4-(6-(1-(3-(5-chloro-2-(1H-tetrazol-1-yl)phenyl)acrylamido)-3-(methylthio)propyl)-3-oxo-2,3-dihydropyridazin-4-yl)phenylcarbamate

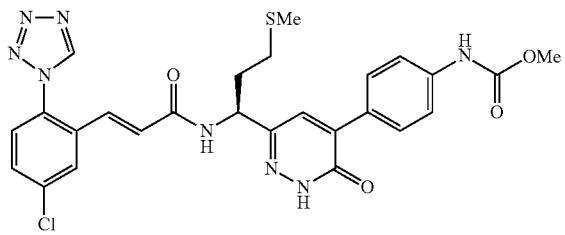

The title compound was prepared using the procedures described in Example 37, by replacing (S)-tert-butyl 4-(dimethoxyphosphoryl)-3-oxo-1-phenylbutan-2-ylcarbamate with 90B. $^1$H NMR (400 MHz, DMSO-D$_6$) δ ppm 13.02 (1 H, s), 9.85-9.92 (2 H, m), 8.67 (1 H, d, J=8.28 Hz), 7.98 (1 H, d, J=2.01 Hz), 7.86 (2 H, d, J=8.78 Hz), 7.71-7.78 (2 H, m), 7.58 (1 H, s), 7.55 (2 H, d, J=8.78 Hz), 6.86-6.93 (1 H, d, J=15.5 Hz), 6.74-6.80 (1 H, d, J=15.5 Hz), 4.95 (1 H, m), 3.68 (3 H, s), 2.49-2.51 (m, 2 H), 1.98-2.09 (5 H, m). MS (ESI) m/z: 581.0 (M+H)$^+$. Analytical HPLC: RT=7.31 min.

Example 131

(S,E)-Methyl 4-(6-(1-(3-(5-chloro-2-(1H-tetrazol-1-yl)phenyl)acrylamido)-2-(pyridin-3-yl)ethyl)-3-oxo-2,3-dihydropyridazin-4-yl)phenylcarbamate

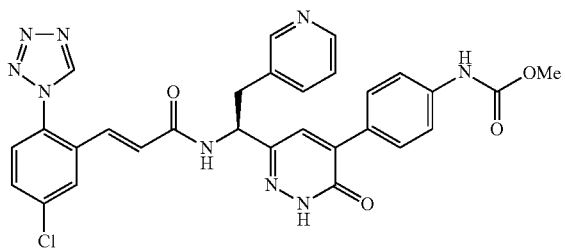

The title compound was prepared using the procedures described in Example 37, by replacing (S)-tert-butyl 4-(dimethoxyphosphoryl)-3-oxo-1-phenylbutan-2-ylcarbamate with 95A. $^1$H NMR (400 MHz, CD$_3$OD) δ ppm 9.52 (1H, s), 8.85-8.91 (2 H, m), 8.77 (1 H, d, J=5.52 Hz), 8.58 (1 H, d, J=8.28 Hz), 8.05 (1H, dd, J=7.91, 5.90 Hz), 7.95 (1 H, d, J=2.26 Hz), 7.84 (2 H, d, J=8.78 Hz), 7.62-7.69 (2 H, m), 7.54-7.60 (3 H, m), 7.03 (1 H, d, J=15.31 Hz), 6.62 (1 H, d, J=15.56 Hz), 5.47-5.54 (1 H, m), 3.76 (3 H, s), 3.67 (1 H, dd, J=14.18, 5.65 Hz), 3.39 (1 H, m). MS (ESI) m/z: 598.1 (M+H)$^+$. Analytical HPLC: RT=5.06 min.

Example 132

(S,E)-Methyl 4-(6-(1-(3-(5-chloro-2-(1H-tetrazol-1-yl)phenyl)acrylamido)-2-(1-methyl-5-(methylsulfinyl)-1H-pyrazol-3-yl)ethyl)-3-oxo-2,3-dihydropyridazin-4-yl)phenylcarbamate

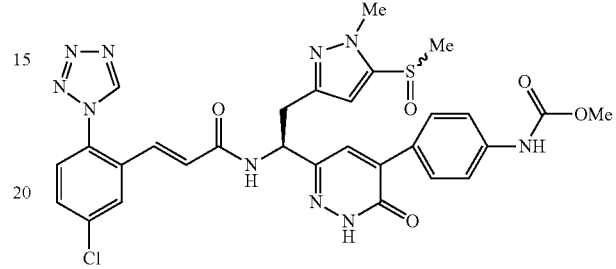

132A. 3-(dimethoxymethyl)-1-methyl-5-(methylthio)-1H-pyrazole: To a solution of 1,1-dimethoxy-4,4-bis(methylthio)but-3-en-2-one (2.6 g, 11.69 mmol), which was prepared according to a modified procedure in literature (Tetrahedron, 2003, 59, 2631-2639), in EtOH (25 mL) was added methylhydrazine (0.616 mL, 11.69 mmol). The reaction mixture was stirred under argon at 80° C. for 4 h. The solvent was removed to give 132A (2.36 g, 100% yield) as a red oil, which was used in next step without further purification. LC-MS (ESI) m/z: 170.9 (M-MeO)$^+$.

132B. 3-(dimethoxymethyl)-1-methyl-5-(methylsulfinyl)-1H-pyrazole: To a solution of 132A (2.36 g, 11.67 mmol) in Acetone (50 mL) was added OXONE® (14.35 g, 23.33 mmol). The reaction mixture was stirred over night. The reaction mixture was filtered through a pad of silica gel, washing with acetone, to remove the solid. The solvent was removed to give 132B (1.89 g 74% yield) as a tan oil. LC-MS indicated a mixture of sulfone and sulfoxide in which the sulfoxide was the majority. The mixture was used in the next step. Sulfoxide: LC-MS (ESI) m/z: 187.2 (M-MeO)$^+$. Sulfone: LC-MS (ESI) m/z: 235.2 (M+H)$^+$.

132C. 1-methyl-5-(methylsulfinyl)-1H-pyrazole-3-carbaldehyde: A solution of 132B (1.89 g, 8.66 mmol) in water (20.00 mL) and acetic acid (20 mL) was stirred under argon at 60° C. for 2 h. The solvent was removed under reduced pressure. Purification by normal phase chromatography gave 132C (1.18 g, 6.85 mmol, 79% yield) as a white solid. LC-MS (ESI) m/z: 173.1 (M+H)$^+$.

132D. (S)-tert-butyl 4-(dimethoxyphosphoryl)-1-(1-methyl-5-(methylsulfinyl)-1H-pyrazol-3-yl)-3-oxobutan-2-ylcarbamate: This compound was prepared by following the procedure described in Intermediate 6, by replacing 1-ethyl-1H-pyrazole-4-carbaldehyde with 132C. LC-MS (ESI) m/z: 460.2 (M+Na)$^+$.

132E. (4-{6-[(S)-1-tert-butoxycarbonylamino-2-(1-methyl-5-methylsulfinyl-1H-pyrazol-3-yl)-ethyl]-3-oxo-2,3-dihydro-pyridazin-4-yl}-phenyl)-carbamic acid methyl ester: The compound was prepared following the procedures described in 37A-C, by replacing (S)-tert-butyl 4-(dimethoxyphosphoryl)-3-oxo-1-phenylbutan-2-ylcarbamate with 132D. LC-MS (ESI) m/z: 531.1 (M+H).

132F. Example 132 was prepared following the procedures described in 37D-E, by replacing 37C with 132E. $^1$H NMR (400 MHz, CD$_3$OD) δ ppm 9.51 (s, 1H) 7.96 (br. s., 1 H) 7.79 (d, J=8.53 Hz, 2 H) 7.65 (dd, J=9.03, 1.25 Hz, 1 H) 7.48-7.59 (m, 4 H) 7.10 (dd, J=15.56, 4.77 Hz, 1 H) 6.63-6.74 (m, 2 H) 5.36 (q, J=7.19 Hz, 1 H) 3.98 (s, 3 H) 3.75 (s, 3 H) 3.28-3.30 (m, 1 H) 3.11-3.23 (m, 1 H) 2.99 (s, 3H). LC-MS (ESI) m/z: 663.5 (M+H)$^+$. Analytical HPLC: RT=5.966 min.

Example 133

(S,E)-Methyl 4-(6-(1-(3-(5-chloro-2-(1H-tetrazol-1-yl)phenyl)acrylamido)-2-(1-methyl-5-(methylsulfonyl)-1H-pyrazol-3-yl)ethyl)-3-oxo-2,3-dihydropyridazin-4-yl)phenylcarbamate

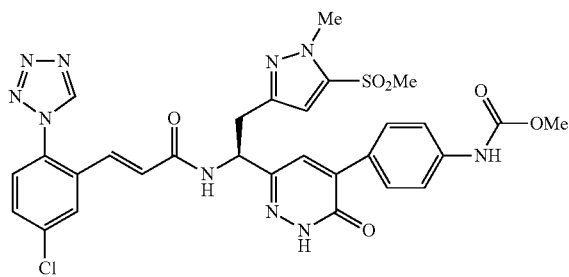

The title compound was prepared following the procedures described in Example 58 and 37D-E, by replacing 56B with 132E. $^1$H NMR (400 MHz, CD$_3$OD) δ ppm 9.50 (s, 1 H) 7.97 (d, J=2.01 Hz, 1 H) 7.79 (d, J=8.78 Hz, 2 H) 7.61-7.68 (m, 1 H) 7.56 (d, J=8.28 Hz, 2 H) 7.50-7.54 (m, 2 H) 7.11 (d, J=15.56 Hz, 1 H) 6.76 (s, 1 H) 6.69 (d, J=15.81 Hz, 1 H) 5.27-5.42 (m, 1 H) 4.04 (s, 3 H) 3.75 (s, 3 H) 3.20 (s, 3 H) 3.11-3.23 (m, 2 H). LC-MS (ESI) m/z: 679.2 (M+H)$^+$. Analytical HPLC: RT=6.813 min.

Example 134

(S,E)-Methyl 4-(6-(1-(3-(5-chloro-2-(1H-tetrazol-1-yl)phenyl)acrylamido)-2-(5-methoxy-1-methyl-1H-pyrazol-3-yl)ethyl)-3-oxo-2,3-dihydropyridazin-4-yl)phenylcarbamate

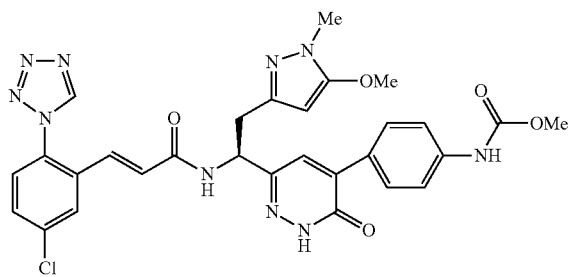

134A. methyl 5-methoxy-1-methyl-1H-pyrazole-3-carboxylate: To a cooled solution (0° C.) of methyl 5-hydroxy-1-methyl-1H-pyrazole-3-carboxylate (1.60 g, 10.25 mmol) and K$_2$CO$_3$ (2.124 g, 15.37 mmol) in DMF (10 mL) was added dropwise MeI (0.703 mL, 11.27 mmol). The reaction mixture was stirred under argon at rt for 5 days. The reaction mixture was diluted with EtOAc, washed with H$_2$O (1×15 mL), saturated NaHCO$_3$ (1×15 mL) and brine (1×15 mL). The organic phase was dried over MgSO$_4$, filtered and concentrated. Purification by normal phase chromatography gave 134A (1.20 g, 7.05 mmol, 68.8% yield) as a white solid. LC-MS (ESI) m/z: 171.2 (M+H)$^+$.

134B. (5-methoxy-1-methyl-1H-pyrazol-3-yl)methanol: To a solution of 134A (1.20 g, 7.05 mmol) in THF (40 mL) were added 2M LiBH$_4$ in THF (5.64 mL, 11.28 mmol) and MeOH (0.456 mL, 11.28 mmol). The reaction mixture was stirred under argon at 40° C. for 4 h. The reaction was cooled to rt and 1N HCl was added to adjust the pH to −1.5 and the reaction was stirred at rt for 1 h. Most of the THF was removed under reduced pressure. The reaction mixture was diluted with EtOAc, washed with saturated NaHCO$_3$ (2×20 mL) and brine (1×20 mL). The organic phase was dried over Na$_2$SO$_4$, filtered and concentrated. Purification by normal phase chromatography gave 134B (0.49 g, 3.45 mmol, 48.9% yield) as a white solid. LC-MS (ESI) m/z: 143.0 (M+H)$^+$.

134C. 5-methoxy-1-methyl-1H-pyrazole-3-carbaldehyde: To a solution of 134B (0.49 g, 3.45 mmol) in chloroform (30 mL) was added MnO$_2$ (2.82 g, 27.6 mmol). The reaction mixture was stirred under argon at reflux for 2 hrs. The mixture was cooled and filtered through a pad of CELITE®. The filtrate was concentrated to give 134C (409 mg, 2.92 mmol, 85% yield) as a white solid. LC-MS (ESI) m/z: 141.1 (M+H)$^+$.

134D. (S)-tert-butyl 4-(dimethoxyphosphoryl)-1-(5-methoxy-1-methyl-1H-pyrazol-3-yl)-3-oxobutan-2-ylcarbamate: This compound was prepared by following the procedure described in Intermediate 6, by replacing 1-ethyl-1H-pyrazole-4-carbaldehyde with 134C. LC-MS (ESI) m/z: 406.1 (M+H)$^+$.

134E. Example 134 was prepared following the procedures described in Example 37 by replacing (S)-tert-butyl 4-(dimethoxyphosphoryl)-3-oxo-1-phenylbutan-2-ylcarbamate with 134D. $^1$H NMR (400 MHz, CD$_3$OD) δ ppm 9.51 (s, 1 H) 7.95 (d, J=2.01 Hz, 1 H) 7.76 (d, J=8.78 Hz, 2 H) 7.64 (dd, J=8.53, 2.26 Hz, 1H) 7.55 (d, J=8.53 Hz, 1 H) 7.53 (d, J=8.78 Hz, 2 H) 7.47 (s, 1 H) 7.12 (d, J=15.56 Hz, 1 H) 6.70 (d, J=15.56 Hz, 1 H) 5.67 (s, 1 H) 5.31 (t, J=7.40 Hz, 1 H) 3.90 (s, 3 H) 3.75 (s, 3 H) 3.54 (s, 3 H) 3.04-3.22 (m, 2 H). LC-MS (ESI) m/z: 631.3 (M+H)$^+$. Analytical HPLC: RT=6.510 min.

Example 135

(S,E)-Methyl 4-(6-(1-(3-(5-chloro-2-(1H-tetrazol-1-yl)phenyl)acrylamido)-2-(6,7-dihydro-5H-pyrazolo[5,1-b][1,3]oxazin-2-yl)ethyl)-3-oxo-2,3-dihydropyridazin-4-yl)phenylcarbamate

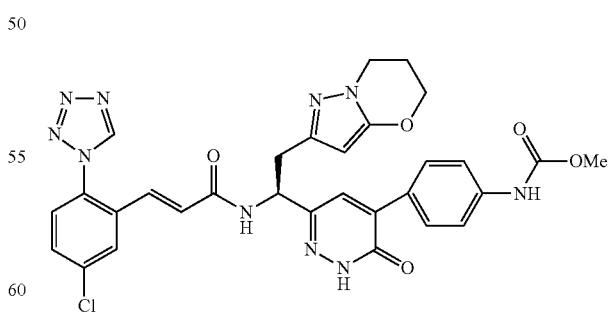

The title compound was prepared following the procedure described in Example 37 by replacing (S)-tert-butyl 4-(dimethoxyphosphoryl)-3-oxo-1-phenylbutan-2-ylcarbamate with 97A. $^1$H NMR (400 MHz, CD$_3$OD) δ ppm 9.50 (s, 1 H) 7.95 (d, J=2.26 Hz, 1 H) 7.77 (d, J=8.78 Hz, 2 H)

7.61-7.68 (m, 1 H) 7.55 (d, J=8.53 Hz, 1 H) 7.53 (d, J=8.53 Hz, 2 H) 7.46 (s, 1 H) 7.12 (d, J=15.56 Hz, 1 H) 6.69 (d, J=15.56 Hz, 1 H) 5.54 (s, 1 H) 5.30 (t, J=7.40 Hz, 1 H) 4.22-4.39 (m, 2 H) 4.09 (t, J=6.27 Hz, 2 H) 3.75 (s, 3 H) 3.14-3.22 (m, 1 H) 3.05-3.14 (m, 1 H) 2.17-2.29 (m, 2 H). LC-MS (ESI) m/z: 643.2 (M+H)+. Analytical HPLC: RT=6.801 min.

Example 136

(S,E)-tert-Butyl 3-(2-(3-(5-chloro-2-(1H-tetrazol-1-yl)phenyl)acrylamido)-2-(5-(4-(methoxycarbonylamino)phenyl)-6-oxo-1,6-dihydropyridazin-3-yl)ethyl)azetidine-1-carboxylate

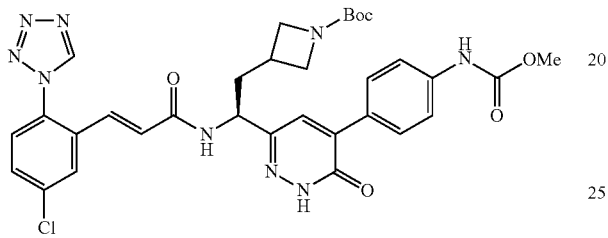

136A. (S)-tert-butyl 3-(2-(benzyloxycarbonylamino)-4-(dimethoxyphosphoryl)-3-oxobutyl)azetidine-1-carboxylate: The compound was prepared according to the procedure described in Intermediate 6 by replacing 1-ethyl-1H-pyrazole-4-carbaldehyde with tert-butyl 3-formylazetidine-1-carboxylate and by replacing Boc-methyl-2-(dimethylphosphono) glycinate with methyl 2-(benzyloxycarbonylamino)-2-(dimethoxyphosphoryl)acetate. MS (ESI) m/z: 385.4 (M+H-Boc)+.

136B. Example 136 was prepared using the procedures described in Example 37, by replacing (S)-tert-butyl 4-(dimethoxyphosphoryl)-3-oxo-1-phenylbutan-2-ylcarbamate with 136A. 1H NMR (400 MHz, CD3OD) δ ppm 9.51 (1H, s), 7.97 (1 H, d, J=2.26 Hz), 7.80-7.84 (2 H, m), 7.63-7.68 (1 H, m), 7.52-7.59 (4 H, m), 7.16 (1 H, d, J=15.56 Hz), 6.70 (1 H, d, J=15.56 Hz), 5.00 (1 H, dd, J=8.53, 6.02 Hz), 3.93-4.03 (2 H, m), 3.75 (3 H, s), 3.56-3.67 (2 H, m), 2.66 (1 H, d, J=6.53 Hz), 2.20-2.29 (1 H, m), 2.09-2.18 (1 H, m), 1.41 (9 H, s). MS (ESI) m/z: 576.3 (M+H-Boc)+. Analytical HPLC: RT=7.4 min.

Example 137

(S,E)-Methyl 4-(6-(2-(azetidin-3-yl)-1-(3-(5-chloro-2-(1H-tetrazol-1-yl)phenyl)acrylamido)ethyl)-3-oxo-2,3-dihydropyridazin-4-yl)phenylcarbamate

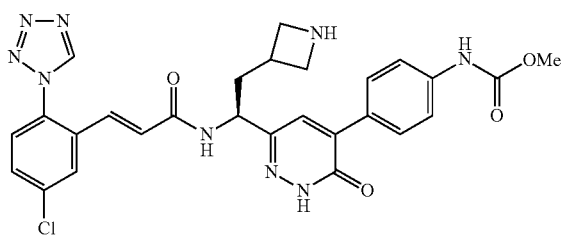

The title compound was prepared using the procedure described in 37D, by replacing 37C with 136B. 1H NMR (400 MHz, CD3OD) δ ppm 9.54 (1 H, s), 9.45 (1 H, s), 7.97 (1 H, d, J=2.26 Hz), 7.82 (2 H, d, J=8.78 Hz), 7.62-7.69 (1 H, m), 7.52-7.61 (4 H, m), 7.17 (1 H, d, J=15.56 Hz), 6.69 (1 H, d, J=15.56 Hz), 4.99-5.07 (1 H, m), 4.07 (2 H, q, J=8.87 Hz), 3.89 (2 H, dd, J=10.54, 8.28 Hz), 3.75 (3 H, s), 2.99-3.10 (1 H, m), 2.35 (1 H, ddd, J=13.93, 8.03, 5.90 Hz), 2.18 (1 H, ddd, J=13.99, 8.60, 7.28 Hz). MS (ESI) m/z: 576.3 (M+H)+. Analytical HPLC: RT=4.7 min.

Example 138 tert-Butyl 3-((S)-2-((E)-3-(5-chloro-2-(1H-tetrazol-1-yl)phenyl)acrylamido)-2-(5-(4-(methoxycarbonylamino)phenyl)-6-oxo-1,6-dihydropyridazin-3-yl)ethyl)piperidine-1-carboxylate (diastereomer mixture)

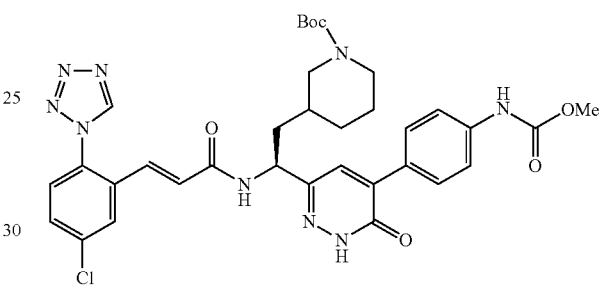

The title compound was prepared using the procedure described in 37C, by replacing 37B with 99C. 1H NMR (400 MHz, CD3OD) δ ppm 9.50 (1 H, d, J=2.51 Hz), 7.96 (1 H, d, J=2.01 Hz), 7.76-7.85 (2 H, m), 7.61-7.67 (1 H, m), 7.51-7.59 (4 H, m), 7.12-7.20 (1 H, m), 6.68-6.75 (1 H, m), 5.07-5.17 (1 H, m), 3.80-3.70 (2 H, m), 3.75 (3 H, s), 3.30-3.25 (2 H, m), 2.79-2.90 (2 H, m), 1.90 (1 H, m), 1.79 (1 H, d, J=7.53 Hz), 1.66 (1 H, d, J=13.55 Hz), 1.51-1.61 (1 H, m), 1.33-1.44 (10H, m). MS (ESI) m/z: 704.5 (M+H)+. Analytical HPLC: RT=7.83 min.

Example 139

(±)-(E)-Methyl 4-(6-(1-(3-(5-chloro-2-(1H-tetrazol-1-yl)phenyl)acrylamido)but-3-enyl)-3-oxo-2,3-dihydropyridazin-4-yl)phenylcarbamate

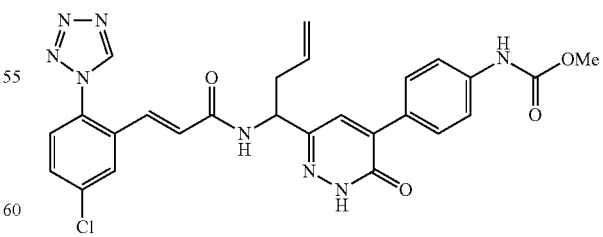

The title compound was prepared following the procedure described in Example 37 by replacing (S)-tert-butyl 4-(dimethoxyphosphoryl)-3-oxo-1-phenylbutan-2-ylcarbamate with (±)-tert-butyl 1-(dimethoxyphosphoryl)-2-oxo-hex-5-en-3-ylcarbamate which was prepared following a similar procedure described in Intermediate 3. ¹H NMR (400 MHz, CD₃OD) δ ppm 9.41 (s, 1 H) 7.86 (d, J=2.01 Hz, 1 H) 7.70 (d, J=8.53 Hz, 2 H) 7.54 (dd, J=8.53, 2.01 Hz, 1 H) 7.39-7.49 (m, 4H) 7.04 (d, J=15.56 Hz, 1 H) 6.63 (d, J=15.56 Hz, 1 H) 5.62-5.82 (m, 1 H) 4.92-5.08 (m, 3 H) 3.65 (s, 3 H) 2.56-2.67 (m, 1 H) 2.45-2.56 (m, 1 H). LC-MS (ESI) m/z: 547.2 (M+H)⁺. Analytical HPLC: RT=6.943 min.

Example 140

[4-(6-{(S)-2-(4-Benzyloxycarbonylamino-phenyl)-1-[(E)-3-(5-chloro-2-tetrazol-1-yl-phenyl)-acryloylamino]-ethyl}-3-oxo-2,3-dihydro-pyridazin-4-yl)-phenyl]-carbamic acid methyl ester

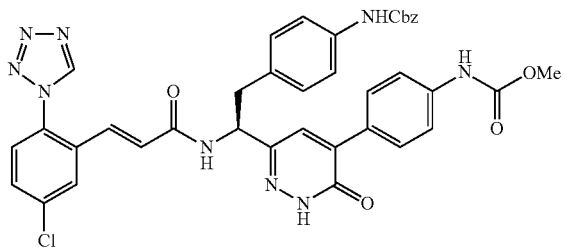

The title compound was prepared using the procedure described in Example 37, by replacing (S)-tert-butyl 4-(dimethoxyphosphoryl)-3-oxo-1-phenylbutan-2-ylcarbamate with [(S)-4-(4-benzyloxycarbonylamino-phenyl)-3-ten-butoxycarbonylamino-2-oxo-butyl]-phosphonic acid dimethyl ester which was prepared using the procedure described in Intermediate 3. ¹H NMR (400 MHz, CD₃OD) δ ppm 9.39 (s, 1 H) 7.85 (d, J=2.26 Hz, 1 H) 7.59 (d, J=8.78 Hz, 2 H) 7.54 (dd, J=8.53, 2.26 Hz, 1 H) 7.45 (d, J=8.53 Hz, 1 H) 7.41 (d, J=8.78 Hz, 2 H) 7.19-7.33 (m, 8 H) 7.03 (d, J=8.53 Hz, 2 H) 6.99 (d, J=15.56 Hz, 1 H) 6.61 (d, J=15.56 Hz, 1 H) 5.09-5.15 (m, 1 H) 5.07 (s, 2 H) 3.64 (s, 3 H) 3.04 (d, J=7.53 Hz, 2 H). LC-MS (ESI) m/z: 746.3 (M+H)⁺. Analytical HPLC: RT=8.194 min.

Example 141

(S,E)-Methyl 4-(6-(2-(1-acetylazetidin-3-yl)-1-(3-(5-chloro-2-(1H-tetrazol-1-yl)phenyl)acrylamido)ethyl)-3-oxo-2,3-dihydropyridazin-4-yl)phenylcarbamate

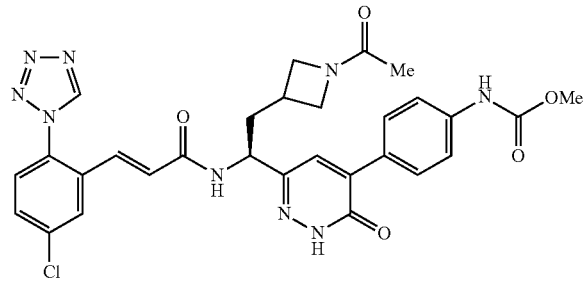

The title compound was prepared using the procedure described in Example 101, by replacing Example 99 with Example 137. ¹H NMR (400 MHz, THF-D₈) δ ppm 9.2 (1 H, s), 8.77 (1 H, s), 7.88 (1 H, d, J=2.26 Hz), 7.78 (2 H, d, J=8.78 Hz), 7.62-7.69 (1 H, m), 7.52-7.61 (4 H, m), 7.17 (1 H, d, J=15.56 Hz), 6.69 (1 H, d, J=15.56 Hz), 4.99-5.07 (1 H, m), 4.07 (2 H, q, J=8.87 Hz), 3.89 (2 H, dd, J=10.54, 8.28 Hz), 3.75 (3 H, s), 2.99-3.10 (1 H, m), 2.35 (1 H, ddd, J=13.93, 8.03, 5.90 Hz), 2.18 (1 H, ddd, J=13.99, 8.60, 7.28 Hz), 2.0 (3 H, s). MS (ESI) m/z: 618.4 (M+H)⁺. Analytical HPLC: RT=5.5 min.

Example 142

(S,E)-Methyl 4-(6-(2-(4-aminophenyl)-1-(3-(5-chloro-2-(1H-tetrazol-1-yl)phenyl)acrylamido)ethyl)-3-oxo-2,3-dihydropyridazin-4-yl)phenylcarbamate, TFA salt

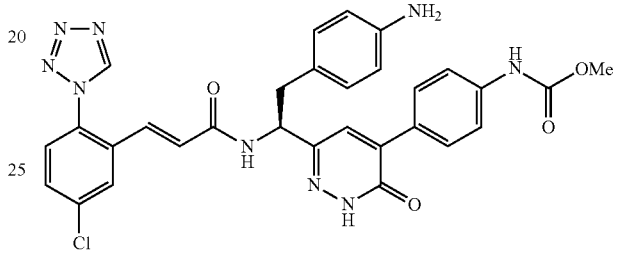

The title compound was prepared using the procedure described in Example 105, by replacing Example 104 with Example 140. ¹H NMR (400 MHz, CD₃OD) δ ppm 9.41 (s, 1 H) 9.35 (br. s, 1 H) 8.73 (br. d, J=8.53 Hz, 1 H) 7.84 (d, J=2.26 Hz, 1 H) 7.68 (d, J=8.78 Hz, 2 H) 7.55 (dd, J=8.53, 2.26 Hz, 1 H) 7.47 (d, J=8.53 Hz, 1 H) 7.40-7.45 (m, 3 H) 7.34 (m, J=8.28 Hz, 2 H) 7.21 (m, J=8.28 Hz, 2H) 6.94 (d, J=15.56 Hz, 1 H) 6.55 (d, J=15.56 Hz, 1 H) 5.15-5.27 (m, 1 H) 3.65 (s, 3 H) 3.24-3.30 (m, 1 H) 3.09 (dd, J=13.68, 8.66 Hz, 1 H). LC-MS (ESI) m/z: 612.3 (M+H)⁺. Analytical HPLC: RT=4.633 min.

Example 143

(S,E)-Methyl 4-(6-(2-(4-acetamidophenyl)-1-(3-(5-chloro-2-(1H-tetrazol-1-yl)phenyl)acrylamido)ethyl)-3-oxo-2,3-dihydropyridazin-4-yl)phenylcarbamate

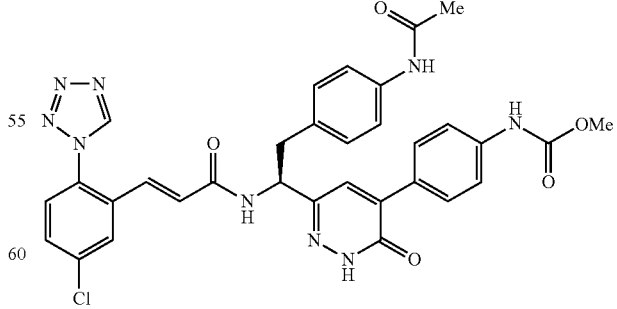

The title compound was prepared using the procedure described in Example 106, by replacing Example 105 with Example 142. ¹H NMR (400 MHz, CD₃OD) δ ppm 9.42 (s, 1 H) 7.89 (d, J=2.01 Hz, 1 H) 7.63 (m, J=8.78 Hz, 2 H) 7.58 (dd, J=8.53, 2.01 Hz, 1 H) 7.49 (d, J=8.53 Hz, 1 H) 7.44 (m, J=8.53 Hz, 2 H) 7.39 (m, J=8.53 Hz, 2 H) 7.26 (s, 1 H) 7.10 (m, J=8.28 Hz, 2 H) 7.02 (d, J=15.56 Hz, 1 H) 6.63 (d, J=15.56 Hz, 1 H) 5.16 (t, J=7.53 Hz, 1 H) 3.68 (s, 3 H) 3.05-3.11 (m, 2 H) 2.04 (s, 3 H). LC-MS (ESI) m/z: 654.2 (M+H)$^+$. Analytical HPLC: RT=6.306 min.

Example 144

Methyl 4-(6-((1S)-1-((E)-3-(5-chloro-2-(1H-tetrazol-1-yl)phenyl)acrylamido)-2-(piperidin-3-yl)ethyl)-3-oxo-2,3-dihydropyridazin-4-yl)phenylcarbamate (diastereomer mixture)

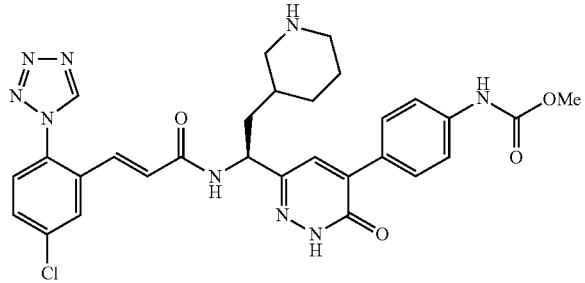

The title compound, as a mixture of diastereomers, was prepared using the procedure described in 37D, by replacing 37C with Example 138. $^1$H NMR (400 MHz, CD$_3$OD) δ ppm 9.55 (1 H, s), 7.96-8.00 (1 H, m), 7.84 (2 H, d, J=8.78 Hz), 7.66-7.71 (1 H, m), 7.58-7.61 (2 H, m), 7.56 (2 H, d, J=8.53 Hz), 7.15-7.22 (1 H, m), 6.71 (1 H, t, J=15.81 Hz), 5.18 (1 H, dd, J=6.02, 2.51 Hz), 3.76 (3 H, s), 3.34-3.43 (2 H, m), 2.86-2.95 (1 H, m), 2.76 (1 H, t, J=11.92 Hz), 2.06 (1 H, m, 1.90-2.00 (3 H, m), 1.78-1.90 (2 H, m), 1.70 (1 H, m). MS (ESI) m/z: 604.2 (M+H)$^+$. Analytical HPLC: RT=5.0 min.

Example 145

(S,E)-3-(3-(5-Chloro-2-(1H-tetrazol-1-yl)phenyl)acrylamido)-3-(5-(4-(methoxycarbonylamino)phenyl)-6-oxo-1,6-dihydropyridazin-3-yl)propanoic acid

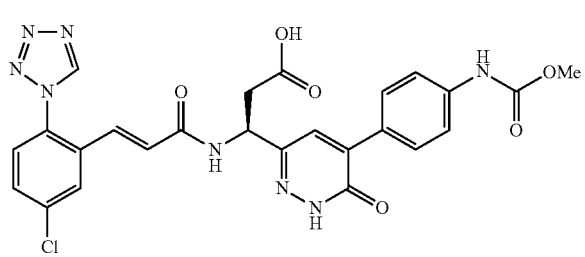

The title compound was prepared using the procedure described in 37E, by replacing 37D with 120B. $^1$H NMR (400 MHz, CD$_3$OD) δ ppm 9.51 (s, 1 H) 7.96 (d, J=2.26 Hz, 1 H) 7.80 (d, J=8.78 Hz, 2 H) 7.64 (dd, J=8.53, 2.26 Hz, 1 H) 7.59 (s, 1 H) 7.50-7.57 (m, 3 H) 7.16 (d, J=15.56 Hz, 1 H) 6.69 (d, J=15.56 Hz, 1 H) 5.36-5.49 (m, 1 H) 3.74 (s, 3 H) 3.07 (dd, J=16.44, 7.40 Hz, 1 H) 2.90 (dd, J=16.44, 6.65 Hz, 1 H). LC-MS (ESI) m/z: 565.1 (M+H)$^+$. Analytical HPLC: RT=5.785 min.

Example 146

(S,E)-tert-Butyl 3-(3-(5-chloro-2-(1H-tetrazol-1-yl)phenyl)acrylamido)-3-(5-(4-(methoxycarbonylamino)phenyl)-6-oxo-1,6-dihydropyridazin-3-yl)propanoate

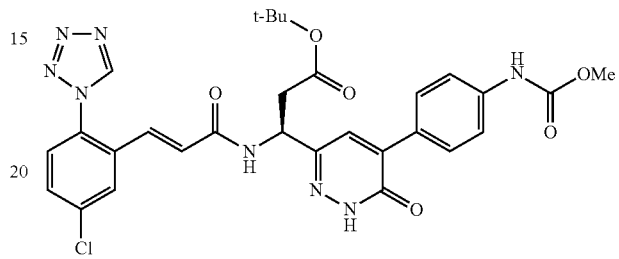

The title compound was prepared using the procedure described in Example 37, by replacing (S)-tert-butyl 4-(dimethoxyphosphoryl)-3-oxo-1-phenylbutan-2-ylcarbamate with (S)-tert-butyl 3-(tert-butoxycarbonylamino)-5-(dimethoxyphosphoryl)-4-oxopentanoate. Procedure 37D was modified by replacing TFA with 4.0N HCl in dioxane for selective deprotection. $^1$H NMR (400 MHz, CD$_3$OD) δ ppm 9.51 (s, 1 H) 7.96 (d, J=2.26 Hz, 1 H) 7.80 (d, J=8.78 Hz, 2 H) 7.64 (dd, J=8.53, 2.26 Hz, 1 H) 7.58 (s, 1 H) 7.51-7.57 (m, 3 H) 7.17 (d, J=15.56 Hz, 1H) 6.68 (d, J=15.56 Hz, 1 H) 5.38-5.49 (m, 1 H) 3.75 (s, 3 H) 2.98 (dd, J=15.81, 7.28 Hz, 1 H) 2.81 (dd, J=15.81, 7.28 Hz, 1 H) 1.40 (s, 9 H). LC-MS (ESI) m/z: 621.2 (M+H)$^+$. Analytical HPLC: RT=7.470 min.

Example 147

Benzyl 3-((S)-2-((E)-3-(5-chloro-2-(1H-tetrazol-1-yl)phenyl)acrylamido)-2-(5-(4-(methoxycarbonylamino)phenyl)-6-oxo-1,6-dihydropyridazin-3-yl)ethyl)pyrrolidine-1-carboxylate (diastereomer mixture)

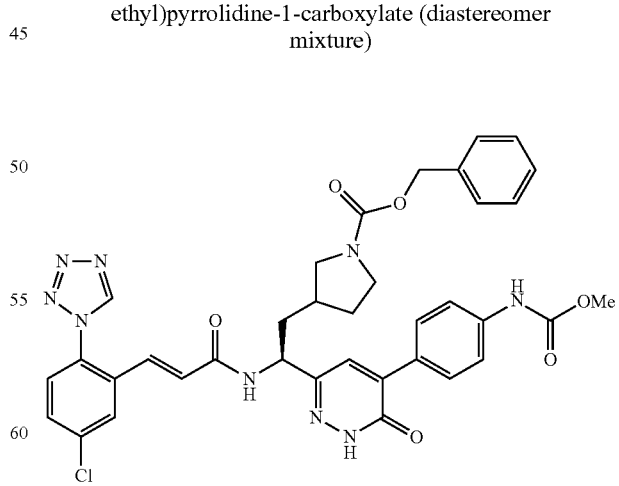

The title compound was prepared using the procedure described in Example 37, by replacing (S)-tert-butyl 4-(dimethoxyphosphoryl)-3-oxo-1-phenylbutan-2-ylcarbamate with 113A. $^1$H NMR (mixture of diastereomers) (400

MHz, CD₃OD) δ ppm 9.45-9.53 (m, 1 H) 8.75 (d, J=6.78 Hz, 1 H) 7.89-8.00 (m, 1H) 7.80 (d, J=7.78 Hz, 2 H) 7.61-7.69 (m, 1 H) 7.48-7.60 (m, 4 H) 7.22-7.39 (m, 5 H) 7.15 (d, J=15.56 Hz, 1 H) 6.64-6.75 (m, 1 H) 5.08 (s, 2 H) 4.99-5.08 (m, 1 H) 3.74 (s, 3 H) 3.45-3.69 (m, 2 H) 3.34-3.37 (m, 1 H) 2.94-3.08 (m, 1 H) 2.16-2.39 (m, 1 H) 1.90-2.14 (m, 3 H) 1.53-1.73 (m, 1 H). LC-MS (ESI) m/z: 724.2 (M+H)⁺. Analytical HPLC: RT=7.821 min.

Example 148

Methyl 4-(6-((1S)-1-((E)-3-(5-chloro-2-(1H-tetrazol-1-yl)phenyl)acrylamido)-2-(1-(cyclopropanecarbonyl)piperidin-3-yl)ethyl)-3-oxo-2,3-dihydropyridazin-4-yl)phenylcarbamate (diastereomer mixture)

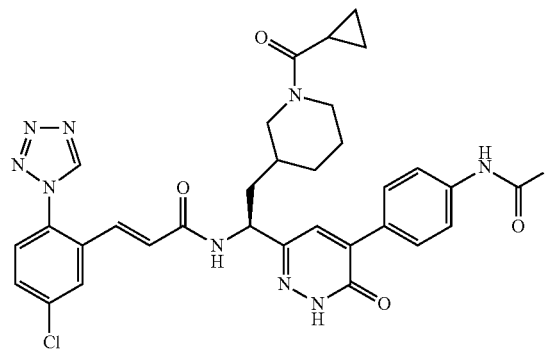

The title compound was prepared using the procedure described in Example 112, by replacing 99D with Example 144. ¹H NMR (400 MHz, CD₃OD) δ ppm 9.51-9.54 (1 H, m), 7.98 (1 H, d, J=2.26 Hz), 7.83 (2 H, d, J=8.53 Hz), 7.63-7.68 (1 H, m), 7.53-7.61 (4 H, m), 7.11-7.20 (1 H, m), 6.69-6.76 (1 H, m), 5.15 (1H, m), 4.28 (1 H, m), 3.78 (3 H, s), 3.33-3.40 (1 H, m), 3.21-3.31 (1 H, m), 3.03 (1H, m), 2.82 (1 H, m),1.92 (4 H, m), 1.70 (1 H, m), 1.43 (2 H, m), 0.78 (4 H, m). MS (ESI) m/z: 672.3 (M+H)⁺. Analytical HPLC: RT=6.7 min.

Example 149

Methyl 3-((S)-2-((E)-3-(5-chloro-2-(1H-tetrazol-1-yl)phenyl)acrylamido)-2-(5-(4-(methoxycarbonylamino)phenyl)-6-oxo-1,6-dihydropyridazin-3-yl)ethyl)piperidine-1-carboxylate (diastereomer mixture)

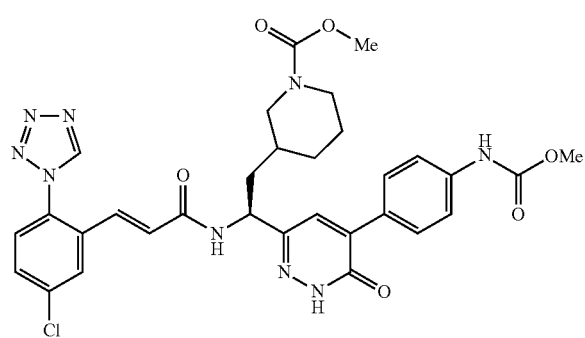

The title compound was prepared using the procedure described in 37C, by replacing 37B with Example 144. ¹H NMR (400 MHz, CD₃CN) δ ppm 9.14 (1 H, s), 7.91-7.84 (4 H, m), 7.66-7.47 (5 H, m), 7.07 (2 H, dd, J=15.54, 4.17 Hz), 6.60 (1H, d, J=15.66 Hz), 5.04 (1 H, d, J=9.35 Hz), 3.98 (1 H, m), 3.85 (1 H, m), 3.75 (3 H, s), 3.57-3.65 (3 H, m), 2.77 (1 H, m), 2.67 (1 H, m), 1.88-1.80 (2 H, m), 1.69 (2 H, m), 1.55 (1 H, m), 1.39 (1 H, m), 1.21 (1 H, m). MS (ESI) m/z: 662.3 (M+H)⁺. Analytical HPLC: RT=6.8 min.

Example 150

(S,E)-Methyl 4-(6-(2-(6-aminopyridin-3-yl)-1-(3-(5-chloro-2-(1H-tetrazol-1-yl)phenyl)acrylamido)ethyl)-3-oxo-2,3-dihydropyridazin-4-yl)phenylcarbamate

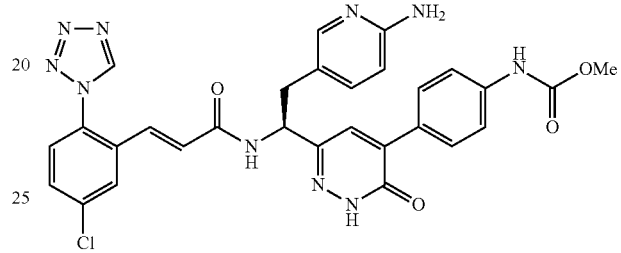

150A. [(S)-3-benzyloxycarbonylamino-4-(6-tert-butoxycarbonylamino-pyridin-3-yl)-2-oxo-butyl]-phosphonic acid dimethyl ester: The compound was prepared according to the procedures described in Intermediate 6, by replacing 1-ethyl-1H-pyrazole-4-carbaldehyde with tert-butyl 5-formylpyridin-2-ylcarbamate and by replacing Boc-methyl-2-(dimethylphosphono) glycinate with methyl 2-(benzyloxycarbonylamino)-2-(dimethoxyphosphoryl)acetate. MS (ESI) m/z: 522.3 (M+H)⁺.

150B. Example 150 was prepared using the procedures described in Example 37, by replacing (S)-tert-butyl 4-(dimethoxyphosphoryl)-3-oxo-1-phenylbutan-2-ylcarbamate with 150A. ¹H NMR (400 MHz, CD₃OD) δ ppm 9.52 (1H, s), 7.96 (1 H, d, J=2.26 Hz), 7.90 (1 H, dd, J=9.16, 2.13 Hz), 7.83 (2 H, d, J=8.78 Hz), 7.71 (1 H, d, J=1.51 Hz), 7.67 (1 H, dd, J=8.53, 2.26 Hz), 7.53-7.61 (4 H, m), 7.11 (1 H, d, J=15.56 Hz), 6.98 (1 H, d, J=9.29 Hz), 6.65 (1 H, d, J=15.56 Hz), 5.31 (1 H, dd, J=8.78, 6.02 Hz), 3.76 (3 H, s), 3.24-3.30 (1 H, m), 3.05 (1 H, dd, J=14.43, 8.91 Hz). MS (ESI) m/z: 613.0 (M+H)⁺. Analytical HPLC: RT=5.03 min.

Example 151

Methyl 4-(6-((1S)-1-((E)-3-(5-chloro-2-(1H-tetrazol-1-yl)phenyl)acrylamido)-2-(pyrrolidin-3-yl)ethyl)-3-oxo-2,3-dihydropyridazin-4-yl)phenylcarbamate, TFA salt (diastereomer mixture)

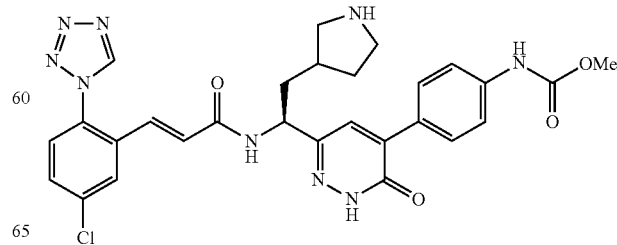

The title compound was prepared using the procedure described in Example 105, by replacing Example 104 with Example 147. ¹H NMR (400 MHz, CD₃OD) δ ppm 9.53 (s, 1 H) 7.97 (t, J=2.01 Hz, 1 H) 7.83 (d, J=8.78 Hz, 2 H) 7.63-7.69 (m, 1 H) 7.57-7.60 (m, 2 H) 7.55 (d, J=8.78 Hz, 2 H) 7.18 (d, J=15.81 Hz, 1 H) 6.67 (d, J=8.78 Hz, 1 H) 5.04-5.20 (m, 1 H) 4.49-4.62 (m, 1 H) 3.75 (s, 3 H) 3.44-3.52 (m, 2 H) 2.92 (ddd, J=11.54, 8.91, 2.38 Hz, 1 H) 2.26-2.43 (m, 1 H) 1.96-2.20 (m, 3 H) 1.56-1.82 (m, 1 H). LC-MS (ESI) m/z: 590.2 (M+H)⁺. Analytical HPLC: RT=4.488 min.

Example 152

Methyl 4-(6-((1S)-2-(1-acetylpyrrolidin-3-yl)-1-((E)-3-(5-chloro-2-(1H-tetrazol-1-yl)phenyl)acrylamido)ethyl)-3-oxo-2,3-dihydropyridazin-4-yl)phenylcarbamate (diastereomer mixture)

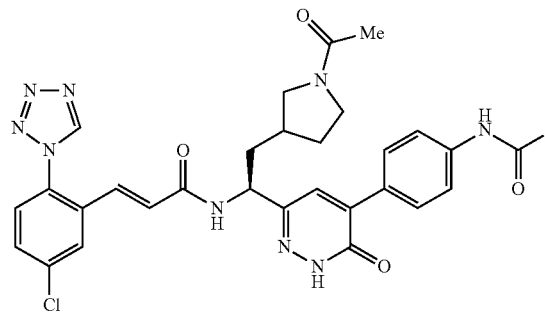

The title compound was prepared using the procedure described in Example 106, by replacing Example 105 with Example 151. ¹H NMR (400 MHz, CD₃OD) δ ppm 9.51 (s, 1 H) 7.94-8.00 (m, 1 H) 7.82 (d, J=8.78 Hz, 2 H) 7.63-7.67 (m, 1 H) 7.52-7.60 (m, 4 H) 7.16 (dd, J=15.56, 5.52 Hz, 1 H) 6.67-6.75 (m, 1 H) 5.01-5.14 (m, 1 H) 3.75 (s, 3 H) 3.66-3.73 (m, 1 H) 3.54-3.64 (m, 1 H) 3.42-3.50 (m, 1 H) 3.14-3.23 (m, 1 H) 1.95-2.13 (m, 5 H) 1.54-1.80 (m, 1 H) 1.05-1.42 (m, 2 H). LC-MS (ESI) m/z: 632.3 (M+H)⁺. Analytical HPLC: RT=5.698 min.

Example 153

Methyl 4-(6-((S)-1-((E)-3-(5-chloro-2-(1H-tetrazol-1-yl)phenyl)acrylamido)-2-(1-(ethylsulfonyl)piperidin-3-yl)ethyl)-3-oxo-2,3-dihydropyridazin-4-yl)phenylcarbamate (diastereomer mixture)

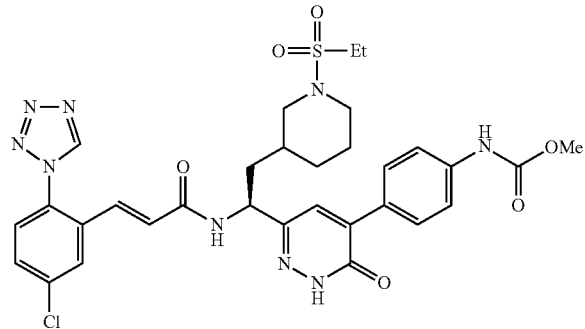

To a suspension of Example 144 (10.7 mg, 0.015 mmol) and potassium carbonate (2.059 mg, 0.015 mmol)/potassium carbonate (5.0 mg, 0.037 mmol) in water (0.35 mL) was added ethanesulfonyl chloride (1.412 µL, 0.015 mmol). The mixture was stirred at rt for 60 min. The mixture was purified by reverse phase chromatography to give Example 153 (2.7 mg, 3.39 µmol, 22.72% yield) as off white solid. ¹H NMR (400 MHz, CD₃OD) δ ppm 9.52 (1 H, s), 7.98 (1 H, t, J=2.51 Hz), 7.83 (2 H, dd, J=9.03, 2.26 Hz), 7.63-7.68 (1 H, m), 7.53-7.62 (4 H, m), 7.17 (1 H, dd, J=15.56, 1.51 Hz), 6.73 (1 H, d, J=15.56 Hz), 5.10-5.19 (1 H, m), 3.76 (3 H, s), 3.69 (1 H, d, J=12.05 Hz), 3.58 (1 H, d, J=1.25 Hz), 3.06-2.79 (4 H, m), 1.98-1.56 (6 H, m), 1.31 (4 H, td, J=15.18, 7.28 Hz).). MS (ESI) m/z: 696.3 (M+H)⁺. Analytical HPLC: RT=6.9 min.

Example 154

Methyl 4-(6-((1S)-1-((E)-3-(5-chloro-2-(1H-tetrazol-1-yl)phenyl)acrylamido)-2-(1-(methylsulfonyl)piperidin-3-yl)ethyl)-3-oxo-2,3-dihydropyridazin-4-yl)phenylcarbamate (diastereomer mixture)

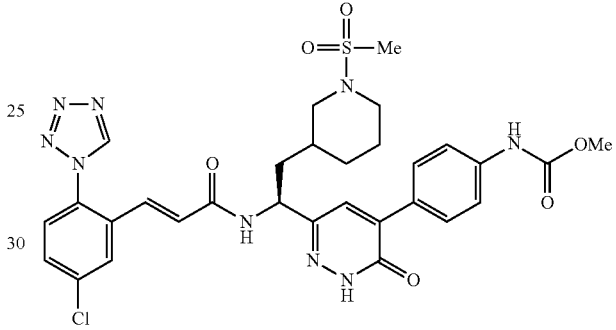

The title compound was prepared using the procedure described in Example 153, by replacing potassium carbonate with sodium carbonate and by replacing ethanesulfonyl chloride with methanesulfonyl chloride. ¹H NMR (400 MHz, CD₃OD) δ ppm 9.52 (1 H, d, J=2.01 Hz), 7.97-8.02 (1 H, m), 7.81-7.86 (2H, m), 7.64-7.68 (1 H, m), 7.53-7.61 (4 H, m), 7.17 (1 H, d, J=15.56 Hz), 6.72 (1H, dd, J=15.56, 2.26 Hz), 5.13 (1 H, dt, J=5.71, 2.79 Hz), 3.76 (3 H, s), 3.58 (1 H, m), 3.49 (1 H, dt, J=3.26, 1.63 Hz), 2.85 (1 H, m), 2.82 (3 H, s), 2.70-2.80 (1 H, m), 2.00 (1 H, m), 1.77-1.88 (4 H, m), 1.60 (1 H, m), 1.20 (1 H, m). MS (ESI) m/z: 682.3 (M+H)⁺. Analytical HPLC: RT=6.6 min.

Example 155

Methyl 4-(6-((S)-1-((E)-3-(5-chloro-2-(1H-tetrazol-1-yl)phenyl)acrylamido)-2-(1-(isopropylsulfonyl)piperidin-3-yl)ethyl)-3-oxo-2,3-dihydropyridazin-4-yl)phenylcarbamate (diastereomer mixture)

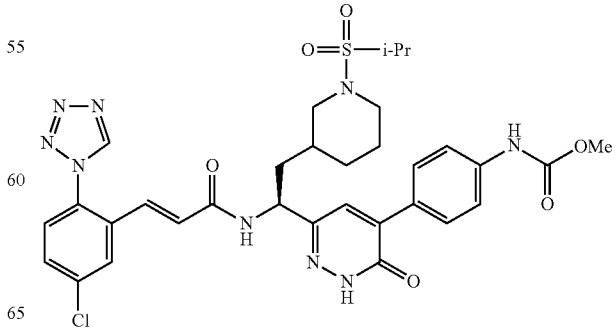

The title compound was prepared using the procedure described in Example 154, by replacing methanesulfonyl chloride with propane-2-sulfonyl chloride. ¹H NMR (400 MHz, CD₃OD) δ ppm 9.51 (1 H, s), 7.97 (1 H, t, J=2.26 Hz), 7.80-7.84 (2 H, m), 7.66-7.52 (5 H, m), 7.15 (1 H, dd, J=15.69, 1.38 Hz), 6.72 (1H, dd, J=15.56, 1.25 Hz), 5.09-5.17 (1 H, m), 3.73-3.77 (3 H, m), 3.56-3.66 (1 H, m), 3.18-3.28 (2 H, m), 2.87 (1 H, m), 1.89-2.00 (1 H, m), 1.79-1.85 (2 H, m), 1.67-1.76 (2 H, m), 1.47-1.58 (1 H, m), 1.25-1.34 (7 H, m). MS (ESI) m/z: 710.3 (M+H)⁺. Analytical HPLC: RT=7.21 min.

Example 156

Methyl 4-(6-((S)-1-((E)-3-(5-chloro-2-(1H-tetrazol-1-yl)phenyl)acrylamido)-2-(1-(cyclopropylsulfonyl)piperidin-3-yl)ethyl)-3-oxo-2,3-dihydropyridazin-4-yl)phenylcarbamate (diastereomer mixture)

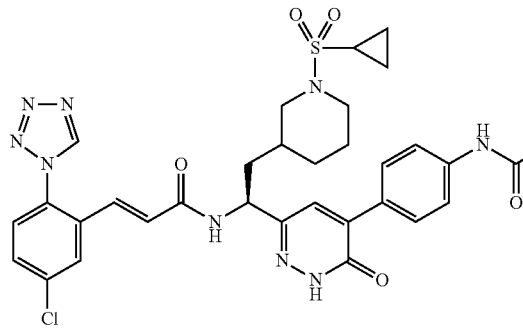

The title compound was prepared using the procedure described in Example 154, by replacing methanesulfonyl chloride with cyclopropanesulfonyl chloride. ¹H NMR (400 MHz, CD₃OD) δ ppm 9.50 (1 H, d, J=2.51 Hz), 7.97 (1 H, t, J=2.64 Hz), 7.79-7.84 (2 H, m), 7.62-7.67 (1 H, m), 7.52-7.60 (4 H, m), 7.16 (1 H, d, J=15.56 Hz), 6.71 (1 H, dd, J=15.56, 2.76 Hz), 5.14 (1 H, d, J=8.28 Hz), 3.75 (3 H, s), 3.68-3.48 (2 H, m), 3.02-2.65 (2 H, m), 2.40-2.47 (1 H, m), 1.99-1.72 (6 H, m), 1.57 (1 H, m), 0.95-1.20 (5 H, m). MS (ESI) m/z: 708.3 (M+H)⁺. Analytical HPLC: RT=7.05 min.

Example 157

Methyl 4-(6-((1S)-1-((E)-3-(5-chloro-2-(1H-tetrazol-1-yl)phenyl)acrylamido)-2-(1-(methylcarbamoyl)piperidin-3-yl)ethyl)-3-oxo-2,3-dihydropyridazin-4-yl)phenylcarbamate (Diastereomer A)

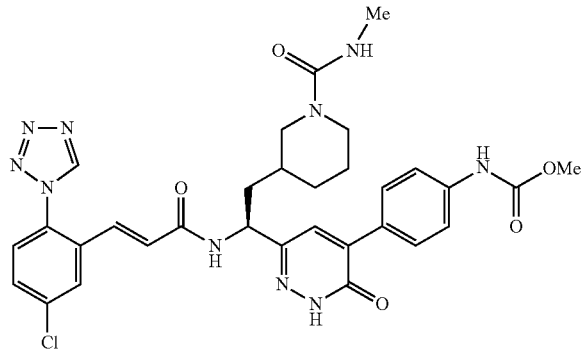

The title compound (diastereomer A) was prepared starting from 144 and using the procedure described in Example 107.

Reverse phase chromatography gave both Example 157 as diastereomer A and Example 158 as diastereomer B. ¹H NMR (400 MHz, CD₃OD) δ ppm 9.51 (1 H, s), 7.97 (1 H, d, J=2.26 Hz), 7.79-7.84 (2 H, m), 7.64 (1 H, dd, J=8.53, 2.26 Hz), 7.51-7.58 (4 H, m), 7.14 (1 H, d, J=15.81 Hz), 6.72 (1 H, d, J=15.56 Hz), 5.12 (1 H, dd, J=9.16, 6.15 Hz), 3.90-3.99 (1 H, m), 3.72-3.78 (4 H, m), 2.78-2.89 (1 H, m), 2.71 (3 H, s), 2.62 (1 H, dd, J=13.05, 10.04 Hz), 1.95 (1 H, s), 1.73-1.84 (2 H, m), 1.62-1.71 (1 H, m), 1.48-1.59 (1 H, m), 1.35-1.46 (1 H, m), 1.17-1.27 (1 H, m). MS (ESI) m/z: 661.3 (M+H)⁺. Analytical HPLC: RT=6.04 min.

Example 158

Methyl 4-(6-((S)-1-((E)-3-(5-chloro-2-(1H-tetrazol-1-yl)phenyl)acrylamido)-2-(1-(methylcarbamoyl)piperidin-3-yl)ethyl)-3-oxo-2,3-dihydropyridazin-4-yl)phenylcarbamate (Diastereomer B)

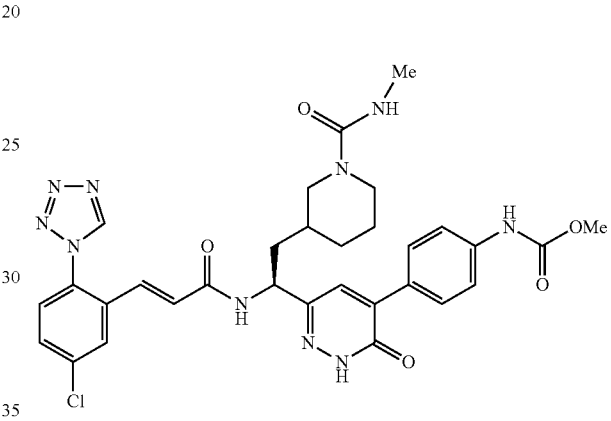

The title compound (diastereomer B) was prepared using the procedure described in Example 157. ¹H NMR (400 MHz, CD₃OD) δ ppm 9.52 (1 H, s), 7.99 (1 H, d, J=2.26 Hz), 7.80-7.84 (2 H, m), 7.63-7.67 (1 H, m), 7.52-7.58 (4 H, m), 7.17 (1 H, d, J=15.56 Hz), 6.74 (1 H, d, J=15.56 Hz), 5.20 (1 H, dd, J=9.66, 5.40 Hz), 3.89 (2 H, m), 3.75 (3 H, s), 2.77-2.88 (1 H, m), 2.68-2.75 (1 H, m), 2.64 (3 H, s), 1.81-1.91 (2 H, m), 1.74 (1 H, ddd, J=14.43, 9.54, 5.14 Hz), 1.65 (1 H, d, J=13.80 Hz), 1.51 (1 H, m), 1.43 (1 H, m), 1.31 (1 H, m). MS (ESI) m/z: 661.3 (M+H)⁺. Analytical HPLC: RT=6.14 min.

Example 159

Methyl 4-(6-((1S)-1-((E)-3-(5-chloro-2-(1H-tetrazol-1-yl)phenyl)acrylamido)-2-(1-isobutyrylpiperidin-3-yl)ethyl)-3-oxo-2,3-dihydropyridazin-4-yl)phenylcarbamate (Diastereomer A)

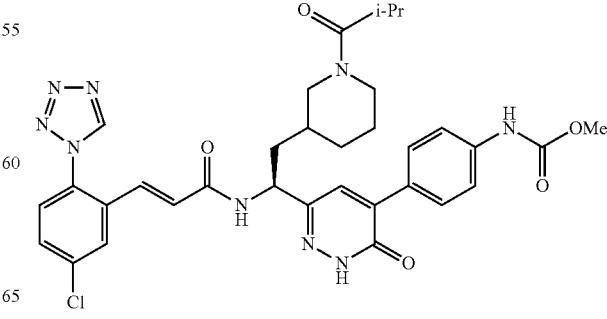

The title compound (diastereomer A) was prepared using the procedure described in Example 117, by replacing Example 99 with Example 144. Reverse phase chromatography gave both Example 159 as diastereomer A and Example 160 as diastereomer B. $^1$H NMR (400 MHz, CD$_3$OD) δ ppm 9.50-9.53 (1 H, m), 7.95-7.99 (1 H, m), 7.79-7.85 (2 H, m), 7.61-7.67 (1 H, m), 7.52-7.60 (4 H, m), 7.16 (1H, t, J=15.94 Hz), 6.67-6.74 (1 H, m), 5.11-5.23 (1 H, m), 3.9-4.4 (2 H, m), 3.76 (3H, s), 2.80-2.92 (2 H, m), 2.60 (1 H, m), 1.83-1.95 (3 H, m), 1.39-1.78 (3 H, m), 1.01-1.10 (6 H, m), 0.94 (1 H, d, J=6.78 Hz). MS (ESI) m/z: 674.4 (M+H)$^+$. Analytical HPLC: RT=6.78 min.

Example 160

Methyl 4-(6-((1S)-1-((E)-3-(5-chloro-2-(1H-tetrazol-1-yl)phenyl)acrylamido)-2-(1-isobutyrylpiperidin-3-yl)ethyl)-3-oxo-2,3-dihydropyridazin-4-yl)phenyl-carbamate (Diastereomer B)

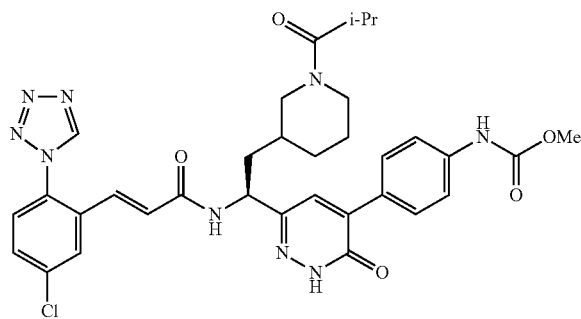

The title compound (diastereomer B) was prepared using the procedure described in Example 159. $^1$H NMR (400 MHz, CD$_3$OD) δ ppm 9.51 (1 H, s), 7.95-7.99 (1 H, m), 7.82 (2 H, d, J=8.78 Hz), 7.62-7.66 (1 H, m), 7.52-7.60 (4 H, m), 7.11-7.20 (1 H, m), 6.67-6.75 (1 H, m), 5.10-5.17 (1 H, m), 4.36 (1 H, m), 3.80-4.02 (1 H, m), 3.75 (3 H, s), 3.11-3.21 (1 H, m), 2.86-2.97 (2 H, m), 2.56-2.67 (1H, m), 1.96 (1 H, s), 1.76-1.88 (2 H, m), 1.52 (1 H, d, J=3.76 Hz), 1.32 (2 H, t, J=7.28 Hz), 1.08 (3 H, d, J=6.53 Hz), 1.04 (3 H, dd, J=9.03, 6.78 Hz). MS (ESI) m/z: 674.4 (M+H)$^+$. Analytical HPLC: RT=6.86 min.

Example 161

(S,E)-Methyl 4-(6-(1-(3-(5-chloro-2-(1H-tetrazol-1-yl)phenyl)acrylamido)-2-(thiazol-4-yl)ethyl)-3-oxo-2,3-dihydropyridazin-4-yl)phenylcarbamate

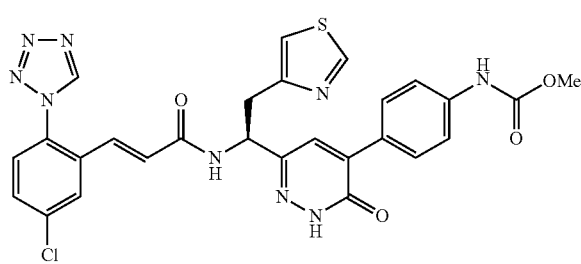

The title compound was prepared using the procedures described in Example 37, by replacing (S)-tert-butyl 4-(dimethoxyphosphoryl)-3-oxo-1-phenylbutan-2-ylcarbamate with 123A. $^1$H NMR (400 MHz, DMSO-D$_6$) δ ppm 12.97 (1 H, s), 9.85 (2 H, s), 9.02 (1 H, d, J=2.02 Hz), 8.70 (1 H, d, J=8.08 Hz), 7.98 (1 H, d, J=2.02 Hz), 7.84 (2 H, d, J=8.84 Hz), 7.70-7.77 (2 H, m), 7.53-7.59 (3 H, m), 7.36 (1 H, d, J=2.02 Hz), 6.84-6.90 (1 H, m), 6.74-6.81 (1 H, m), 5.27 (1 H, q, J=7.92 Hz), 3.70 (3 H, s), 3.27-3.37 (2 H, m). MS (ESI) m/z: 604.0 (M+H)$^+$. Analytical HPLC: RT=6.27 min.

Example 162

(S,E)-Methyl 4-(6-(1-(3-(5-chloro-2-(1H-tetrazol-1-yl)phenyl)acrylamido)-2-(4-methylthiazol-2-yl)ethyl)-3-oxo-2,3-dihydropyridazin-4-yl)phenylcarbamate

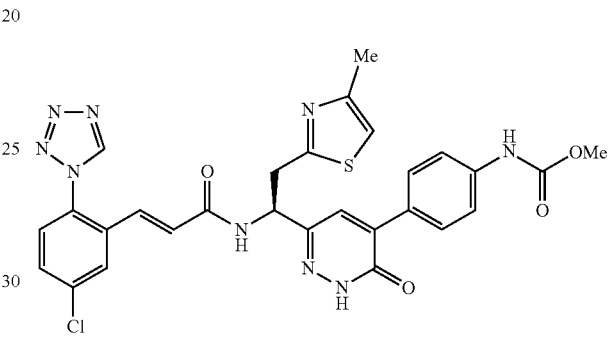

The title compound was prepared using the procedures described in Examples 37, by replacing (S)-tert-butyl 4-(dimethoxyphosphoryl)-3-oxo-1-phenylbutan-2-ylcarbamate with 126A. $^1$H NMR (400 MHz, CD$_3$OD) δ ppm 9.51 (1 H, s), 7.96 (1 H, d, J=2.26 Hz), 7.78-7.82 (2 H, m), 7.63-7.68 (1 H, m), 7.52-7.59 (4 H, m), 7.09-7.15 (2 H, m), 6.68 (1 H, d, J=15.81 Hz), 5.47 (1 H, dd, J=7.91, 6.40 Hz), 3.75 (3 H, s), 3.69-3.74 (1 H, m), 3.57 (1 H, dd, J=14.81, 8.03 Hz), 2.40 (3 H, d, J=1.00 Hz). MS (ESI) m/z: 618.1 (M+H)$^+$. Analytical HPLC: RT=6.14 min.

Example 163

(S,E)-Methyl 4-(6-(1-(3-(3-chloro-2-fluoro-6-(1H-tetrazol-1-yl)phenyl)acrylamido)-2-(4-methylthiazol-2-yl)ethyl)-3-oxo-2,3-dihydropyridazin-4-yl)phenyl-carbamate

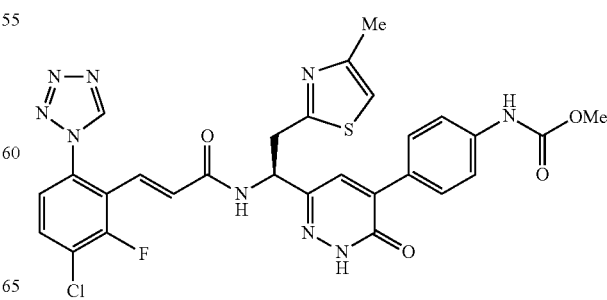

The title compound was prepared using the procedures described in 37A-D and 48C, by replacing (S)-tert-butyl 4-(dimethoxyphosphoryl)-3-oxo-1-phenylbutan-2-ylcarbamate with 126A. In addition, in procedure 48C, Intermediate 1B was replaced with Intermediate 7. $^1$H NMR (400 MHz, CD$_3$OD-DMSO-D$_6$) δ ppm 9.57 (1 H, s), 7.77-7.87 (3 H, m), 7.54-7.60 (3 H, m), 7.50 (1 H, d, J=8.53 Hz), 7.13 (1 H, s), 6.97 (1 H, d, J=15.81 Hz), 6.69 (1 H, d, J=15.81 Hz), 5.38-5.44 (1 H, m), 3.74 (3 H, s), 3.68 (1 H, ms), 3.55 (1 H, m), 2.38 (3 H, s). MS (ESI) m/z: 636.1 (M+H)$^+$. Analytical HPLC: RT=6.3 min.

Example 164

[4-(6-{(S)-2-tert-Butoxycarbonylamino-1-[(E)-3-(5-chloro-2-tetrazol-1-yl-phenyl)-acryloylamino]-ethyl}-3-oxo-2,3-dihydro-pyridazin-4-yl)-phenyl]-carbamic acid methyl ester

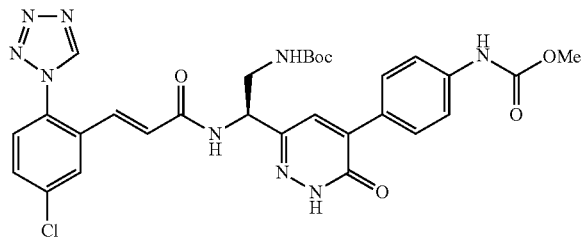

The title compound was prepared using the procedure described in Example 37, by replacing (S)-tert-butyl 4-(dimethoxyphosphoryl)-3-oxo-1-phenylbutan-2-ylcarbamate with ((S)-3-Benzyloxycarbonylamino-4-tert-butoxycarbonylamino-2-oxo-butyl)-phosphonic acid dimethyl ester (prepared using the procedure described in Intermediate 3, by replacing Intermediate 3A with (S)-2-Benzyloxycarbonylamino-3-tert-butoxycarbonylamino-propionic acid methyl ester).

$^1$H NMR (400 MHz, CD$_3$OD) δ ppm 9.52 (s, 1 H) 7.98 (d, J=2.26 Hz, 1 H) 7.83 (d, J=8.78 Hz, 2 H) 7.65 (dd, J=8.53, 2.26 Hz, 1 H) 7.52-7.59 (m, 4 H) 7.15 (d, J=15.56 Hz, 1 H) 6.75 (d, J=15.56 Hz, 1 H) 5.06-5.18 (m, 1 H) 3.75 (s, 3 H) 3.45-3.59 (m, 2 H) 1.35 (s, 9 H). LC-MS (ESI) m/z: 636.1 (M+H)$^+$. Analytical HPLC: RT=7.123 min.

Example 165

(S,E)-Methyl 4-(6-(1-(3-(5-chloro-2-(1H-tetrazol-1-yl)phenyl)acrylamido)-2-pivalamidoethyl)-3-oxo-2,3-dihydropyridazin-4-yl)phenylcarbamate

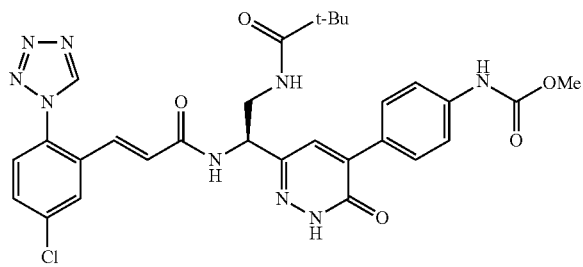

165A. {4-[6-((S)-2-amino-1-benzyloxycarbonylamino-ethyl)-3-oxo-2,3-dihydro-pyridazin-4-yl]-phenyl}-carbamic acid methyl ester, TFA salt: To a solution of {(S)-2-tert-Butoxycarbonylamino-1-[5-(4-methoxycarbonylamino-phenyl)-6-oxo-1,6-dihydro-pyridazin-3-yl]-ethyl}-carbamic acid benzyl ester (44 mg, 0.082 mmol), an intermediate of example 164, in CH$_2$Cl$_2$ (2 mL) was added TFA (1.0 mL, 12.98 mmol). The reaction mixture was stirred under argon at rt for 30 min. The solvent was removed and the residue was dried in vacuo to give 165A.

165B. (4-{6-[(S)-1-benzyloxycarbonylamino-2-(2,2-dimethyl-propionylamino)-ethyl]-3-oxo-2,3-dihydro-pyridazin-4-yl}-phenyl)-carbamic acid methyl ester: To a cooled solution (0° C.) of 165A in CH$_2$Cl$_2$ (3 mL) was added TEA (0.1 mL, 0.717 mmol) and pivaloyl chloride (14.80 mg, 0.123 mmol). The reaction was stirred for 1 h. The solvent was removed. Purification by normal phase chromatography gave 165B (34 mg, 0.065 mmol, 80% yield) as a tan solid. LC-MS (ESI) m/z: 522.2 (M+H)$^+$.

165C. Example 165 was prepared following the procedures described in 37B and 1D, by replacing 37A with 165B. $^1$H NMR (400 MHz, CD$_3$OD) δ ppm 9.52 (s, 1 H) 7.98 (d, J=2.26 Hz, 1 H) 7.79-7.86 (m, 2 H) 7.62-7.68 (m, 1 H) 7.51-7.58 (m, 4 H) 7.14 (d, J=15.56 Hz, 1 H) 6.74 (d, J=15.81 Hz, 1 H) 5.20 (t, J=6.90 Hz, 1 H) 3.75 (s, 3 H) 3.60-3.72 (m, 2 H) 1.09 (s, 9 H). LC-MS (ESI) m/z: 620.1 (M+H)$^+$. Analytical HPLC: RT=6.645 min.

Example 166

(S,E)-Methyl 4-(6-(1-(3-(5-chloro-2-(1H-tetrazol-1-yl)phenyl)acrylamido)-2-(2-oxooxazolidin-3-yl)ethyl)-3-oxo-2,3-dihydropyridazin-4-yl)phenylcarbamate

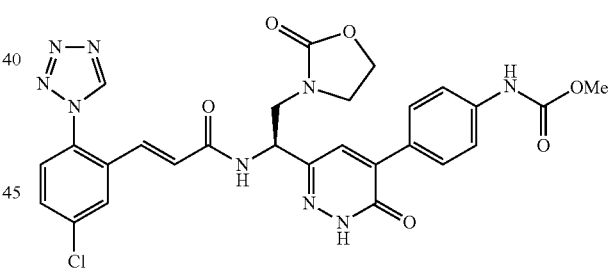

166A. (4-{6-[(S)-1-benzyloxycarbonylamino-2-(2-hydroxy-ethylamino)-ethyl]-3-oxo-2,3-dihydro-pyridazin-4-yl}-phenyl)-carbamic acid methyl ester: To a solution of 165A (0.103 g, 0.186 mmol) in THF (5 mL) were added 2-hydroxyacetaldehyde (0.011 g, 0.186 mmol) and NaBH(OAc)$_3$ (0.059 g, 0.279 mmol). The reaction mixture was stirred under argon at rt for 1.5 h. The reaction was quenched by adding 1.0N HCl (1 mL). The reaction mixture was diluted with EtOAc, washed with saturated NaHCO$_3$ (2×10 mL) and brine (1×10 mL). The organic phase was dried over sodium sulfate, filtered and concentrated to give a slightly brown solid of 166A, which was used in next step without further purification. LC-MS (ESI) m/z: 482.1 (M+H)$^+$.

166B. (4-{6-[(S)-1-benzyloxycarbonylamino-2-(2-oxo-oxazolidin-3-yl)-ethyl]-3-oxo-2,3-dihydro-pyridazin-4-yl}-phenyl)-carbamic acid methyl ester: To a solution of 166A (90 mg, 0.186 mmol) in CH$_2$Cl$_2$ (5 mL) and DMF (2 mL) were added CDI (60.3 mg, 0.372 mmol) and TEA (0.1 mL, 0.717 mmol). The reaction mixture was stirred over night. The solvent was removed. Purification by reverse phase chromatography gave 166B (27 mg, 0.053 mmol, 28.6% yield) as a light yellow solid. LC-MS (ESI) m/z: 508.1 (M+H)+.

166C. Example 166 was prepared following the procedures described in 165C, by replacing 165B with 166B. ¹H NMR (400 MHz, CD₃OD) δ ppm 9.53 (s, 1H) 7.99 (d, J=2.01 Hz, 1 H) 7.83 (d, J=8.78 Hz, 2 H) 7.63-7.68 (m, 1 H) 7.62 (s, 1H) 7.51-7.59 (m, 3 H) 7.16 (d, J=15.56 Hz, 1 H) 6.73 (d, J=15.81 Hz, 1 H) 5.39 (dd, J=8.66, 5.65 Hz, 1 H) 4.22-4.39 (m, 2 H) 3.76-3.86 (m, 2 H) 3.75 (s, 3 H) 3.61-3.72 (m, 2 H). LC-MS (ESI) m/z: 606.1 (M+H)+. Analytical HPLC: RT=5.995 min.

Example 167

(E)-Methyl 4-(6-(1-(3-(5-chloro-2-(1H-tetrazol-1-yl)phenyl)acrylamido)-2-(2-isopropylthiazol-4-yl)ethyl)-3-oxo-2,3-dihydropyridazin-4-yl)phenylcarbamate

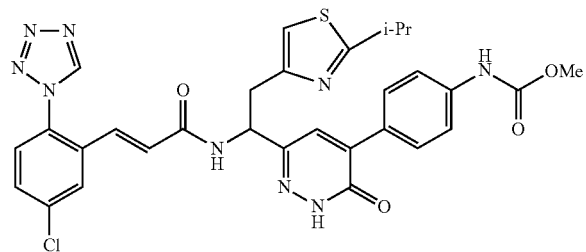

167A. diethyl 2-acetamido-2-((2-isopropylthiazol-4-yl)methyl)malonate: 167A was prepared following a modified procedure described by T. B. Stensbol (*J. Med. Chem.* 2002, 45(1):19-31). To a cooled suspension (0° C.) of sodium hydride (79 mg, 1.968 mmol) in dry DMF (3 mL) was slowly added a solution of diethyl acetamidomalonate (386 mg, 1.777 mmol) in dry DMF (2 mL). The mixture was allowed to warm to rt, and stirring was continued until a clear solution was obtained and no more hydrogen gas evolved (1.5 hrs). Then a solution of 4-(chloromethyl)-2-isopropylthiazole (223 mg, 1.269 mmol) in dry DMF (0.5 mL) was added, and the mixture was stirred at rt overnight. The reaction was quenched with saturated NH₄Cl (15 mL)/water at 0° C., warmed to rt and extracted with EtOAc (1×). The organic layer was washed with water (3×), brine, dried (Na₂SO₄), filtered, and concentrated to give 167A (455 mg, 1.277 mmol, 101% yield) as a light-brown waxy solid. MS (ESI) m/z: 356.5 (M+H)+.

167B. 2-amino-3-(2-isopropylthiazol-4-yl)propanoic acid: A suspension of 167A (500 mg, 1.262 mmol) in aq. 4 N HCl (7891 µL, 31.6 mmol) was heated at 160° C. in a microwave for 5 min. The mixture was concentrated with toluene/dioxane to give 167B (271 mg, 1.262 mmol, 100% yield) as a white solid. MS (ESI) m/z: 215.8 (M+H)+.

167C. 2-(tert-butoxycarbonylamino)-3-(2-isopropylthiazol-4-yl)propanoic acid: To a solution of 167B (0.677 g, 2.7 mmol) in dioxane (15 mL) and aq. 1N NaOH (7.56 mL, 7.56 mmol) was added di-tert-butyl dicarbonate (1.061 g, 4.86 mmol). The mixture was stirred at rt for 4 h. The mixture was concentrated to remove most of the excess solvent. Next aq.HCl (1N) was added to adjust pH ~4, then extracted with EtOAc (3×). The combined organic layers were washed with brine (2×), dried (Na₂SO₄), filtered, and concentrated to give 167C (1.02 g, 3.24 mmol, 120% yield) as an oil (some solvent). MS (ESI) m/z: 315.2 (M+H)+.

167D. methyl 2-(tert-butoxycarbonylamino)-3-(2-isopropylthiazol-4-yl)propanoate: The compound was prepared according to the procedure described in Example 90A, by replacing (S)-2-(tert-butoxycarbonylamino)-4-(methylthio)butanoic acid with 167C. MS (ESI) m/z: 329.1 (M+H)+.

167E. tert-butyl 4-(dimethoxyphosphoryl)-1-(2-isopropylthiazol-4-yl)-3-oxobutan-2-ylcarbamate: The compound was prepared according to the procedure described in Intermediate 3, by replacing Intermediate 3A with 167D and by replacing diethyl methylphosphonate with dimethyl methylphosphonate. MS (ESI) m/z: 443.1 (M+Na)+.

167F. Example 167 was prepared using the procedures described in Example 37, by replacing (5)-tert-butyl 4-(dimethoxyphosphoryl)-3-oxo-1-phenylbutan-2-ylcarbamate with 167E. ¹H NMR (400 MHz, CD₃OD) δ ppm 9.50 (1 H, s), 7.94 (1 H, d, J=2.26 Hz), 7.73-7.78 (2 H, m), 7.61-7.66 (1 H, m), 7.53 (3 H, dd, J=12.42, 8.66 Hz), 7.46 (1 H, s), 7.18 (1 H, s), 7.08 (1 H, d, J=15.56 Hz), 6.69 (1H, d, J=15.56 Hz), 5.42 (1 H, dd, J=8.41, 6.40 Hz), 3.74 (3 H, s), 3.35-3.42 (1 H, m), 3.26-3.30 (2 H, m), 1.35 (6 H, dd, J=6.90, 1.88 Hz). MS (ESI) m/z: 646.3 (M+H)+. Analytical HPLC: RT=7.04 min.

Example 168

(E)-Methyl 4-(6-(1-(3-(5-chloro-2-(1H-tetrazol-1-yl)phenyl)acrylamido)-2-(5-cyclopropyl-1,3,4-thiadiazol-2-yl)ethyl)-3-oxo-2,3-dihydropyridazin-4-yl)phenylcarbamate

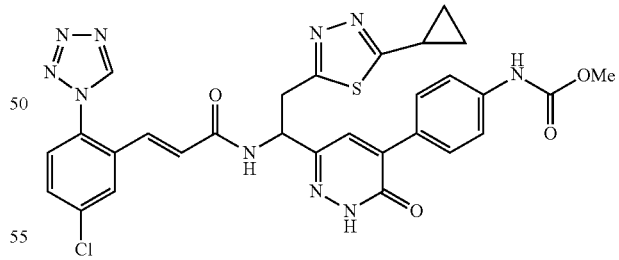

Example 168 was prepared using the procedures described in Example 167, by replacing 4-(chloromethyl)-2-isopropylthiazole with 2-(chloromethyl)-5-cyclopropyl-1,3,4-thiadiazole. ¹H NMR (400 MHz, DMSO-d₆) δ ppm 9.82 (1 H, s), 9.80 (1 H, s), 8.78 (1 H, d, J=8.28 Hz), 7.92 (1 H, d, J=2.01 Hz), 7.80 (2 H, d, J=8.78 Hz), 7.64-7.71 (2 H, m), 7.57 (1 H, s), 7.48 (2 H, d, J=9.03 Hz), 6.80-6.86 (1 H, m), 6.66-6.72 (1 H, m), 5.19 (1 H, d, J=6.53 Hz), 3.62 (3 H, s), 3.57 (1 H, dd, J=14.93, 6.15 Hz), 3.42-3.49 (1 H, m), 2.36-2.40 (1 H, m), 1.07-1.13 (2 H, m), 0.89 (2 H, ddd, J=6.96, 4.45, 4.14 Hz). MS (ESI) m/z: 645.1 (M+H)+. Analytical HPLC: RT=6.75 min.

Example 169

(R,E)-Methyl 4-(6-(1-(3-(5-chloro-2-(1H-tetrazol-1-yl)phenyl)acrylamido)-2-(methylthio)ethyl)-3-oxo-2,3-dihydropyridazin-4-yl)phenylcarbamate

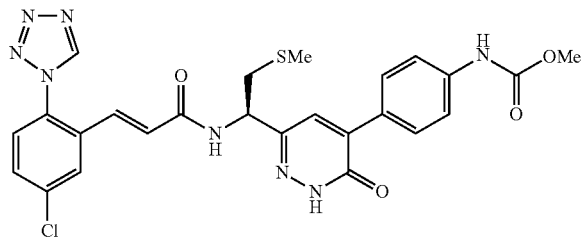

169A. {4-[6-((R)-1-tert-Butoxycarbonylamino-2-methylsulfanyl-ethyl)-3-oxo-2,3-dihydro-pyridazin-4-yl]-phenyl}-carbamic acid methyl ester: This compound was prepared according to the procedures described in 37A, 37B and 37C, by replacing (S)-tert-butyl 4-(dimethoxyphosphoryl)-3-oxo-1-phenylbutan-2-ylcarbamate with (R)-tert-butyl 4-(dimethoxyphosphoryl)-1-(methylthio)-3-oxobutan-2-ylcarbamate.

169B: Example 169 was prepared using the procedures described in 37D and 37E, by replacing 37C with 169A. $^1$H NMR (400 MHz, CD$_3$OD) δ ppm 9.51 (s, 1 H) 7.96 (d, J=2.26 Hz, 1 H) 7.77-7.84 (m, 2 H) 7.64 (dd, J=8.53, 2.26 Hz, 1 H) 7.60 (s, 1 H) 7.50-7.58 (m, 3 H) 7.16 (d, J=15.56 Hz, 1 H) 6.74 (d, J=15.56 Hz, 1 H) 5.13-5.28 (m, 1 H) 3.74 (s, 3 H) 3.07 (dd, J=13.80, 6.53 Hz, 1 H) 2.95 (dd, J=13.80, 8.03 Hz, 1 H) 2.13 (s, 3 H). LC-MS (ESI) m/z: 567.0 (M+H)+. Analytical HPLC: RT=6.868 min.

Example 170

(R,E)-Methyl 4-(6-(1-(3-(5-chloro-2-(1H-tetrazol-1-yl)phenyl)acrylamido)-2-(methylsulfonyl)ethyl)-3-oxo-2,3-dihydropyridazin-4-yl)phenylcarbamate

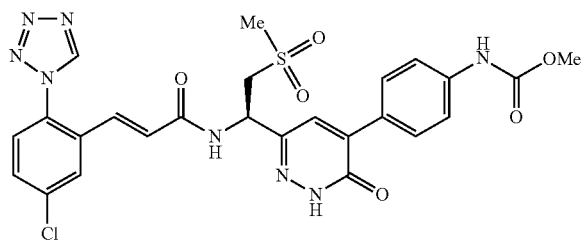

170A. {4-[6-((R)-1-tert-Butoxycarbonylamino-2-methanesulfonyl-ethyl)-3-oxo-2,3-dihydro-pyridazin-4-yl]-phenyl}-carbamic acid methyl ester: To a cooled (0° C.) solution of 169A (100 mg, 0.230 mmol) in dichloromethane (15 mL) was added mCPBA (238 mg, 1.381 mmol). The reaction was stirred under argon at 0° C. for 1 h. The reaction was diluted with EtOAc, washed with saturated NaHCO$_3$ and brine. The organic phase was dried over magnesium sulfate, filtered and concentrated to give 170A in quantitative yield. LC-MS (ESI) m/z: 467.0.

170B: Example 170 was prepared using the procedures described in 37D and 37E, by replacing 37C with 170A. $^1$H NMR (400 MHz, CD$_3$OD) δ ppm 9.52 (s, 1H) 7.98 (d, J=2.26 Hz, 1 H) 7.82 (d, J=9.03 Hz, 2 H) 7.65 (dd, J=8.53, 2.26 Hz, 1 H) 7.61 (s, 1 H) 7.57 (d, J=8.53 Hz, 1 H) 7.54 (d, J=8.78 Hz, 2 H) 7.19 (d, J=15.56 Hz, 1 H) 6.68 (d, J=15.56 Hz, 1 H) 5.65 (dd, J=8.28, 5.27 Hz, 1 H) 3.95 (dd, J=14.56, 5.27 Hz, 1 H) 3.75 (s, 3 H) 3.69 (dd, J=14.68, 8.41 Hz, 1 H) 3.05 (s, 3 H). LC-MS (ESI) m/z: 599.0 (M+H)+. Analytical HPLC: RT=6.278 min.

Example 171

(E)-Methyl 4-(6-(2-(5-tert-butyl-1,2,4-oxadiazol-3-yl)-1-(3-(5-chloro-2-(1H-tetrazol-1-yl)phenyl)acrylamido)ethyl)-3-oxo-2,3-dihydropyridazin-4-yl)phenylcarbamate

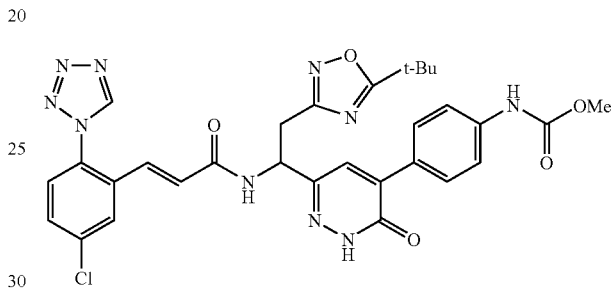

Example 171 was prepared using the procedures described in Example 167, by replacing 4-(chloromethyl)-2-isopropylthiazole with 5-tert-butyl-3-(chloromethyl)-1,2,4-oxadiazole. $^1$H NMR (400 MHz, DMSO-d$_6$) δ ppm 12.99 (1 H, s), 9.78-9.88 (2 H, m), 8.70 (1 H, d, J=8.53 Hz), 7.91 (1 H, d, J=2.01 Hz), 7.80 (2 H, d, J=8.78 Hz), 7.63-7.73 (2 H, m), 7.56 (1 H, s), 7.48 (2 H, d, J=8.78 Hz), 6.78-6.88 (1 H, m), 6.66-6.74 (1 H, m), 5.25 (1 H, d, J=7.53 Hz), 3.62 (3 H, s), 3.19 (2 H, dd, J=16.06, 7.28 Hz), 1.23 (9 H, s). MS (ESI) m/z: 645.2 (M+H)+. Analytical HPLC: RT=7.84 min.

Example 172

(R,E)-Methyl 4-(6-(1-(3-(5-chloro-2-(1H-tetrazol-1-yl)phenyl)acrylamido)-2-(neopentylthio)ethyl)-3-oxo-2,3-dihydropyridazin-4-yl)phenylcarbamate

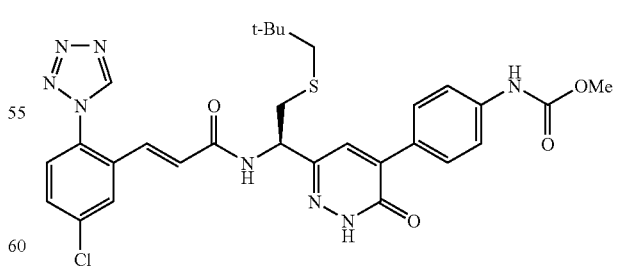

172A. (R)-2-Acetamido-3-(neopentylthio)propanoic acid: The compound was prepared according to a modified procedure described in literature (David A. Perrey, et al., *Tetrahedron Lett.*, 2001, 1859-1861). LC-MS (ESI) m/z: 234.1 (M+H)+.

172B. (R)-Methyl 2-acetamido-3-(neopentylthio)propanoate: The compound was prepared following the procedure described in 90A by replacing (S)-2-(tert-butoxycarbonylamino)-4-(methylthio)butanoic acid with 172A and by replacing toluene/methanol with dichloromethane. LC-MS (ESI) m/z: 248.1 (M+H)+.

172C. (R)-Methyl 4-(6-(1-acetamido-2-(neopentylthio)ethyl)-3-oxo-2,3-dihydropyridazin-4-yl)phenylcarbamate: The compound was prepared using the procedures described in 37A, 37B, and 37C, by replacing (S)-tert-butyl 4-(dimethoxyphosphoryl)-3-oxo-1-phenylbutan-2-ylcarbamate with (R)-dimethyl 3-acetamido-4-(neopentylthio)-2-oxobutylphosphonate (which was prepared according to procedure described in Intermediate 3, by replacing intermediate 3A with 172B.) LC-MS (ESI) m/z: 433.0 (M+H)+.

172D. (R)-Methyl 4-(6-(1-amino-2-(neopentylthio)ethyl)-3-oxo-2,3-dihydropyridazin-4-yl)phenylcarbamate, TFA salt: A suspension of 172C (50 mg, 0.116 mmol) in 4M HCl (4 mL, 16.00 mmol) was stirred at reflux for 16 h. The reaction was cooled. Methanol was added to dissolve the solid in the reaction mixture. Purification by reverse phase chromatography gave 172D (22 mg, 0.044 mmol, 37.7% yield) as a light brown solid. LC-MS (ESI) m/z: 391.0 (M+H)+.

172E: Example 172 was prepared by following the procedure described in 1D, by replacing 1C with 172D. $^1$H NMR (400 MHz, CD$_3$OD) δ ppm 9.42 (s, 1 H) 7.88 (d, J=2.26 Hz, 1 H) 7.72 (d, J=8.78 Hz, 2 H) 7.53-7.58 (m, 1 H) 7.50 (s, 1 H) 7.46 (t, J=8.28 Hz, 3 H) 7.06 (d, J=15.56 Hz, 1 H) 6.65 (d, J=15.56 Hz, 1 H) 5.00-5.12 (m, 1 H) 3.65 (s, 3 H) 2.94-3.02 (m, 1 H) 2.85-2.93 (m, 1 H) 2.43 (s, 2 H) 0.86 (s, 9 H). LC-MS (ESI) m/z: 623.2 (M+H)+. Analytical HPLC: RT=9.366 min.

Example 173

(S,E)-Methyl 4-(6-(1-(3-(5-chloro-2-(1H-tetrazol-1-yl)phenyl)acrylamido)-2-(4,5-dimethylthiazol-2-yl)ethyl)-3-oxo-2,3-dihydropyridazin-4-yl)phenylcarbamate

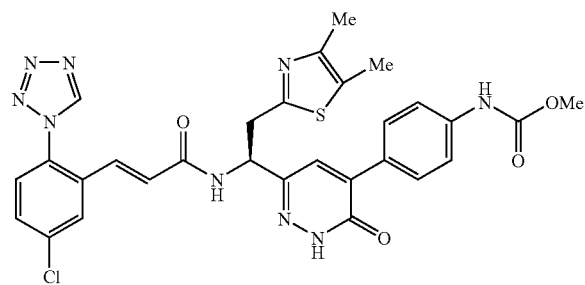

Example 173 was prepared using the procedures described in 126A and Example 162, by replacing 4-methylthiazole-2-carbaldehyde with 4,5-dimethylthiazole-2-carbaldehyde. $^1$H NMR (400 MHz, DMSO-d$_6$) δ ppm 9.88 (1 H, s), 9.85 (1 H, s), 8.81 (1 H, d, J=8.28 Hz), 7.98 (1 H, d, J=2.01 Hz), 7.86 (2 H, d, J=8.78 Hz), 7.70-7.76 (2 H, m), 7.62 (1 H, s), 7.54 (2 H, d, J=8.78 Hz), 6.85-6.91 (1 H, m), 6.72-6.78 (1 H, m), 5.17-5.26 (1 H, m), 3.68 (3 H, s), 3.41-3.49 (1 H, m), 3.31-3.40 (1 H, m), 2.26 (3 H, s), 2.18 (3 H, s). MS (ESI) m/z: 632.2 (M+H)+. Analytical HPLC: RT=6.5 min.

Example 174

(R,E)-Methyl 4-(6-(1-(3-(5-chloro-2-(1H-tetrazol-1-yl)phenyl)acrylamido)-2-(neopentylsulfonyl)ethyl)-3-oxo-2,3-dihydropyridazin-4-yl)phenylcarbamate

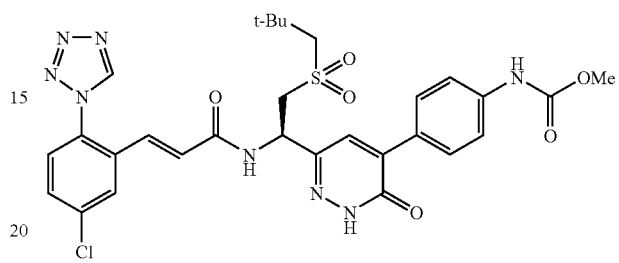

174A. (R)-Methyl 4-(6-(1-acetamido-2-(neopentylsulfonyl)ethyl)-3-oxo-2,3-dihydropyridazin-4-yl)phenylcarbamate: The compound was prepared following the procedure described in 170A, by replacing 169A with 172C. LC-MS (ESI) m/z: 465.0 (M+H)+.

174B: Example 174 was prepared by following the procedures described in 172D and 172E, by replacing 172C with 174A. $^1$H NMR (400 MHz, CD$_3$OD) δ ppm 9.43 (s, 1 H) 7.89 (d, J=2.26 Hz, 1 H) 7.73 (d, J=9.03 Hz, 2 H) 7.54-7.59 (m, 1 H) 7.53 (s, 1 H) 7.47 (dd, J=9.79, 8.78 Hz, 3 H) 7.11 (d, J=15.56 Hz, 1 H) 6.61 (d, J=15.56 Hz, 1 H) 5.56 (dd, J=7.91, 5.40 Hz, 1 H) 3.79 (dd, J=14.43, 5.40 Hz, 1 H) 3.67 (s, 3 H) 3.55 (dd, J=14.56, 8.03 Hz, 1 H) 3.10 (s, 2 H) 1.10 (s, 9 H). LC-MS (ESI) m/z: 655.1 (M+H)+. Analytical HPLC: RT=8.073 min.

Example 175

(S,E)-Methyl 4-(6-(1-(3-(5-chloro-2-(1H-tetrazol-1-yl)phenyl)acrylamido)-3-(3,3-difluoropyrrolidin-1-yl)-3-oxopropyl)-3-oxo-2,3-dihydropyridazin-4-yl)phenylcarbamate

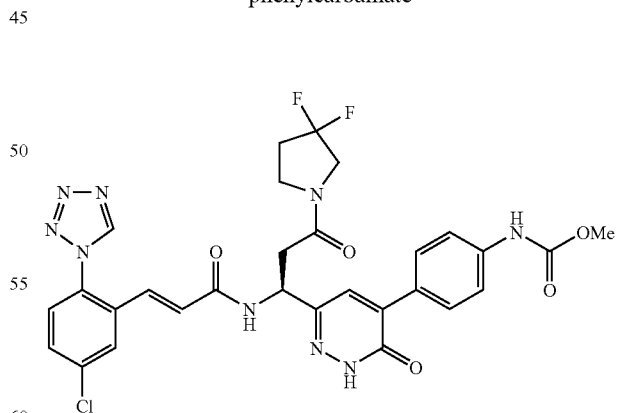

175A. (S)-3-(tert-Butoxycarbonylamino)-3-(5-(4-(methoxycarbonylamino)phenyl)-6-oxo-1,6-dihydropyridazin-3-yl)propanoic acid: To a solution of 120B (1.7 g, 3.81 mmol) in dichloromethane (40 mL) were added TEA (1.593 mL, 11.43 mmol) and BOC$_2$O (0.973 mL, 4.19 mmol) at rt. The reaction was stirred under argon at rt. overnight. The solvent was removed. The residue was diluted with EtOAc and then washed with 1M HCl (2×20 mL) and brine (1×20 mL). The organic phase was dried over sodium sulfate, filtered and concentrated to give 175A (1.4 g, 85% yield) as a dark brown solid. LC-MS (ESI) m/z: 433.0 (M+H)+.

175B. (4-{6-[(S)-1-tert-Butoxycarbonylamino-3-(3,3-difluoro-pyrrolidin-1-yl)-3-oxo-propyl]-3-oxo-2,3-dihydro-pyridazin-4-yl}-phenyl)-carbamic acid methyl ester: To a solution of 175A (100 mg, 0.231 mmol) in DMF (2 mL) were added 3,3-difluoropyrrolidine, HCl salt (33 mg, 0.231 mmol), HOBt (17.7 mg, 0.116 mmol), DIEA (0.1 mL, 0.573 mmol) and EDC (66 mg, 0.347 mmol) at rt. The reaction was stirred under argon at rt. overnight. The reaction was diluted with water and MeOH. Purification by reverse phase chromatography gave 175B (55.3 mg, 0.106 mmol, 45.9% yield) as a tan solid. LC-MS (ESI) m/z: 522.2 (M+H)+.

175C. Example 175 was prepared by following the procedures described in 37D and 37E, by replacing 37C with 175B. $^1$H NMR (400 MHz, CD$_3$OD) δ ppm 9.52 (s, 1 H) 7.97 (d, J=2.02 Hz, 1 H) 7.82 (d, J=8.59 Hz, 2 H) 7.64-7.69 (m, 1 H) 7.62 (s, 1 H) 7.53-7.60 (m, 3 H) 7.18 (d, J=15.66 Hz, 1 H) 6.70 (d, J=15.41 Hz, 1 H) 5.51 (dd, J=7.58, 6.06 Hz, 1 H) 4.00 (t, J=12.88 Hz, 1 H) 3.85 (dt, J=7.33, 3.66 Hz, 1 H) 3.77 (s, 3 H) 3.59-3.76 (m, 2 H) 3.05-3.20 (m, 1 H) 2.89-3.00 (m, 1 H) 2.45-2.60 (m, 1 H) 2.41 (dt, J=13.90, 6.95 Hz, 1 H). $^{19}$F NMR (376 MHz, CD$_3$OD) δ ppm −103.60 (s, 1 F)-104.34 (s, 1 F). LC-MS (ESI) m/z: 654.1 (M+H)+. Analytical HPLC: RT=7.145 min.

Example 176

Methyl 4-(6-((S)-1-((E)-3-(5-chloro-2-(1H-tetrazol-1-yl)phenyl)acrylamido)-3-((S)-3-fluoropyrrolidin-1-yl)-3-oxopropyl)-3-oxo-2,3-dihydropyridazin-4-yl)phenylcarbamate

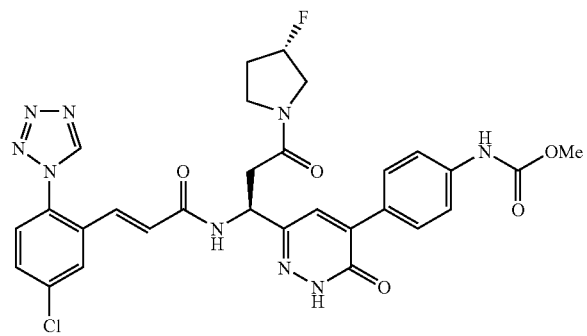

Example 176 was prepared by following the procedures described in 175B and 175C, by replacing 3,3-difluoropyrrolidine, HCl salt with (S)-3-fluoropyrrolidine, HCl salt. $^1$H NMR (400 MHz, CD$_3$OD) δ ppm 9.51 (d, J=1.65 Hz, 1 H) 7.95 (d, J=2.20 Hz, 1 H) 7.77-7.81 (m, 2 H) 7.61-7.65 (m, 1 H) 7.60 (s, 1 H) 7.55 (d, J=8.79 Hz, 1 H) 7.52 (d, J=8.79 Hz, 2 H) 7.15 (d, J=15.94 Hz, 1 H) 6.69 (dd, J=15.67, 3.02 Hz, 1 H) 5.43-5.52 (m, 1 H) 5.13-5.41 (m, 1 H) 3.74 (s, 3 H) 3.61-3.86 (m, 4 H) 3.08-3.19 (m, 1 H) 2.88-2.99 (m, 1 H) 2.16-2.38 (m, 2 H). $^{19}$F NMR (376 MHz, CD$_3$OD) δ ppm −179.42 (s, 1 F)-179.81 (s, 1 F). LC-MS (ESI) m/z: 636.1 (M+H)+. Analytical HPLC (low pH, 254 nm): Sunfire, RT=6.570 min.

Example 177

(S,E)-Methyl 4-(6-(1-(3-(5-chloro-2-(1H-tetrazol-1-yl)phenyl)acrylamido)-3-(3,3-difluoroazetidin-1-yl)-3-oxopropyl)-3-oxo-2,3-dihydropyridazin-4-yl)phenylcarbamate

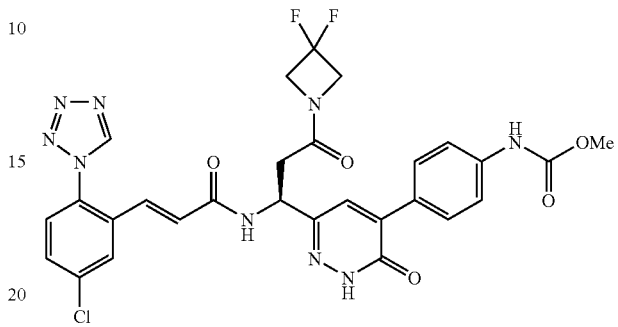

Example 177 was prepared by following the procedures described in 175B and 175C, by replacing 3,3-difluoropyrrolidine, HCl salt with 3,3-difluoroazetidine, HCl salt. $^1$H NMR (400 MHz, CD$_3$OD) δ ppm 9.52 (s, 1 H) 7.97 (d, J=2.27 Hz, 1 H) 7.81 (d, J=8.84 Hz, 2 H) 7.63-7.68 (m, 1 H) 7.60 (s, 1 H) 7.57 (d, J=8.59 Hz, 1 H) 7.54 (d, J=8.59 Hz, 2 H) 7.19 (d, J=15.41 Hz, 1 H) 6.70 (d, J=15.66 Hz, 1 H) 5.40-5.57 (m, 1 H) 4.59-4.75 (m, 2 H) 4.31 (t, J=12.13 Hz, 2 H) 3.76 (s, 3 H) 2.99 (dd, J=15.66, 7.58 Hz, 1 H) 2.83 (dd, J=15.41, 6.32 Hz, 1 H). $^{19}$F NMR (376 MHz, CD$_3$OD) δ ppm −103.48 (s, 2 F). LC-MS (ESI) m/z: 640.0 (M+H)+. Analytical HPLC: RT=6.963 min.

Example 178

(S,E)-Methyl 4-(6-(2-benzamido-1-(3-(5-chloro-2-(1H-tetrazol-1-yl)phenyl)acrylamido)ethyl)-3-oxo-2,3-dihydropyridazin-4-yl)phenylcarbamate

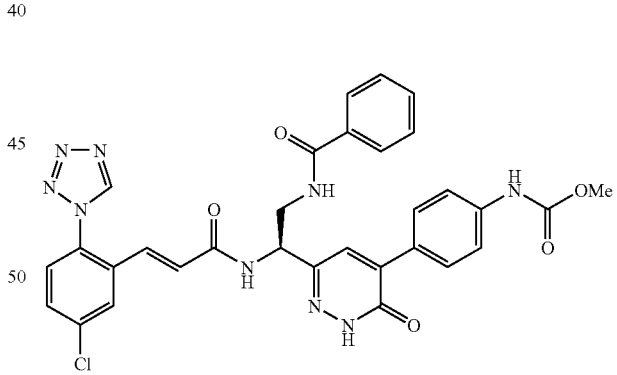

178A. {4-[6-((S)-2-Benzoylamino-1-benzyloxycarbonylamino-ethyl)-3-oxo-2,3-dihydro-pyridazin-4-yl]-phenyl}-carbamic acid methyl ester: To a solution of 165A (40 mg, 0.073 mmol) in DMF (2 mL) were added benzoyl chloride (15 mg, 0.109 mmol) and TEA (0.05 mL, 0.363 mmol) at rt. The reaction was stirred under argon at rt overnight. The reaction mixture was diluted with water and MeOH. Purification by reverse phase chromatography gave 178A (41 mg, 0.077 mmol, 100% yield) as a white solid. LC-MS (ESI) m/z: 542.1 (M+H)+.

178C. Example 178 was prepared by following the procedures described in 4D and 1D, by replacing 4C with 178B. $^1$H NMR (400 MHz, DMF-d7) δ ppm 12.91 (s, 1 H) 9.73 (s, 1 H)

9.69 (s, 1 H) 8.69 (d, J=8.28 Hz, 1 H) 8.55 (t, J=5.90 Hz, 1 H) 7.90 (d, J=2.01 Hz, 1 H) 7.81 (d, J=8.78 Hz, 2 H) 7.71-7.76 (m, 2 H) 7.60-7.68 (m, 3 H) 7.49 (d, J=8.78 Hz, 2 H) 7.34-7.40 (m, 1 H) 7.26-7.33 (m, 2 H) 6.93 (d, J=15.56 Hz, 1 H) 6.84 (d, J=15.56 Hz, 1 H) 5.08-5.23 (m, 1 H) 3.65-3.84 (m, 2H) 3.57 (s, 3 H). LC-MS (ESI) m/z: 640.0 (M+H)⁺. Analytical HPLC: RT=7.306 min.

Example 179

(S,E)-Methyl 4-(6-(2-(3-(1H-pyrazol-1-yl)phenylsulfonamido)-1-(3-(5-chloro-2-(1H-tetrazol-1-yl)phenyl)acrylamido)ethyl)-3-oxo-2,3-dihydropyridazin-4-yl)phenylcarbamate

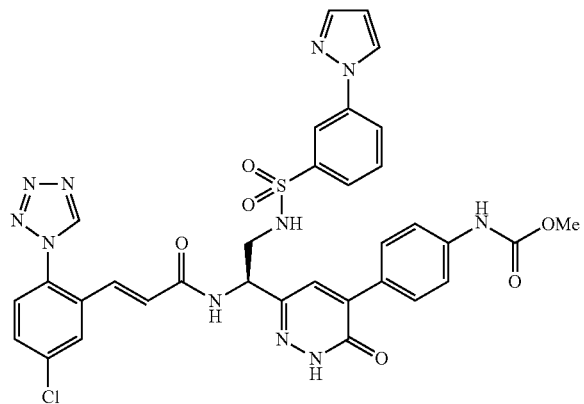

Example 179 was prepared by following the procedure described in Example 178, by replacing benzoyl chloride with 3-(1H-pyrazol-1-yl)benzene-1-sulfonyl chloride. ¹H NMR (400 MHz, DMF-d₇) δ ppm 13.28 (s, 1 H) 10.08 (s, 1 H) 10.04 (s, 1 H) 8.91 (d, J=8.28 Hz, 1 H) 8.84 (d, J=2.26 Hz, 1 H) 8.58 (t, J=1.76 Hz, 1H) 8.35 (ddd, J=7.91, 2.13, 1.26 Hz, 1 H) 8.24-8.27 (m, 2 H) 8.17 (d, J=8.78 Hz, 2H) 7.95-8.03 (m, 4 H) 7.89-7.94 (m, 2 H) 7.85 (d, J=8.78 Hz, 2 H) 7.22-7.30 (m, 1 H) 7.09-7.18 (m, 1 H) 6.79 (dd, J=2.51, 1.76 Hz, 1 H) 5.25-5.46 (m, 1 H) 3.92 (s, 3H) 3.65-3.71 (m, 2 H). LC-MS (ESI) m/z: 742.3 (M+H)⁺. Analytical HPLC: RT=7.683 min.

Example 180

(S,E)-Methyl 4-(6-(1-(3-(5-chloro-2-(1H-tetrazol-1-yl)phenyl)acrylamido)-2-(1,3-dimethyl-1H-pyrazole-4-sulfonamido)ethyl)-3-oxo-2,3-dihydropyridazin-4-yl)phenylcarbamate

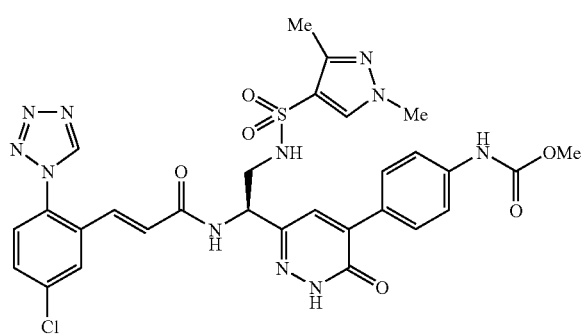

Example 180 was prepared by following the procedures described in Example 178, by replacing benzoyl chloride with 5-chloro-1,3-dimethyl-1H-pyrazole-4-sulfonyl chloride. ¹H NMR (400 MHz, CD₃CN) δ ppm 10.99 (s, 1 H) 9.06 (s, 1 H) 7.83 (d, J=2.26 Hz, 2 H) 7.76 (d, J=8.78 Hz, 2 H) 7.70 (s, 1 H) 7.50-7.57 (m, 1 H) 7.40-7.49 (m, 3 H) 7.31 (s, 1 H) 7.10 (d, J=7.78 Hz, 1 H) 6.96 (d, J=15.81 Hz, 1 H) 6.53 (d, J=15.56 Hz, 1 H) 5.71 (t, J=6.53 Hz, 1 H) 4.92 (dt, J=7.72, 5.80 Hz, 1 H) 3.63 (s, 3 H) 3.62 (s, 3 H) 3.13-3.34 (m, 2 H) 2.16 (s, 3 H). LC-MS (ESI) m/z: 694.1 (M+H)⁺. Analytical HPLC: RT=6.653 min.

Example 181

(E)-Methyl 4-(3-chloro-6-(1-(3-(5-chloro-2-(1H-tetrazol-1-yl)phenyl)acrylamido)-2-(2-isopropylthiazol-4-yl)ethyl)pyridazin-4-yl)phenylcarbamate

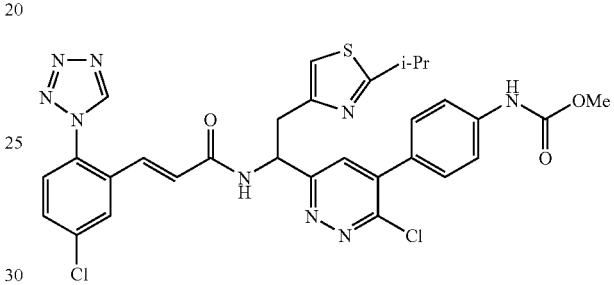

Example 181 was prepared using the procedures described in 37A, 37B, 37C, 38A, and 38B, by replacing (S)-tert-butyl 4-(dimethoxyphosphoryl)-3-oxo-1-phenylbutan-2-ylcarbamate with 167E. ¹H NMR (400 MHz, CD₃OD) δ ppm 9.50 (1H, s), 7.96 (1 H, d, J=2.26 Hz), 7.58-7.66 (3 H, m), 7.53-7.58 (2 H, m), 7.45-7.49 (2 H, m), 7.12-7.15 (1 H, m), 7.08 (1 H, d, J=15.56 Hz), 6.75 (1 H, d, J=15.56 Hz), 5.66 (1 H, t, J=7.40 Hz), 3.76 (3 H, s), 3.45 (2 H, t, J=7.65 Hz), 3.25-3.29 (1 H, m), 1.33 (6 H, d, J=7.03 Hz). MS (ESI) m/z: 664.2 (M+H)⁺. Analytical HPLC: RT=8.2 min.

Example 182

(R,E)-Methyl 4-(3-chloro-6-(1-(3-(5-chloro-2-(1H-tetrazol-1-yl)phenyl)acrylamido)-2-(methylsulfonyl)ethyl)pyridazin-4-yl)phenylcarbamate

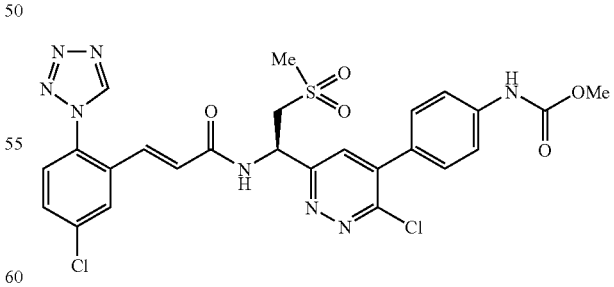

Example 182 was prepared by following the procedures described in Example 38, by replacing 37C with 170A. ¹H NMR (400 MHz, CD₃OD) δ ppm 9.42 (s, 1 H) 7.89 (d, J=2.26 Hz, 1 H) 7.68 (s, 1 H) 7.54-7.58 (m, 1 H) 7.51-7.54 (m, 2H) 7.42-7.49 (m, 3 H) 7.07 (d, J=15.56 Hz, 1 H) 6.63 (d, J=15.56 Hz, 1 H) 5.80 (td, J=8.03, 5.27 Hz, 1 H) 3.99 (dd, J=14.56, 5.52 Hz, 1 H) 3.80 (dd, J=14.43, 8.41 Hz, 1H) 3.66 (s, 3 H) 2.98 (s, 3 H). LC-MS (ESI) m/z: 616.9 (M+H)+. Analytical HPLC: RT=7.131 min.

Examples 1-9 and 11-182 were tested in the Factor XIa assay described above and found having Factor XIa inhibitory activity. Table 1 below lists Factor XIa Ki values measured for the following examples.

TABLE 1

| Example Number | Factor XIa Ki (nM) |
|---|---|
| 2 | 2.0 |
| 3 | 630 |
| 8 | 1164 |
| 11 | 52 |
| 20 | 2.9 |
| 27 | 4.0 |
| 36 | 20 |
| 40 | 156 |
| 51 | 405 |
| 60 | 3370 |
| 61 | 1678 |
| 71 | 9.4 |
| 78 | 0.84 |
| 80 | 3326 |
| 89 | 141 |
| 90 | 67 |
| 94 | 27 |
| 97 | 17 |
| 99 | 746 |
| 112 | 6365 |
| 116 | 327 |
| 118 | 55 |
| 123 | 57 |
| 132 | 76 |
| 136 | 503 |
| 146 | 5.5 |
| 147 | 5152 |
| 154 | 176 |

While the foregoing specification teaches the principles of the present invention, which examples provided for the purpose of illustration, it will be understood that the practice of the invention encompasses all of the usual variations, adaptations and/or modifications as come within the scope of the following claims and their equivalents.

What is claimed is:

1. A compound of Formula (I):

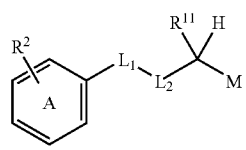

(I)

or a stereoisomer, a tautomer, or a pharmaceutically acceptable salt thereof, wherein:

A is phenyl further substituted with 0-3 $R^1$, or pyridyl further substituted with 0-3 $R^1$;

$L_1$ is —CH($R^5$)CH$_2$—, —CH(NR$^7$R$^8$)CH$_2$—, —C($R^5$)=CH—, —C≡C—, —OCH$_2$—, —CR$^5$R$^6$NH—, —CH$_2$O—, —SCH$_2$—, —S(O)CH$_2$—, —SO$_2$CH$_2$—, —CH$_2$NR$^{10}$—, or —NHNH—;

$L_2$ is —CONH— or —NHCO—;

provided that when $L_1$ is —NHNH—, —OCH$_2$—, or —SCH$_2$—, then $L_2$ is —CONH—;

M is selected from the group consisting of:

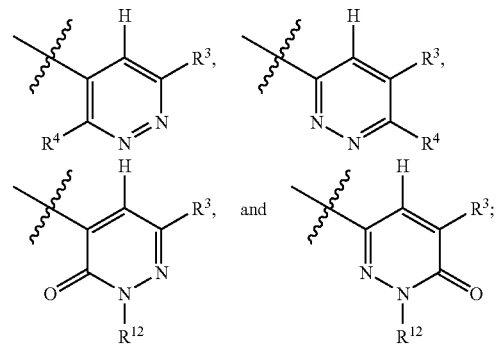

$R^1$ is, independently at each occurrence, F, Cl, Br, I, OCF$_3$, CHF$_2$, CF$_3$, —(CH$_2$)$_r$OR$^a$, —(CH$_2$)$_r$SR$^a$, CN, NO$_2$, —(CH$_2$)$_r$NR$^7$R$^8$, —(CH$_2$)$_r$C(O)OR$^a$, —(CH$_2$)$_r$OC(O)R$^a$, —C(=NR$^8$)NR$^8$R$^9$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —NR$^8$C(O)NR$^8$R$^c$, —S(O)$_p$NR$^8$R$^9$, —S(O)R$^c$, —S(O)$_2$R$^c$, or C$_{1-6}$ alkyl substituted with 0-1 R$^{13}$;

$R^2$ is H, —(CH$_2$)$_r$C(O)R$^a$, —(CH$_2$)$_r$OR$^a$, —(CH$_2$)$_r$NR$^7$R$^8$, C$_{1-6}$ alkyl substituted with 0-1 R$^{2a}$, —(CH$_2$)$_r$-3- to 7-membered carbocycle substituted with 0-2 R$^{2b}$, or —(CH$_2$)$_r$-5- to 7-membered heterocycle comprising carbon atoms and 1-4 heteroatoms selected from N, O, and S(O)$_p$, wherein said heterocycle is substituted with 0-2 R$^{2b}$;

$R^{2a}$ is F, OCF$_3$, CF$_3$, OR$^a$, SR$^a$, CN, —NR$^7$R$^8$, —C(O) NR$^8$R$^9$, —NR$^8$C(O)R$^c$, —NR$^8$C(O)OR$^c$, —NR$^8$C(O) NR$^8$R$^c$, —S(O)$_p$NR$^8$R$^9$, —NR$^8$SO$_2$R$^c$, or —(CF$_2$)$_r$CF$_3$;

$R^{2b}$ is, independently at each occurrence, =O, F, Br, Cl, OCF$_3$, CF$_3$, —(CH$_2$)$_r$OR$^a$, —(CH$_2$)$_r$SR$^a$, —(CH$_2$)$_r$CN, —(CH$_2$)$_r$NR$^7$R$^8$, —(CH$_2$)$_r$C(O)OR$^a$, —(CH$_2$)$_r$OC(O) R$^a$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —(CH$_2$)$_r$S(O)$_p$NR$^8$R$^9$, —(CH$_2$)$_r$NR$^8$SO$_2$R$^c$, C$_{1-4}$ alkyl or —(CF$_2$)$_r$CF$_3$;

$R^3$ is, independently at each occurrence, —(CH$_2$)$_r$—C$_{3-10}$ carbocycle substituted with 0-3 R$^{3a}$ and 0-1 R$^{3d}$, or —(CH$_2$)$_r$-5- to 12-membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

$R^{3a}$ is, independently at each occurrence, F, Cl, Br, I, OCF$_3$, CF$_3$, —(CH$_2$)$_r$CN, NO$_2$, —(CH$_2$)$_r$OR$^a$, —(CH$_2$)$_r$SR$^a$, —(CH$_2$)$_r$NR$^7$R$^8$, —NHC(O)NR$^8$R$^9$, —(CH$_2$)$_r$C(O) OR$^a$, —C(O)C$_{1-4}$ alkyl, —(CH$_2$)$_r$NR$^8$C(O)R$^a$, —(CH$_2$)$_r$NR$^8$CO$_2$R$^c$, —(CH$_2$)$_r$S(O)$_p$NR$^8$R$^9$, —(CH$_2$)$_r$NR$^8$S(O)$_p$R$^c$, —NHSO$_2$CF$_3$, —S(O)R$^c$, —S(O)$_2$R$^c$, —(CH$_2$)$_r$OC(O)R$^c$, —(CH$_2$)$_r$C(O)NR$^8$R$^9$, —(CH$_2$)$_r$OC(O)NR$^8$R$^9$, C$_{1-4}$ haloalkyl, C$_{1-4}$ haloalkyloxy-, C$_{1-6}$ alkyl, C$_{3-6}$ cycloalkyl substituted by 0-1 R$^{3d}$, —(CH$_2$)$_r$—C$_{6-10}$ carbocycle substituted by 0-3 R$^{3d}$ or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

$R^{3d}$ is, independently at each occurrence, H, =O, F, Cl, Br, CN, NO$_2$, —(CH$_2$)$_r$NR$^7$R$^8$, —(CH$_2$)$_r$OR$^a$, —C(O)R$^a$, —C(O)OR$^a$, —OC(O)R$^a$, —NR$^8$C(O)R$^c$, —C(O) NR$^8$R$^9$, —S(O)2NR$^8$R$^9$, —NR$^7$R$^8$, —NR$^8$S(O) 2NR$^8$R$^9$, —NR$^8$S(O)$_2$R$^c$, —S(O)$_p$R$^c$, —(CF$_2$)$_r$CF$_3$, C$_{1-6}$ alkyl substituted with 0-2 R$^e$, C$_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, F, Cl, Br, I, $OCF_3$, $CF_3$, CN, $NO_2$, —$(CH_2)_rOR^a$, —$(CH_2)_rSR^a$, —$(CH_2)_rC(O)R^a$, —$(CH_2)_rC(O)OR^a$, —$OC(O)R^a$, —$(CH_2)_rNR^7R^8$, —$NR^8(CH_2)_rC(O)OR^a$, —$(CH_2)_rC(O)NR^8R^9$, —$(CH_2)_rNR^8C(O)R^c$, —$(CH_2)_rNR^8C(O)_2R^b$, —$(CH_2)_rNR^8C(O)NR^8R^9$, —$S(O)_pNR^8R^9$, —$NR^8S(O)_pR^c$, —$(CH_2)_rS(O)_2R^c$, —$(CH_2)_rOP(O)(OR^a)_2$, $C_{1-4}$ alkyl substituted with 0-2 $R^{4a}$, or $C_{2-4}$ alkenyl substituted with 0-2 $R^{4a}$;

$R^{4a}$ is, independently at each occurrence, H, F, =O, $C_{1-6}$ alkyl, $OR^a$, $SR^a$, $CF_3$, CN, $NO_2$, —$C(O)R^a$, —$C(O)OR^a$, —$NR^7R^8$, —$C(O)NR^8R^9$, —$NR^8C(O)R^c$, —$S(O)_pNR^8R^9$, —$NR^8S(O)_pR^c$, —$S(O)_pR^c$, or —$S(O)_2R^c$;

$R^5$ is, independently at each occurrence, H, F, $CF_3$, —$(CH_2)_rOR^a$, =O, —$(CH_2)_rNR^7R^8$, —$S(O)_pNR^8R^9$, —$(CH_2)_rCO_2R^a$, —$(CH_2)_rCONR^8R^9$, or $C_{1-4}$ alkyl;

$R^6$ is, independently at each occurrence, H, F, or $C_{1-4}$ alkyl;

$R^7$ is, independently at each occurrence, H, $C_{1-6}$ alkyl, —$(CH_2)_n$—$C_{3-10}$ carbocycle, —$(CH_2)_n$-(5- to 10-membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are substituted with 0-2 $R^f$; wherein said heteroaryl comprises: carbon atoms and 1-4 heteroatoms selected from N, O, and $S(O)_p$;

$R^8$ is, independently at each occurrence, H, $C_{1-6}$ alkyl, —$(CH_2)_n$-phenyl, or —$(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

alternatively, $R^8$ and $R^9$, when attached to the same nitrogen, combine to form a 5- to 12-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H or $C_{1-6}$ alkyl substituted with 0-3 $R^{10a}$;

$R^{10a}$ is, independently at each occurrence, H, =O, $C_{1-4}$ alkyl, $OR^a$, $SR^a$, F, $CF_3$, CN, $NO_2$, —$C(O)R^a$, —$C(O)OR^a$, —$C(O)NR^8R^9$, —$NR^8C(O)R^c$, —$S(O)_pNR^8R^9$, —$NR^8S(O)_pR^c$, or —$S(O)_pR^c$;

$R^{11}$ is $C_{1-4}$ haloalkyl, $C_{1-6}$ alkyl substituted with 0-3 $R^{11a}$, $C_{2-6}$ alkenyl substituted with 0-3 $R^{11a}$, $C_{2-6}$ alkynyl substituted with 0-3 $R^{11a}$, —$(CH_2)_s$—$C_{3-10}$ carbocycle substituted with 0-3 $R^{11b}$, or —$(CH_2)_s$-4- to 10-membered heterocycle comprising: carbon atoms and 1-4 heteroatoms selected from N, O, and $S(O)_p$, wherein said heterocycle is substituted with 0-3 $R^{11b}$;

$R^{11a}$ is, independently at each occurrence H, =O, $OR^a$, $SR^a$, F, $CF_3$, CN, $NO_2$, —$C(O)R^a$, —$C(O)OR^a$, —$NR^7R^8$, —$C(O)NR^8R^9$, —$NR^8C(O)R^c$, —$NR^8C(O)OR^c$, —$NR^8CHO$, —$S(O)_pNR^8R^9$, —$NR^8S(O)_pR^c$, —$S(O)_pR^c$, $C_{1-4}$ alkyl, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, —$CH_2OR^a$, F, Cl, Br, CN, $NO_2$, $CF_3$, $OCF_3$, $OCHF_2$, —$C(CH_3)_2OR^a$, —$C(O)R^a$, —$C(O)OR^a$, —$NR^7R^8$, —$C(O)NR^8R^9$, —$NR^7C(O)R^b$, —$NR^8C(O)_2R^c$, —$NR^8C(O)NR^8R^9$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

R12 is, independently at each occurrence, H, $C_{1-6}$ alkyl substituted with 0-2 $R^f$, or —$(CH_2)_n$-phenyl;

$R^{13}$ is F, $OCF_3$, $CF_3$, $OR^a$, $SR^a$, CN, —$NR^7R^8$, —$C(O)NR^8R^9$, —$NR^8C(O)R^c$, —$S(O)_pNR^8R^9$, —$NR^8SO_2R^c$, or —$(CF_2)_rCF_3$;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10-membered heterocycle comprising carbon atoms and 1-4 heteroatoms selected from N, O, and $S(O)_p$; wherein said alkyl, cycloalkyl, aryl or heterocycle groups are substituted with 0-2 $R^f$;

$R^b$ is, independently at each occurrence, $CF_3$, OH, $C_{1-4}$ alkoxy, $C_{1-6}$ alkyl substituted with 0-2 $R^d$, —$(CH_2)_r$—$C_{3-10}$ carbocycle substituted with 0-2 $R^d$, or —$(CH_2)_r$-5- to 10-membered heterocycle comprising: carbon atoms and 1-4 heteroatoms selected from N, O, and $S(O)_p$ and substituted with 0-3 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, $(C_{6-10}$ aryl)-$C_{1-4}$ alkyl, or (5- to 10-membered heteroaryl)-$C_{1-4}$ alkyl, wherein said aryl is substituted with 0-3 $R^f$ and said heteroaryl comprises: carbon atoms and 1-4 heteroatoms selected from N, O, and $S(O)_p$ and substituted with 0-3 $R^f$;

$R^d$ is, independently at each occurrence, H, =O, =$NR^8$, $OR^a$, F, Cl, Br, I, CN, $NO_2$, —$NR^7R^8$, —$C(O)R^a$, —$C(O)OR^a$, —$OC(O)R^a$, —$NR^8C(O)R^c$, —$C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^7R^8$, —$C(O)R^a$, —$C(O)OR^a$, —$NR^8C(O)R^c$, —$C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^f$ is, independently at each occurrence, H, =O, —$(CH_2)_rOR^g$, F, Cl, Br, I, CN, $NO_2$, —$NR^gR^g$, —$C(O)R^g$, —$C(O)OR^g$, —$OC(O)R^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, —$(CH_2)_n$-phenyl, or —$(CH_2)_n$-5- to 10-membered heterocycle comprising carbon atoms and 1-4 heteroatoms selected from N, O, and $S(O)_p$;

$R^g$ is, independently at each occurrence, H, $C_{1-6}$ alkyl, or —$(CH_2)_r$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4.
s, at each occurrence, is selected from 1, 2, 3, and 4.

2. A compound according to claim 1, wherein:
$R^2$ is, H, —$(CH_2)_rC(O)R^a$, —$(CH_2)_rOR^a$, —$(CH_2)_rNR^7R^8$, $C_{1-6}$ alkyl substituted with 0-1 $R^{2a}$, —$(CH_2)_r$—$C_{3-6}$ cycloalkyl substituted with 0-2 $R^{2b}$, —$(CH_2)_r$-phenyl substituted with 0-2 $R^{2b}$, or —$(CH_2)_r$-5-7 membered heterocycle comprising carbon atoms and 1-4 heteroatoms selected from N, O, and $S(O)_p$, wherein said heterocycle is substituted with 0-2 $R^{2b}$;

$R^3$ is, independently at each occurrence, —$(CH_2)_r$-phenyl substituted with 0-2 $R^{3a}$ and 0-1 $R^{3d}$, —$(CH_2)_r$-naphthyl substituted with 0-2 $R^{3a}$ and 0-1 $R^{3d}$, —$(CH_2)_r$-1,2,3,4-tetrahydronaphthyl substituted with 0-2 $R^{3a}$ and 0-1 $R^{3d}$, or —$(CH_2)_r$-5- to 12-membered heterocycle substituted with 0-2 $R^{3a}$ and 0-1 $R^{3d}$, wherein said heterocycle is selected from the group consisting of: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

$R^4$ is, independently at each occurrence, H, F, Cl, Br, $OCF_3$, $CF_3$, CN, $NO_2$, —$(CH_2)_rOR^a$, —$(CH_2)_rSR^a$, —$(CH_2)_rC(O)R^a$, —$(CH_2)_rC(O)OR^a$, —$(CH_2)_rNR^7R^8$, —$(CH_2)_rC(O)NR^8R^9$, —$(CH_2)_rS(O)_2R^c$, $C_{1-4}$ alkyl substituted with 0-2 $R^{4a}$, or $C_{2-4}$ alkenyl substituted with 0-2 $R^{4a}$; and $R^{11}$ is —$CH_2OR^a$, —$CH_2CH_2OR^a$, —$CH_2S(O)_pR^c$, —$CH_2CH_2S(O)_pR^c$, —$CH_2NR^7R^8$, —$CH_2CH_2NR^7R^8$, —$CH_2C(O)R^a$, —$CH_2CH_2C(O)R^a$, —$CH_2C(O)OR^a$, —$CH_2CH_2C(O)OR^a$, —$CH_2C(O)NR^8R^9$, —$CH_2CH_2C(O)NR^8R^9$, —$CH_2NR^8C(O)R^c$, —$CH_2CH_2NR^8C(O)R^c$, —$CH_2NR^8C(O)OR^c$, —$CH_2CH_2NR^8C(O)OR^c$, —$CH_2NHS(O)_2$(3-(pyrazol-1-yl)-Ph), —$CH_2NHS(O)_2$(1,3-dimethyl-pyrazol-4-yl), $C_{1-4}$ haloalkyl, $C_{1-6}$ alkyl substituted with 0-2 $R^{11a}$, $C_{2-6}$ alkyl substituted with 0-2 $R^{11a}$, —$(CH_2)_s$—$C_{3-6}$ cycloalkyl substituted with 0-2 $R^{11b}$, —$(CH_2)_s$-phenyl substituted with 0-3 $R^{11b}$, or —$(CH_2)_s$-4- to 10-membered heterocycle comprising: carbon atoms and 1-4 heteroatoms selected from N, O, and $S(O)_p$, wherein said heterocycle is substituted with 0-3 $R^{11b}$.

3. A compound according to claim 1, wherein:
$L_1$ is —$CH_2CH_2$—, —CH=CH—, —C(Me)=CH—, —C≡C—, —$CH_2NH$—, —$CH_2O$—, —NHNH—, —$SCH_2$—, —$SO_2CH_2$— or —$OCH_2$—;
$L_2$ is —CONH— or —NHCO—;
provided that when $L_1$ is —NHNH—, —$OCH_2$—, or —$SCH_2$— then $L_2$ is —CONH—;
$R^3$ is, independently at each occurrence, —$(CH_2)_r$-phenyl substituted with 0-3 $R^{3a}$, —$(CH_2)_r$-pyridyl substituted with 0-3 $R^{3a}$, —$(CH_2)_r$-thiazolyl substituted with 0-2 $R^{3a}$, or

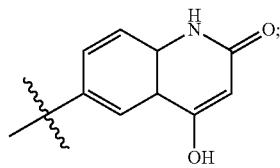

$R^4$ is, independently at each occurrence, H, F, Cl, Br, $OCF_3$, $CF_3$, CN, $NO_2$, —$(CH_2)_rOR^a$, —$CH(OH)CH_2OH$, —$(CH_2)_rSR^a$, $C(O)R^a$, $C(O)OR^a$, —$(CH_2)_rNR^7R^8$, —$(CH_2)_rS(O)_2R^c$, $C(O)NR^8R^9$, $C_{1-4}$ alkyl substituted with 0-2 $R^{4a}$, or $C_{2-4}$ alkenyl substituted with 0-2 $R^{4a}$; and $R^{11}$ is —$CH_2OR^a$, —$CH_2CH_2OR^a$, —$CH_2S(O)_pR^c$, —$CH_2CH_2S(O)_pR^c$, —$CH_2NR^7R^8$, —$CH_2CH_2NR^7R^8$, —$CH_2C(O)R^a$, —$CH_2CH_2C(O)R^a$, —$CH_2C(O)OR^a$, —$CH_2CH_2C(O)OR^a$, —$CH_2C(O)NR^8R^9$, —$CH_2CH_2C(O)NR^8R^9$, —$CH_2NR^8C(O)R^c$, —$CH_2CH_2NR^8C(O)R^c$, —$CH_2NR^8C(O)OR^c$, —$CH_2CH_2NR^8C(O)OR^c$, —$CH_2NHS(O)_2$(3-(pyrazol-1-yl)-Ph), —$CH_2NHS(O)_2$(1,3-dimethyl-pyrazol-4-yl), $C_{1-6}$ alkyl, $C_{2-6}$ alkenyl, —$(CH_2)_s$-phenyl substituted with 0-2 $R^{11b}$, or —$(CH_2)_s$-4 to 6-membered heterocycle substituted with 0-2 $R^{11b}$, wherein said heterocycle is selected from the group consisting of: azetidine, oxazolidin-2-one, pyrrolidine, pyrazole, thiazole, thiadiazole, oxazole, oxadiazole, imidazole, piperidine, piperazine, and pyridine;

alternatively, $R^{11}$ is

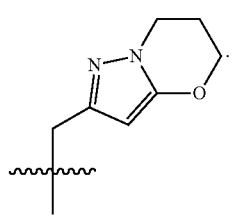

4. A compound according to claim 1, wherein the compound is of Formula (II):

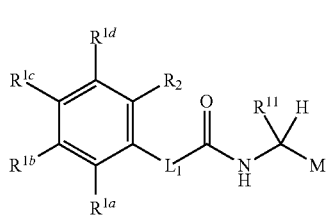

(II)

or a stereoisomer, a tautomer, or a pharmaceutically acceptable salt thereof, wherein:
M is selected from the group consisting of:

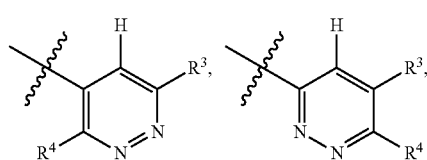

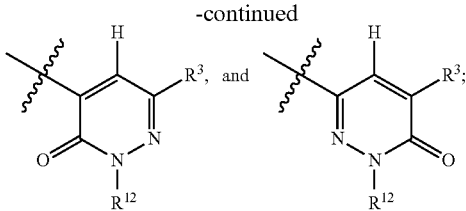

L₁ is —CH₂CH₂—, —CH=CH—, —C≡C—, —OCH₂—, —CH₂NH—, —CH₂O—, or —SCH₂—;

$R^{1a}$, $R^{1b}$, $R^{1c}$, and $R^{1d}$ are, independently at each occurrence, H, F, Cl, Br, CF₃, —(CH₂)ᵣOR$^a$, CN, —(CH₂)ᵣNR⁷R⁸, or C₁₋₄ alkyl;

$R^2$ is —(CH₂)ᵣC(O)R$^a$, —(CH₂)ᵣOR$^a$, —(CH₂)ᵣNR⁷R⁸, or 5-membered heterocycle comprising carbon atoms and 1-4 heteroatoms selected from N, O, and S(O)ₚ, wherein said heterocycle is substituted with 0-2 $R^{2b}$;

$R^{2b}$ is, independently at each occurrence, F, Br, Cl, OCF₃, CF₃, OR$^a$, SR$^a$, CN, NR⁷R⁸, C(O)OR$^a$, or C₁₋₄ alkyl;

$R^3$ is, independently at each occurrence, —(CH₂)ᵣ-phenyl substituted with 0-3 $R^{3a}$, —(CH₂)ᵣ-pyridyl substituted with 0-3 $R^{3a}$, —(CH₂)ᵣ-thiazolyl substituted with 0-2 $R^{3a}$, or

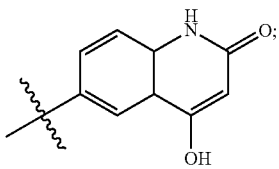

$R^{3a}$ is, independently at each occurrence, F, Cl, Br, I, OCF₃, CF₃, CN, NO₂, OR$^a$, SR$^a$, NR⁷R⁸, —NHC(O)NR⁸R⁹, —(CH₂)ᵣC(O)OR$^a$, —C(O)C₁₋₄ alkyl, —(CH₂)ᵣNR⁸C(O)R$^a$, —(CH₂)ᵣNR⁸CO₂R$^c$, —C(O)NR⁸R⁹, C₁₋₄ haloalkyl, C₁₋₄ haloalkyloxy-, C₁₋₆ alkyl, C₃₋₆ cycloalkyl, —(CH₂)ᵣ-phenyl,

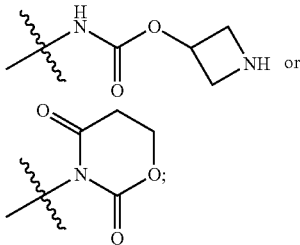

$R^4$ is, independently at each occurrence, H, F, Cl, Br, I, OCF₃, CF₃, CN, NO₂, —(CH₂)ᵣOR$^a$, —CH(OH)CH₂OH, —(CH₂)ᵣSR$^a$, C(O)R$^a$, C(O)OR$^a$, —(CH₂)ᵣS(O)₂R$^c$, —(CH₂)ᵣNR⁷R⁸, C(O)NR⁸R⁹, C₁₋₄ alkyl, or C₂₋₄ alkenyl;

$R^7$ is, independently at each occurrence, H, C₁₋₄ alkyl substituted with 0-1 OH, or benzyl;

$R^8$ is, independently at each occurrence, H, C₁₋₄ alkyl substituted with 0-1 OH, or benzyl;

alternatively, R⁷ and R⁸, when attached to the same nitrogen, combine to form a 5- to 6-membered heterocycle comprising: carbon atoms and 0-2 additional heteroatoms selected from N, O, and S(O)ₚ; wherein said heterocycle is substituted with 0-2 R$^f$;

$R^9$ is, independently at each occurrence, H, C₁₋₆ alkyl, or benzyl; alternatively, R⁸ and R⁹, when attached to the same nitrogen, combine to form a 5- to 6-membered heterocycle comprising: carbon atoms and 0-2 additional heteroatoms selected from N, O, and S(O)ₚ, wherein said heterocycle is substituted with 0-2 R$^d$;

$R^{11}$ is —CH₂OR$^a$, —CH₂CH₂OR$^a$, —CH₂S(O)ₚR$^c$, —CH₂CH₂S(O)ₚR$^c$, —CH₂NR⁷R⁸, —CH₂CH₂NR⁷R⁸, —CH₂C(O)R$^a$, —CH₂CH₂C(O)R$^a$, —CH₂C(O)OR$^a$, —CH₂CH₂C(O)OR$^a$, —CH₂C(O)NR⁸R⁹, —CH₂CH₂C(O)NR⁸R⁹, —CH₂NR⁸C(O)R$^c$, —CH₂CH₂NR⁸C(O)R$^c$, —CH₂NR⁸C(O)OR$^c$, —CH₂CH₂NR⁸C(O)OR$^c$, —CH₂NHS(O)₂(3-(pyrazol-1-yl)-Ph), —CH₂NHS(O)₂(1,3-dimethyl-pyrazol-4-yl), C₁₋₆ alkyl, C₂₋₆ alkenyl, —(CH₂)ₛ-phenyl substituted with 0-2 $R^{11b}$, or —(CH₂)ₛ-4 to 6-membered heterocycle substituted with 0-2 $R^{11b}$, wherein said heterocycle is selected from the group consisting of: azetidine, oxazolidin-2-one, pyrrolidine, pyrazole, thiazole, thiadiazole, oxazole, oxadiazole, imidazole, piperidine, piperazine, and pyridine;

alternatively, $R^{11}$ is

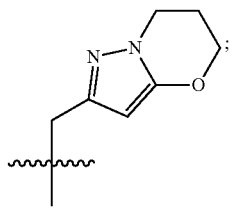

$R^{11b}$ is, independently at each occurrence H, F, CF₃, CN, NO₂, NH₂, C₁₋₄ alkyl, OMe, OEt, —C(O)R$^a$, —C(O)OR$^a$, —S(O)ₚR$^c$, —C(O)NHMe, —NHCOMe, —NHCONHMe, —NHCOCH₂N(Me)₂, —NHC(O)OBn, cyclopropyl, or cyclopropylmethyl;

$R^{12}$ is, independently at each occurrence, H, C₁₋₄ alkyl substituted with 0-2 R$^f$, or benzyl;

$R^a$ is, independently at each occurrence, H, C₁₋₄ alkyl substituted with 0-2 R$^f$, C₃₋₆ cycloalkyl substituted with 0-2 R$^f$, —(CH₂)ᵣ-phenyl substituted with 0-2 R$^f$, or —(CH₂)ᵣ-5- to 6-membered heterocycle comprising carbon atoms and 1-4 heteroatoms selected from N, O, and S(O)ₚ; wherein said heterocycle is substituted with 0-2 R$^f$;

$R^c$ is, independently at each occurrence, C₁₋₆ alkyl substituted with 0-2 R$^f$, C₃₋₆ cycloalkyl, or phenyl;

$R^d$ is, independently at each occurrence, H, =O, =NR⁸, OR$^a$, F, Cl, Br, I, CN, NO₂, —NR⁷R⁸, —C(O)R$^a$, —C(O)OR$^a$, —OC(O)R$^a$, —NR⁸C(O)R$^c$, —C(O)NR⁸R⁹, —SO₂NR⁸R⁹, —NR⁸SO₂NR⁸R⁹, —NR⁸SO₂—C₁₋₄ alkyl, —NR⁸SO₂CF₃, —NR⁸SO₂-phenyl, —S(O)₂CF₃, —S(O)ₚ—C₁₋₄ alkyl, —S(O)ₚ-phenyl, —(CF₂)ᵣCF₃, C₁₋₆ alkyl substituted with 0-2 R$^e$, C₂₋₆ alkenyl substituted with 0-2 R$^e$, or C₂₋₆ alkynyl substituted with 0-2 R$^e$;

$R^e$ is, independently at each occurrence, =O, OR$^a$, F, Cl, Br, I, CN, NO₂, —NR⁷R⁸, —C(O)R$^a$, —C(O)OR$^a$, —NR⁸C(O)R$^c$, —C(O)NR⁸R⁹, —SO₂NR⁸R⁹, —NR⁸SO₂NR⁸R⁹, —NR⁸SO₂—C₁₋₄ alkyl, —NR⁸SO₂CF₃, —NR⁸SO₂-phenyl, —S(O)₂CF₃, —S(O)ₚ—C₁₋₄ alkyl, —S(O)ₚ-phenyl, or —(CF₂)ᵣCF₃;

$R^f$ is, independently at each occurrence, H, =O, —(CH₂)ᵣOR$^g$, F, Cl, Br, I, CN, NO₂, —NR$^g$R$^g$, —C(O)R$^g$, —C(O)OR$^g$, —OC(O)R$^g$, —NR$^g$C(O)R$^g$, —C(O)

NR^gR^g, —SO₂NR^gR^g, —NR^gSO₂NR^gR^g, —NR^gSO₂—C₁₋₄ alkyl, —NR^gSO₂CF₃, —NR^gSO₂-phenyl, —S(O)₂CF₃, —S(O)ₚ—C₁₋₄ alkyl, —S(O)ₚ-phenyl, —(CF₂)ᵣCF₃, C₁₋₆ alkyl, C₂₋₆ alkenyl, C₂₋₆ alkynyl, —(CH₂)ₙ-phenyl, or —(CH₂)ₙ-5- to 10-membered heterocycle comprising carbon atoms and 1-4 heteroatoms selected from N, O, and S(O)ₚ;

R^g is, independently at each occurrence, H, C₁₋₆ alkyl, or —(CH₂)ₚ-phenyl;

p, at each occurrence, is selected from 0, 1, and 2; and r, at each occurrence, is selected from 0, 1, 2, 3, and 4.

5. A compound according to claim 4, wherein:

L₁ is —CH₂CH₂—, or —CH═CH—;

R^{1a}, R^{1b}, R^{1c}, and R^{1d} are, independently at each occurrence, H, F, Cl, or Me;

R² is 5-membered heterocycle selected from the group consisting of imidazole, triazole, and tetrazole; wherein said heterocycle is substituted with 0-2 R^{2b};

R³ is, independently at each occurrence, phenyl substituted with 0-2 R^{3a};

R⁴ is, independently at each occurrence, H, F, Cl, CN, C₁₋₄ alkyl, C₂₋₄ alkenyl, OH, —CH₂OH, —CH(OH)CH₂OH, —O—C₁₋₄ alkyl, —CH₂O(C₁₋₄ alkyl), —NH(C₁₋₄ alkyl), —N(C₁₋₄ alkyl)₂, —CH₂NH(C₁₋₄ alkyl), —CH₂N(C₁₋₄ alkyl)₂, —S—C₁₋₄ alkyl, —CH₂S(C₁₋₄ alkyl), —S(O)₂—C₁₋₄ alkyl, —CH₂S(O)₂—C₁₋₄ alkyl, C(O)OH, C(O)NR⁸R⁹, or C(O)O(C₁₋₄ alkyl); and R¹¹ is C₁₋₆ alkyl, C₂₋₆ alkenyl, benzyl substituted with 0-2 R^{11b}, —CH₂O(C₁₋₆ alkyl), —CH₂CH₂O(C₁₋₆ alkyl), —CH₂S(O)ₚ(C₁₋₆ alkyl), —CH₂CH₂S(O)ₚ(C₁₋₆ alkyl), —CH₂C(O)OH, —CH₂C(O)O(C₁₋₄ alkyl), —CH₂NHC(O)(C₁₋₄ alkyl), —CH₂NHC(O)O(C₁₋₄ alkyl), —CH₂NH(C₁₋₄ alkyl), —CH₂N(C₁₋₄ alkyl)₂, —CH₂C(O)NH(C₁₋₄ alkyl substituted with 0-1 OH), —CH₂C(O)N(C₁₋₄ alkyl)₂, —CH₂NHC(O)Ph, —CH₂C(O)(pyrrolidin-1-yl), —CH₂C(O)(3-OH-pyrrolidin-1-yl), —CH₂C(O)(4-OH-piperidin-1-yl), —CH₂C(O)(4-Me-piperazin-1-yl), —CH₂NHS(O)₂(3-(pyrazol-1-yl)-Ph), —CH₂NHS(O)₂(1,3-dimethyl-pyrazol-4-yl), or —CH₂-4- to 6-membered heterocycle substituted with 0-2 R^{11b}, wherein said heterocycle is selected from the group consisting of: azetidine, oxazolidin-2-one, pyrrolidine, pyrazole, thiazole, thiadiazole, oxadiazole, piperidine, and pyridine;

alternatively, R¹¹ is

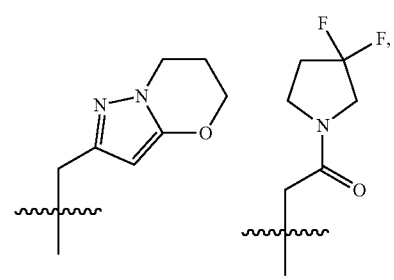

6. A compound according to claim 1, wherein the compound is of Formula (III):

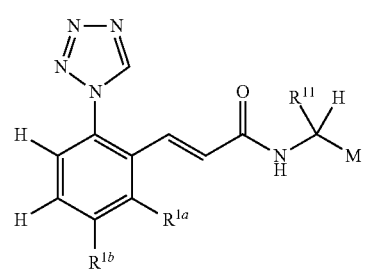

(III)

or a stereoisomer, a tautomer, or a pharmaceutically acceptable salt thereof, wherein:

M is selected from the group consisting of:

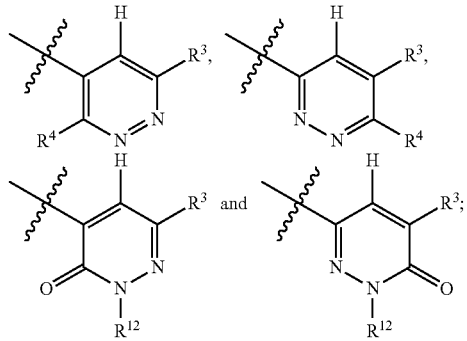

R^{1a} is H or F;

R^{1b} is Cl or Me;

R³ is, independently at each occurrence, —(CH₂)ᵣ-phenyl substituted with 0-2 R^{3a}, —(CH₂)ᵣ-pyridyl substituted with 0-2 R^{3a}, —(CH₂)ᵣ-thiazolyl substituted with 0-2 R^{3a}, or

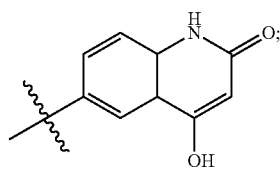

R^{3a} is, independently at each occurrence, F, NH₂, —NHC(O)OMe, —NHC(O)OEt, —NHC(O)CH₂OH, —NHC(O)O(CH₂)₂C(O)OH, —NHC(O)OCH₂C(O)NH₂, —NHC(O)O(CH₂)₂C(O)NH₂, —NHC(O)CH₂OC(O)

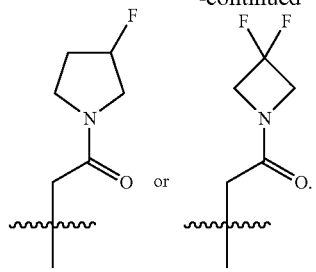

Me, —NHC(O)O(CH₂)₂OH, —NHC(O)O(CH₂)₂OMe, —NHC(O)NHC(CH₂)₂OH, —NHC(O)NHC(Me)₂CH₂OH,

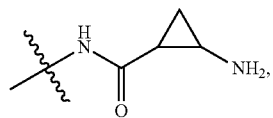

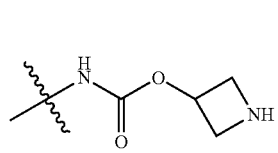 or 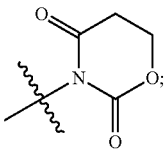

R⁴ is, independently at each occurrence, H, F, Cl, Me, Et, —CH═CH₂, OH, —CH₂OH, —CH(OH)CH₂OH, OMe, OEt, SMe, —CH₂SMe, SEt, SO₂Me, —CH₂SO₂Me, SO₂Et, CN, C(O)OH, C(O)OMe, —CH₂N(Me)₂, C(O)NH₂, or C(O)NHMe;

R¹¹ is selected from the group consisting of: C₁₋₄ alkyl, C₂₋₄ alkenyl, benzyl, 3-F-benzyl, 4-F-benzyl, 4-NH₂-benzyl, 4-NHCOMe-benzyl, 4-NHCONHMe-benzyl, 4-NHCOCH₂N(Me)₂-benzyl, —CH₂SMe, —CH₂S(neopentyl), —(CH₂)₂SMe, —(CH₂)₂S(O)Me, —CH₂S(O)₂Me, —CH₂S(O)₂(neopentyl), —(CH₂)₂S(O)₂Me, —CH₂C(O)OH, —CH₂C(O)OMe, —CH₂C(O)O(t-Bu), —CH₂NHC(O)Me, —CH₂NHC(O)(t-Bu), —CH₂NHC(O)Ph, —CH₂NHS(O)₂(3-(pyrazol-1-yl)-Ph), —CH₂NHS(O)₂(1,3-dimethyl-pyrazol-4-yl), —CH₂NHC(O)O(t-Bu), —CH₂NH(i-Pr), —CH₂C(O)NH(CH₂CH₂OH), —CH₂C(O)NH(t-Bu), —CH₂C(O)N(Me)₂, —CH₂C(O)NMe(i-Pr), —CH₂C(O)(pyrrolidin-1-yl), —CH₂C(O)(3-OH-pyrrolidin-1-yl), —CH₂C(O)(4-OH-piperidin-1-yl), —CH₂C(O)(4-Me-piperazin-1-yl), (azetidin-3-yl)methyl, (1-acetyl-azetidin-3-yl)methyl, (1-Et-pyrazol-3-yl)methyl, (4-Me-thiazol-2-yl)methyl, (thiazol-4-yl)methyl, (2-isopropyl-thiazol-4-yl)methyl, (5-methoxy-1-Me-1H-pyrazol-3-yl)methyl, (1-Me-5-(methylsulfinyl)-1H-pyrazol-3-yl)methyl, (1-Me-5-(methylsulfonyl)-1H-pyrazol-3-yl)methyl, (pyrrolidin-3-yl)methyl, (1-Et-pyrrolidin-3-yl)methyl, (1-acetyl-pyrrolidin-3-yl)methyl, (1-(cyclopropylmethyl)-pyrrolidin-3-yl)methyl, (2-(i-Pr)-thiazol-4-yl)methyl, (4,5-dimethylthiazol-2-yl)methyl, (5-cyclopropyl-1,3,4-thiadiazol-2-yl)methyl, (5-(t-Bu)-1,2,4-oxadiazol-3-yl)methyl, (piperidin-3-yl)methyl, (piperidin-4-yl)ethyl, (1-acetyl-piperidin-3-yl)methyl, (1-propionyl-piperidin-3-yl)methyl, (1-isobutyryl-piperidin-3-yl)methyl, (1-(cyclopropanecarbonyl)-piperidin-3-yl)methyl, (pyrid-3-yl)methyl, (6-Me-pyrid-3-yl)methyl, (6-NH₂-pyrid-3-yl)methyl, (pyrid-4-yl)methyl,

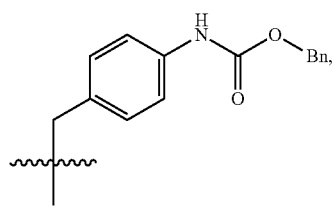

-continued

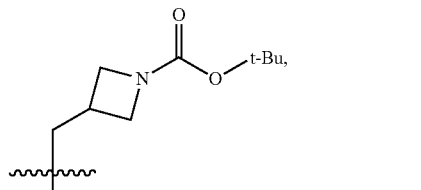

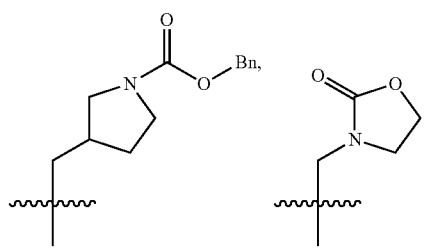

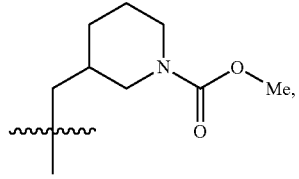

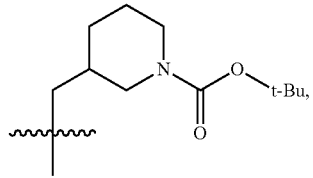

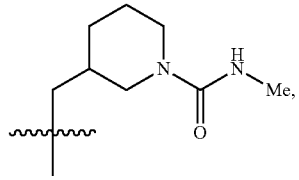

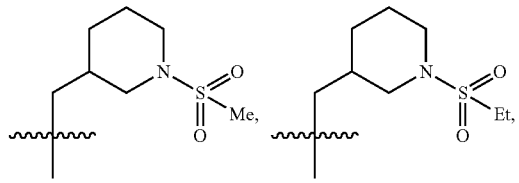

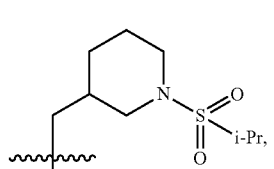

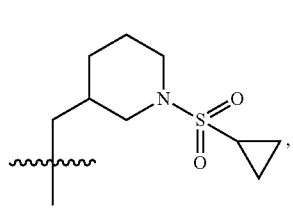

-continued

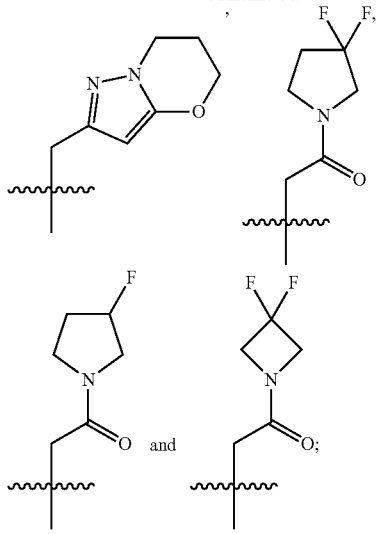

R$^{12}$ is, independently at each occurrence, H, Me, —CH$_2$CH$_2$OH, —CH$_2$C(O)OH, or —CH$_2$C(O)OMe; and r, at each occurrence, is selected from 0, 1, and 2.

7. A compound according to claim 6, wherein:

R$^3$ is, independently at each occurrence, phenyl substituted with 0-2 R$^{3a}$, pyridyl substituted with 0-2 R$^{3a}$, thiazolyl substituted with 0-2 R$^{3a}$, or

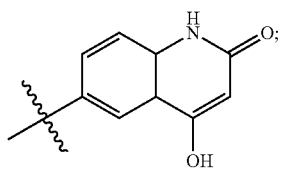

R$^{3a}$ is, independently at each occurrence, NH$_2$, —NHC(O)OMe, —NHC(O)OEt, —NHC(O)CH$_2$OH, —NHC(O)OCH$_2$C(O)NH$_2$, —NHC(O)O(CH$_2$)$_2$C(O)NH$_2$, —NHC(O)CH$_2$OC(O)Me, —NHC(O)O(CH$_2$)$_2$OH, —NHC(O)O(CH$_2$)$_2$OMe, —NHC(O)NHC(CH$_2$)$_2$OH, —NHC(O)NHC(Me)$_2$CH$_2$OH,

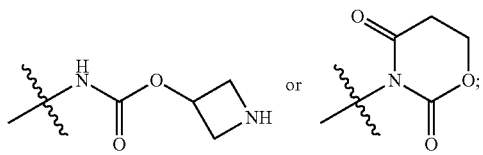

R$^4$ is, independently at each occurrence, H, F, Cl, Me, Et, —CH=CH$_2$, OH, —CH$_2$OH, —CH(OH)CH$_2$OH, OMe, OEt, SMe, —CH$_2$SMe, SEt, SO$_2$Me, —CH$_2$SO$_2$Me, SO$_2$Et, CN, C(O)OH, C(O)OMe, —CH$_2$N(Me)$_2$, C(O)NH$_2$, or C(O)NHMe;

R$^{11}$ is selected from the group consisting of: C$_{1-4}$ alkyl, C$_{2-4}$ alkenyl, benzyl, 3-F-benzyl, 4-F-benzyl, 4-NH$_2$-benzyl, 4-NHCOMe-benzyl, 4-NHCONHMe-benzyl, 4-NHCOCH$_2$N(Me)$_2$-benzyl, —CH$_2$SMe, —(CH$_2$)$_2$SMe, —(CH$_2$)$_2$S(O)Me, —CH$_2$S(O)$_2$Me, —(CH$_2$)$_2$S(O)$_2$Me, —CH$_2$C(O)OH, —CH$_2$C(O)OMe, —CH$_2$C(O)O(t-Bu), —CH$_2$NHC(O)Me, —CH$_2$NHC(O)(t-Bu), —CH$_2$NHC(O)O(t-Bu), —CH$_2$NH(i-Pr), —CH$_2$C(O)NH(CH$_2$CH$_2$OH), —CH$_2$C(O)NH(t-Bu), —CH$_2$C(O)N(Me)$_2$, —CH$_2$C(O)NMe(i-Pr), —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), (azetidin-3-yl)methyl, (1-acetyl-azetidin-3-yl)methyl, (1-Et-pyrazol-3-yl)methyl, (4-Me-thiazol-2-yl)methyl, (thiazol-4-yl)methyl, (2-isopropyl-thiazol-4-yl)methyl, (5-methoxy-1-Me-1H-pyrazol-3-yl)methyl, (1-Me-5-(methylsulfinyl)-1H-pyrazol-3-yl)methyl, (1-Me-5-(methylsulfonyl)-1H-pyrazol-3-yl)methyl, (pyrrolidin-3-yl)methyl, (1-Et-pyrrolidin-3-yl)methyl, (1-acetyl-pyrrolidin-3-yl)methyl, (1-(cyclopropylmethyl)-pyrrolidin-3-yl)methyl, (2-(i-Pr)-thiazol-4-yl)methyl, (4,5-dimethylthiazol-2-yl)methyl, (5-cyclopropyl-1,3,4-thiadiazol-2-yl)methyl, (5-(t-Bu)-1,2,4-oxadiazol-3-yl)methyl, (piperidin-3-yl)methyl, (piperidin-4-yl)ethyl, (1-acetyl-piperidin-3-yl)methyl, (1-propionyl-piperidin-3-yl)methyl, (1-isobutyryl-piperidin-3-yl)methyl, (1-(cyclopropanecarbonyl)-piperidin-3-yl)methyl, (pyrid-3-yl)methyl, (6-Me-pyrid-3-yl)methyl, (6-NH$_2$-pyrid-3-yl)methyl, (pyrid-4-yl)methyl,

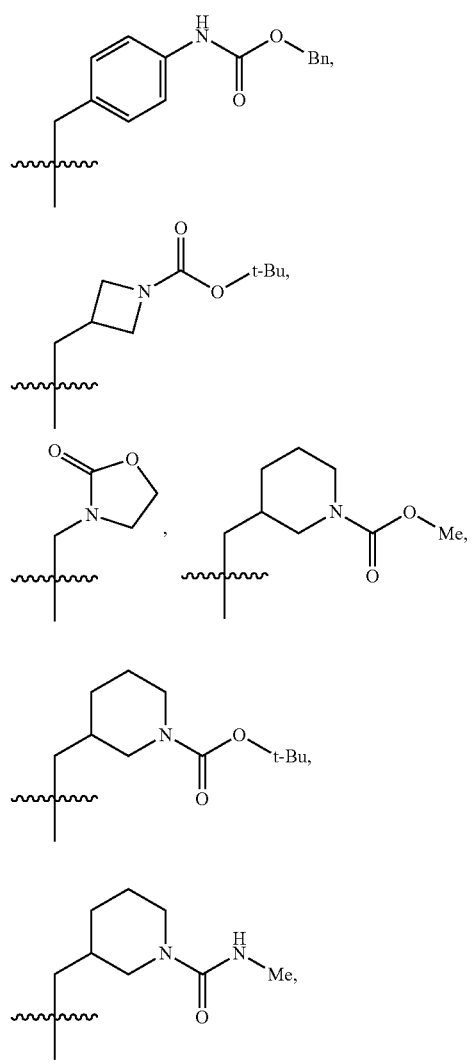

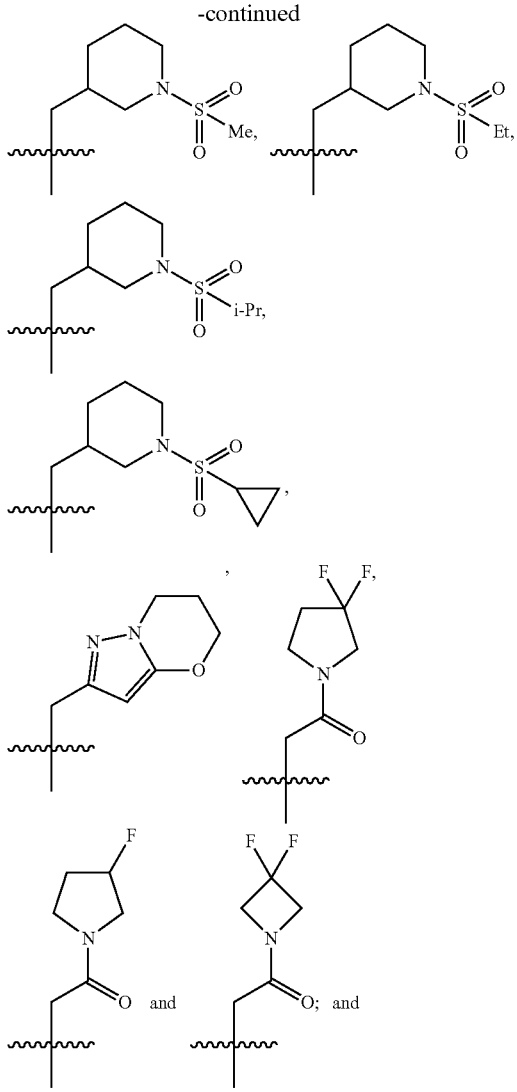

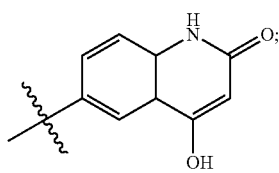

$R^{12}$ is, independently at each occurrence, H, Me, —CH$_2$CH$_2$OH, —CH$_2$C(O)OH, or —CH$_2$C(O)OMe.

8. A compound according to claim 6, wherein:

$R^3$ is, independently at each occurrence, phenyl substituted with 0-2 $R^{3a}$, or $R^{3a}$ is, independently at each occurrence, NH$_2$, —NHC(O)OMe, —NHC(O)OCH$_2$C(O)NH$_2$, —NHC(O)O(CH$_2$)$_2$C(O)NH$_2$, —NHC(O)O(CH$_2$)$_2$OH, —NHC(O)O(CH$_2$)$_2$OMe, or —NHC(O)NHC(CH$_2$)$_2$OH;

$R^4$ is, independently at each occurrence, H, F, Cl, Me, Et, —CH=CH$_2$, OH, —CH$_2$OH, —CH(OH)CH$_2$OH, OMe, SMe, —CH$_2$SMe, SEt, SO$_2$Me, —CH$_2$SO$_2$Me, SO$_2$Et, CN, C(O)OH, C(O)OMe, —CH$_2$N(Me)$_2$, C(O)NH$_2$, or C(O)NHMe;

$R^{11}$ is selected from the group consisting of: benzyl, 3-F-benzyl, 4-F-benzyl, 4-NH$_2$-benzyl, 4-NHCOMe-benzyl, 4-NHCONHMe-benzyl, 4-NHCOCH$_2$N(Me)$_2$-benzyl, —CH$_2$C(O)OMe, —CH$_2$C(O)O(t-Bu), —CH$_2$NHC(O)Me, —CH$_2$C(O)NH(CH$_2$CH$_2$OH), —CH$_2$C(O)NH(t-Bu), —CH$_2$C(O)N(Me)$_2$, —CH$_2$C(O)NMe(i-Pr), —CH$_2$C(O)(pyrrolidin-1-yl), —CH$_2$C(O)(3-OH-pyrrolidin-1-yl), —CH$_2$C(O)(4-OH-piperidin-1-yl), —CH$_2$C(O)(4-Me-piperazin-1-yl), (1-Et-pyrazol-3-yl)methyl, (4-Me-thiazol-2-yl)methyl, (thiazol-4-yl)methyl, (5-methoxy-1-Me-1H-pyrazol-3-yl)methyl, (4,5-dimethylthiazol-2-yl)methyl, (5-cyclopropyl-1,3,4-thiadiazol-2-yl)methyl, (1-acetyl-piperidin-3-yl)methyl, (1-propionyl-piperidin-3-yl)methyl, (1-isobutyryl-piperidin-3-yl)methyl, (pyrid-3-yl)methyl, (6-NH$_2$-pyrid-3-yl)methyl, (pyrid-4-yl)methyl,

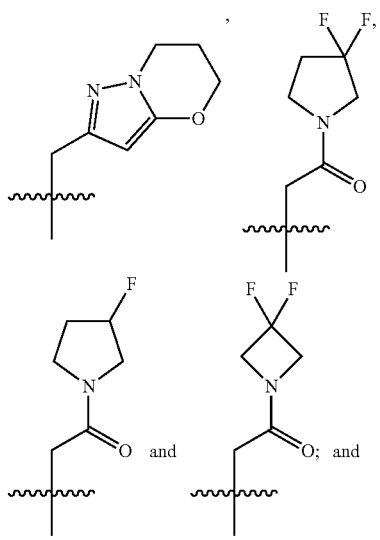

$R^{12}$ is, independently at each occurrence, H, Me, —CH$_2$CH$_2$OH, or —CH$_2$C(O)OH.

9. A pharmaceutical composition, comprising: a pharmaceutically acceptable carrier and a compound of claim 1, or a stereoisomer, a tautomer, or a pharmaceutically acceptable salt thereof.

* * * * *

UNITED STATES PATENT AND TRADEMARK OFFICE
CERTIFICATE OF CORRECTION

PATENT NO.        : 8,324,199 B2                              Page 1 of 1
APPLICATION NO.   : 12/921177
DATED             : December 4, 2012
INVENTOR(S)       : James R. Corte et al.

It is certified that error appears in the above-identified patent and that said Letters Patent is hereby corrected as shown below:

In the Claims:

Claim 1:

Column 192, line 20, change "R12" to -- $R^{12}$ --.

Claim 4:

Column 197, line 10, change "—$(CH_2)_p$-phenyl;" to -- —$(CH_2)_n$-phenyl; --.

Signed and Sealed this
Eleventh Day of February, 2014

Michelle K. Lee
*Deputy Director of the United States Patent and Trademark Office*